(12) United States Patent
Hubschwerlen et al.

(10) Patent No.: US 8,618,092 B2
(45) Date of Patent: Dec. 31, 2013

(54) TRICYCLIC OXAZOLIDINONE ANTIBIOTIC COMPOUNDS

(75) Inventors: Christian Hubschwerlen, Durmenach (FR); Daniel Ritz, Allschwil (CH); Georg Rueedi, Allschwil (CH); Jean-Philippe Surivet, Kembs (FR); Cornelia Zumbrunn-Acklin, Basel (CH)

(73) Assignee: Actelion Pharmaceuticals Ltd., Allschweil (CH)

( * ) Notice: Subject to any disclaimer, the term of this patent is extended or adjusted under 35 U.S.C. 154(b) by 211 days.

(21) Appl. No.: 13/123,218

(22) PCT Filed: Oct. 6, 2009

(86) PCT No.: PCT/IB2009/054357
§ 371 (c)(1),
(2), (4) Date: Apr. 7, 2011

(87) PCT Pub. No.: WO2010/041194
PCT Pub. Date: Apr. 15, 2010

(65) Prior Publication Data
US 2011/0195961 A1 Aug. 11, 2011

(30) Foreign Application Priority Data

Oct. 7, 2008 (WO) .................. PCT/IB2008/054109
Mar. 13, 2009 (WO) .................. PCT/IB2009/051059
Jun. 30, 2009 (WO) .................. PCT/IB2009/052843

(51) Int. Cl.
*A61K 31/54* (2006.01)
*A61K 31/535* (2006.01)

(52) U.S. Cl.
USPC ................... 514/224.2; 514/229.2; 514/230.5

(58) Field of Classification Search
USPC .......... 514/250, 224.2, 229.2, 230.5
See application file for complete search history.

(56) References Cited

U.S. PATENT DOCUMENTS

| 5,298,518 | A | 3/1994 | Miyake et al. |
| 2007/0060558 | A1 | 3/2007 | Sanchez et al. |
| 2010/0113448 | A1 | 5/2010 | Itai et al. |
| 2010/0331318 | A1 | 12/2010 | Hubschwerlen et al. |

FOREIGN PATENT DOCUMENTS

| EP | 0 106 816 | 4/1984 |
| EP | 0518672 | 12/1992 |
| EP | 1 980 251 | 10/2008 |
| WO | WO 98/17672 | 4/1998 |
| WO | WO 00/21948 | 4/2000 |
| WO | WO 01/30782 | 5/2001 |

(Continued)

OTHER PUBLICATIONS

Greene et al., Index of Protective Groups in Organic Synthesis, 3$^{rd}$ Edition (1999).
Greene et al., Protective Groups in Organic Synthesis, 3$^{rd}$ Edition, pp. 494-653 (Publisher: John Wiley and Sons, Inc., New York, N.Y.) (1999).

(Continued)

*Primary Examiner* — San-Ming Hui
(74) *Attorney, Agent, or Firm* — Hunton & Williams LLP

(57) ABSTRACT

The invention relates to antibacterial compounds of formula I

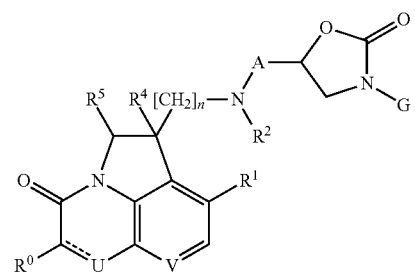

wherein "‒‒‒‒‒" is a bond or is absent, V is CH, CR$^6$ or N; R$^0$ is H or, if "‒‒‒‒‒" is a bond, may also be alkoxy; R$^1$ is notably H or halogen; U is CH or N when "‒‒‒‒‒" is a bond, or, if "‒‒‒‒‒" is absent, U is CH$_2$, NH or NR$^9$; R$^2$ is H, alkylcarbonyl or —CH$_2$—R$^3$; R$^3$ is H, alkyl or hydroxyalkyl; R$^4$ is H or, if n is not 0 and R$^5$ is H, may also be OH; R$^5$ is H, alkyl, hydroxyalkyl, aminoalkyl, alkoxyalkyl, carboxy or alkoxycarbonyl; R$^6$ is hydroxyalkyl, carboxy, alkoxycarbonyl or —(CH$_2$)$_q$—NR$^7$R$^8$, q being 1, 2 or 3 and each of R$^7$ and R$^8$ independently being H or alkyl or R$^7$ and R$^8$ forming with the N atom bearing them a ring; R$^9$ is alkyl or hydroxyalkyl; A is —(CH$_2$)$_p$—, —CH$_2$CH$_2$CH(OH)— or —COCH$_2$CH(OH)—; G is substituted phenyl or G$^1$ or G$^2$

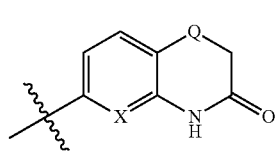

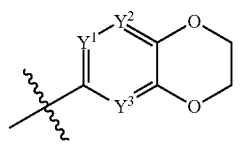

wherein Q is O or S and X is CH or N; and Y$^1$, Y$^2$ and Y$^3$ may each be CH or N; and n is 0 when A is —CH$_2$CH$_2$CH(OH)— or —COCH$_2$CH(OH)—, and n is 0, 1 or 2 when A is —(CH$_2$)$_p$—, p being 1, 2, 3 or 4, with the proviso that the sum of n and p is then 2, 3 or 4;
and to salts of such compounds.

23 Claims, No Drawings

(56) References Cited

FOREIGN PATENT DOCUMENTS

| | | |
|---|---|---|
| WO | WO 02/08224 | 1/2002 |
| WO | WO 2004/002490 | 1/2004 |
| WO | WO 2004/058144 | 7/2004 |
| WO | WO 2005/019177 | 3/2005 |
| WO | WO 2006/021448 | 3/2006 |
| WO | WO 2006/032466 | 3/2006 |
| WO | WO 2006/046552 | 5/2006 |
| WO | WO 2006/125974 | 11/2006 |
| WO | WO 2007/016610 | 2/2007 |
| WO | WO 2007/071936 | 6/2007 |
| WO | WO 2007/081597 | 7/2007 |
| WO | WO 2007/107965 | 9/2007 |
| WO | WO 2007/115947 | 10/2007 |
| WO | WO 2007/122258 | 11/2007 |
| WO | WO 2007/144423 | 12/2007 |
| WO | WO 2008/003690 | 1/2008 |
| WO | WO 2008/026172 | 3/2008 |
| WO | WO 2008/065198 | 6/2008 |
| WO | WO 2008/078305 | 7/2008 |
| WO | WO 2008/116815 | 10/2008 |
| WO | WO 2008/120003 | 10/2008 |
| WO | WO 2008/125594 | 10/2008 |
| WO | WO 2008/126024 | 10/2008 |
| WO | WO 2008/126034 | 10/2008 |
| WO | WO 2008/128942 | 10/2008 |
| WO | WO 2008/128953 | 10/2008 |
| WO | WO 2008/128962 | 10/2008 |
| WO | WO 2008/148867 | 12/2008 |
| WO | WO 2008/150827 | 12/2008 |
| WO | WO 2008/152603 | 12/2008 |
| WO | WO 2009/000745 | 12/2008 |
| WO | WO 2009/077989 | 6/2009 |
| WO | WO 2009/087153 | 7/2009 |
| WO | WO 2009/104147 | 8/2009 |
| WO | WO 2009/104159 | 8/2009 |

OTHER PUBLICATIONS

Greene et al., Protective Groups in Organic Synthesis, 3rd Edition, pp. 17-245, particularly pp. 23-147, 133-139 and 142-143 (Publisher: John Wiley and Sons, Inc., New York, N.Y.) (1999).
Benz, Comprehensive Organic Synthesis, B.M. Trost, 1. Fleming, Eds; Pergamon Press: New York, vol. 6, pp. 381-417 (1991).
Selwood et al., Bioorganic & Medicinal Chemistry Letters, vol. 6, No. 8, pp. 991-994 (1996).
Cha et al., Chemical Reviews, vol. 95, No. 6, pp. 1761-1795 (1995).
Kolb et al., Chemical Reviews, vol. 94, No. 8, pp. 2483-2547 (1994).
Talbot et al., Clinical Infectious Diseases, vol. 42, pp. 657-668 (2006).
Larock, Comprehensive Organic Transformations, A guide to Functional Group Preparations; 2nd Edition, Wiley-VC; New York, Chichester, Weinheim, Brisbane, Singapore, Toronto, Section: nitriles, carboxylic acids and derivatives, pp. 1941-1949 (1999).
Larock, Comprehensive Organic Transformations, A guide to Functional Group Preparations; 2nd Edition, Wiley-VC; New York, Chichester, Weinheim, Brisbane, Singapore, Toronto, Section: nitriles, carboxylic acids and derivatives, pp. 1653-1655 (1999).
Larock, Comprehensive Organic Transformations, A guide to Functional Group Preparations; 2nd Edition, Wiley-VC; New York, Chichester, Weinheim, Brisbane, Singapore, Toronto, 1999. Section: nitriles, carboxylic acids and derivatives, pp. 1646-1648.
Larock, Comprehensive Transformations, A guide to Functional Group Preparations; 2nd Edition, Wiley-VC; New York, Chichester, Weinheim, Brisbane, Singapore, Toronto, Section: Amines, pp. 779-784 (1999).
Larock, Comprehensive Organic Transformations, A guide to Functional Group Preparations; 2nd Edition, Wiley-VC; New York, Chichester, Weinheim, Brisbane, Singapore, Toronto, Section: Amines, pp. 1057-1087 (1999).
Mancuso et al., The Journal of Organic Chemistry, vol. 43, No. 12, pp. 2480-2482 (1978).
Dess et al., The Journal of Organic Chemistry, vol. 48, No. 22, pp. 4155-4156 (1983).
Abdel-Megeid et al., Egyptian Journal of Chemistry, vol. 20, No. 5, pp. 427-439 (1977).
Gould, International Journal of Pharmaceutics, vol. 33, pp. 201-217 (1986).
Svetlik, Journal of Organic Chemistry, vol. 55, pp. 4740-4744 (1990).
Kumar et al., Journal of Organic Chemistry, vol. 59, pp. 4760-4764 (1994).
Liu et al., Journal of Organic Chemistry, vol. 70, pp. 2847-2850 (2005).
Chang et al., Journal of Medicinal Chemistry, vol. 36, pp. 2558-2568 (1993).
Albert et al., Journal of Organic Chemistry, vol. 73, pp. 1093-1098 (2008).
Mitsunobu, Synthesis, pp. 1-28 (1981).
Chen et al., Organic Chemistry, vol. 8, No. 24, pp. 5609-5612 (2006).
Bravo et al., Organic Letters, vol. 5, No. 12, pp. 2123-2126 (2003).
Bartoli et al., Organic Letters, vol. 6, No. 22, pp. 3973-3975 (2004).
Johannes et al., Organic Letters, vol. 7, No. 18, pp. 3997-4000 (2005).
Andreou et al., Organic Letters, vol. 7, No. 19, pp. 4083-4086 (2005).
Bartoli et al., Organic Letters, vol. 7, No. 10, pp. 1983-1985 (2005).
Index of Remington, The Science and Practice of Pharmacy, 21st Edition, Part 5, "Pharmaceutical Manufacturing" [published by Lippincott Williams & Wilkins]) (2005).
Bal et al., Tetrahedron, vol. 37, pp. 2091-2096 (1981).
International Search Report for International Application No. PCT/IB2009/054357, mailed Jan. 15, 2010.
Written Opinion for International Application No. PCT/IB2009/054357, mailed Jan. 15, 2010.
Wikler, Matthew, "Methods for Dilution Antimicrobial Susceptibility Tests for Bacteria that Grow Aerobically", approved standard, 7th ed., Clinical and Laboratory Standards Institute (CLSI), Document M7-A7, vol. 26, No. 2, (64 pages), Wayne, PA, USA, 2006.
Turner, J. "A General Approach to the Synthesis of 1,6-,1,7-, and 1,8-Naphthyridines" J. Org. Chem. 55(15), pp. 4744-4750, 1990.
Brickner, Current Pharmaceutical Design, vol. 2, pp. 175-194 (1996).
Curran et al., Tetrahedron, vol. 49, No. 22, pp. 4841-4858 (1993).
Fatiadi, Synthesis, pp. 85-127 (1987).
Larock, Comprehensive Organic Transformations. A Guide to Functional Group Preparations, 2nd Edition, Wiley-VC; New York, Chichester, Weinheim, Brisbane, Singapore, Toronto, Section Aldehydes and Ketones, pp. 1235-1236 and 1238-1246 (1999).
Roma et al., Heterocycles, vol. 25, No. 1, pp. 329-332 (1987).
Schaus et al., Journal of the American Chemical Society, vol. 124, pp. 1307-1315 (2002).
Shi et al., Accounts of Chemical Research, 37, pp. 488-496 (2004).
Tokunaga et al., Science, vol. 277, pp. 936-938 (1997).
Vanrheenen et al., Tetrahedron Letters, vol. 23, pp. 1973-1976 (1976).
Vourloumis et al., Tetrahedron Letters, vol. 44, No. 14, pp. 2807-2811 (2003).
Yin et al., Organic Letters, vol. 2, No. 8, pp. 1101-1104 (2000).
Zaragoza et al., Journal of Medicinal Chemistry, vol. 48, pp. 306 (2005).
International Search Report for International Application No. PCT/IB2009/050675 mailed Sep. 17, 2009.
Statement of Substance filed Jul. 26, 2012 in the US Patent and Trademark Office in U.S. Appl. No. 12/918,749, filed Aug. 20, 2010.

TRICYCLIC OXAZOLIDINONE ANTIBIOTIC COMPOUNDS

CROSS-REFERENCE TO RELATED APPLICATIONS

This application is the national phase application of PCT/IB2009/054357, filed Oct. 6, 2009, which claims the benefit of PCT/IB2008/054109, filed Oct. 7, 2008, and PCT/IB2009/051059, filed Mar. 13, 2009, and PCT/IB2009/052843, filed Jun. 30, 2009, the contents of each are hereby incorporated by reference in their entirety.

FIELD OF THE INVENTION

The present invention concerns tricyclic oxazolidinone antibiotic compounds, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

BRIEF SUMMARY OF THE INVENTION

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:
  *S. aureus* is resistant to β-lactams, quinolones and now even to vancomycin;
  *S. pneumoniae* is becoming resistant to penicillin or quinolone antibiotics and even to new macrolides;
  *Enteroccocci* are quinolone and vancomycin resistant and β-lactam antibiotics are inefficacious against these strains;
  Enterobacteriaceae are cephalosporin and quinolone resistant;
  *P. aeruginosa* are β-lactam and quinolone resistant.

Furthermore, the incidence of multi-drug-resistant Gram-negative strains such as Enterobacteriaceae and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella* species and *Pseudomonas aeruginosa* (*Clinical Infectious Diseases* (2006), 42, 657-68).

In addition, microorganisms that are causing persistent infections are increasingly being recognized as causative agents or cofactors of severe chronic diseases like peptic ulcers or heart diseases.

Azatricyclic antibiotic compounds have already been described in WO 2007/071936 and WO 2007/122258 (disclosing 3-oxo-1,2-dihydro-3H-2a,6-diaza-acenaphthyl ene-1-methyl derivatives), WO 2007/081597 (disclosing 4-oxo-1,2-dihydro-4H-pyrrolo[3,2,1-ij]quinoline-1-methyl derivatives), WO 2007/115947 (disclosing 3-oxo-5,6-dihydro-3H-pyrrolo[1,2,3-de]quinoxaline-6-methyl derivatives) and WO 2008/003690 (disclosing notably 1-(7-oxo-5,6,9a,9b-tetrahydro-4H,7H-1,6a-diaza-phenalen-5-yl)-piperidine-4-yl and 1-(5-oxo-2,3,7a, 10b-tetrahydro-1H,5H-pyrido quinolin-2-yl)-piperidine-4-yl derivatives). More recently, further azatricyclic antibiotics have been described in WO 2008/120003, WO 2008/128942, WO 2008/128953, WO 2008/128962, WO 2009/000745 and WO 2009/087153 (all filed before, but published after the earliest priority date(s) of the present application).

Quinoline, naphthyridine or quinoxaline spirooxazolidinone antibiotic compounds have already been described in WO 2008/026172. More recently, other antibiotic compounds comprising an oxazolidinone motif have been disclosed in WO 2008/126024, WO 2008/126034, WO 2009/077989 and WO 2009/104159 (all filed before, but published after the earliest priority date(s) of the present application).

Moreover, azatricyclic antibiotics comprising an oxazolidinone motif have been described in WO 2009/104147 (the priority or filing dates of which are earlier than some of or all those of the present application, while the publication took place after the priority dates of the present application).

The Applicants have now found a new family of tricyclic antibiotic compounds corresponding to the formula I described hereafter.

Various embodiments of the invention are presented hereafter:

DETAILED DESCRIPTION OF PREFERRED EMBODIMENTS i) The invention firstly relates to compounds of formula I

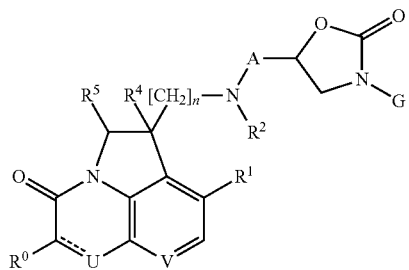

wherein
"_____" is a bond or is absent;
$R^0$ represents H or, in the case "_____" is a bond, may also represent $(C_1\text{-}C_3)$alkoxy (in particular methoxy);
$R^1$ represents H, halogen (notably F, Cl or Br), cyano, $(C_1\text{-}C_3)$alkyl (notably methyl) or ethynyl;
U represents CH or N when "_____" is a bond, or, in case "_____" is absent, U represents $CH_2$, NH or $NR^9$;
V represents CH, $CR^6$ or N;
$R^2$ represents H, $(C_1\text{-}C_3)$alkylcarbonyl or a group of the formula $—CH_2—R^3$;
$R^3$ represents H, $(C_1\text{-}C_3)$alkyl or $(C_1\text{-}C_3)$hydroxyalkyl;
$R^4$ represents H or, in the cases wherein n is not 0 and $R^5$ is H, may also represent OH;

R⁵ represents H, $(C_1-C_3)$alkyl (notably methyl), $(C_1-C_3)$hydroxyalkyl (notably hydroxymethyl), $(C_1-C_3)$amino alkyl (notably amino methyl), $(C_1-C_3)$alkoxy $(C_1-C_3)$alkyl (notably methoxymethyl), carboxy or $(C_1-C_3)$alkoxycarbonyl (notably methoxycarbonyl);

R⁶ represents $(C_1-C_3)$hydroxyalkyl (notably hydroxymethyl), carboxy, $(C_1-C_3)$alkoxycarbonyl or a group —$(CH_2)_q$—NR⁷R⁸ wherein q is 1, 2 or 3 and each of R⁷ and R⁸ independently represents H or $(C_1-C_3)$alkyl or R⁷ and R⁸ form together with the nitrogen atom bearing them a pyrrolidinyl, piperidinyl, morpholinyl or thiomorpholinyl ring;

R⁹ represents $(C_1-C_3)$alkyl (notably methyl), 2-hydroxyethyl, 2-hydroxy-propyl or 3-hydroxy-propyl;

A represents —$(CH_2)_p$—, —$CH_2CH_2CH(OH)$— or —$COCH_2CH(OH)$—;

G represents a phenyl group which is substituted once or twice in the meta and/or para position(s) by substituents selected independently from $(C_1-C_4)$alkyl, $(C_1-C_3)$alkoxy and a halogen (notably F), whereby a $(C_1-C_3)$alkoxy substituent is preferably a straight chain $(C_1-C_3)$alkoxy and in para position, or G is a group having one of the formulae G¹ and G² below

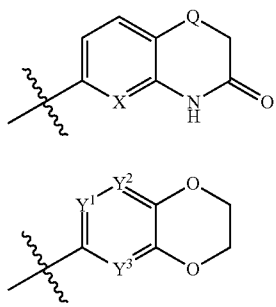

wherein

Q is O or S and X is CH or N; and

Y¹, Y² and Y³ each represent CH, or Y¹ and Y³ each represent CH and Y² represents N, or Y¹ represents N, Y² represents CH or N and Y³ represents CH, or Y¹ and Y² each represent CH and Y³ represents N; and n is 0 when A represents —$CH_2CH_2CH(OH)$— or —$COCH_2CH(OH)$—, and n is 0, 1 or 2 when A represents $(CH_2)_p$, p being 1, 2, 3 or 4, with the proviso that the sum of n and p is then 2, 3 or 4 (i.e. when n is 0, p is not 1, when n is 1, p is not 4 and when n is 2, p is neither 3 nor 4);

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "$(C_1-C_x)$alkyl" (x being an integer) refers to a straight or branched chain alkyl group containing 1 to x carbon atoms. For example, a $(C_1-C_4)$alkyl group contains from one to four carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "alkoxy", used alone or in combination, refers to a straight or branched chain alkoxy group containing from one to four carbon atoms. The term "$(C_x-C_y)$alkoxy" (x and y each being an integer) refers to an alkoxy group as defined before containing x to y carbon atoms. For example, a $(C_1-C_3)$alkoxy group contains from one to three carbon atoms. Representative examples of alkoxy groups include methoxy, ethoxy, n-propoxy and iso-propoxy. Preferred are methoxy and ethoxy.

The term "hydroxyalkyl" refers to a straight or branched chain alkyl group containing from one to four carbon atoms wherein one of the hydrogen atoms has been replaced by a hydroxy group. The term "$(C_1-C_x)$hydroxyalkyl" (x being an integer) refers to an hydroxyalkyl group wherein the alkyl group contains 1 to x carbon atoms. Representative examples of $(C_1-C_3)$hydroxyalkyl groups include, but are not limited to, hydroxymethyl, 2-hydroxy-ethyl, 1-hydroxy-ethyl and 2-hydroxy-propyl. Preferred $(C_1-C_3)$hydroxyalkyl groups are hydroxymethyl and 2-hydroxy-propyl. The most preferred $(C_1-C_3)$hydroxyalkyl group is hydroxymethyl.

The term "aminoalkyl" refers to a straight or branched chain alkyl group containing from one to four carbon atoms wherein one of the hydrogen atoms has been replaced by an amino group. The term "$(C_1-C_x)$aminoalkyl" (x being an integer) refers to an aminoalkyl group wherein the alkyl group contains 1 to x carbon atoms. Representative examples of $(C_1-C_3)$aminoalkyl groups include, but are not limited to, aminomethyl, 2-amino-ethyl, 1-amino-ethyl and 2-amino-propyl. Preferred $(C_1-C_3)$aminoalkyl groups are aminomethyl and 2-amino-propyl. The most preferred $(C_1-C_3)$aminoalkyl group is aminomethyl.

The term "alkoxyalkyl" refers to an alkoxyalkyl group wherein the alkoxy group is a $(C_1-C_4)$alkoxy group and the alkyl group is a $(C_1-C_4)$alkyl group. The term "$(C_1-C_x)$alkoxy$(C_1-C_y)$alkyl" (x and y being each independently an integer) refers to an alkoxyalkyl group wherein the alkoxy group contains 1 to x carbon atoms and the alkyl group contains 1 to y carbon atoms. Representative examples of $(C_1-C_3)$alkoxy$(C_1-C_3)$alkyl groups include, but are not limited to, methoxymethyl and ethoxymethyl. The most preferred $(C_1-C_3)$alkoxy$(C_1-C_3)$alkyl group is methoxymethyl.

The term "alkylcarbonyl" refers to an alkylcarbonyl group wherein the alkyl is a straight or branched chain alkyl group containing from one to four carbon atoms. The term "$(C_1-C_x)$alkylcarbonyl" (x being an integer) refers to an alkylcarbonyl group wherein the alkyl is a straight or branched chain alkyl group containing 1 to x carbon atoms. Representative examples of $(C_1-C_3)$alkylcarbonyl groups include acetyl, ethylcarbonyl, 1-propyl-carbonyl and 2-propyl-carbonyl. Preferred $(C_1-C_3)$alkylcarbonyl groups are acetyl and ethylcarbonyl. The most preferred $(C_1-C_3)$alkylcarbonyl group is acetyl.

The term "alkoxycarbonyl" refers to an alkoxycarbonyl group wherein the alkoxy group is a straight or branched chain alkoxy group containing from one to four carbon atoms. The term "$(C_1-C_x)$alkoxycarbonyl" (x being an integer) refers to an alkoxycarbonyl group wherein the alkoxy is a straight or branched chain alkoxy group containing 1 to x carbon atoms. Representative examples of $(C_1-C_3)$alkoxycarbonyl groups include methoxycarbonyl, ethoxycarbonyl, 1-propoxy-carbonyl and 2-propoxy-carbonyl. Preferred $(C_1-C_3)$alkylcarbonyl groups are methoxycarbonyl and ethoxycarbonyl. The most preferred (C₁-C₃)alkylcarbonyl group is ethoxycarbonyl.

The term "halogen" refers to fluorine, chlorine, bromine or iodine, and preferably to fluorine or chlorine.

When in the formula

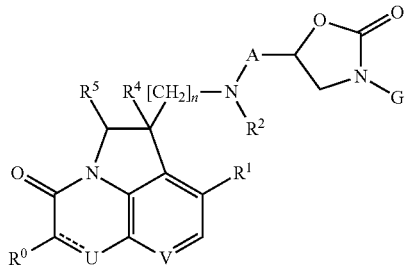

A represents the radical —CH₂CH₂CH(OH)—, this means specifically that the CH₂ part of said radical is attached to the neighbouring nitrogen while the CH(OH) part of said radical is attached to the oxazolidinone ring.

This is applicable mutatis mutandis to all radicals that make A radicals (e.g. to the radicals A' mentioned in the preparation methods). As a further example, in the substructure A, if it is stated that A represents —COCH₂CH (OH)—, it is thereby meant that the CO group of said radical is attached to the neighbouring nitrogen while the CH(OH) part of said radical is attached to the oxazolidinone ring. In other words, the left part of a radical is always attached to the right part of the radical that is next to the left.

In this text, a bond interrupted by a wavy line shows a point of attachment of the radical drawn to the rest of the molecule. For example, the radical drawn below

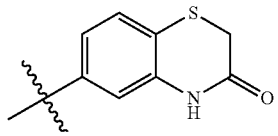 [SMILES: *c1ccc2c(c1)NC(=O)CS2]

is the 3-oxo-3,4-dihydro-2H-benzo[1,4]thiazin-6-yl group.

The compounds of formula I according to this invention may contain one or more stereogenic or asymmetric centers, such as one or more asymmetric carbon atoms. The compounds of formula I may thus be present as mixtures of stereoisomers or, preferably, as pure stereoisomers. Mixtures of stereoisomers may be separated in a manner known to a person skilled in the art.

Whenever the absolute stereochemistry indication "(R)" or "(S)" is omitted in the name of a compound although there is a corresponding asymmetric carbon atom, it is meant thereby that this compound name refers to either the (R)-configured compound or the (S)-configured compound.

The relative configuration of stereoisomers having two asymmetric centers is indicated in this text by using the wording (R*,R*) to refer to either the (R,R)-configured stereomer or the (S,S)-configured stereomer and the wording (R*,S*) to refer to either the (R,S)-configured stereomer or the (S,R)-configured stereomer. Thus, for example, (1R*,2R*)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester refers to either (1R,2R)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester or (1S,2S)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester.

The present invention also includes isotopically labelled, especially ²H (deuterium) labelled compounds of formula I, which compounds are identical to the compounds of formula I except that one or more atoms have each been replaced by an atom having the same atomic number but an atomic mass different from the atomic mass usually found in nature. Isotopically labelled, especially ²H (deuterium) labelled compounds of formula I and salts thereof are within the scope of the present invention. Substitution of hydrogen with the heavier isotope ²H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one variant of the invention, the compounds of formula I are not isotopically labelled, or they are labelled only with one or more deuterium atoms. In a sub-variant, the compounds of formula I are not isotopically labelled at all. Isotopically labelled compounds of formula I may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) The invention relates notably to compounds of formula I according to embodiment i) that are also compounds of formula $I_{P3}$

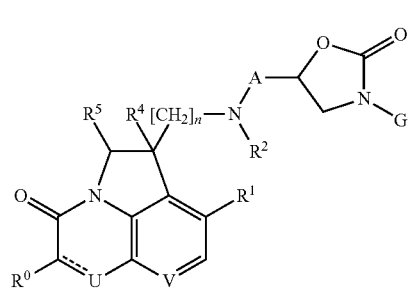

wherein

"------" is a bond or is absent;

R⁰ represents H or, in the case "------" is a bond, may also represent (C₁-C₃)alkoxy (in particular methoxy);

$R^1$ represents H, halogen (notably F or Br), cyano or $(C_1\text{-}C_3)$alkyl (notably methyl);

U represents CH or N when "_____" is a bond, or, in case "_____" is absent, U represents $CH_2$ or NH;

V represents CH, $CR^6$ or N;

$R^2$ represents H, $(C_1\text{-}C_3)$alkylcarbonyl or a group of the formula $—CH_2—R^3$;

$R^3$ represents H, $(C_1\text{-}C_3)$alkyl or $(C_1\text{-}C_3)$hydroxyalkyl;

$R^4$ represents H or, in the cases wherein n is not 0 and $R^5$ is H, may also represent OH;

$R^5$ represents H, $(C_1\text{-}C_3)$alkyl (notably methyl), $(C_1\text{-}C_3)$hydroxyalkyl (notably hydroxymethyl), $(C_1\text{-}C_3)$alkoxy$(C_1\text{-}C_3)$alkyl (notably methoxymethyl) or $(C_1\text{-}C_3)$alkoxycarbonyl (notably methoxycarbonyl);

$R^6$ represents $(C_1\text{-}C_3)$hydroxyalkyl (notably hydroxymethyl), carboxy, $(C_1\text{-}C_3)$alkoxycarbonyl or a group $—(CH_2)_q—NR^7R^8$ wherein q is 1, 2 or 3 and each of $R^7$ and $R^8$ independently represents H or $(C_1\text{-}C_3)$alkyl or $R^7$ and $R^8$ form together with the nitrogen atom bearing them a pyrrolidinyl, piperidinyl, morpholinyl or thiomorpholinyl ring;

A represents $—(CH_2)_p—$, $—CH_2CH_2CH(OH)—$ or $—COCH_2CH(OH)—$;

G represents a phenyl group which is substituted once or twice in the meta and/or para position(s) by substituents selected independently from $(C_1\text{-}C_4)$alkyl, $(C_1\text{-}C_3)$alkoxy and a halogen (notably F), whereby a $(C_1\text{-}C_3)$alkoxy substituent is preferably a straight chain $(C_1\text{-}C_3)$alkoxy and in para position, or G is a group having one of the formulae $G^1$ and $G^2$ below

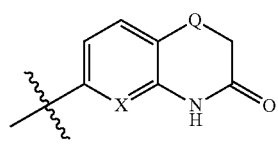

$G^1$

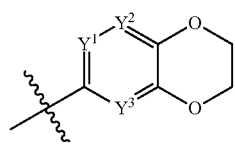

$G^2$ wherein

Q is O or S and X is CH or N; and $Y^1$, $Y^2$ and $Y^3$ each represent CH, or $Y^1$ and $Y^3$ each represent CH and $Y^2$ represents N, or $Y^1$ represents N, $Y^2$ represents CH or N and $Y^3$ represents CH, or $Y^1$ and $Y^2$ each represent CH and $Y^3$ represents N; and n is 0 when A represents $—CH_2CH_2CH(OH)—$ or $—COCH_2CH(OH)—$, and n is 0, 1 or 2 when A represents $(CH_2)_p$, p being 1, 2, 3 or 4, with the proviso that the sum of n and p is then 2, 3 or 4 (i.e. when n is 0, p is not 1, when n is 1, p is not 4 and when n is 2, p is neither 3 nor 4);

and to salts (in particular pharmaceutically acceptable salts) of compounds of formula $I_{P3}$.

iii) The invention furthermore relates notably to compounds of formula I according to embodiment i) or ii) that are also compounds of formula $I_{P2}$

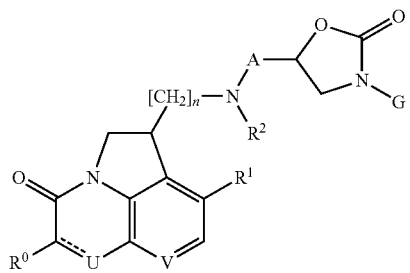

$I_{P2}$ wherein

"_____" is a bond or is absent;

$R^0$ represents H or, in the case "_____" is a bond, may also represent $(C_1\text{-}C_3)$alkoxy (in particular methoxy);

$R^1$ represents H or halogen (notably F);

U represents CH or N when "_____" is a bond, or, in case "_____" is absent, U represents $CH_2$ or NH;

V represents CH or N;

$R^2$ represents H or a group of the formula $—CH_2—R^3$, $R^3$ being hydrogen, $(C_1\text{-}C_3)$alkyl or $(C_1\text{-}C_3)$hydroxyalkyl;

A represents $—(CH_2)_p—$, $—CH_2CH_2CH(OH)—$ or $—COCH_2CH(OH)—$;

G represents a phenyl group which is substituted once or twice in the meta and/or para position(s) by substituents selected independently from $(C_1\text{-}C_4)$alkyl, $(C_1\text{-}C_3)$alkoxy and a halogen (notably F), whereby a $(C_1\text{-}C_3)$alkoxy substituent is preferably a straight chain $(C_1\text{-}C_3)$alkoxy and in para position, or G is a group having one of the formulae $G^1$ and $G^2$ below

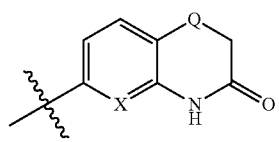

$G^1$

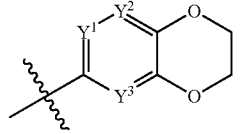

$G^2$ wherein

Q is O or S and X is CH or N; and $Y^1$, $Y^2$ and $Y^3$ each represent CH, or $Y^1$ and $Y^3$ each represent CH and $Y^2$ represents N, or $Y^1$ represents N, $Y^2$ represents CH or N and $Y^3$ represents CH, or $Y^1$ and $Y^2$ each represent CH and $Y^3$ represents N; and n is 0 when A represents $—CH_2CH_2CH(OH)—$ or $—COCH_2CH(OH)—$, and n is 0, 1 or 2 when A represents $(CH_2)_p$, p being 1, 2, 3 or 4, with the proviso that the sum of n and p is then 2, 3 or 4 (i.e. when n is 0, p is not 1, when n is 1, p is not 4 and when n is 2, p is neither 3 nor 4);

and to salts (in particular pharmaceutically acceptable salts) of compounds of formula $I_2$.

iv) The invention yet relates to compounds of formula I as defined in embodiment i), ii) or iii) that are also compounds of formula $I_{P1}$

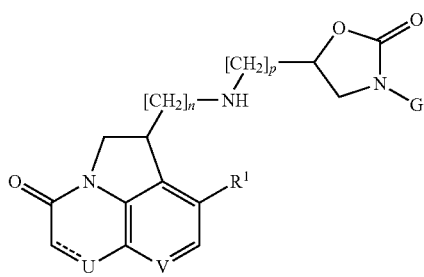

$I_{P1}$

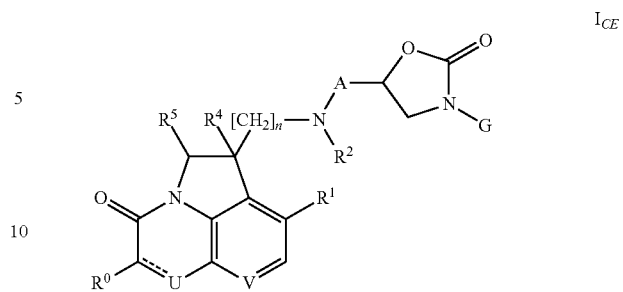

$I_{CE}$ wherein

"_____" is a bond or is absent;

R¹ represents H or halogen (notably F);

V represents CH or N;

U represents CH or N, or, in case "_____" is absent, U represents $CH_2$ or NH;

G represents a phenyl group which is substituted once or twice in the meta and/or para position(s) by substituents selected independently from $(C_1-C_4)$alkyl, $(C_1-C_3)$alkoxy and a halogen (notably F), whereby a $(C_1-C_3)$alkoxy substituent is preferably a straight chain $(C_1-C_3)$alkoxy and in para position, or G is a group having one of the formulae $G^1$ and $G^2$ below

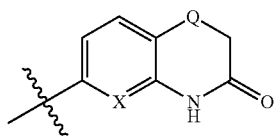

$G^1$

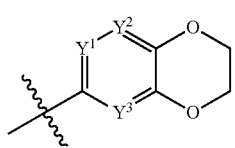

$G^2$ wherein

Q is O or S and X is CH or N; and $Y^1$, $Y^2$ and $Y^3$ each represent CH, or $Y^1$ and $Y^3$ each represent CH and $Y^2$ represents N, or $Y^1$ represents N, $Y^2$ represents CH or N and $Y^3$ represents CH, or $Y^1$ and $Y^2$ each represent CH and $Y^3$ represents N; and n is 0, 1 or 2 and p is 1, 2 or 3, with the proviso that the sum of n and p is either 2 or 3 (i.e. when n is 0, p is 2 or 3, when n is 1, p is 1 or 2 and when n is 2, p is 1);

and to salts (in particular pharmaceutically acceptable salts) of compounds of formula $I_P$.

v) In particular, the invention relates to compounds of formula I as defined in embodiment i) that are also compounds of formula $I_{CE}$ wherein "_____" is a bond, V represents CH and U represents CH or N, or "_____" is a bond, V represents $CR^6$ and U represents CH, or also "_____" is a bond, V represents N and U represents CH, or "_____" is absent, V represents CH and U represents $CH_2$, NH or $NR^9$;

R⁰ represents H or, in the case "_____" is a bond, may also represent $(C_1-C_3)$alkoxy (in particular methoxy);

R¹ represents H, halogen (notably F, Cl or Br), cyano, $(C_1-C_3)$alkyl (notably methyl) or ethynyl;

V represents CH, $CR^6$ or N;

R² represents H, acetyl or a group of the formula $—CH_2—R^3$;

R³ represents hydrogen, $(C_1-C_3)$alkyl or $(C_1-C_3)$hydroxyalkyl;

R⁴ represents H or, in the cases wherein n is not 0 and R⁵ is H, may also represent OH;

R⁵ represents H, $(C_1-C_3)$alkyl (notably methyl), $(C_1-C_3)$hydroxyalkyl (notably hydroxymethyl), $(C_1-C_3)$amino alkyl (notably amino methyl), $(C_1-C_3)$alkoxy$(C_1-C_3)$alkyl (notably methoxymethyl), carboxy or $(C_1-C_3)$alkoxycarbonyl (notably methoxycarbonyl);

R⁶ represents $(C_1-C_3)$hydroxyalkyl (notably hydroxymethyl), carboxy, $(C_1-C_3)$alkoxycarbonyl or a group $—(CH_2)_q—NR^7R^8$ wherein q is 1, 2 or 3 (notably 1) and each of R⁷ and R⁸ independently represents H or $(C_1-C_3)$alkyl or R⁷ and R⁸ form together with the nitrogen atom bearing them a pyrrolidinyl or piperidinyl ring (notably a pyrrolidinyl ring);

R⁹ represents $(C_1-C_3)$alkyl (notably methyl), 2-hydroxyethyl, 2-hydroxy-propyl or 3-hydroxy-propyl;

A represents $—(CH_2)_p—$, $—CH_2CH_2CH(OH)—$ or $—COCH_2CH(OH)—$;

G represents a phenyl group which is substituted once or twice in the meta and/or para position(s) by substituents selected independently from $(C_1-C_4)$alkyl, $(C_1-C_3)$alkoxy and a halogen (notably F), whereby a $(C_1-C_3)$alkoxy substituent is preferably a straight chain $(C_1-C_3)$alkoxy and in para position, or G is a group having one of the formulae $G^1$ and $G^2$, below

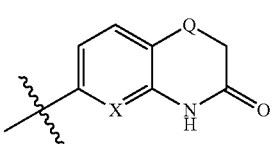

$G^1$

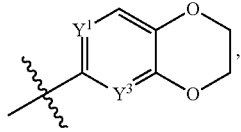

wherein
Q is O or S and X is CH or N; and
each of $Y^1$ and $Y^3$ represents CH, or one of $Y^1$ and $Y^3$ represents N and the other represents CH; and
n is 0 when A represents —$CH_2CH_2CH(OH)$— or —$COCH_2CH(OH)$—, and n is 0, 1 or 2 when A represents $(CH_2)_p$, p being 1, 2, 3 or 4, with the proviso that the sum of n and p is then 2, 3 or 4 (i.e. when n is 0, p is not 1, when n is 1, p is not 4 and when n is 2, p is neither 3 nor 4);
and to salts (in particular pharmaceutically acceptable salts) of compounds of formula $I_{CE}$.

vi) Also in particular, the invention relates to compounds of formula I as defined in embodiment i), ii) or v) that are also compounds of formula $I_{CEP3}$

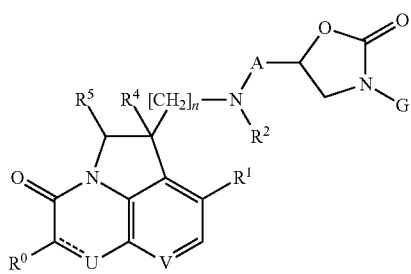

$I_{CE3}$ wherein
"_____" is a bond, V represents CH and U represents CH or N, or "_____" is a bond, V represents $CR^6$ and U represents CH, or also "_____" is a bond, V represents N and U represents CH, or
"_____" is absent, V represents CH and U represents $CH_2$ or NH;
$R^0$ represents H or, in the case "_____" is a bond, may also represent $(C_1-C_3)$alkoxy (in particular methoxy);
$R^1$ represents H, halogen (notably F or Br), cyano or $(C_1-C_3)$alkyl (notably methyl);
V represents CH, $CR^6$ or N;
$R^2$ represents H, acetyl or a group of the formula —$CH_2$—$R^3$;
$R^3$ represents hydrogen, $(C_1-C_3)$alkyl or $(C_1-C_3)$hydroxyalkyl;
$R^4$ represents H or, in the cases wherein n is not 0 and $R^5$ is H, may also represent OH;
$R^5$ represents H, $(C_1-C_3)$alkyl (notably methyl), $(C_1-C_3)$hydroxyalkyl (notably hydroxymethyl), $(C_1-C_3)$alkoxy$(C_1-C_3)$alkyl (notably methoxymethyl) or $(C_1-C_3)$alkoxycarbonyl (notably methoxycarbonyl);
$R^6$ represents $(C_1-C_3)$hydroxyalkyl (notably hydroxymethyl), carboxy, $(C_1-C_3)$alkoxycarbonyl or a group —$(CH_2)_q$—$NR^7R^8$ wherein q is 1, 2 or 3 (notably 1) and each of $R^7$ and $R^8$ independently represents H or $(C_1-C_3)$alkyl or $R^7$ and $R^8$ form together with the nitrogen atom bearing them a pyrrolidinyl or piperidinyl ring (notably a pyrrolidinyl ring);
A represents —$(CH_2)_p$—, —$CH_2CH_2CH(OH)$— or —$COCH_2CH(OH)$—;

G represents a phenyl group which is substituted once or twice in the meta and/or para position(s) by substituents selected independently from $(C_1-C_4)$alkyl, $(C_1-C_3)$alkoxy and a halogen (notably F), whereby a $(C_1-C_3)$alkoxy substituent is preferably a straight chain $(C_1-C_3)$alkoxy and in para position, or G is a group having one of the formulae $G^1$ and $G^{2'}$ below

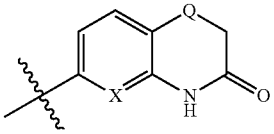

$G^1$

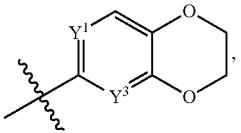

$G^2$ wherein
Q is O or S and X is CH or N; and
each of $Y^1$ and $Y^3$ represents CH, or one of $Y^1$ and $Y^3$ represents N and the other represents CH; and
n is 0 when A represents —$CH_2CH_2CH(OH)$— or —$COCH_2CH(OH)$—, and n is 0, 1 or 2 when A represents $(CH_2)_p$, p being 1, 2, 3 or 4, with the proviso that the sum of n and p is then 2, 3 or 4 (i.e. when n is 0, p is not 1, when n is 1, p is not 4 and when n is 2, p is neither 3 nor 4);
and to salts (in particular pharmaceutically acceptable salts) of compounds of formula $I_{CE}$.

vii) The invention furthermore relates to compounds of formula I as defined in embodiment i), ii), iii), v) or vi) that are also compounds of formula $I_{CEP2}$

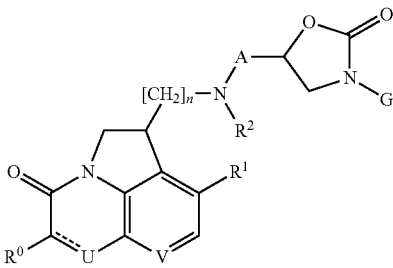

$I_{CEP2}$ wherein
"_____" is a bond, V represents CH and U represents CH or N or V represents N and U represents CH, or "_____" is absent, V represents CH and U represents $CH_2$ or NH;
$R^0$ represents H or, in the case "_____" is a bond, may also represent $(C_1-C_3)$alkoxy (in particular methoxy);
$R^1$ represents H or halogen (notably F);
$R^2$ represents H or a group of the formula —$CH_2$—$R^3$, $R^3$ being $(C_1-C_3)$hydroxyalkyl;
A represents —$(CH_2)_p$—, —$CH_2CH_2CH(OH)$— or —$COCH_2CH(OH)$—;
G represents a phenyl group which is substituted once in a meta position and once in the para position by substituents selected independently from $(C_1-C_4)$alkyl and a halogen (notably F), G represents a phenyl group which is substituted in the para position by a substituent selected from (C$_1$-C$_4$)alkyl and (C$_1$-C$_3$)alkoxy, or also G is a group having one of the formulae G$^1$ and G$^{2'}$ below

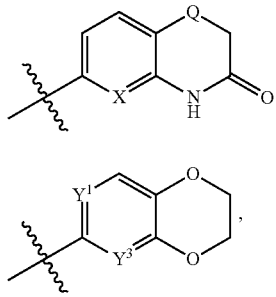

wherein
X represents CH or N and Q represents O or S;
each of Y$^1$ and Y$^3$ represents CH, or one of Y$^1$ and Y$^3$ represents N and the other represents CH;
n is 0 when A represents —CH$_2$CH$_2$CH(OH)— or —COCH$_2$CH(OH)—, and n is 0, 1 or 2 when A represents (CH$_2$)$_p$, p being 1, 2, 3 or 4, with the provisos that when n is 0, p is 2 or 3, when n is 1, p is 1, 2 or 3 and when n is 2, p is 1;
and to salts (in particular pharmaceutically acceptable salts) of compounds of formula I$_{CEP2}$.
viii) The invention yet relates to compounds of formula I as defined in one of embodiments i) to vii) that are also compounds of formula I$_{CEP1}$

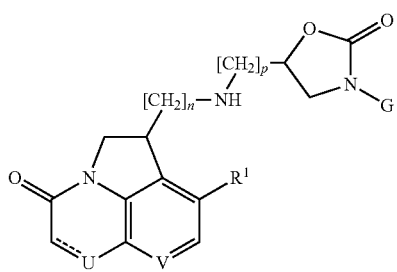

wherein
R$^1$ represents H or halogen (notably F);
"_____" is a bond, V represents CH and U represents CH or N or V represents N and U represents CH, or "_____" is absent, V represents CH and U represents CH$_2$;
G represents a phenyl group which is substituted once in a meta position and once in the para position by substituents selected independently from (C$_1$-C$_4$)alkyl and a halogen (notably F), or G is a group having one of the formulae G$^{1'}$ and G$^{2'}$ below

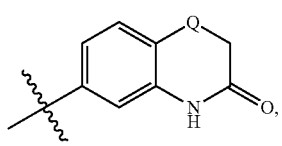

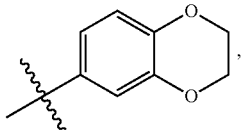

wherein Q represents O or S;
n is 0, 1 or 2 and p is 1, 2 or 3, with the proviso that the sum of n and p is either 2 or 3 (i.e. when n is 0, p is 2 or 3, when n is 1, p is 1 or 2 and when n is 2, p is 1);
and to salts (in particular pharmaceutically acceptable salts) of compounds of formula I$_{CEP1}$.
ix) According to one main variant of this invention, the compounds of formula I as defined in one of embodiments i) to viii) above will be such that R$^1$ represents halogen (notably F, Cl or Br, preferably F or Br and in particular F).
x) According to another main variant of this invention, the compounds of formula I as defined in one of embodiments i) to viii) above will be such that R$^1$ represents H.
xi) According to a further main variant of this invention, the compounds of formula I as defined in embodiment i), ii), v) or vi) above will be such that R$^1$ represents (C$_1$-C$_3$)alkyl (notably methyl).
xii) According to yet a further main variant of this invention, the compounds of formula I as defined in embodiment i) or v) above will be such that R$^1$ represents ethynyl.
xiii) One main embodiment of this invention relates to the compounds of formula I as defined in one of embodiments i) to xii) above wherein V represents CH (and notably to compounds of formula I as defined in embodiment iv) or viii) wherein V represents CH and R$^1$ represents fluorine).
xiv) Another main embodiment of this invention relates to the compounds of formula I as defined in one of embodiments i) to xii) above wherein V represents N (and notably to compounds of formula I as defined in embodiment iv) or viii) wherein V represents N and R$^1$ represents fluorine).
xv) A further main embodiment of this invention relates to the compounds of formula I as defined in embodiment i), ii), v) or vi) above wherein V represents CR$^6$.
xvi) According to one sub-embodiment of embodiment xv) above, R$^6$ will represent (C$_1$-C$_3$)hydroxyalkyl (notably hydroxymethyl).
xvii) According to another sub-embodiment of embodiment xv) above, R$^6$ will represent carboxy.
xviii) According to yet another sub-embodiment of embodiment xv) above, R$^6$ will represent (C$_1$-C$_3$)alkoxycarbonyl (notably ethoxycarbonyl).
xix) According to a further sub-embodiment of embodiment xv) above, R$^6$ will represent a group —(CH$_2$)$_q$—NR$^7$R$^8$ wherein q is 1, 2 or 3 (in particular 1) and each of R$^7$ and R$^8$ independently represents H or (C$_1$-C$_3$)alkyl or R$^7$ and R$^8$ form together with the nitrogen atom bearing them a pyrrolidinyl, piperidinyl, morpholinyl or thiomorpholinyl ring, and in particular a pyrrolidinyl or piperidinyl ring (such a group —(CH$_2$)$_q$—NR$^7$R$^8$ being notably dimethylaminomethyl or pyrrolidin-1-ylmethyl).
xx) A further embodiment of this invention relates to the compounds of formula I as defined in one of embodiments i) to xix) above wherein "_____" is a bond; such embodiment thus notably relates to compounds of formula I as defined in embodiment iv) or viii) wherein "_____" is a bond and:
R$^1$ represents fluorine, or
R$^1$ represents fluorine and V represents CH, or
R$^1$ represents fluorine and V represents N.

xxi) One sub-embodiment of embodiment xx) above relates to the compounds of formula I as defined in embodiment xx) above wherein U represents CH (and notably to the compounds of formula I as defined in embodiment xiv) above wherein U represents CH and $R^0$ represents H).

xxii) Another sub-embodiment of embodiment xx) above relates to the compounds of formula I as defined in embodiment xx) above wherein U represents N.

xxiii) According to one variant of sub-embodiment xxii), the compounds of formula I as defined in embodiment xxii) above will be such that $R^0$ represents H (and notably such that $R^0$ represents H and V represents CH).

xxiv) According to the other variant of sub-embodiment xxii), the compounds of formula I as defined in embodiment xxii) above will be such that $R^0$ represents $(C_1-C_3)$alkoxy (and in particular methoxy); this particular variant relates notably to compounds of formula I as defined in one of embodiments i) to iii) or v) to vii) wherein $R^0$ represents $(C_1-C_3)$alkoxy (and in particular methoxy) and:
- $R^1$ represents halogen (and preferably F), or
- $R^1$ represents H, or
- $R^1$ represents halogen (and preferably F) and V represents CH, or
- $R^1$ represents halogen (and preferably F) and V represents N, or
- $R^1$ represents H and V represents CH, or
- $R^1$ represents H and V represents N, or
- V represents CH, or
- V represents N.

xxv) Yet a further embodiment of this invention relates to the compounds of formula I as defined in one of embodiments i) to xix) above wherein "_____" is absent and U represents $CH_2$ or NH (notably $CH_2$); such embodiment thus notably to compounds of formula I as defined in embodiment iv) or viii) wherein "_____" is absent, U represents $CH_2$ and:
- $R^1$ represents fluorine, or
- $R^1$ represents fluorine and V represents CH, or
- $R^1$ represents fluorine and V represents N, or
- V represents CH, or
- V represents N.

xxvi) One particular embodiment of this invention relates to the compounds of formula I as defined in embodiment i), ii), v) or vi), or as defined in embodiment i), ii), v) or vi) taken together with any of embodiments ix) to xxv), wherein $R^4$ represents H.

xxvii) One sub-embodiment of embodiment xxvi) relates to compounds of formula I as defined in embodiment xxvi) wherein each of $R^4$ and $R^5$ represents H.

xxviii) Another particular embodiment of this invention relates to the compounds of formula I as defined in embodiment i), ii), v) or vi), or as defined in embodiment i), ii), v) or vi) taken together with any of embodiments ix) to xxv), wherein n is 1 or 2, $R^4$ represents OH and $R^5$ represents H.

xxix) Yet another particular embodiment of this invention relates to the compounds of formula I as defined in embodiment i) or v), or as defined in embodiment i) or v) taken together with any of embodiments ix) to xxv), wherein $R^5$ represents $(C_1-C_3)$alkyl (notably methyl), $(C_1-C_3)$hydroxyalkyl (notably hydroxymethyl), $(C_1-C_3)$aminoalkyl (notably aminomethyl), $(C_1-C_3)$alkoxy$(C_1-C_3)$alkyl (notably methoxymethyl), carboxy or $(C_1-C_3)$alkoxycarbonyl (notably methoxycarbonyl).

xxx) In particular, the compounds of formula I as defined in embodiment xxix) will be compounds of formula I as defined in embodiment ii) or vi), or as defined in embodiment ii) or vi) taken together with any of embodiments ix) to xxv), wherein $R^5$ represents $(C_1-C_3)$alkyl (notably methyl), $(C_1-C_3)$hydroxyalkyl (notably hydroxymethyl), $(C_1-C_3)$alkoxy$(C_1-C_3)$alkyl (notably methoxymethyl) or $(C_1-C_3)$alkoxycarbonyl (notably methoxycarbonyl).

xxxi) According to one variant of embodiment xxix) or xxx), $R^5$ will represent $(C_1-C_3)$alkyl (notably methyl).

xxxii) According to another variant of embodiment xxix) or xxx), $R^5$ will represent $(C_1-C_3)$hydroxyalkyl (notably hydroxymethyl or 1-hydroxy-1-methyl-ethyl and in particular hydroxymethyl).

xxxiii) According to yet another variant of embodiment xxix) or xxx), $R^5$ will represent $(C_1-C_3)$alkoxy$(C_1-C_3)$alkyl (notably methoxymethyl).

xxxiv) According to a further variant of embodiment xxix), $R^5$ will represent $(C_1-C_3)$alkoxycarbonyl (notably methoxycarbonyl).

xxxv) According to yet a further variant of embodiment xxix), $R^5$ will represent $(C_1-C_3)$aminoalkyl (notably aminomethyl).

xxxvi) According to yet a further variant of embodiment xxix), $R^5$ will represent carboxy.

xxxvii) According to one main variant of this invention, the compounds of formula I as defined in one of embodiments i) to xxxvi) will be such that A represents $—(CH_2)_p—$(whereby in such case the compounds of formula I wherein n is 0 and p is 2 or 3, or n is 1 and p is 1, 2 or 3, or n is 2 and p is 1 will in a general manner be preferred).

xxxviii) According to one sub-embodiment of embodiment xxxvii), the compounds of formula I as defined in embodiment xxxvii) will be such that the sum of n and p is 2.

xxxix) According to one variant of embodiment xxxviii), the compounds of formula I will be such that n is 0 and p is 2.

xl) According to another variant of embodiment xxxviii), the compounds of formula I will be such that n is 1 and p is 1.

xli) According to another sub-embodiment of embodiment xxxvii), the compounds of formula I as defined in embodiment xxxvii) will be such that the sum of n and p is 3 (and notably such that the sum of n and p is 3, each of $R^0$, $R^4$ and $R^5$ represents H and G is a group of the formula $G^1$ or $G^2$ as defined in embodiment i), ii) or iii)).

xlii) According to one variant of embodiment xli), the compounds of formula I will be such that n is 0 and p is 3.

xliii) The compounds of formula I as defined in embodiment xlii) will notably be such that "_____" is a bond, each of $R^0$, $R^4$ and $R^5$ represents H, $R^1$ represents H or F (in particular F), V represents CH, U represents CH or N and G is a group of the formula $G^1$ or $G^2$ as defined in embodiment i), ii) or iii) (and in particular a group of the formula $G^1$ as defined in embodiment i), ii) or iii), notably such a group of the formula $G^1$ wherein X is CH and Q is S).

xliv) According to another variant of embodiment xli), the compounds of formula I will be such that n is 1 and p is 2.

xlv) The compounds of formula I as defined in embodiment xliv) will notably be such that "_____" is a bond, each of $R^0$, $R^4$ and $R^5$ represents H, $R^1$ represents H or F (in particular F), V represents CH, U represents CH or N and G is a group of the formula $G^1$ or $G^2$ as defined in embodiment i), ii) or iii) (and in particular a group of the formula $G^1$ as defined in embodiment i), ii) or iii), notably such a group of the formula $G^1$ wherein X is CH and Q is S).

xlvi) According to yet another variant of embodiment xli), the compounds of formula I will be such that n is 2 and p is 1.

xlvii) The compounds of formula I as defined in embodiment xlvi) will notably be such that "_____" is a bond, each of $R^0$, $R^4$ and $R^5$ represents H, $R^1$ represents H or F (in particular F), V represents CH, U represents CH or N and G is a group of the formula $G^1$ or $G^2$ as defined in embodiment i), ii) or iii) (and in particular a group of the formula $G^1$ as defined in embodiment i), ii) or iii), notably such a group of the formula $G^1$ wherein X is CH and Q is S).

xlviii) According to another sub-embodiment of embodiment xxxvii), the compounds of formula I as defined in embodiment xxxvii) will be such that the sum of n and p is 4.

il) According to one variant of embodiment xlviii), the compounds of formula I will be such that n is 0 and p is 4.

l) According to another variant of embodiment xlviii), the compounds of formula I will be such that n is 1 and p is 3.

li) According to yet another variant of embodiment xlviii), the compounds of formula I will be such that n is 2 and p is 2.

lii) Another main variant of this invention relates to the compounds of formula I as defined in embodiment i), ii), iii), v), vi) or vii) wherein A represents —$CH_2CH_2CH(OH)$—, or to the compounds of formula I as defined in embodiment i), ii), iii), v), vi) or vii) taken together with any of embodiments ix) to xxxvi) wherein A represents —$CH_2CH_2CH(OH)$—.

liii) Yet another main variant of this invention relates to the compounds of formula I as defined in embodiment i), ii), iii), v), vi) or vii) wherein A represents —$COCH_2CH(OH)$—, or to the compounds of formula I as defined in embodiment i), ii), iii), v), vi) or vii) taken together with any of embodiments vii) to xxxvi) wherein A represents —$COCH_2CH(OH)$—.

liv) A further embodiment of this invention relates to the compounds of formula I as defined in embodiment i), ii), iii), v), vi) or vii) wherein $R^2$ represents H, or to the compounds of formula I as defined in embodiment i), ii), iii), v), vi) or vii) taken together with any of embodiments ix) to liii) wherein $R^2$ represents H.

lv) Yet a further embodiment of this invention relates to the compounds of formula I as defined in embodiment i), ii), iii), v), vi) or vii) wherein $R^2$ represents a group of the formula —$CH_2$—$R^3$, $R^3$ being hydrogen, $(C_1$-$C_3)$alkyl or $(C_1$-$C_3)$hydroxyalkyl, or to the compounds of formula I as defined in embodiment i), ii), iii), v), vi) or vii) taken together with any of embodiments ix) to liii) wherein $R^2$ represents a group of the formula —$CH_2$—$R^3$, $R^3$ being hydrogen, $(C_1$-$C_3)$alkyl or $(C_1$-$C_3)$hydroxyalkyl (and in particular to the compounds of formula I as defined in embodiment iii) or vii) wherein $R^2$ represents a group of the formula —$CH_2$—$R^3$, $R^3$ being $(C_1$-$C_3)$alkyl or $(C_1$-$C_3)$hydroxyalkyl, or to the compounds of formula I as defined in embodiment iii) or vii) taken together with any of embodiments ix), x), xiii), xiv), xx) to xxv) and xxxvii) to liii) wherein $R^2$ represents a group of the formula —$CH_2$—$R^3$, $R^3$ being $(C_1$-$C_3)$alkyl or $(C_1$-$C_3)$hydroxyalkyl).

lvi) According to one variant of embodiment lv), the compounds of formula I as defined in embodiment lv) will be such that $R^2$ represents a group of the formula —$CH_2$—$R^3$ wherein $R^3$ is hydrogen or $(C_1$-$C_3)$alkyl.

lvii) According to another variant of embodiment lv), the compounds of formula I as defined in embodiment lv) will be such that $R^2$ represents a group of the formula —$CH_2$—$R^3$ wherein $R^3$ is $(C_1$-$C_3)$hydroxyalkyl (in particular such that $R^2$ represents a group 2-hydroxy-ethyl or 3-hydroxy-propyl).

lviii) Yet a further embodiment of this invention relates to the compounds of formula I as defined in embodiment i), ii), v) or vi) wherein $R^2$ represents $(C_1$-$C_3)$alkylcarbonyl (notably acetyl), or to the compounds of formula I as defined in embodiment i), ii), v) or vi) taken together with any of embodiments ix) to liii) wherein $R^2$ represents $(C_1$-$C_3)$alkylcarbonyl (notably acetyl).

lix) According to one particular embodiment of this invention, the compounds of formula I as defined in embodiments i) to lviii) above will be such that G represents a group of the formula $G^1$, or, in the embodiments referring to embodiment viii), the group $G^{1'}$.

lx) Preferably, the compounds of formula I as defined in embodiment lix) above will be such that X, if present, represents CH (that is, G represents 3-oxo-3,4-dihydro-2H-benzo[1,4]thiazin-6-yl or 3-oxo-3,4-dihydro-2H-benzo[1,4]oxazin-6-yl); a particular sub-embodiment of this embodiment will relate to compounds of formula I as defined in embodiment iv) or viii) wherein G represents 3-oxo-3,4-dihydro-2H-benzo[1,4]thiazin-6-yl or 3-oxo-3,4-dihydro-2H-benzo[1,4]oxazin-6-yl and:

$R^1$ represents fluorine, or

V represents CH, or

V represents N, or $R^1$ represents fluorine and V represents CH, or $R^1$ represents fluorine and V represents N, or $R^1$ represents fluorine and "_____" is a bond, or $R^1$ represents fluorine, "_____" is a bond and V represents CH, $R^1$ represents fluorine, "_____" is a bond and V represents N, "_____" is absent and U represents $CH_2$, or $R^1$ represents fluorine, "_____" is absent and U represents $CH_2$, or $R^1$ represents fluorine, V represents CH, "_____" is absent and U represents $CH_2$, or $R^1$ represents fluorine, V represents N, "_____" is absent and U represents $CH_2$.

lxi) According to another particular embodiment of this invention, the compounds of formula I as defined in embodiments i) to lviii) above will be such that G represents a group of the formula $G^2$, or, in the embodiments referring to embodiment v), vi), vii) or viii), the group $G^{2'}$.

lxii) According to a variant of embodiment lxi), the compounds of formula I as defined in embodiment lxi) above will be such that either each of $Y^1$, $Y^2$ and $Y^3$, if present, represents CH, or one of $Y^1$ and $Y^3$, if present, represents N and $Y^2$ and the other of $Y^1$ and $Y^3$, if present, each represent CH (that is, G represents 2,3-dihydro-[1,4]dioxino[2,3-c]pyridin-7-yl, 2,3-dihydro-[1,4]dioxino[2,3-b]pyridin-6-yl or 2,3-dihydro-benzo[1,4]dioxin-6-yl).

lxiii) Preferably, the compounds of formula I as defined in embodiment lxii) above will be such that each of $Y^1$, $Y^2$ and $Y^3$, if present, represents CH (that is, G represents 2,3-dihydro-benzo[1,4]dioxin-6-yl).

lxiv) According to yet another particular embodiment of this invention, the compounds of formula I as defined in embodiments i) to lviii) above will be such that G represents a phenyl group which is substituted once or twice in the meta and/or para position(s) by substituents selected independently from $(C_1$-$C_4)$alkyl, $(C_1$-$C_3)$alkoxy and a halogen (notably F), whereby a $(C_1$-$C_3)$alkoxy substituent, if present, is preferably a straight chain $(C_1$-$C_3)$alkoxy and in para position, or, in the embodiments referring to embodiment vii) or viii), such that G represents a phenyl group which is substituted once in a meta position and once in the para position by substituents selected independently from $(C_1$-$C_4)$alkyl and a halogen (notably F).

lxv) Preferably, the compounds of formula I as defined in embodiment lxiv) above will be such that G represents a phenyl group which is substituted once or twice in the meta and/or para position(s) by substituents selected independently from methyl, ethyl, methoxy, ethoxy and halogen (notably F), whereby a methoxy or ethoxy substituent, if present, is in para position, or, in the embodiments referring to embodiment vii) or viii), such that G represents a phenyl group which is substituted once in a meta position and once in the para position by substituents selected independently from methyl and fluorine.

lxvi) In particular, the compounds of formula I as defined in embodiment lxiv) or lxv) above will be such that G represents 3-fluoro-4-methyl-phenyl.

lxvii) Yet a further embodiment of this invention relates to compounds of formula I as defined in embodiment i), ii), v) or vi) wherein:

"_____" is a bond, V represents CH and U represents CH or N, or "_____" is absent and U represents NH;

$R^0$ represents H or, in the case "_____" is a bond, may also represent ($C_1$-$C_3$)alkoxy (in particular methoxy);

$R^1$ represents H or halogen (notably H, F or Br, and in particular H or F);

$R^2$ represents H;

each of $R^4$ and $R^5$ represents H;

n is 0;

A represents —$(CH_2)_p$—, p being 3;

G is a group having the formula $G^1$ below

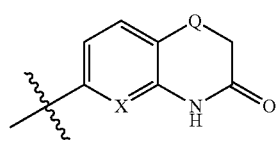

wherein X is CH or N and Q is O or S;

and to salts (in particular pharmaceutically acceptable salts) of such compounds.

lxviii) According to one sub-embodiment of embodiment lxvii), the compounds of formula I as defined in embodiment lxiv) will be such that "_____" is a bond, V represents CH and U represents CH or N.

lxix) According to another sub-embodiment of embodiment lxvii), the compounds of formula I as defined in embodiment lxiv) will be such that "_____" is absent and U represents NH.

lxx) Yet a further embodiment of this invention relates to compounds of formula I as defined in embodiment i), ii), v) or vi) wherein:

"_____" is a bond, V represents CH and U represents CH or N, or "_____" is absent and U represents NH;

$R^0$ represents H or, in the case "_____" is a bond, may also represent ($C_1$-$C_3$)alkoxy (in particular methoxy);

$R^1$ represents H or halogen (notably F or Br, in particular F);

$R^2$ represents H;

$R^4$ represents H;

$R^5$ represents H, ($C_1$-$C_3$)alkyl (notably methyl), ($C_1$-$C_3$) hydroxyalkyl (notably hydroxymethyl), ($C_1$-$C_3$)alkoxy ($C_1$-$C_3$)alkyl (notably methoxymethyl) or ($C_1$-$C_3$) alkoxycarbonyl (notably acetyl);

n is 0;

A represents —$(CH_2)_p$—, p being 3; and

G is a group having the formula $G^{2'}$ below

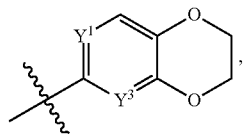

wherein each of $Y^1$ and $Y^3$ represents CH, or one of $Y^1$ and $Y^3$ represents N and the other represents CH (and in particular wherein each of $Y^1$ and $Y^3$ represents CH);

and to salts (in particular pharmaceutically acceptable salts) of such compounds.

lxxi) According to one sub-embodiment of embodiment lxx), the compounds of formula I as defined in embodiment lxx) will be such that "_____" is a bond, V represents CH and U represents CH or N.

lxxii) According to another sub-embodiment of embodiment lxx), the compounds of formula I as defined in embodiment lxx) will be such that "_____" is absent and U represents NH.

lxxiii) One main embodiment of this invention relates to the compounds of formula I as defined in one of embodiments i) to xxvii) or xxix) to xxxvii), and in particular according to embodiment i) or v)), wherein n is 0 (and notably wherein n is 0, A represents $(CH_2)_p$ and p is 2 or 3).

lxxiv) Another main embodiment of this invention relates to the compounds of formula I as defined in one of embodiments i) to xxvii) or xxix) to xxxvii), and in particular according to embodiment i) or v)), wherein n is 1 (and notably wherein n is 1, A represents $(CH_2)_p$ and p is 1 or 2).

lxxv) Yet another main embodiment of this invention relates to the compounds of formula I as defined in one of embodiments i) to xxvii) or xxix) to xxxvii), and in particular according to embodiment i) or v)), wherein n is 2 (and notably wherein n is 2, A represents $(CH_2)_p$ and p is 1 or 2).

lxxvi) Yet a further embodiment of this invention relates to the compounds of formula I as defined in embodiment i) or v) wherein:

"_____" is a bond and V represents CH and U represents CH or N or V represents N and U represents CH;

$R^0$ represents H;

$R^1$ represents H or fluorine (in particular fluorine);

$R^2$ represents H;

$R^4$ represents H;

$R^5$ represents H, methyl, hydroxymethyl or aminomethyl (and in particular H);

n is 0 and A represents —$(CH_2)_p$— wherein p is 2, 3 or 4, or n is 1 and A represents —$(CH_2)_p$— wherein p is 1, 2 or 3; and G is a group having the formula $G^1$ below

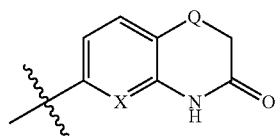

wherein X is CH or N and Q is O or S;
and to salts (in particular pharmaceutically acceptable salts) of such compounds.

lxxvii) Yet another embodiment of this invention relates to compounds of formula I as defined in embodiment i) or v) wherein:

"----" is absent and U represents NH or NR$^9$ wherein R$^9$ is methyl (and in particular NH);

R$^0$ represents H;

R$^1$ represents H or fluorine (in particular fluorine);

R$^2$ represents H;

each of R$^4$ and R$^5$ represents H;

n is 0 and A represents —(CH$_2$)$_p$— wherein p is 2, 3 or 4, or n is 1 and A represents —(CH$_2$)$_p$— wherein p is 1, 2 or 3; and G is a group having the formula G$^1$ below

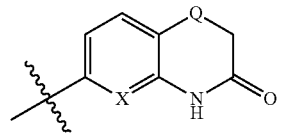

wherein X is CH or N and Q is O or S;

and to salts (in particular pharmaceutically acceptable salts) of such compounds.

lxxviii) According to one particular variant of this invention, the compounds of formula I as defined in embodiments i) to lxxvii) above will be such that their stereochemistry is as drawn below

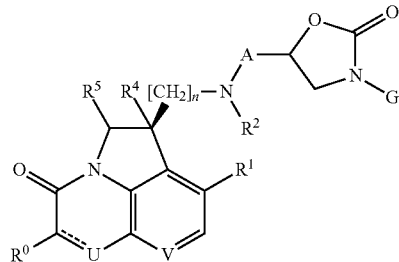

or, in the particular case of compounds of formula I$_{P2}$, such that their stereochemistry is as drawn below

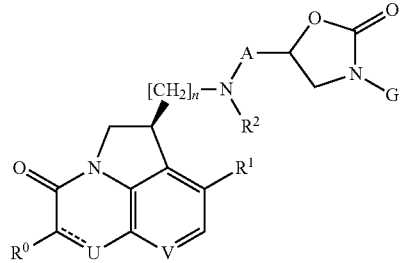

or also, in the particular case of compounds of formula I$_{P1}$, such that their stereochemistry is as drawn below

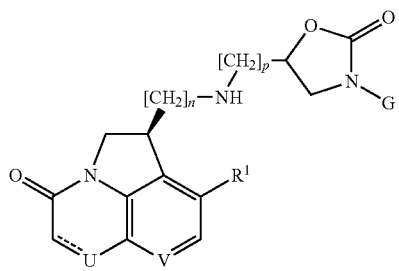

lxxix) According to one sub-variant of embodiment lxxviii), the compounds of formula I as defined in embodiment lxxviii) will be such that their stereochemistry is as drawn below

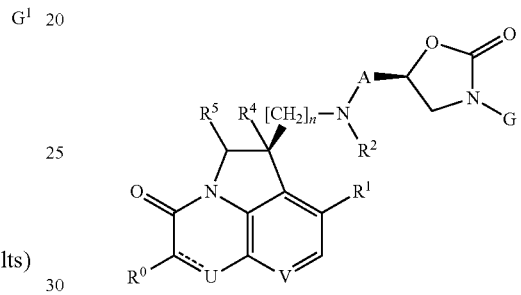

or, in the particular case of compounds of formula I$_{P2}$, such that their stereochemistry is as drawn below

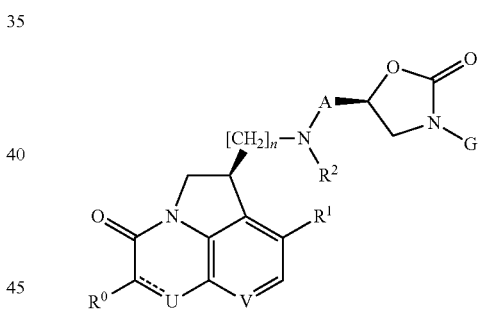

or also, in the particular case of compounds of formula I$_{P1}$, such that their stereochemistry is as drawn below

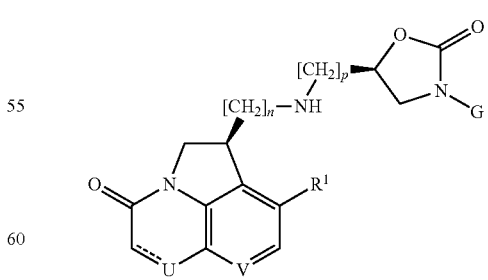

lxxx) According to the other sub-variant of embodiment lxxviii), the compounds of formula I as defined in embodiment lxxviii) will be such that their stereochemistry is as drawn below

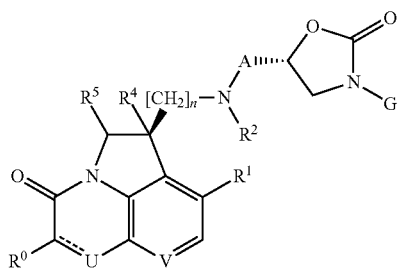

or, in the particular case of compounds of formula I$_{P2}$, such that their stereochemistry is as drawn below

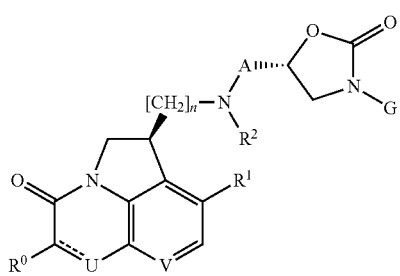

or also, in the particular case of compounds of formula I$_{P1}$, such that their stereochemistry is as drawn below

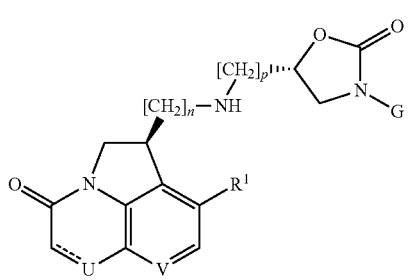

lxxxi) According to another particular variant of this invention, the compounds of formula I as defined in embodiments i) to lxxvii) above will be such that their stereochemistry is as drawn below

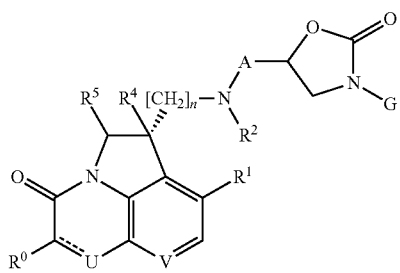

or, in the particular case of compounds of formula I$_{P2}$, such that their stereochemistry is as drawn below

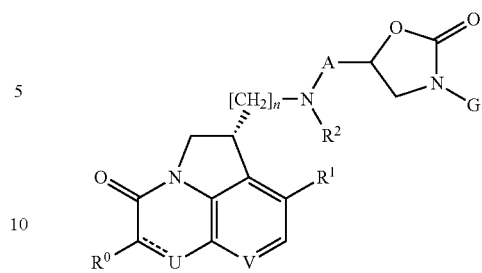

or also, in the particular case of compounds of formula I$_{P1}$, such that their stereochemistry is as drawn below

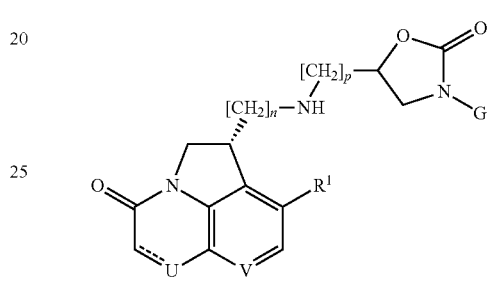

lxxxii) According to one sub-variant of embodiment lxxxi), the compounds of formula I as defined in embodiment lxxxi) will be such that their stereochemistry is as drawn below

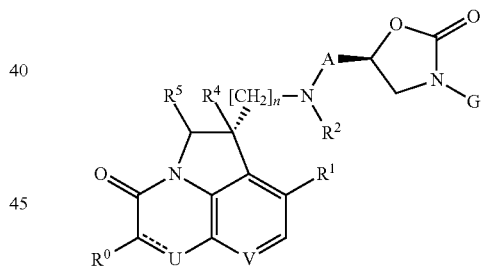

or, in the particular case of compounds of formula I$_{P2}$, such that their stereochemistry is as drawn below

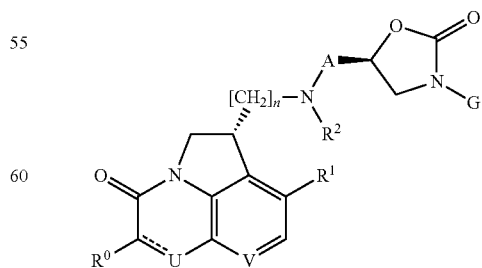

or also, in the particular case of compounds of formula I$_{P1}$, such that their stereochemistry is as drawn below

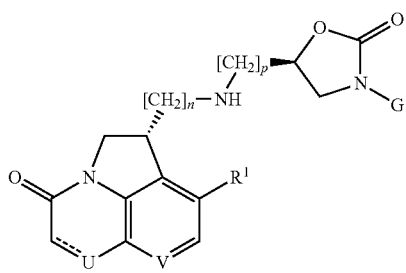

lxxxiii) According to the other sub-variant of embodiment lxxxi), the compounds of formula I as defined in embodiment lxxxi) will be such that their stereochemistry is as drawn below

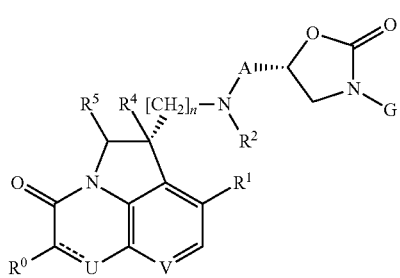

or, in the particular case of compounds of formula I$_{P2}$, such that their stereochemistry is as drawn below

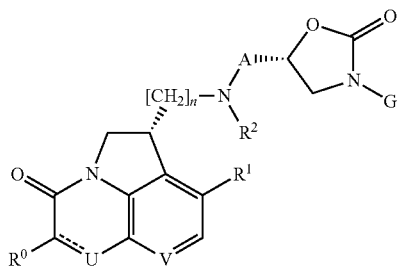

or also, in the particular case of compounds of formula I$_{P1}$, such that their stereochemistry is as drawn below

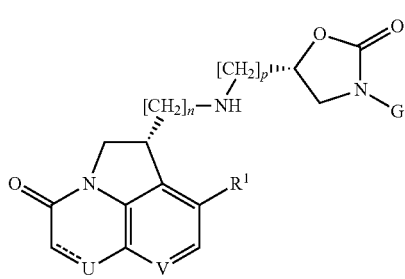

lxxxiv) According to yet another particular variant of this invention, the compounds of formula I as defined in embodiments i) to lxxvii) above will be such that their stereochemistry is as drawn below

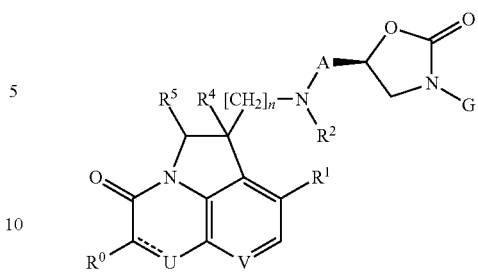

or, in the particular case of compounds of formula I$_{P2}$, such that their stereochemistry is as drawn below

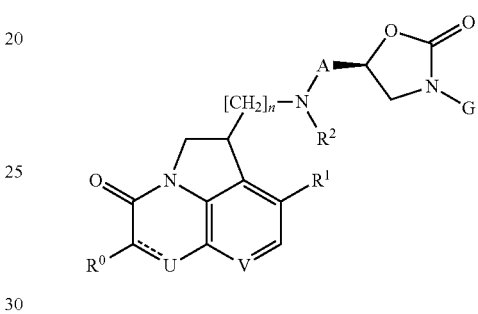

or also, in the particular case of compounds of formula I$_{P1}$, such that their stereochemistry is as drawn below

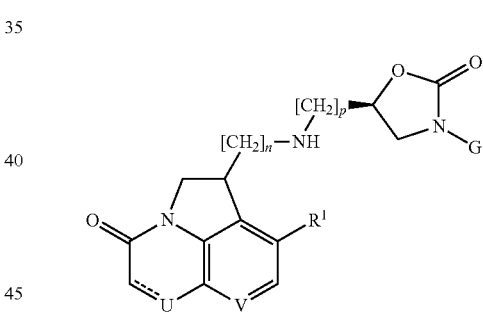

lxxxv) According to yet another particular variant of this invention, the compounds of formula I as defined in embodiments i) to lxxvii) above will be such that their stereochemistry is as drawn below

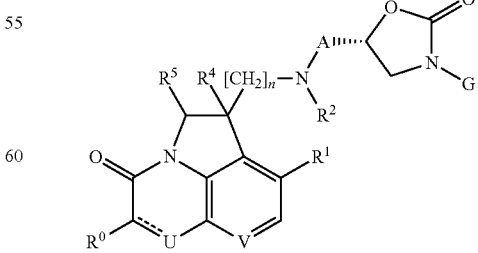

or, in the particular case of compounds of formula I$_{P2}$, such that their stereochemistry is as drawn below

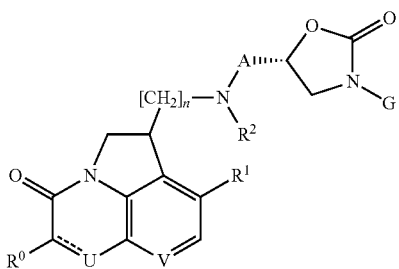

or also, in the particular case of compounds of formula I$_{P1}$, such that their stereochemistry is as drawn below

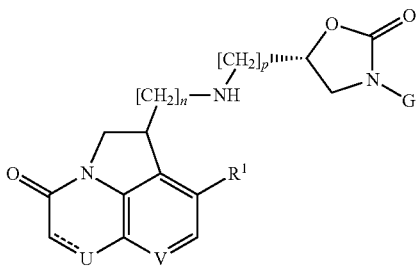

lxxxvi) Particularly preferred are the following compounds of formula I as defined in one of embodiments i) to viii):

9-fluoro-1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

9-fluoro-1-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

9-fluoro-1-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

9-fluoro-1-({2-[3-(3-fluoro-4-methyl-phenyl)-2-oxo-oxazolidin-5-yl]-ethylamino}-methyl)-1,2-dihydro-pyrrolo[3,2,1-ij]quinolin-4-one;

1-(2-{[(R)-3-(2,3-dihydro-benzo[1,4]dioxin-6-yl)-2-oxo-oxazolidin-5-ylmethyl]-amino}-ethyl)-9-fluoro-1,2-dihydro-pyrrolo[3,2,1-ij]quinolin-4-one;

9-fluoro-1-(2-{[(S)-2-oxo-3-(3-oxo-3,4-dihydro-2H-benzo[1,4]thiazin-6-yl)-oxazolidin-1-ylmethyl]-amino}-ethyl)-1,2-dihydro-pyrrolo[3,2,1-ij]quinolin-4-one;

9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2-dihydro-pyrrolo[3,2,1-ij]quinolin-4-one;

9-fluoro-1-(2-{[(R)-2-oxo-3-(3-oxo-3,4-dihydro-2H-benzo[1,4]thiazin-6-yl)-oxazolidin-1-ylmethyl]-amino}-ethyl)-1,2-dihydro-pyrrolo[3,2,1-ij]quinolin-4-one;

9-fluoro-1-(2-{[(R)-3-(3-fluoro-4-methyl-phenyl)-2-oxo-oxazolidin-5-ylmethyl]-amino}-ethyl)-1,2-dihydro-pyrrolo[3,2,1-ij]quinolin-4-one;

9-fluoro-1-{3-[(R)-2-oxo-3-(3-oxo-3,4-dihydro-2H-benzo[1,4]oxazin-6-yl)-oxazolidin-1-yl]-propylamino}-1,2-dihydro-pyrrolo[3,2,1-ij]quinolin-4-one;

9-fluoro-1-{3-[(R)-2-oxo-3-(3-oxo-3,4-dihydro-2H-benzo[1,4]thiazin-6-yl)-oxazolidin-1-yl]-propylamino}-1,2-dihydro-pyrrolo[3,2,1-ij]quinolin-4-one;

9-fluoro-1-{2-[2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;

(4R)-4-({2-[(R)-2-oxo-3-(3-oxo-3,4-dihydro-2H-benzo[1,4]thiazin-6-yl)-oxazolidin-1-yl]-ethylamino}-methyl)-4,5-dihydro-pyrrolo[3,2,1-de][1,5]naphthyridin-7-one;

3-fluoro-4-(2-{[(S)-2-oxo-3-(3-oxo-3,4-dihydro-2H-benzo[1,4]thiazin-6-yl)-oxazolidin-1-ylmethyl]-amino}-ethyl)-4,5-dihydro-pyrrolo[3,2,1-de][1,5]naphthyridin-7-one;

3-fluoro-4-(2-{[(R)-2-oxo-3-(3-oxo-3,4-dihydro-2H-benzo[1,4]thiazin-6-yl)-oxazolidin-1-ylmethyl]-amino}-ethyl)-4,5-dihydro-pyrrolo[3,2,1-de][1,5]naphthyridin-7-one;

(4R)-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(4R)-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

9-fluoro-1-(2-{[(S)-2-oxo-3-(3-oxo-3,4-dihydro-2H-benzo[1,4]thiazin-6-yl)-oxazolidin-5-ylmethyl]-amino}-ethyl)-1,2,5,6-tetrahydro-pyrrolo[3,2,1-ij]quinolin-4-one;

9-fluoro-1-({2-[(R)-2-oxo-3-(3-oxo-3,4-dihydro-2H-benzo[1,4]thiazin-6-yl)-oxazolidin-1-yl]-ethylamino}-methyl)-1,2,5,6-tetrahydro-pyrrolo[3,2,1-ij]quinolin-4-one;

9-fluoro-1-(2-{[(R)-2-oxo-3-(3-oxo-3,4-dihydro-2H-benzo[1,4]thiazin-6-yl)-oxazolidin-1-ylmethyl]-amino}-ethyl)-1,2,5,6-tetrahydro-pyrrolo[3,2,1-ij]quinolin-4-one;

9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2,5,6-tetrahydro-pyrrolo[3,2,1-ij]quinolin-4-one;

1-(2-{[(R)-3-(2,3-dihydro-benzo[1,4]dioxin-6-yl)-2-oxo-oxazolidin-5-ylmethyl]-amino}-ethyl)-9-fluoro-1,2,5,6-tetrahydro-pyrrolo[3,2,1-ij]quinolin-4-one;

9-fluoro-1-(2-{[(R)-3-(3-fluoro-4-methyl-phenyl)-2-oxo-oxazolidin-5-ylmethyl]-amino}-ethyl)-1,2,5,6-tetrahydro-pyrrolo[3,2,1-ij]quinolin-4-one;

3-fluoro-4-({2-[(R)-2-oxo-3-(3-oxo-3,4-dihydro-2H-benzo[1,4]thiazin-6-yl)-oxazolidin-1-yl]-ethylamino}-methyl)-4,5-dihydro-pyrrolo[3,2,1-de][1,5]naphthyridin-7-one;

9-fluoro-1-({2-[(S)-2-oxo-3-(3-oxo-3,4-dihydro-2H-benzo[1,4]thiazin-6-yl)-oxazolidin-1-yl]-ethylamino}-methyl)-1,2,5,6-tetrahydro-pyrrolo[3,2,1-ij]quinolin-4-one;

9-fluoro-1-({[(S)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

1-({[(R)-3-(2,3-dihydro-benzo[1,4]dioxin-6-yl)-2-oxo-oxazolidin-5-ylmethyl]-amino}-methyl)-9-fluoro-1,2-dihydro-pyrrolo[3,2,1-ij]quinolin-4-one;

9-fluoro-1-({[(R)-2-oxo-3-(3-oxo-3,4-dihydro-2H-benzo[1,4]oxazin-6-yl)-oxazolidin-1-ylmethyl]-amino}-methyl)-1,2-dihydro-pyrrolo[3,2,1-ij]quinolin-4-one;

9-fluoro-1-({[(R)-3-(3-fluoro-4-methyl-phenyl)-2-oxo-oxazolidin-5-ylmethyl]-amino}-methyl)-1,2-dihydro-pyrrolo[3,2,1-ij]quinolin-4-one;

as well as the salts (in particular the pharmaceutically acceptable salts) thereof lxxxvii) A further object of this invention thus relates to the following compounds of formula I as defined in one of embodiments i) to viii):

(1R)-9-fluoro-1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(1S)-9-fluoro-1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(1R)-9-fluoro-1-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(1S)-9-fluoro-1-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;
(1R)-9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(1S)-9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(1R)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(1S)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(1R)-9-fluoro-1-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;
(1S)-9-fluoro-1-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;
(1R)-9-fluoro-1-({2-[(R)-3-(3-fluoro-4-methyl-phenyl)-2-oxo-oxazolidin-5-yl]-ethylamino}-methyl)-1,2-dihydro-pyrrolo[3,2,1-ij]quinolin-4-one;
(1R)-9-fluoro-1-({2-[(S)-3-(3-fluoro-4-methyl-phenyl)-2-oxo-oxazolidin-5-yl]-ethylamino}-methyl)-1,2-dihydro-pyrrolo[3,2,1-ij]quinolin-4-one;
(1S)-9-fluoro-1-({2-[(R)-3-(3-fluoro-4-methyl-phenyl)-2-oxo-oxazolidin-5-yl]-ethylamino}-methyl)-1,2-dihydro-pyrrolo[3,2,1-ij]quinolin-4-one;
(1S)-9-fluoro-1-({2-[(S)-3-(3-fluoro-4-methyl-phenyl)-2-oxo-oxazolidin-5-yl]-ethylamino}-methyl)-1,2-dihydro-pyrrolo[3,2,1-ij]quinolin-4-one;
(1R)-1-(2-{[(R)-3-(2,3-dihydro-benzo[1,4]dioxin-6-yl)-2-oxo-oxazolidin-5-ylmethyl]-amino}-ethyl)-9-fluoro-1,2-dihydro-pyrrolo[3,2,1-ij]quinolin-4-one;
(1S)-1-(2-{[(R)-3-(2,3-dihydro-benzo[1,4]dioxin-6-yl)-2-oxo-oxazolidin-5-ylmethyl]-amino}-ethyl)-9-fluoro-1,2-dihydro-pyrrolo[3,2,1-ij]quinolin-4-one;
(1R)-9-fluoro-1-(2-{[(S)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;
(1S)-9-fluoro-1-(2-{[(S)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;
(1R)-9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2-dihydro-pyrrolo[3,2,1-ij]quinolin-4-one;
(1S)-9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2-dihydro-pyrrolo[3,2,1-ij]quinolin-4-one;
(1R)-9-fluoro-1-(2-{[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;
(1S)-9-fluoro-1-(2-{[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;
(1R)-9-fluoro-1-(2-{[(R)-3-(3-fluoro-4-methyl-phenyl)-2-oxo-oxazolidin-5-ylmethyl]-amino}-ethyl)-1,2-dihydro-pyrrolo[3,2,1-ij]quinolin-4-one;
(1S)-9-fluoro-1-(2-{[(R)-3-(3-fluoro-4-methyl-phenyl)-2-oxo-oxazolidin-5-ylmethyl]-amino}-ethyl)-1,2-dihydro-pyrrolo[3,2,1-ij]quinolin-4-one;
(1R)-9-fluoro-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;
(1S)-9-fluoro-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;
(1R)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1S)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1R)-9-fluoro-1-{2-[(R)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;
(1R)-9-fluoro-1-{2-[(S)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;
(1S)-9-fluoro-1-{2-[(R)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;
(1S)-9-fluoro-1-{2-[(S)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;
(4R)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
(4R)-3-fluoro-4-(2-{[(S)-2-oxo-3-(3-oxo-3,4-dihydro-2H-benzo[1,4]thiazin-6-yl)-oxazolidin-5-ylmethyl]-amino}-ethyl)-4,5-dihydro-pyrrolo[3,2,1-de][1,5]naphthyridin-7-one;
(4S)-3-fluoro-4-(2-{[(S)-2-oxo-3-(3-oxo-3,4-dihydro-2H-benzo[1,4]thiazin-6-yl)-oxazolidin-5-ylmethyl]-amino}-ethyl)-4,5-dihydro-pyrrolo[3,2,1-de][1,5]naphthyridin-7-one;
(4R)-3-fluoro-4-(2-{[(R)-2-oxo-3-(3-oxo-3,4-dihydro-2H-benzo[1,4]thiazin-6-yl)-oxazolidin-5-ylmethyl]-amino}-ethyl)-4,5-dihydro-pyrrolo[3,2,1-de][1,5]naphthyridin-7-one;
(4S)-3-fluoro-4-(2-{[(R)-2-oxo-3-(3-oxo-3,4-dihydro-2H-benzo[1,4]thiazin-6-yl)-oxazolidin-5-ylmethyl]-amino}-ethyl)-4,5-dihydro-pyrrolo[3,2,1-de][1,5]naphthyridin-7-one;
(4R)-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;
(4R)-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;
(6R)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(6S)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(6R)-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(6S)-6-{3-[(R)-2-oxo-3-(3-oxo-3,4-dihydro-2H-benzo[1,4]
oxazin-6-yl)-oxazolidin-5-yl]-propylamino}-5,6-dihydro-pyrrolo[1,2,3-de]quinoxalin-3-one;
(1R)-9-fluoro-1-(2-{[(S)-2-oxo-3-(3-oxo-3,4-dihydro-2H-benzo[1,4]thiazin-6-yl)-oxazolidin-5-ylmethyl]-amino}-ethyl)-1,2,5,6-tetrahydro-pyrrolo[3,2,1-ij]quinolin-4-one;
(1S)-9-fluoro-1-(2-{[(S)-2-oxo-3-(3-oxo-3,4-dihydro-2H-benzo[1,4]thiazin-6-yl)-oxazolidin-5-ylmethyl]-amino}-ethyl)-1,2,5,6-tetrahydro-pyrrolo[3,2,1-ij]quinolin-4-one;
(1R)-9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2,5,6-tetrahydro-pyrrolo[3,2,1-ij]quinolin-4-one;
(1S)-9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2,5,6-tetrahydro-pyrrolo[3,2,1-ij]quinolin-4-one;
(1R)-9-fluoro-1-(2-{[(R)-2-oxo-3-(3-oxo-3,4-dihydro-2H-benzo[1,4]thiazin-6-yl)-oxazolidin-5-ylmethyl]-amino}-ethyl)-1,2,5,6-tetrahydro-pyrrolo[3,2,1-ij]quinolin-4-one;
(1S)-9-fluoro-1-(2-{[(R)-2-oxo-3-(3-oxo-3,4-dihydro-2H-benzo[1,4]thiazin-6-yl)-oxazolidin-5-ylmethyl]-amino}-ethyl)-1,2,5,6-tetrahydro-pyrrolo[3,2,1-ij]quinolin-4-one;
(1R)-9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2,5,6-tetrahydro-pyrrolo[3,2,1-ij]quinolin-4-one;
(1S)-9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2,5,6-tetrahydro-pyrrolo[3,2,1-ij]quinolin-4-one;
(1R)-1-(2-{[(R)-3-(2,3-dihydro-benzo[1,4]dioxin-6-yl)-2-oxo-oxazolidin-5-ylmethyl]-amino}-ethyl)-9-fluoro-1,2,5,6-tetrahydro-pyrrolo[3,2,1-ij]quinolin-4-one;
(1S)-1-(2-{[(R)-3-(2,3-dihydro-benzo[1,4]dioxin-6-yl)-2-oxo-oxazolidin-5-ylmethyl]-amino}-ethyl)-9-fluoro-1,2,5,6-tetrahydro-pyrrolo[3,2,1-ij]quinolin-4-one;
(1R)-9-fluoro-1-(2-{[(R)-3-(3-fluoro-4-methyl-phenyl)-2-oxo-oxazolidin-5-ylmethyl]-amino}-ethyl)-1,2,5,6-tetrahydro-pyrrolo[3,2,1-ij]quinolin-4-one;
(1S)-9-fluoro-1-(2-{[(R)-3-(3-fluoro-4-methyl-phenyl)-2-oxo-oxazolidin-5-ylmethyl]-amino}-ethyl)-1,2,5,6-tetrahydro-pyrrolo[3,2,1-ij]quinolin-4-one;
(4R)-3-fluoro-4-{2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
(4S)-3-fluoro-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
(1R)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2,5,6-tetrahydro-pyrrolo[3,2,1-ij]quinolin-4-one;
(1S)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2,5,6-tetrahydro-pyrrolo[3,2,1-ij]quinolin-4-one;
(1R)-9-fluoro-1-({[(S)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;
(1S)-9-fluoro-1-({[(S)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;
(1R)-1-({[(R)-3-(2,3-dihydro-benzo[1,4]dioxin-6-yl)-2-oxo-oxazolidin-5-ylmethyl]-amino}-methyl)-9-fluoro-1,2-dihydro-pyrrolo[3,2,1-ij]quinolin-4-one;
(1S)-1-({[(R)-3-(2,3-dihydro-benzo[1,4]dioxin-6-yl)-2-oxo-oxazolidin-5-ylmethyl]-amino}-methyl)-9-fluoro-1,2-dihydro-pyrrolo[3,2,1-ij]quinolin-4-one;
(1R)-9-fluoro-1-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;
(1S)-9-fluoro-1-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;
(1R)-9-fluoro-1-({[(R)-3-(3-fluoro-4-methyl-phenyl)-2-oxo-oxazolidin-5-ylmethyl]-amino}-methyl)-1,2-dihydro-pyrrolo[3,2,1-ij]quinolin-4-one;
(1S)-9-fluoro-1-({[(R)-3-(3-fluoro-4-methyl-phenyl)-2-oxo-oxazolidin-5-ylmethyl]-amino}-methyl)-1,2-dihydro-pyrrolo[3,2,1-ij]quinolin-4-one;
as well as to the salts (in particular the pharmaceutically acceptable salts) thereof lxxxviii) Further particularly preferred compounds of formula I as defined in embodiment i), ii), iii), v), vi) or vii) are the following compounds:

4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
1-({[(R)-3-(4-ethoxy-phenyl)-2-oxo-oxazolidin-5-ylmethyl]-amino}-methyl)-9-fluoro-1,2-dihydro-pyrrolo[3,2,1-ij]quinolin-4-one;
9-fluoro-1-({[(R)-2-oxo-3-(4-propyl-phenyl)-oxazolidin-5-ylmethyl]-amino}-methyl)-1,2-dihydro-pyrrolo[3,2,1-ij]quinolin-4-one;
1-({[(R)-3-(4-butyl-phenyl)-2-oxo-oxazolidin-5-ylmethyl]-amino}-methyl)-9-fluoro-1,2-dihydro-pyrrolo[3,2,1-ij]quinolin-4-one;
(S)-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;
(S)-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;
(S)-4-{2-[(S)-2-oxo-3-(3-oxo-3,4-dihydro-2H-benzo[1,4]thiazin-6-yl)-oxazolidin-5-yl]-ethylamino}-4,5-dihydro-pyrrolo[3,2,1-de][1,5]naphthyridin-7-one;
1-({2-[3-(2,3-dihydro-[1,4]dioxino[2,3-c]pyridin-7-yl)-2-oxo-oxazolidin-5-yl]-ethylamino}-methyl)-9-fluoro-1,2-dihydro-pyrrolo[3,2,1-ij]quinolin-4-one;
1-({2-[3-(2,3-dihydro-[1,4]dioxino[2,3-b]pyridin-6-yl)-2-oxo-oxazolidin-5-yl]-ethylamino}-methyl)-9-fluoro-1,2-dihydro-pyrrolo[3,2,1-ij]quinolin-4-one;
1-({2-[(R)-3-(4-ethoxy-phenyl)-2-oxo-oxazolidin-5-yl]-ethylamino}-methyl)-9-fluoro-1,2-dihydro-pyrrolo[3,2,1-ij]quinolin-4-one;
9-fluoro-1-({2-[(R)-2-oxo-3-(4-propyl-phenyl)-oxazolidin-5-yl]-ethylamino}-methyl)-1,2-dihydro-pyrrolo[3,2,1-ij]quinolin-4-one;
1-({2-[(R)-3-(2,3-dihydro-benzo[1,4]dioxin-6-yl)-2-oxo-oxazolidin-5-yl]-ethylamino}-methyl)-9-fluoro-1,2-dihydro-pyrrolo[3,2,1-ij]quinolin-4-one;
9-fluoro-1-({2-[2-oxo-3-(3-oxo-3,4-dihydro-2H-pyrido[3,2-b][1,4]oxazin-6-yl)-oxazolidin-5-yl]-ethylamino}-methyl)-1,2-dihydro-pyrrolo[3,2,1-ij]quinolin-4-one;
(S)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(S)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

9-fluoro-1-({3-[(R)-2-oxo-3-(3-oxo-3,4-dihydro-2H-benzo[1,4]thiazin-6-yl)-oxazolidin-1-yl]-propylamino}-methyl)-1,2-dihydro-pyrrolo[3,2,1-ij]quinolin-4-one;

9-fluoro-1-({3-[(R)-2-oxo-3-(3-oxo-3,4-dihydro-2H-benzo[1,4]oxazin-6-yl)-oxazolidin-5-yl]-propylamino}-methyl)-1,2-dihydro-pyrrolo[3,2,1-ij]quinolin-4-one;

1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(S)-6-{2-[(R)-2-oxo-3-(3-oxo-3,4-dihydro-2H-benzo[1,4]thiazin-6-yl)-oxazolidin-5-yl]-ethylamino}-5,6-dihydro-pyrrolo[1,2,3-de]quinoxalin-3-one;

(S)-6-{2-[(S)-2-oxo-3-(3-oxo-3,4-dihydro-2H-benzo[1,4]thiazin-6-yl)-oxazolidin-5-yl]-ethylamino}-5,6-dihydro-pyrrolo[1,2,3-de]quinoxalin-3-one;

6-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one;

(S)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(S)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

9-fluoro-1-{2-[(R)-2-oxo-3-(4-propyl-phenyl)-oxazolidin-5-yl]-ethylamino}-1,2-dihydro-pyrrolo[3,2,1-ij]quinolin-4-one;

1-({2-[(S)-3-(2,3-dihydro-benzo[1,4]dioxin-6-yl)-2-oxo-oxazolidin-5-yl]-ethylamino}-methyl)-9-fluoro-1,2-dihydro-pyrrolo[3,2,1-ij]quinolin-4-one;

1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

1-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

(R)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(R)-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(S)-7-fluoro-6-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-5,6-dihydro-pyrrolo[1,2,3-de]quinoxalin-3-one;

(S)-7-fluoro-6-((2-hydroxy-ethyl)-{3-[(R)-2-oxo-3-(3-oxo-3,4-dihydro-2H-benzo[1,4]oxazin-6-yl)-oxazolidin-5-yl]-propyl}-amino)-5,6-dihydro-pyrrolo[1,2,3-de]quinoxalin-3-one;

9-fluoro-1-(2-{(3-hydroxy-propyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;

9-fluoro-1-(2-{(2-hydroxy-ethyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;

9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-7-fluoro-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;

(S)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;

(S)-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-6-{3-[(R)-2-oxo-3-(3-oxo-3,4-dihydro-2H-pyrido[3,2-b][1,4]oxazin-6-yl)-oxazolidin-1-yl]-propylamino}-5,6-dihydro-pyrrolo[1,2,3-de]quinoxalin-3-one;

(S)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(R)-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-7-fluoro-6-{3-[(S)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(S)-7-fluoro-6-{3-[(S)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

1-({[(S)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one;

1-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;

1-({3-[2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one;

3-fluoro-4-{2-[(S)-2-oxo-3-(3-oxo-3,4-dihydro-2H-benzo[1,4]thiazin-6-yl)-oxazolidin-5-yl]-ethylamino}-4,5-dihydro-pyrrolo[3,2,1-de][1,5]naphthyridin-7-one;

(S)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;

(S)-1-{2-[(R)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;

(S)-1-{2-[(S)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;

(S)-1-{2-[(S)-2-oxo-3-(3-oxo-3,4-dihydro-2H-benzo[1,4]oxazin-6-yl)-oxazolidin-5-yl]-ethylamino}-1,2-dihydro-pyrrolo[3,2,1-ij]quinolin-4-one;

9-fluoro-1-[((3-hydroxy-propyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one;

9-fluoro-1-[((2-hydroxy-ethyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one;

9-fluoro-1-((3-hydroxy-propyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

9-fluoro-1-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

3-fluoro-4-{3-[(R)-2-oxo-3-(3-oxo-3,4-dihydro-2H-benzo[1,4]thiazin-6-yl)-oxazolidin-1-yl]-propylamino}-4,5-dihydro-pyrrolo[3,2,1-de][1,5]naphthyridin-7-one;

3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

3-fluoro-4-{3-[(S)-2-oxo-3-(3-oxo-3,4-dihydro-2H-benzo[1,4]thiazin-6-yl)-oxazolidin-1-yl]-propylamino}-4,5-dihydro-pyrrolo[3,2,1-de][1,5]naphthyridin-7-one;

3-fluoro-4-{3-[(S)-2-oxo-3-(3-oxo-3,4-dihydro-2H-benzo[1,4]oxazin-6-yl)-oxazolidin-1-yl]-propylamino}-4,5-dihydro-pyrrolo[3,2,1-de][1,5]naphthyridin-7-one;

3-fluoro-4-({[(R)-2-oxo-3-(3-oxo-3,4-dihydro-2H-benzo[1,4]oxazin-6-yl)-oxazolidin-1-ylmethyl]-amino}-methyl)-4,5-dihydro-pyrrolo[3,2,1-de][1,5]naphthyridin-7-one;

3-fluoro-4-({2-[(S)-2-oxo-3-(3-oxo-3,4-dihydro-2H-benzo[1,4]thiazin-6-yl)-oxazolidin-1-yl]-ethylamino}-methyl)-4,5-dihydro-pyrrolo[3,2,1-de][1,5]naphthyridin-7-one;

3-fluoro-4-({[(R)-2-oxo-3-(3-oxo-3,4-dihydro-2H-benzo[1,4]thiazin-6-yl)-oxazolidin-5-ylmethyl]-amino}-methyl)-4,5-dihydro-pyrrolo[3,2,1-de][1,5]naphthyridin-7-one;

3-fluoro-4-({[(S)-2-oxo-3-(3-oxo-3,4-dihydro-2H-benzo[1,4]thiazin-6-yl)-oxazolidin-1-ylmethyl]-amino}-methyl)-4,5-dihydro-pyrrolo[3,2,1-de][1,5]naphthyridin-7-one;

3-fluoro-4-({2-[(S)-2-oxo-3-(3-oxo-3,4-dihydro-2H-benzo[1,4]oxazin-6-yl)-oxazolidin-1-yl]-ethylamino}-methyl)-4,5-dihydro-pyrrolo[3,2,1-de][1,5]naphthyridin-7-one;

3-fluoro-4-({2-[(R)-2-oxo-3-(3-oxo-3,4-dihydro-2H-benzo[1,4]oxazin-6-yl)-oxazolidin-1-yl]-ethylamino}-methyl)-4,5-dihydro-pyrrolo[3,2,1-de][1,5]naphthyridin-7-one;

(R)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(R)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

6-({[(S)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one;

1-{2-[(S)-3-(2,3-dihydro-benzo[1,4]dioxin-6-yl)-2-oxo-oxazolidin-5-yl]-ethylamino}-9-fluoro-1,2-dihydro-pyrrolo[3,2,1-ij]quinolin-4-one;

N-((S)-9-fluoro-4-oxo-1,2-dihydro-4H-pyrrolo[3,2,1-ij]quinolin-1-yl)-3-hydroxy-3-[2-oxo-3-(3-oxo-3,4-dihydro-2H-benzo[1,4]thiazin-6-yl)-oxazolidin-5-yl]-propionamide;

(R)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

6-({[(R)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one;

(R)-7-fluoro-2-methoxy-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(R)-7-fluoro-2-methoxy-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

9-fluoro-1-{3-hydroxy-3-[2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-6-{3-[(R)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one;

as well as the salts (in particular the pharmaceutically acceptable salts) thereof lxxxix) A further object of this invention thus relates to the following compounds of formula I as defined in embodiment i), ii), iii), v), vi) or vii):

(R)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(R)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-1-({[(R)-3-(4-ethoxy-phenyl)-2-oxo-oxazolidin-5-ylmethyl]-amino}-methyl)-9-fluoro-1,2-dihydro-pyrrolo[3,2,1-ij]quinolin-4-one;

(S)-1-({[(R)-3-(4-ethoxy-phenyl)-2-oxo-oxazolidin-5-ylmethyl]-amino}-methyl)-9-fluoro-1,2-dihydro-pyrrolo[3,2,1-ij]quinolin-4-one;

(R)-9-fluoro-1-({[(R)-2-oxo-3-(4-propyl-phenyl)-oxazolidin-5-ylmethyl]-amino}-methyl)-1,2-dihydro-pyrrolo[3,2,1-ij]quinolin-4-one;

(S)-9-fluoro-1-({[(R)-2-oxo-3-(4-propyl-phenyl)-oxazolidin-5-ylmethyl]-amino}-methyl)-1,2-dihydro-pyrrolo[3,2,1-ij]quinolin-4-one;

(R)-1-({[(R)-3-(4-butyl-phenyl)-2-oxo-oxazolidin-5-ylmethyl]-amino}-methyl)-9-fluoro-1,2-dihydro-pyrrolo[3,2,1-ij]quinolin-4-one;

(S)-1-({[(R)-3-(4-butyl-phenyl)-2-oxo-oxazolidin-5-ylmethyl]-amino}-methyl)-9-fluoro-1,2-dihydro-pyrrolo[3,2,1-ij]quinolin-4-one;

(S)-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(S)-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(S)-4-{2-[(S)-2-oxo-3-(3-oxo-3,4-dihydro-2H-benzo[1,4]thiazin-6-yl)-oxazolidin-5-yl]-ethylamino}-4,5-dihydro-pyrrolo[3,2,1-de][1,5]naphthyridin-7-one;

(R)-1-({2-[(R)-3-(2,3-dihydro-[1,4]dioxino[2,3-c]pyridin-7-yl)-2-oxo-oxazolidin-5-yl]-ethylamino}-methyl)-9-fluoro-1,2-dihydro-pyrrolo[3,2,1-ij]quinolin-4-one;

(R)-1-({2-[(S)-3-(2,3-dihydro-[1,4]dioxino[2,3-c]pyridin-7-yl)-2-oxo-oxazolidin-5-yl]-ethylamino}-methyl)-9-fluoro-1,2-dihydro-pyrrolo[3,2,1-ij]quinolin-4-one;

(S)-1-({2-[(R)-3-(2,3-dihydro-[1,4]dioxino[2,3-c]pyridin-7-yl)-2-oxo-oxazolidin-5-yl]-ethylamino}-methyl)-9-fluoro-1,2-dihydro-pyrrolo[3,2,1-ij]quinolin-4-one;

(S)-1-({2-[(S)-3-(2,3-dihydro-[1,4]dioxino[2,3-c]pyridin-7-yl)-2-oxo-oxazolidin-5-yl]-ethylamino}-methyl)-9-fluoro-1,2-dihydro-pyrrolo[3,2,1-ij]quinolin-4-one;

(R)-1-({2-[(R)-3-(2,3-dihydro-[1,4]dioxino[2,3-b]pyridin-6-yl)-2-oxo-oxazolidin-5-yl]-ethylamino}-methyl)-9-fluoro-1,2-dihydro-pyrrolo[3,2,1-ij]quinolin-4-one;

(R)-1-({2-[(S)-3-(2,3-dihydro-[1,4]dioxino[2,3-b]pyridin-6-yl)-2-oxo-oxazolidin-5-yl]-ethylamino}-methyl)-9-fluoro-1,2-dihydro-pyrrolo[3,2,1-ij]quinolin-4-one;

(S)-1-({2-[(R)-3-(2,3-dihydro-[1,4]dioxino[2,3-b]pyridin-6-yl)-2-oxo-oxazolidin-5-yl]-ethylamino}-methyl)-9-fluoro-1,2-dihydro-pyrrolo[3,2,1-ij]quinolin-4-one;

(S)-1-({2-[(S)-3-(2,3-dihydro-[1,4]dioxino[2,3-b]pyridin-6-yl)-2-oxo-oxazolidin-5-yl]-ethylamino}-methyl)-9-fluoro-1,2-dihydro-pyrrolo[3,2,1-ij]quinolin-4-one;

(R)-1-({2-[(R)-3-(4-ethoxy-phenyl)-2-oxo-oxazolidin-5-yl]-ethylamino}-methyl)-9-fluoro-1,2-dihydro-pyrrolo[3,2,1-ij]quinolin-4-one;

(S)-1-({2-[(R)-3-(4-ethoxy-phenyl)-2-oxo-oxazolidin-5-yl]-ethylamino}-methyl)-9-fluoro-1,2-dihydro-pyrrolo[3,2,1-ij]quinolin-4-one;

(R)-9-fluoro-1-({2-[(R)-2-oxo-3-(4-propyl-phenyl)-oxazolidin-5-yl]-ethylamino}-methyl)-1,2-dihydro-pyrrolo[3,2,1-ij]quinolin-4-one;

(S)-9-fluoro-1-({2-[(R)-2-oxo-3-(4-propyl-phenyl)-oxazolidin-5-yl]-ethylamino}-methyl)-1,2-dihydro-pyrrolo[3,2,1-ij]quinolin-4-one;

(R)-1-({2-[(R)-3-(2,3-dihydro-benzo[1,4]-dioxin-6-yl)-2-oxo-oxazolidin-5-yl]-ethylamino}-methyl)-9-fluoro-1,2-dihydro-pyrrolo[3,2,1-ij]quinolin-4-one;

(S)-1-({2-[(R)-3-(2,3-dihydro-benzo[1,4]dioxin-6-yl)-2-oxo-oxazolidin-5-yl]-ethylamino}-methyl)-9-fluoro-1,2-dihydro-pyrrolo[3,2,1-ij]quinolin-4-one;

(R)-9-fluoro-1-({2-[(R)-2-oxo-3-(3-oxo-3,4-dihydro-2H-pyrido[3,2-b][1,4]oxazin-6-yl)-oxazolidin-5-yl]-ethylamino}-methyl)-1,2-dihydro-pyrrolo[3,2,1-ij]quinolin-4-one;

(R)-9-fluoro-1-({2-[(S)-2-oxo-3-(3-oxo-3,4-dihydro-2H-pyrido[3,2-b][1,4]oxazin-6-yl)-oxazolidin-5-yl]-ethylamino}-methyl)-1,2-dihydro-pyrrolo[3,2,1-ij]quinolin-4-one;

(S)-9-fluoro-1-({2-[(R)-2-oxo-3-(3-oxo-3,4-dihydro-2H-pyrido[3,2-b][1,4]oxazin-6-yl)-oxazolidin-5-yl]-ethylamino}-methyl)-1,2-dihydro-pyrrolo[3,2,1-ij]quinolin-4-one;

(S)-9-fluoro-1-({2-[(S)-2-oxo-3-(3-oxo-3,4-dihydro-2H-pyrido[3,2-b][1,4]oxazin-6-yl)-oxazolidin-5-yl]-ethylamino}-methyl)-1,2-dihydro-pyrrolo[3,2,1-ij]quinolin-4-one;

(S)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(S)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-9-fluoro-1-({3-[(R)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one;

(S)-9-fluoro-1-({3-[(R)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one;

(R)-9-fluoro-1-({3-[(R)-2-oxo-3-(3-oxo-3,4-dihydro-2H-benzo[1,4]oxazin-6-yl)-oxazolidin-5-yl]-propylamino}-methyl)-1,2-dihydro-pyrrolo[3,2,1-ij]quinolin-4-one;

(S)-9-fluoro-1-({3-[(R)-2-oxo-3-(3-oxo-3,4-dihydro-2H-benzo[1,4]oxazin-6-yl)-oxazolidin-5-yl]-propylamino}-methyl)-1,2-dihydro-pyrrolo[3,2,1-ij]quinolin-4-one;

(R)-1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(S)-1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(S)-6-{2-[(R)-2-oxo-3-(3-oxo-3,4-dihydro-2H-benzo[1,4]thiazin-6-yl)-oxazolidin-5-yl]-ethylamino}-5,6-dihydro-pyrrolo[1,2,3-de]quinoxalin-3-one;

(S)-6-{2-[(S)-2-oxo-3-(3-oxo-3,4-dihydro-2H-benzo[1,4]thiazin-6-yl)-oxazolidin-5-yl]-ethylamino}-5,6-dihydro-pyrrolo[1,2,3-de]quinoxalin-3-one;

(R)-6-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one;

(S)-6-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one;

(S)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(S)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(R)-9-fluoro-1-{2-[(R)-2-oxo-3-(4-propyl-phenyl)-oxazolidin-5-yl]-ethylamino}-1,2-dihydro-pyrrolo[3,2,1-ij]quinolin-4-one;

(S)-9-fluoro-1-{2-[(R)-2-oxo-3-(4-propyl-phenyl)-oxazolidin-5-yl]-ethylamino}-1,2-dihydro-pyrrolo[3,2,1-ij]quinolin-4-one;

(R)-1-({2-[(S)-3-(2,3-dihydro-benzo[1,4]dioxin-6-yl)-2-oxo-oxazolidin-5-yl]-ethylamino}-methyl)-9-fluoro-1,2-dihydro-pyrrolo[3,2,1-ij]quinolin-4-one;

(S)-1-({2-[(S)-3-(2,3-dihydro-benzo[1,4]dioxin-6-yl)-2-oxo-oxazolidin-5-yl]-ethylamino}-methyl)-9-fluoro-1,2-dihydro-pyrrolo[3,2,1-ij]quinolin-4-one;

(R)-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(S)-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

(R)-1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

(S)-1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one;

(R)-1-({[(R)-2-oxo-3-(3-oxo-3,4-dihydro-2H-benzo[1,4]thiazin-6-yl)-oxazolidin-1-ylmethyl]-amino}-methyl)-1,2-dihydro-pyrrolo[3,2,1-ij]quinolin-4-one;

(S)-1-({[(R)-2-oxo-3-(3-oxo-3,4-dihydro-2H-benzo[1,4]thiazin-6-yl)-oxazolidin-1-ylmethyl]-amino}-methyl)-1,2-dihydro-pyrrolo[3,2,1-ij]quinolin-4-one;

(R)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(R)-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(S)-7-fluoro-6-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-5,6-dihydro-pyrrolo[1,2,3-de]quinoxalin-3-one;

(S)-7-fluoro-6-((2-hydroxy-ethyl)-{3-[(R)-2-oxo-3-(3-oxo-3,4-dihydro-2H-benzo[1,4]oxazin-6-yl)-oxazolidin-5-yl]-propyl}-amino)-5,6-dihydro-pyrrolo[1,2,3-de]quinoxalin-3-one;

(R)-9-fluoro-1-(2-{(3-hydroxy-propyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;

(S)-9-fluoro-1-(2-{(3-hydroxy-propyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;

(R)-9-fluoro-1-(2-{(2-hydroxy-ethyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;

(S)-9-fluoro-1-(2-{(2-hydroxy-ethyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-7-fluoro-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;

(S)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;

(S)-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-6-{3-[(R)-2-oxo-3-(3-oxo-3,4-dihydro-2H-pyrido[3,2-b][1,4]oxazin-6-yl)-oxazolidin-1-yl]-propylamino}-5,6-dihydro-pyrrolo[1,2,3-de]quinoxalin-3-one;

(S)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(R)-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-7-fluoro-6-{3-[(S)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(S)-7-fluoro-6-{3-[(S)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(R)-1-({[(S)-2-oxo-3-(3-oxo-3,4-dihydro-2H-benzo[1,4]thiazin-6-yl)-oxazolidin-1-ylmethyl]-amino}-methyl)-1,2-dihydro-pyrrolo[3,2,1-ij]quinolin-4-one;

(S)-1-({[(S)-2-oxo-3-(3-oxo-3,4-dihydro-2H-benzo[1,4]thiazin-6-yl)-oxazolidin-1-ylmethyl]-amino}-methyl)-1,2-dihydro-pyrrolo[3,2,1-ij]quinolin-4-one;

(R)-1-({[(R)-2-oxo-3-(3-oxo-3,4-dihydro-2H-benzo[1,4]oxazin-6-yl)-oxazolidin-1-ylmethyl]-amino}-methyl)-1,2-dihydro-pyrrolo[3,2,1-ij]quinolin-4-one;

(S)-1-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one;

(R)-1-({3-[(R)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one;

(R)-1-({3-[(S)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one;

(S)-1-({3-[(R)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one;

(S)-1-({3-[(S)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one;

(R)-3-fluoro-4-{2-[(S)-2-oxo-3-(3-oxo-3,4-dihydro-2H-benzo[1,4]thiazin-6-yl)-oxazolidin-5-yl]-ethylamino}-4,5-dihydro-pyrrolo[3,2,1-de][1,5]naphthyridin-7-one;

(S)-3-fluoro-4-{2-[(S)-2-oxo-3-(3-oxo-3,4-dihydro-2H-benzo[1,4]thiazin-6-yl)-oxazolidin-5-yl]-ethylamino}-4,5-dihydro-pyrrolo[3,2,1-de][1,5]naphthyridin-7-one;

(S)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;

(S)-1-{2-[(R)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;

(S)-1-{2-[(S)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;

(S)-1-{2-[(S)-2-oxo-3-(3-oxo-3,4-dihydro-2H-benzo[1,4]oxazin-6-yl)-oxazolidin-5-yl]-ethylamino}-1,2-dihydro-pyrrolo[3,2,1-ij]quinolin-4-one;

(R)-9-fluoro-1-[((3-hydroxy-propyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one;

(S)-9-fluoro-1-[((3-hydroxy-propyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one;

(R)-9-fluoro-1-[((2-hydroxy-ethyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one;

(S)-9-fluoro-1-[((2-hydroxy-ethyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one;

(R)-9-fluoro-1-((3-hydroxy-propyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

(S)-9-fluoro-1-((3-hydroxy-propyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

(R)-9-fluoro-1-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

(S)-9-fluoro-1-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

(R)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(R)-3-fluoro-4-({[(R)-2-oxo-3-(3-oxo-3,4-dihydro-2H-benzo[1,4]oxazin-6-yl)-oxazolidin-5-ylmethyl]-amino}-methyl)-4,5-dihydro-pyrrolo[3,2,1-de][1,5]naphthyridin-7-one;

(S)-3-fluoro-4-({[(R)-2-oxo-3-(3-oxo-3,4-dihydro-2H-benzo[1,4]oxazin-6-yl)-oxazolidin-5-ylmethyl]-amino}-methyl)-4,5-dihydro-pyrrolo[3,2,1-de][1,5]naphthyridin-7-one;

(R)-3-fluoro-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(S)-3-fluoro-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

(R)-3-fluoro-4-({[(R)-2-oxo-3-(3-oxo-3,4-dihydro-2H-benzo[1,4]thiazin-6-yl)-oxazolidin-5-ylmethyl]-amino}-methyl)-4,5-dihydro-pyrrolo[3,2,1-de][1,5]naphthyridin-7-one;

(S)-3-fluoro-4-({[(R)-2-oxo-3-(3-oxo-3,4-dihydro-2H-benzo[1,4]thiazin-6-yl)-oxazolidin-1-ylmethyl]-amino}-methyl)-4,5-dihydro-pyrrolo[3,2,1-de][1,5]naphthyridin-7-one;

(R)-3-fluoro-4-({[(S)-2-oxo-3-(3-oxo-3,4-dihydro-2H-benzo[1,4]thiazin-6-yl)-oxazolidin-1-ylmethyl]-amino}-methyl)-4,5-dihydro-pyrrolo[3,2,1-de][1,5]naphthyridin-7-one;

(S)-3-fluoro-4-({[(S)-2-oxo-3-(3-oxo-3,4-dihydro-2H-benzo[1,4]thiazin-6-yl)-oxazolidin-1-ylmethyl]-amino}-methyl)-4,5-dihydro-pyrrolo[3,2,1-de][1,5]naphthyridin-7-one;

(R)-3-fluoro-4-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;

(S)-3-fluoro-4-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;

(R)-3-fluoro-4-({2-[(R)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;

(S)-3-fluoro-4-({2-[(R)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one;

(R)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(R)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(R)-6-({[(S)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one;

(S)-6-({[(S)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one;

(R)-1-{2-[(S)-3-(2,3-dihydro-benzo[1,4]dioxin-6-yl)-2-oxo-oxazolidin-5-yl]-ethylamino}-9-fluoro-1,2-dihydro-pyrrolo[3,2,1-ij]quinolin-4-one;

(S)-1-{2-[(S)-3-(2,3-dihydro-benzo[1,4]dioxin-6-yl)-2-oxo-oxazolidin-5-yl]-ethylamino}-9-fluoro-1,2-dihydro-pyrrolo[3,2,1-ij]quinolin-4-one;

(R)-N-((S)-9-fluoro-4-oxo-1,2-dihydro-4H-pyrrolo[3,2,1-ij]quinolin-1-yl)-3-hydroxy-3-[(R)-2-oxo-3-(3-oxo-3,4-dihydro-2H-benzo[1,4]thiazin-6-yl)-oxazolidin-5-yl]-propionamide;

(R)-N-((S)-9-fluoro-4-oxo-1,2-dihydro-4H-pyrrolo[3,2,1-ij]quinolin-1-yl)-3-hydroxy-3-[(S)-2-oxo-3-(3-oxo-3,4-dihydro-2H-benzo[1,4]thiazin-6-yl)-oxazolidin-5-yl]-propionamide;

(S)-N-((S)-9-fluoro-4-oxo-1,2-dihydro-4H-pyrrolo[3,2,1-ij]quinolin-1-yl)-3-hydroxy-3-[(R)-2-oxo-3-(3-oxo-3,4-dihydro-2H-benzo[1,4]thiazin-6-yl)-oxazolidin-5-yl]-propionamide;

(S)-N-((S)-9-fluoro-4-oxo-1,2-dihydro-4H-pyrrolo[3,2,1-ij]quinolin-1-yl)-3-hydroxy-3-[(S)-2-oxo-3-(3-oxo-3,4-dihydro-2H-benzo[1,4]thiazin-6-yl)-oxazolidin-5-yl]-propionamide;

(R)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-6-({[(R)-2-oxo-3-(3-oxo-3,4-dihydro-2H-benzo[1,4]thiazin-6-yl)-oxazolidin-1-ylmethyl]-amino}-methyl)-5,6-dihydro-pyrrolo[1,2,3-de]quinoxalin-3-one;

(S)-6-({[(R)-2-oxo-3-(3-oxo-3,4-dihydro-2H-benzo[1,4]thiazin-6-yl)-oxazolidin-1-ylmethyl]-amino}-methyl)-5,6-dihydro-pyrrolo[1,2,3-de]quinoxalin-3-one;

(R)-7-fluoro-2-methoxy-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;

(R)-7-fluoro-2-methoxy-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;

(1R)-9-fluoro-1-{(3R)-3-hydroxy-3-[(5R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R)-9-fluoro-1-{(3R)-3-hydroxy-3-[(5S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R)-9-fluoro-1-{(3S)-3-hydroxy-3-[(5R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R)-9-fluoro-1-{(3S)-3-hydroxy-3-[(5S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S)-9-fluoro-1-{(3R)-3-hydroxy-3-[(5R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S)-9-fluoro-1-{(3R)-3-hydroxy-3-[(5S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S)-9-fluoro-1-{(3S)-3-hydroxy-3-[(5R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S)-9-fluoro-1-{(3S)-3-hydroxy-3-[(5S)-2-oxo-3-(3-oxo-3,4-dihydro-2H-benzo[1,4]thiazin-6-yl)-propylamino}-1,2-dihydro-pyrrolo[3,2,1-ij]quinolin-4-one;

(S)-6-{3-[(R)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one;

as well as to the salts (in particular the pharmaceutically acceptable salts) thereof xc) Yet further particularly preferred compounds of formula I as defined in embodiment ii) or vi) are the following compounds:

6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;

9-bromo-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-9-carbonitrile;

4-oxo-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-4H-pyrrolo[3,2,1-ij]quinoline-9-carbonitrile;

(R)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-7-carboxylic acid ethyl ester;

(R)-7-hydroxymethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-4-oxo-1-{3-[(S)-2-oxo-3-(3-oxo-3,4-dihydro-2H-benzo[1,4]thiazin-6-yl)-oxazolidin-1-yl]-propylamino}-1,2-dihydro-4H-pyrrolo[3,2,1-ij]quinoline-7-carboxylic acid;

(R)-7-dimethylamino methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-benzo[1,4]thiazin-6-yl)-oxazolidin-5-yl]-propylamino}-7-pyrrolidin-1-ylmethyl-1,2-dihydro-pyrrolo[3,2,1-ij]quinolin-4-one;

9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-7-fluoro-6-{3-[(S)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;

(R)-7-fluoro-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;

(R)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-1-{3-[(S)-2-oxo-3-(3-oxo-3,4-dihydro-2H-pyrido[3,2-b][1,4]thiazin-6-yl)-oxazolidin-1-yl]-propylamino}-1,2-dihydro-pyrrolo[3,2,1-ij]quinolin-4-one;

(S)-1-{3-[(R)-2-oxo-3-(3-oxo-3,4-dihydro-2H-pyrido[3,2-b][1,4]thiazin-6-yl)-oxazolidin-1-yl]-propylamino}-1,2-dihydro-pyrrolo[3,2,1-ij]quinolin-4-one;

(R)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(R)-3-fluoro-4-{3-[(R)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-pyrido[3,2-b][1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-pyrido[3,2-b][1,4]oxazin-6-yl)-oxazolidin-5-yl]-propylamino}-4,5-dihydro-pyrrolo[3,2,1-de][1,5]naphthyridin-7-one;

9-methyl-1-{3-[(R)-2-oxo-3-(3-oxo-3,4-dihydro-2H-benzo[1,4]thiazin-6-yl)-oxazolidin-1-yl]-propylamino}-1,2-dihydro-pyrrolo[3,2,1-ij]quinolin-4-one;

9-fluoro-1-(methyl-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

6-({2-[(S)-2-oxo-3-(3-oxo-3,4-dihydro-2H-benzo[1,4]oxazin-6-yl)-oxazolidin-5-yl]-ethylamino}-methyl)-5,6-dihydro-pyrrolo[1,2,3-de]quinoxalin-3-one;

(RS)-6-({2-[(R)-2-oxo-3-(3-oxo-3,4-dihydro-2H-benzo[1,4]oxazin-6-yl)-oxazolidin-5-yl]-ethylamino}-methyl)-5,6-dihydro-pyrrolo[1,2,3-de]quinoxalin-3-one;

6-({2-[(R)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one;

(R)-1-{2-[(S)-2-oxo-3-(3-oxo-3,4-dihydro-2H-benzo[1,4]oxazin-6-yl)-oxazolidin-5-yl]-ethylamino}-1,2-dihydro-pyrrolo[3,2,1-ij]quinolin-4-one;

(R)-1-{2-[(R)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one;

9-fluoro-1-{4-[(S)-2-oxo-3-(3-oxo-3,4-dihydro-2H-benzo[1,4]thiazin-6-yl)-oxazolidin-5-yl]-butylamino}-1,2-dihydro-pyrrolo[3,2,1-ij]quinolin-4-one;

(S)-7-fluoro-6-{3-[(S)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one;

(1R*,2R*)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;

(1R*,2R*)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;

(1R*,2R*)-2-hydroxy methyl-1-{3-[(R)-2-oxo-3-(3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2R*)-2-hydroxymethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2R*)-2-methoxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2S*)-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2S*)-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2S*)-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(1R*,2S*)-2-methyl-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(1R*,2R*)-2-(1-hydroxy-1-methyl-ethyl)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one;

N-(9-fluoro-4-oxo-1,2-dihydro-4H-pyrrolo[3,2,1-ij]quinolin-1-yl)-N-{3-[(R)-2-oxo-3-(3-oxo-3,4-dihydro-2H-benzo[1,4]thiazin-6-yl)-oxazolidin-5-yl]-propyl}-acetamide;

(S)-4-hydroxy-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;

9-fluoro-1-hydroxy-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

as well as the salts (in particular the pharmaceutically acceptable salts) thereof xci) Yet a further object of this invention thus relates to the following compounds of formula I as defined in embodiment ii) or vi):

(R)-6-{3-[(R)-2-oxo-3-(3-oxo-3,4-dihydro-2H-pyrido[3,2-b][1,4]thiazin-6-yl)-oxazolidin-1-yl]-propylamino}-5,6-dihydro-pyrrolo[1,2,3-de]quinoxalin-3-one;

(S)-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;

(R)-9-bromo-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-bromo-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-4-oxo-1-{3-[(R)-2-oxo-3-(3-oxo-3,4-dihydro-2H-benzo[1,4]thiazin-6-yl)-oxazolidin-1-yl]-propylamino}-1,2-dihydro-4H-pyrrolo[3,2,1-ij]quinoline-9-carbonitrile;

(S)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-9-carbonitrile;

(R)-4-oxo-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-4H-pyrrolo[3,2,1-ij]quinoline-9-carbonitrile;

(S)-4-oxo-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-4H-pyrrolo[3,2,1-ij]quinoline-9-carbonitrile;

(R)-4-oxo-1-{3-[(S)-2-oxo-3-(3-oxo-3,4-dihydro-2H-benzo[1,4]thiazin-6-yl)-oxazolidin-1-yl]-propylamino}-1,2-dihydro-4H-pyrrolo[3,2,1-ij]quinoline-7-carboxylic acid ethyl ester;

(R)-7-hydroxymethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-7-carboxylic acid;

(R)-7-dimethylamino methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-benzo[1,4]thiazin-6-yl)-oxazolidin-5-yl]-propylamino}-7-pyrrolidin-1-ylmethyl-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-7-fluoro-6-{3-[(S)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;

(R)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-pyrido[3,2-b][1,4]oxazin-6-yl)-oxazolidin-1-yl]-propylamino}-1,2-dihydro-pyrrolo[3,2,1-ij]quinolin-4-one;

(S)-1-{3-[(S)-2-oxo-3-(3-oxo-3,4-dihydro-2H-pyrido[3,2-b][1,4]thiazin-6-yl)-oxazolidin-1-yl]-propylamino}-1,2-dihydro-pyrrolo[3,2,1-ij]quinolin-4-one;

(S)-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(R)-3-fluoro-4-{3-[(R)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(R)-3-fluoro-4-{3-[(S)-2-oxo-3-(3-oxo-3,4-dihydro-2H-pyrido[3,2-b][1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(R)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one;

(S)-3-fluoro-4-{3-[(S)-2-oxo-3-(3-oxo-3,4-dihydro-2H-pyrido[3,2-b][1,4]oxazin-6-yl)-oxazolidin-5-yl]-propylamino}-4,5-dihydro-pyrrolo[3,2,1-de][1,5]naphthyridin-7-one;

(R)-9-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-9-fluoro-1-(methyl-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

(S)-9-fluoro-1-(methyl-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one;

(R)-6-({2-[(S)-2-oxo-3-(3-oxo-3,4-dihydro-2H-benzo[1,4] oxazin-6-yl)-oxazolidin-5-yl]-ethylamino}-methyl)-5,6-dihydro-pyrrolo[1,2,3-de]quinoxalin-3-one;
(S)-6-({2-[(S)-2-oxo-3-(3-oxo-3,4-dihydro-2H-benzo[1,4] oxazin-6-yl)-oxazolidin-5-yl]-ethylamino}-methyl)-5,6-dihydro-pyrrolo[1,2,3-de]quinoxalin-3-one;
(R)-6-({2-[(R)-2-oxo-3-(3-oxo-3,4-dihydro-2H-benzo[1,4] oxazin-6-yl)-oxazolidin-5-yl]-ethylamino}-methyl)-5,6-dihydro-pyrrolo[1,2,3-de]quinoxalin-3-one;
(S)-6-({2-[(R)-2-oxo-3-(3-oxo-3,4-dihydro-2H-benzo[1,4] oxazin-6-yl)-oxazolidin-5-yl]-ethylamino}-methyl)-5,6-dihydro-pyrrolo[1,2,3-de]quinoxalin-3-one;
(R)-6-({2-[(R)-2-oxo-3-(3-oxo-3,4-dihydro-2H-benzo[1,4] thiazin-6-yl)-oxazolidin-5-yl]-ethylamino}-methyl)-5,6-dihydro-pyrrolo[1,2,3-de]quinoxalin-3-one;
(S)-6-({2-[(R)-2-oxo-3-(3-oxo-3,4-dihydro-2H-benzo[1,4] thiazin-6-yl)-oxazolidin-5-yl]-ethylamino}-methyl)-5,6-dihydro-pyrrolo[1,2,3-de]quinoxalin-3-one;
(R)-1-{2-[(S)-2-oxo-3-(3-oxo-3,4-dihydro-2H-benzo[1,4] oxazin-6-yl)-oxazolidin-5-yl]-ethylamino}-1,2-dihydro-pyrrolo[3,2,1-ij]quinolin-4-one;
(R)-1-{2-[(R)-2-oxo-3-(3-oxo-3,4-dihydro-2H-benzo[1,4] thiazin-6-yl)-oxazolidin-5-yl]-ethylamino}-1,2-dihydro-pyrrolo[3,2,1-ij]quinolin-4-one;
(R)-9-fluoro-1-{4-[(R)-2-oxo-3-(3-oxo-3,4-dihydro-2H-benzo[1,4]thiazin-6-yl)-oxazolidin-5-yl]-butylamino}-1,2-dihydro-pyrrolo[3,2,1-ij]quinolin-4-one;
(R)-9-fluoro-1-{4-[(S)-2-oxo-3-(3-oxo-3,4-dihydro-2H-benzo[1,4]thiazin-6-yl)-oxazolidin-5-yl]-butylamino}-1,2-dihydro-pyrrolo[3,2,1-ij]quinolin-4-one;
(S)-9-fluoro-1-{4-[(R)-2-oxo-3-(3-oxo-3,4-dihydro-2H-benzo[1,4]thiazin-6-yl)-oxazolidin-5-yl]-butylamino}-1,2-dihydro-pyrrolo[3,2,1-ij]quinolin-4-one;
(S)-9-fluoro-1-{4-[(S)-2-oxo-3-(3-oxo-3,4-dihydro-2H-benzo[1,4]thiazin-6-yl)-oxazolidin-5-yl]-butylamino}-1,2-dihydro-pyrrolo[3,2,1-ij]quinolin-4-one;
(S)-7-fluoro-6-{3-[(S)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one;
(1R,2R)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;
(1S,2S)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;
(1R,2R)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;
(1S,2S)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;
(1R,2R)-2-hydroxy methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1S,2S)-2-hydroxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1R,2R)-2-hydroxy methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1S,2S)-2-hydroxymethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1R,2R)-2-methoxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1S,2S)-2-methoxy methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1R,2S)-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1S,2R)-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1R,2S)-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1S,2R)-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1R,2S)-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;
(1S,2R)-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;
(1R,2S)-2-methyl-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;
(1S,2R)-2-methyl-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;
(1R,2R)-2-(1-hydroxy-1-methyl-ethyl)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(1S,2S)-2-(1-hydroxy-1-methyl-ethyl)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one;
N—((R)-9-fluoro-4-oxo-1,2-dihydro-4H-pyrrolo[3,2,1-ij] quinolin-1-yl)-N-{3-[(R)-2-oxo-3-(3-oxo-3,4-dihydro-2H-benzo[1,4]thiazin-6-yl)-oxazolidin-5-yl]-propyl}-acetamide;
N-((S)-9-fluoro-4-oxo-1,2-dihydro-4H-pyrrolo[3,2,1-ij] quinolin-1-yl)-N-{3-[(R)-2-oxo-3-(3-oxo-3,4-dihydro-2H-benzo[1,4]thiazin-6-yl)-oxazolidin-5-yl]-propyl}-acetamide;
(S)-4-hydr oxy-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one;
(R)-9-fluoro-1-hydroxy-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;
(S)-9-fluoro-1-hydroxy-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one;

as well as to the salts (in particular the pharmaceutically acceptable salts) thereof xcii) Yet other particularly preferred compounds of formula I as defined in embodiment i) or v) are the following compounds:

1-({[(S)-2-oxo-3-(3-oxo-3,4-dihydro-2H-pyrido[3,2-b][1,4]thiazin-6-yl)-oxazolidin-1-ylmethyl]-amino}-methyl)-1,2-dihydro-pyrrolo[3,2,1-ij]quinolin-4-one;

1-({2-[(S)-2-oxo-3-(3-oxo-3,4-dihydro-2H-pyrido[3,2-b][1,4]thiazin-6-yl)-oxazolidin-1-yl]-ethylamino}-methyl)-1,2-dihydro-pyrrolo[3,2,1-ij]quinolin-4-one;

9-chloro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

9-chloro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

9-ethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

9-ethynyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2R*)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;

(1R*,2R*)-9-fluoro-2-hydroxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2S*)-9-fluoro-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2S*)-9-fluoro-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R*,2S*)-9-fluoro-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(1R*,2R*)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid;

9-fluoro-1-({2-[(S)-2-oxo-3-(3-oxo-3,4-dihydro-2H-benzo[1,4]oxazin-6-yl)-oxazolidin-1-yl]-ethylamino}-methyl)-1,2,5,6-tetrahydro-pyrrolo[3,2,1-ij]quinolin-4-one;

(1R*,2S*)-2-amino methyl-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

9-fluoro-1-({2-[(R)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

9-fluoro-1-({2-[(S)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;

7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one;

7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-methyl-1,2,5,6-tetrahydro-pyrrolo[1,2,3-de]quinoxalin-3-one;

7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-(3-hydroxypropyl)-1,2,5,6-tetrahydro-pyrrolo[1,2,3-de]quinoxalin-3-one;

as well as the salts (in particular the pharmaceutically acceptable salts) thereof xciii) Yet another object of this invention thus relates to the following compounds of formula I as defined in embodiment i) or v):

(R)-1-({[(S)-2-oxo-3-(3-oxo-3,4-dihydro-2H-pyrido[3,2-b][1,4]thiazin-6-yl)-oxazolidin-5-ylmethyl]-amino}-methyl)-1,2-dihydro-pyrrolo[3,2,1-ij]quinolin-4-one;

(S)-1-({[(S)-2-oxo-3-(3-oxo-3,4-dihydro-2H-pyrido[3,2-b][1,4]thiazin-6-yl)-oxazolidin-5-ylmethyl]-amino}-methyl)-1,2-dihydro-pyrrolo[3,2,1-ij]quinolin-4-one;

(R)-1-({2-[(S)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

(S)-1-({2-[(S)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

(R)-9-chloro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-9-chloro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-chloro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-chloro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-9-ethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-ethyl-1-{3-[(R)-2-oxo-3-(3-oxo-3,4-dihydro-2H-benzo[1,4]thiazin-6-yl)-oxazolidin-1-yl]-propylamino}-1,2-dihydro-pyrrolo[3,2,1-ij]quinolin-4-one;

(R)-9-ethynyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-ethynyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R,2R)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;

(1S,2S)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester;

(1R,2R)-9-fluoro-2-hydroxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S,2S)-9-fluoro-2-hydroxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R,2S)-9-fluoro-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S,2R)-9-fluoro-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R,2S)-9-fluoro-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S,2R)-9-fluoro-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1R,2S)-9-fluoro-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(1S,2R)-9-fluoro-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(1R,2R)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid;

(1S,2S)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid;

(R)-9-fluoro-1-({2-[(S)-2-oxo-3-(3-oxo-3,4-dihydro-2H-benzo[1,4]oxazin-6-yl)-oxazolidin-5-yl]-ethylamino}-methyl)-1,2,5,6-tetrahydro-pyrrolo[3,2,1-ij]quinolin-4-one;

(S)-9-fluoro-1-({2-[(S)-2-oxo-3-(3-oxo-3,4-dihydro-2H-benzo[1,4]oxazin-6-yl)-oxazolidin-5-yl]-ethylamino}-methyl)-1,2,5,6-tetrahydro-pyrrolo[3,2,1-ij]quinolin-4-one;

(1R,2S)-2-amino methyl-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(1S,2R)-2-amino methyl-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-({2-[(R)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

(S)-9-fluoro-1-({2-[(R)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

(R)-9-fluoro-1-({2-[(S)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

(S)-9-fluoro-1-({2-[(S)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;

(S)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one;

(S)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-methyl-1,2,5,6-tetrahydro-pyrrolo[1,2,3-de]quinoxalin-3-one;

(S)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-methyl-1,2,5,6-tetrahydro-pyrrolo[1,2,3-de]quinoxalin-3-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-(3-hydroxypropyl)-1,2,5,6-tetrahydro-pyrrolo[1,2,3-de]quinoxalin-3-one;

(S)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-(3-hydroxypropyl)-1,2,5,6-tetrahydro-pyrrolo[1,2,3-de]quinoxalin-3-one;

as well as to the salts (in particular the pharmaceutically acceptable salts) thereof xciv) The invention further relates to the compounds of formula I as defined in embodiment i) or v) which are selected from the group consisting of the compounds listed in embodiment lxxxvi), the compounds listed in embodiment lxxxviii), the compounds listed in embodiment xc) and the compounds listed in embodiment xcii), as well as to the salts (in particular the pharmaceutically acceptable salts) of such compounds. In particular, it also relates to the groups of compounds of formula I selected from the group consisting of the compounds listed in embodiment lxxxvi), the compounds listed in embodiment lxxxviii), the compounds listed in embodiment xc) and the compounds listed in embodiment xcii), which groups of compounds furthermore correspond to one of embodiments ix) to lxxxv), as well as to the salts (in particular the pharmaceutically acceptable salts) of such compounds.

xcv) The invention moreover relates to the compounds of formula I as defined in embodiment i) or v) which are selected from the group consisting of the compounds listed in embodiment lxxxvii), the compounds listed in embodiment lxxxix), the compounds listed in embodiment xci) and the compounds listed in embodiment xciii), as well as to the salts (in particular the pharmaceutically acceptable salts) of such compounds. In particular, it also relates to the groups of compounds of formula I selected from the group consisting of the compounds listed in embodiment lxxxvii), the compounds listed in embodiment lxxxix), the compounds listed in embodiment xci) and the compounds listed in embodiment xciii), which groups of compounds furthermore correspond to one of embodiments ix) to lxxxv), as well as to the salts (in particular the pharmaceutically acceptable salts) of such compounds.

The compounds of formula I according to the invention, i.e. according to one of embodiments i) to xcv) above, are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neisserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp. including *Acinetobacter baumanii, Stenotrophomonas maltophilia, Neisseria meningitidis, Bacillus cereus, Bacillus anthracis, Clostridium difficile, Corynebacterium* spp., *Propionibacterium acnes* and *bacteroide* spp.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of formula I according to this invention, or the pharmaceutically acceptable salt thereof, may be used for the preparation of a medicament, and are suitable, for the prevention or treatment (and notably for the treatment) of a bacterial infection.

One aspect of this invention therefore relates to the use of a compound of formula I according to one of embodiments i) to xcv), or of a pharmaceutically acceptable salt thereof, for the manufacture of a medicament for the prevention or treatment (and notably for the treatment) of a bacterial infection. Another aspect of this invention relates to a compound of formula I according to one of embodiments i) to xcv), or of a pharmaceutically acceptable salt thereof, for the prevention or treatment (and notably for the treatment) of a bacterial infection.

Accordingly, the compounds of formula I according to one of embodiments i) to xcv), or the pharmaceutically acceptable salts thereof, may be used for the preparation of a medicament, and are suitable, for the prevention or treatment (and notably for the treatment) of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment (especially for the treatment) of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment (and notably for the treatment) of a bacterial infection in a patient comprising the administration to said patient of a pharmaceutically active amount of a compound of formula I according to one of embodiments i) to xcv), or a pharmaceutically acceptable salt of such a compound.

Besides, any preferences and (sub-)embodiments indicated for the compounds of formula I (whether for the compounds themselves, salts thereof, compositions containing the compounds or salts thereof, uses of the compounds or salts thereof, etc.) apply mutatis mutandis to compounds of formula $I_{CE}$, $I_{P1}$, $I_{CEP1}$, $I_{P2}$, $I_{CEP2}$, $I_{P3}$ or $I_{CEP3}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

PREPARATION OF COMPOUNDS OF FORMULA I

Abbreviations:

The following abbreviations are used throughout the specification and the examples:

Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
Alloc allyloxycarbonyl
AIBN azobisisobutyronitrile
aq. aqueous
9-BBN 9-borabicyclo[3.3.1]nonane
Boc tert-butoxycarbonyl
Bs 4-bromobenzenesulfonyl (brosylate)
Bu n-butyl
Cbz benzyloxycarbonyl
CC column chromatography over silica gel
CDI 1,1'-carbonyldiimidazole
DAD diode array detection
DBU 1,8-diazabicyclo[5.4.0]undec-7-ene
DCC N,N'-dicyclohexylcarbodiimide
DCE 1,2-dichloroethane
DEA diethylamine
DCM dichloromethane
$(DHQ)_2PHAL$ 1,4-bis(dihydroquinine)phthalazine
$(DHQD)_2PHAL$ 1,4-bis(dihydroquinidine)phthalazine
DIAD diisopropylazodicarboxylate
DIBAH diisobutylaluminium hydride
DIPEA N,N-diisopropylethylamine
DMAP 4-dimethylaminopyridine
DMF N,N-dimethylformamide
DMSO dimethylsulfoxide
DPEphos bis(2-diphenylphosphinophenyl)ether
DPPA diphenyl phosphorylazide
EA ethyl acetate
EDC 1-(3-dimethylaminopropyl)-3-ethylcarbodiimide hydrochloride
ee enantiomeric excess
ELSD Evaporative Light Scattering Detector
ESI Electron Spray Ionisation
eq. equivalent
ether diethyl ether
Et ethyl
EtOH ethanol
Fmoc 9-fluorenylmethoxycarbonyl
HATU O-(7-azabenzotriazol-1-yl)-N,N,N',N'-tetramethyluronium hexafluorophosphate
Hept heptane
Hex hexane
HOBT 1-hydroxybenzotriazole hydrate
HPLC high pressure liquid chromatography
HV high vacuum KHMDS potassium hexamethyldisilazide
LAH lithium aluminium hydride
LC liquid chromatography
LDA lithium diisopropylamide
LiHMDS lithium hexamethyldisilazide
MCPBA meta-chloroperbenzoic acid
Me methyl
MeCN acetonitrile
MeOH methanol
MS Mass Spectroscopy
Ms methanesulfonyl (mesyl)
n-BuLi n-butyl lithium
NBS N-bromosuccinimide
Nf nonafluorobutanesulfonyl
Ns 4-nitrobenzenesulfonyl (nosylate)
NMO N-methyl-morpholine N-oxide
org. organic
o-Tol ortho-tolyl
Pd/C palladium on carbon
Pd(OH)$_2$/C palladium dihydroxide on carbon
Ph phenyl
Pht phthaloyl
Pyr pyridine
quant. quantitative
rac racemic
rt room temperature
sat. saturated
TBAF tetrabutylammonium fluoride
TBDMS tert-butyldimethylsilyl
TBME tert-butylmethylether
TBDPS tert-butyldiphenylsilyl
tBu tert-butyl
TEA triethylamine
TEMPO 2,2,6,6-tetramethyl-1-piperidinyloxy
Tf trifluoromethanesulfonyl (triflyl)
TFA trifluoroacetic acid
THF tetrahydrofuran
TLC thin layer chromatography
TMEDA tetramethylethylenediamine
TMS trimethylsilyl
$t_R$ retention time
Ts para-toluenesulfonyl
General Reaction Techniques:
General Reaction Technique 1 (Alkylation of an Amine):

Ammonia or the appropriate amine derivatives is/are reacted with the appropriate derivatives having a side group $L^1$, $L^2$, $L^3$ or $L^4$, wherein $L^1$, $L^2$, $L^3$ or $L^4$ represents OMs, OTf, OTs, ONs, ONf, OBs, Cl, Br or I, in presence of an inorganic base such as K$_2$CO$_3$ or an org. base such as TEA in a solvent such as THF, DMF or DMSO between 0° C. and +80° C. Further details can be found in *Comprehensive Organic Transformations. A guide to Functional Group Preparations;* 2$^{nd}$ Edition, R. C. Larock, Wiley-VC; New York, Chichester, Weinheim, Brisbane, Singapore, Toronto, (1999). Section Amines p. 779.
General Reaction Technique 2 (Reductive Amination):

A solution of amine (1 mmol) and aldehyde or ketone (1 mmol) in DCE/MeOH 1:1 (10 mL) is stirred at rt overnight possibly in presence of a desiccant such as MgSO$_4$ or 3 Å molecular sieves. NaBH$_4$ (2-5 eq.) is added and the reaction allowed to proceed for one hour. The reaction is diluted with DCM and aq. NH$_4$OH. The org. phase is washed with water, dried over MgSO$_4$ and concentrated. Alternatively, a solution of amine (1 mmol) and aldehyde or ketone (1 mmol) in DCE/MeOH 1:1 (10 mL) is treated with NaBH(OAc)$_3$ (2 eq.). The mixture is stirred at rt until complete conversion. The reaction is diluted with DCM and aq. NH$_4$OH. The org. phase is washed with water, dried over MgSO$_4$ and concentrated.
General Reaction Technique 3 (Activation of an Alcohol):

The alcohol is reacted with MSCl, TfCl, NfCl, NsCl, BsCl or TsCl in presence of an organic base such as TEA, DIPEA or Pyr in a dry aprotic solvent such as DCM, THF or Pyr between −10° C. and rt. Alternatively, the alcohol can also be reacted with Ms$_2$O or Tf$_2$O. The activated intermediate can be further transformed into its corresponding iodo or bromo derivative by reaction of the activated alcohol with NaI or NaBr in a solvent such as acetone.
General Reaction Technique 4 (Removal of Amino Protecting Groups):

The benzyl carbamates are deprotected by hydrogenolysis over a noble metal catalyst (e.g. Pd/C or Pd(OH)$_2$/C). The Boc group is removed under acidic conditions such as HCl in an organic solvent such as MeOH or dioxane, or TFA neat or diluted in a solvent such DCM. Further general methods to remove amine protecting groups have been described in T. W. Greene, P. G. M. Wuts, *Protecting Groups in Organic Synthesis,* 3$^{rd}$ Ed (1999), 494-653 (Publisher: John Wiley and Sons, Inc., New York, N.Y.).
General Reaction Technique 5 (Ester, Ketone or Aldehyde Reduction):

The ester is reduced with a boron or aluminium hydride reducing agent such as LiBH$_4$ or LAH in a solvent such as THF between −20° C. and 40° C. Alternatively, the ester function is hydrolyzed into its corresponding acid using an alkali hydroxide such as NaOH, KOH or LiOH in water or in a mixture of water with polar protic or aprotic organic solvent such as THF or MeOH between −10° C. and 50° C. The resulting carboxylic acid is further reduced into the corresponding alcohol using a borane derivative such as a BH$_3$.THF complex in a solvent such as THF between −10° C. and 40° C.

The aldehyde and the ketone are reduced with a boron or aluminium hydride reducing agent such as NaBH$_4$, LiBH$_4$ or LAH in a solvent such as THF between −20° C. and 40° C. Further details can be found in *Comprehensive Organic Transformations. A guide to Functional Group Preparations;* 2nd Edition, R. C. Larock, Wiley-VC; New York, Chichester, Weinheim, Brisbane, Singapore, Toronto, (1999). Section Alcohols and phenols, p. 1057-1087.
General Reaction Technique 6 (Cis-Dihydroxylation):

The diol is obtained by dihydroxylation of the corresponding ethylenic derivative using a catalytic amount of potassium osmate in the presence a co-oxidant such as NMO in an aq. solvent such as an acetone-water or DCM-water mixture (see Cha, J. K., *Chem. Rev.* (1995), 95, 1761-1795). The chiral cis-diols are obtained by using AD-mix α or AD-mix β in presence of methanesulfonamide in a water/2-methyl-2 propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.
General Reaction Technique 7 (Protection of Alcohols):

The alcohols are protected as silyl ethers (usually TBDMS or TBDPS ethers). The alcohol is reacted with the required silyl chloride reagent (TBDMSCl or TBDPSCl) in presence of a base such as imidazole or TEA in a solvent such as DCM or DMF between +10° C. and +40° C. Further strategies to introduce other alcohol protecting groups have been described in T. W. Greene, P. G. M. Wuts, *Protecting Groups in Organic Synthesis,* 3rd Ed (1999), 23-147 (Publisher: John Wiley and Sons, Inc., New York, N.Y.).

General Reaction Technique 8 (Removal of Hydroxy Protecting Groups):

The silyl ether groups are removed either using fluoride anion sources such as TBAF in THF between 0° C. and +40° C. or HF in MeCN between 0° C. and +40° C. or using acidic conditions such as AcOH in THF/MeOH or HCl in MeOH. Further methods to remove the TBDMS and TBDPS groups are given in T. W. Greene, P. G. M. Wuts, *Protecting Groups in Organic Synthesis*, 3rd Ed (1999), 133-139 and 142-143 respectively (Publisher: John Wiley and Sons, Inc., New York, N.Y.). Further general methods to remove alcohol protecting groups are described in T. W. Greene, P. G. M. Wuts, *Protecting Groups in Organic Synthesis*, 3rd Ed (1999), 23-147 (Publisher: John Wiley and Sons, Inc., New York, N.Y.). In the particular case of alkylcarboxy protecting group, the free alcohol can be obtained by the action of an inorganic base such as $K_2CO_3$ in a solvent such as MeOH.

General Reaction Technique 9 (Formation of Aldehydes):

The alcohols can be transformed into their corresponding aldehydes through oxidation under Swern (see D. Swern et al., *J. Org. Chem.* (1978), 43, 2480-2482) or Dess Martin (see D. B. Dess and J. C. Martin, *J. Org. Chem.* (1983), 48, 4155) conditions respectively. Alternatively, the esters can be transformed into their corresponding aldehydes by controlled reduction with a bulky hydride reagent such as DIBAH.

General Reaction Technique 10 (Amine Protection):

Amines are usually protected as carbamates such as Alloc, Cbz, Boc or Fmoc. They are obtained by reacting the amine with allyl or benzyl chloroformate, di tert-butyl dicarbonate or FmocCl in presence of a base such as NaOH, TEA, DMAP or imidazole. They can also be protected as N-benzyl derivatives by reaction with benzyl bromide or chloride in presence of a base such as $Na_2CO_3$ or TEA. Alternatively, N-benzyl derivatives can be obtained through reductive amination in presence of benzaldehyde and a borohydride reagent such as $NaBH_4$, $NaBH_3CN$ or $NaBH(OAc)_3$ in a solvent such as MeOH, DCE or THF. Further strategies to introduce other amine protecting groups have been described in T. W. Greene, P. G. M. Wuts, *Protecting Groups in Organic Synthesis*, 3rd Ed (1999), 494-653 (Publisher: John Wiley and Sons, Inc., New York, N.Y.).

General Reaction Technique 11 (Hydrogenation of a Double Bond):

The unsaturated derivatives dissolved in a solvent such as MeOH, EA or THF are hydrogenated over a noble metal catalyst such as Pd/C or $PtO_2$, or over Raney Ni. At the end of the reaction the catalyst is filtered off and the filtrate is evaporated under reduced pressure. Alternatively the reduction can be performed by catalytic transfer hydrogenation using Pd/C and ammonium formate as hydrogen source.

General Reaction Technique 12 (Reduction of Azides into Amines):

The azides are hydrogenated over a noble metal catalyst such as Pd/C in solvent such as MeOH or EA. In case the molecule is containing an unsaturated double or triple bond, the reduction can be performed using $PPh_3$ in presence of water as described in *J. Med. Chem.* (1993), 36, 2558-68.

General Reaction Technique 13 (Amide Formation):

The carboxylic acid is reacted with the amine in presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and +60° C. (see G. Benz in Comprehensive Organic Synthesis, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between 20° and +60° C. Further activating agents can be found in *Comprehensive Organic Transformations. A guide to Functional Group Preparations;* 2nd Edition, R. C. Larock, Wiley-VC; New York, Chichester, Weinheim, Brisbane, Singapore, Toronto, 1999. Section nitriles, carboxylic acids and derivatives p. 1941-1949.

General Reaction Technique 14 (Oxidation of Alcohols/Aldehydes into Acids):

Aldehydes can be oxidized into their corresponding acids by a variety of methods as described in *Comprehensive Organic Transformations. A guide to Functional Group Preparations;* 2nd Edition, R. C. Larock, Wiley-VC; New York, Chichester, Weinheim, Brisbane, Singapore, Toronto, 1999. Section nitriles, carboxylic acids and derivatives, p. 1653-1655. Among them, potassium permanganate in an acetone-water mixture (see Synthesis 1987, 85) or sodium chlorite in 2-methyl-2-propanol in presence of 2-methyl-2-butene (see Tetrahedron 1981, 37, 2091-2096) are frequently used.

Alcohols can be directly oxidized into their corresponding acids by a variety of methods as described in *Comprehensive Organic Transformations. A guide to Functional Group Preparations;* 2nd Edition, R. C. Larock, Wiley-VC; New York, Chichester, Weinheim, Brisbane, Singapore, Toronto, 1999. Section nitriles, carboxylic acids and derivatives p. 1646-1648. Among them, [bis(acetoxy)iodo]benzene in presence of TEMPO, the Jones reagents ($CrO_3/H_2SO_4$), $NaIO_4$ in presence of $RuCl_3$, $KMnO_4$ or pyridine $H_2Cr_2O_7$ are frequently used.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to r) hereafter describe general methods for preparing compounds of formula I. If not indicated otherwise, the generic groups or integers n, p, $R^0$, $R^1$, U, V, $R^4$, $R^5$, $R^2$, A and G are as defined for formula I. General synthetic methods used repeatedly throughout the text below are referenced to and described in the above section entitled "General synthetic methods". Other abbreviations used are defined in the experimental section. In some instances the generic groups $R^0$, $R^1$, $R^2$, $R^4$, $R^5$, U, A and G might be incompatible with the assembly illustrated in the procedures and schemes below and so will require the use of protecting groups. The use of protecting groups is well known in the art (see for example "Protective Groups in Organic Synthesis", T. W. Greene, P. G. M. Wuts, Wiley-Interscience, 1999).

a) The compounds of formula I wherein $R^2$ represents H and A represents —$(CH_2)_p$— can be manufactured in accordance with the present invention by reacting the compounds of formula II

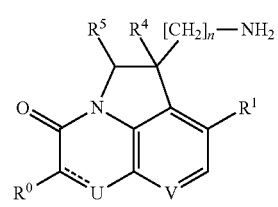

II with the compounds of formula III

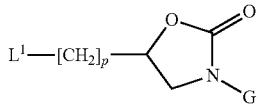

III wherein $L^1$ is a halogen such as bromine or iodine, or a group $OSO_2R^a$ wherein $R^a$ is alkyl, $CF_3$ or tolyl, following general reaction technique 1.

b) The compounds of formula I wherein $R^2$ represents H and A represents —$CH_2CH_2CH(OH)$— or —$(CH_2)_p$—, p being 3 or 4, can be manufactured in accordance with the present invention by reacting the compounds of formula II as defined in section a) with the aldehydes of formula IV

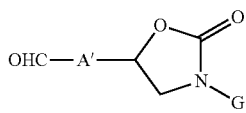

IV wherein A' represents —$(CH_2)_{p-1}$— or —$CH_2CH(OPG)$-, PG being a silyl protecting group such as TBDMS or TBDPS, following general reaction technique 2, the compounds thus obtained being if necessary deprotected using general reaction technique 8.

c) The compounds of formula I wherein $R^2$ represents H, n represents 1 or 2 and A represents —$(CH_2)_p$—, p being 1, 2 or 3, can further be manufactured in accordance with the present invention by reacting the compounds of formula V

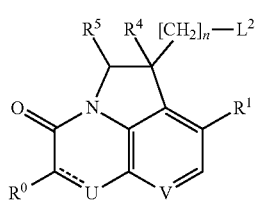

V wherein $L^2$ is a halogen such as bromine or iodine, or a group $OSO_2R^a$ wherein $R^a$ is alkyl, $CF_3$ or tolyl, with the amines of formula VI

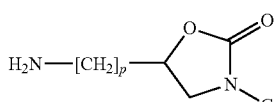

VI following general reaction technique 1.

d) The compounds of formula I wherein $R^2$ represents H, A represents —$(CH_2)_p$— and n is 1 or 2 can be manufactured in accordance with the present invention by reacting the compounds of formula VII

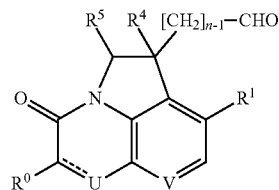

VII with the previously mentioned amines of formula VI following general reaction technique 2.

e) The compounds of formula I wherein "_____" is absent, $R^0$ represents H and U is $CH_2$ or NH can be obtained by hydrogenation of a compound of formula I wherein "_____" is a bond and U is CH or N over a noble metal catalyst such as Pd/C, following general reaction technique 11. In the case wherein U is N the transformation can also be performed by reduction with a hydride reagent such as $NaBH_4$.

f) The compounds of formula I wherein each of $R^4$ and $R^5$ represents H and A represents —$(CH_2)_p$— can moreover be obtained by reacting the compounds of formula VIII

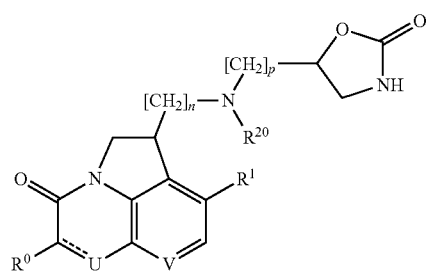

VIII wherein $R^{20}$ represents H, $CH_2R^{3'}$ or an amino protecting group such as Cbz, Boc or Fmoc and $R^{3'}$ represents hydrogen or $(C_1-C_3)$alkyl or also $R^{3'}$ represents a $(C_1-C_3)$hydroxyalkyl group the hydroxy of which is protected in the form of a silyl ether (e.g. as a TBDMS or TBDPS ether), with the compounds of formula IX $G-L^3$    IX wherein $L^3$ represents halogen. In the case of compounds of formula IX wherein G is a group $G^1$ and X is N or G is a group $G^2$ and $Y^1$ and/or $Y^3$ is/are N, the reaction can be performed in the presence of NaH. This reaction can also be performed under conditions described for the metal catalyzed N-arylation of 2-oxazolidinones or amides. In particular by using CuI and 1,1,1-tris(hydroxymethyl)ethane in presence of $Cs_2CO_3$ (*Org. Lett.* (2006), 8, 5609-5612), or $Pd(OAc)_2$ and DPEphos in presence of $K_3PO_4$. The compounds thus obtained are if necessary deprotected using general reaction technique 8.

g) The compounds of formula I wherein $R^2$ does not represent H can furthermore be obtained by reacting the compounds of formula X

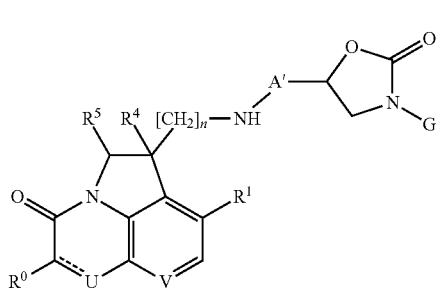

X wherein A' represents —$(CH_2)_p$— or —$CH_2CH(OPG)$-, PG being a silyl protecting group such as TBDMS or TBDPS, with the compounds of formula XI

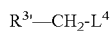

XI wherein $L^4$ represents halogen or the group $OSO_2R^a$ wherein $R^a$ is alkyl, $CF_3$ or tolyl and $R^{3'}$ represents hydrogen or $(C_1-C_3)$alkyl or also $R^{3'}$ represents a $(C_1-C_3)$hydroxyalkyl group, the hydroxy of which is protected in the form of a silyl ether (e.g. as a TBDMS or TBDPS ether), following general reaction technique 1, the compounds thus obtained being if necessary deprotected using general reaction technique 8. In the particular case wherein $R^{3'}$ is H, the reaction can also be performed by reaction of the compounds of formula X as defined above with dimethylsulfate.

h) The compounds of formula I wherein $R^2$ does not represent H can also be obtained by reacting the compounds of formula X as defined above with the compounds of formula XII

XII wherein $R^{3'}$ represents hydrogen or $(C_1-C_3)$alkyl or also $R^{3'}$ represents a $(C_1-C_3)$hydroxyalkyl group, the hydroxy of which is protected in the form of a silyl ether (e.g. as a TBDMS or TBDPS ether), following general reaction technique 2, the compounds thus obtained being if necessary deprotected using general reaction technique 8.

i) The compounds of formula I wherein $R^2$ does not represent H can also be obtained by reacting the compounds of formula X as defined above with the compounds of formula XIIa

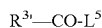

XIIa wherein $R^{3'}$ represents $(C_1-C_3)$alkyl or $(C_1-C_3)$hydroxyalkyl group, the hydroxy of which is protected in the form of a silyl ether (e.g. as a TBDMS or TBDPS ether) and $L^5$ represents halogen or OH, following general reaction technique 13; the compounds thus obtained being if necessary deprotected using general reaction technique 8. In the particular case wherein $R^{3'}$ is methyl, the reaction can also be performed by reacting the compounds of formula X as defined above with acetic acid anhydride.

j) The compounds of formula I wherein $R^2$ does not represent H can furthermore be obtained by reacting the compounds of formula XIII

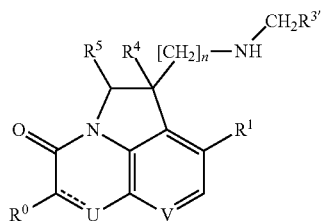

XIII wherein $R^{3'}$ represents hydrogen or $(C_1-C_3)$alkyl or also $R^{3'}$ represents a $(C_1-C_3)$hydroxyalkyl group, the hydroxy of which is protected in the form of a silyl ether (e.g. as a TBDMS or TBDPS ether), with the compounds of formula XIV

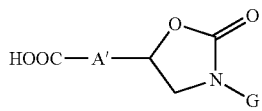

XIV wherein A' represents —$(CH_2)_{p-1}$— or —$CH_2CH(OPG)$-, PG being a silyl protecting group such as TBDMS or TBDPS, following general reaction technique 13, the compounds thus obtained being if necessary deprotected using general reaction technique 8.

k) The compounds of formula I wherein $R^2$ does not represent H can be obtained by reacting the compounds of formula XIII as defined above with the compounds of formula III as defined above following general reaction technique 1. The compounds thus obtained being if necessary deprotected using general reaction technique 8.

l) The compounds of formula I wherein $R^2$ does not represent H can furthermore be obtained by reacting the compounds of formula V with the compounds of formula XV

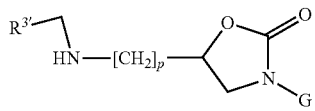

XV wherein $R^{3'}$ represents hydrogen or $(C_1-C_3)$alkyl or also $R^{3'}$ represents a $(C_1-C_3)$hydroxyalkyl group, the hydroxy of which is protected in the form of a silyl ether (e.g. as a TBDMS or TBDPS ether), following general reaction technique 1, the compounds thus obtained being if necessary deprotected using general reaction technique 8.

m) The compounds of formula I wherein $R^2$ does not represent H can be obtained by reacting the compounds of formula VII as defined above with the compounds of formula XV as defined above following general reaction technique 2, the compounds thus obtained being if necessary deprotected using general reaction technique 8.

n) The compounds of formula I wherein V is $CR^6$ and $R^6$ represents carboxy can be obtained by hydrolysis of the derivatives of formula I wherein $R^6$ represents either alkoxycarbonyl (under acidic or basic conditions) or benzyloxycarbonyl (under hydrogenolysis conditions).

o) The compounds of formula I wherein V is $CR^6$ and $R^6$ represents —$CH_2OH$ can be obtained by reduction of the derivatives of formula I wherein $R^6$ represents either alkoxycarbonyl or benzyloxycarbonyl using general reaction technique 5.

p) The compounds of formula I wherein $R^5$ represents carboxy can be obtained from the corresponding compounds of formula I wherein $R^5$ represents ($C_1$-$C_3$)alkoxycarbonyl by treatment with an aq. HCl solution.

q) The compounds of formula I wherein $R^5$ represents ($C_1$-$C_3$)aminoalkyl can be obtained by reacting the compounds of formula XVI

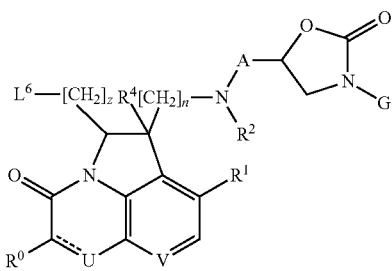

wherein z represents an integer from 1 to 3 and $L^6$ represents halogen or the group $OSO_2R^a$ wherein $R^a$ is alkyl, $CF_3$ or tolyl, with sodium azide followed by transforming the intermediate azides into the corresponding amines of formula I using general reaction technique 12.

r) The compounds of formula I wherein "_____" is absent, U represents $NR^9$, $R^9$ represents ($C_1$-$C_3$)alkyl, 2-hydroxy-ethyl, 2-hydroxy-propyl or 3-hydroxy-propyl, $R^0$ represents H, $R^2$ represents H and A represents —$(CH_2)_p$— or —$CH_2CH_2CH(OH)$— can be obtained by removal of the amino protecting group $PG^0$ from the compounds of formula XVII

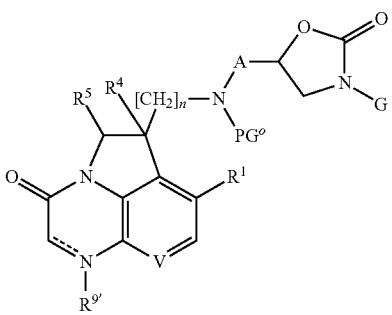

wherein $PG^0$ represents an amino protecting group such as Ac, Boc, Cbz or Fmoc and $R^{9'}$ represents ($C_1$-$C_3$)alkyl or also $R^{9'}$ represents a 2-hydroxy-ethyl, 2-hydroxy-propyl or 3-hydroxy-propyl group, the hydroxy of which group has been protected in the form of a silyl ether (e.g. as a TBDMS or TBDPS ether), using general reaction technique 4, this reaction being followed, in the case wherein $R^{9'}$ is a ($C_2$-$C_3$)hydroxyalkyl group, the hydroxy group of which has been protected in the form of a silyl ether, by removal of the silyl protecting group using general reaction technique 8.

With reference to the reactions mentioned at preceding sections a) to r), in addition to the cases already indicated, the use of hydroxy or amino protecting groups (see general reaction techniques 7 and 8 for hydroxy protecting groups and general reaction techniques 10 and 4 for amino protecting groups) is likely to be required in the following cases:

when $R^5$ represents ($C_1$-$C_3$)hydroxyalkyl or ($C_1$-$C_3$)aminoalkyl;

when $R^6$ represents ($C_1$-$C_3$)hydroxyalkyl or a group —$(CH_2)_q$—$NR^7R^8$ wherein at least one of $R^7$ and $R^8$ represents H;

when "_____" is absent and U represents $NR^9$ wherein $R^9$ represents 2-hydroxy-ethyl, 2-hydroxy-propyl or 3-hydroxy-propyl.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1 (R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min. Whenever the compounds of formula I are obtained in the form of mixtures of diasteromers they may be separated by an appropriate combination of silica gel chromatography, HPLC and crystallization techniques.

PREPARATION OF THE COMPOUNDS OF FORMULAE II TO XV

The compounds of formula II can be prepared either by reaction of the compounds of formula V with sodium azide followed by transformation into the corresponding amines of formula II using general reaction technique 12 or as described in Schemes 1, 1a, 1b, 1c, 1d and 1e hereafter.

The compounds of formula II wherein each of $R^4$ and $R^5$ represents H can be prepared as described in Scheme 1 hereafter.

Scheme 1

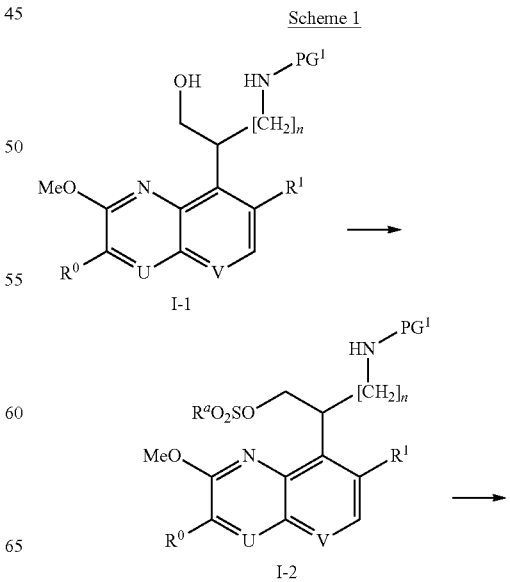

-continued

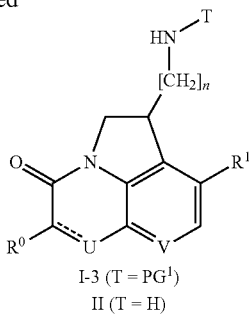

I-3 (T = PG¹)
II (T = H)

In Scheme 1, PG¹ represents an amino protecting group such as Boc or Fmoc and R^a represents alkyl, CF₃ or tolyl.

The protected amino alcohol derivatives of formula I-1 can be transformed into the corresponding mesylates, triflates or tosylates using general reaction technique 3. The resulting sulfonates of formula I-2 can be ring closed between rt and 110° C. affording the tricyclic derivatives of formula I-3. Then the amino protecting group can be removed using general reaction technique 4 to give the compounds of formula II wherein "_____" is a bond.

The compounds of formula II wherein "_____" is absent and U represents $CH_2$ or NH can be prepared by using derivatives identical to the compounds of formula I-1 except that U represents CH or N and PG¹ represents Cbz. The same synthetic sequence can be used, except that, during the last step, the hydrogenation reaction reduces both the CH=CH or CH=N double bond and removes the Cbz protecting group. In the case of compounds of formula II wherein "_____" is absent and U represents NH, the reduction of the CH=N double bond can also be carried out using a hydride reagent such as $NaBH_4$.

The compounds of formula II wherein R⁴ represents H and R⁵ represents $(C_1-C_3)$alkyl, $(C_1-C_3)$hydroxyalkyl, $(C_1-C_3)$alkoxy$(C_1-C_3)$alkyl or $(C_1-C_3)$alkoxycarbonyl can be prepared as described in Scheme 1a hereafter.

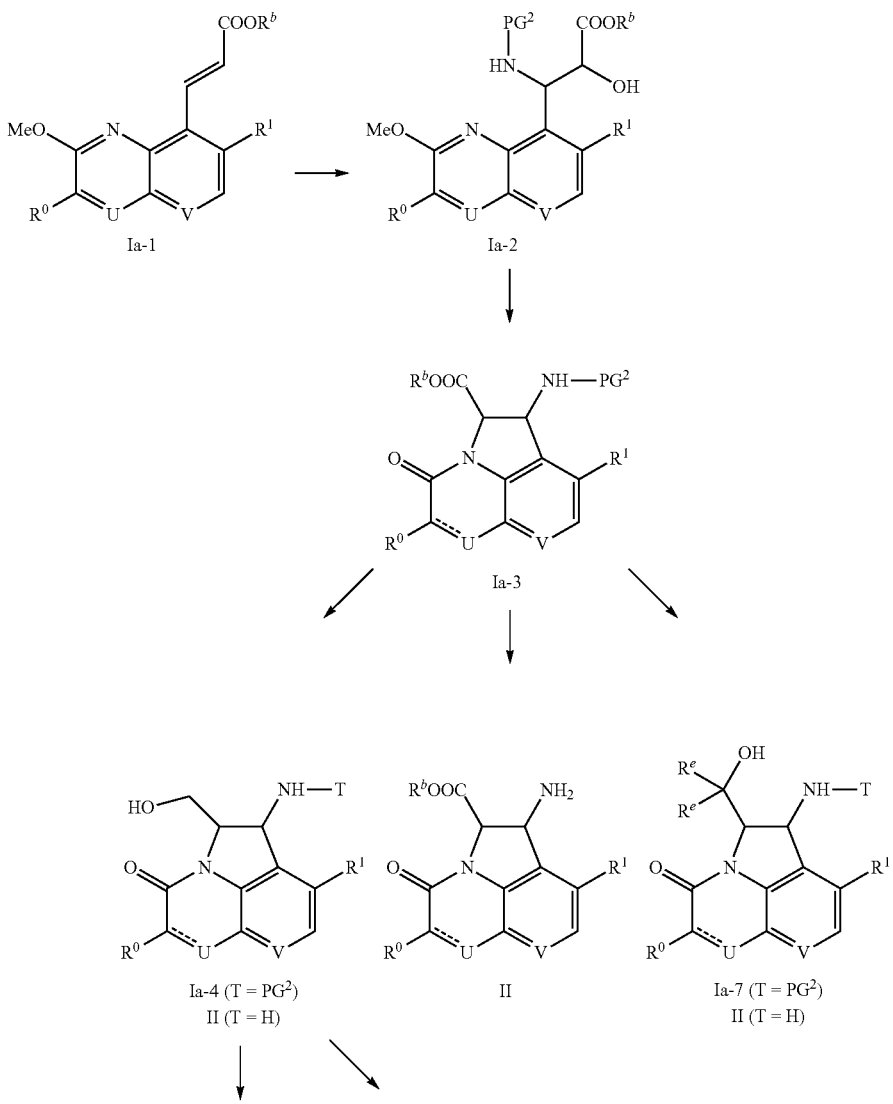

Scheme 1a

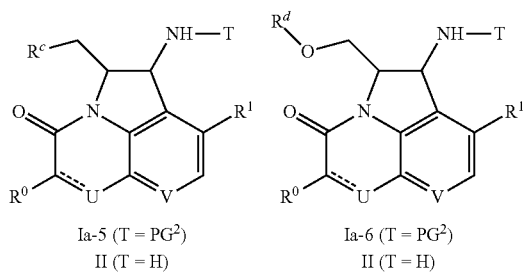

Ia-5 (T = PG²)
II (T = H)

Ia-6 (T = PG²)
II (T = H)

In Scheme 1a, PG² represents an amino protecting group such as Boc or Fmoc, $R^b$ represents alkyl or benzyl, $R^c$ represents hydrogen or alkyl and each of $R^d$ and $R^e$ represents alkyl.

The compounds of formula II wherein $R^4$ represents H and $R^5$ is ($C_1$-$C_3$)alkoxycarbonyl can be obtained by oxyamination of the acrylate derivatives of formula Ia-1 ($K_2OsO_4$, BocNClNa and either (DHQD)$_2$PHAL or (DQD)$_2$PHAL as described in *J. Org. Chem.* (2005), 70, 2847-2850). The intermediates of formula Ia-2 can be cyclised into the derivatives of formula Ia-3 using general reaction technique 3 (including heating at 50-70° C.). The corresponding compounds of formula II can then be obtained by removal of the protecting group using general reaction technique 4.

The compounds of formula II wherein $R^5$ is hydroxymethyl can be obtained by reduction of the ester function of the intermediates of formula Ia-3 using general reaction technique 5. The corresponding compounds of formula II can then be obtained by removal of the protecting group in the compounds of formula Ia-4 using general reaction technique 4.

The compounds of formula II wherein $R^5$ is methyl can be obtained by activation of the alcohol function of intermediates Ia-4 using general reaction technique 3 followed by reaction with a hydride reagent such as LAH or Bu$_3$SnH. More generally, the compounds of formula II wherein $R^5$ is ($C_1$-$C_3$)alkyl can be obtained by oxidation of the intermediates of formula Ia-4 into the corresponding aldehydes following general reaction technique 9 followed by sequential Wittig reaction with alkylidene triphenylphosphorane and catalytic hydrogenation following general reaction technique 11. The protecting group of the intermediates of formula Ia-5 thus obtained can then be removed using general reaction technique 4, providing the corresponding compounds of formula II.

The compounds of formula II wherein $R^5$ is alkoxymethyl can be obtained by reacting the anions of the compounds of formula Ia-4 (generated by reaction with NaH) with the corresponding halogenides of formula $R^d$—X ($R^d$ being alkyl and X being halogen). The protecting group of the intermediates of formula Ia-6 thus obtained can then be removed using general reaction technique 4, providing the corresponding compounds of formula II.

The compounds of formula II wherein $R^5$ is dialkylhydroxymethyl can be obtained reacting the esters of formula Ia-3 with a Grignard reagent of formula $R^e$—MgX wherein $R^e$ is alkyl and X represents halogen. The protecting group of the intermediates of formula Ia-7 thus obtained can then be removed using general reaction technique 4, providing the corresponding compounds of formula II.

The compounds of formulae II and V wherein $R^4$ represents OH can be prepared as described in Scheme 1b hereafter.

Scheme 1b

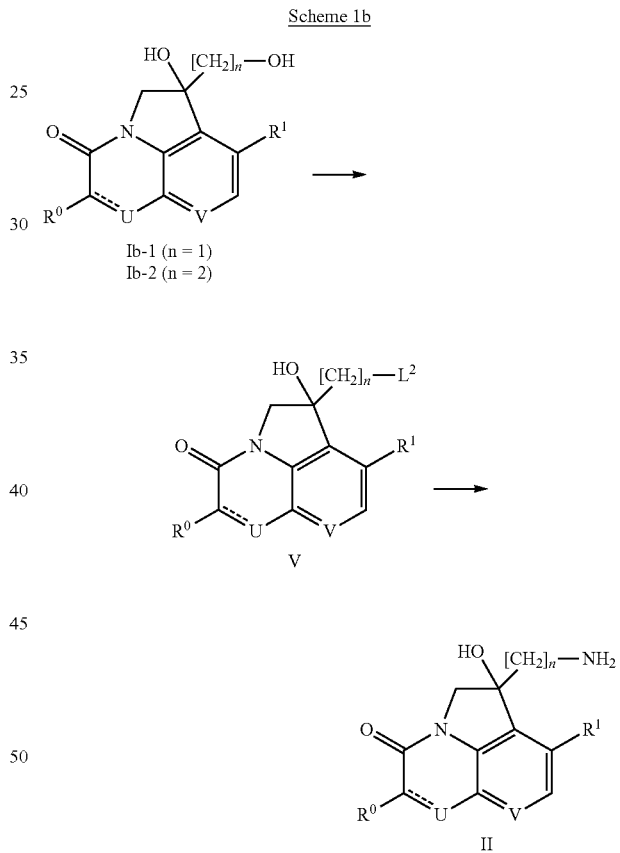

Ib-1 (n = 1)
Ib-2 (n = 2)

V

II

Accordingly, the compounds of formula V wherein $R^4$ represents OH and n is 1 or 2 can be obtained by activation of the primary alcohols of formula Ib-1 or Ib-2 using general reaction technique 3 followed by reaction with NaN$_3$. The compounds of formula V can then be transformed into the amines of formula II using general reaction technique 12.

Besides, the compounds of formula II wherein each of $R^4$ and $R^5$ represents H and V represents CR⁶, $R^6$ representing hydroxymethyl or a group —CH$_2$—NR⁷R⁸, can be prepared as described in Scheme 1c hereafter.

Scheme 1c

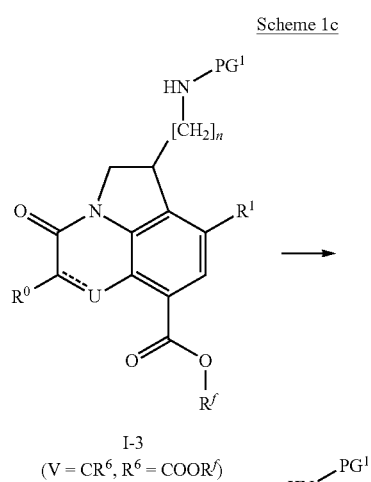

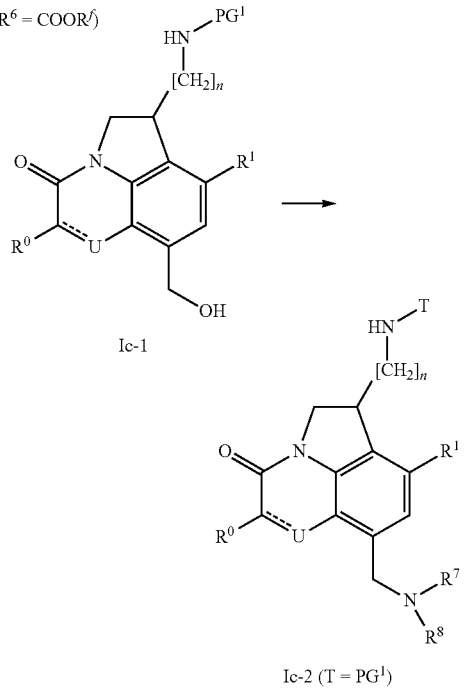

In Scheme 1c, $PG^1$ represents an amino protecting group such as Boc or Fmoc, $R^f$ represents alkyl, each of $R^7$ and $R^8$ independently represents H or $(C_1-C_3)$alkyl or $R^7$ and $R^8$ together with the nitrogen atom bearing them form a pyrrolidinyl, piperidinyl, morpholinyl or thiomorpholinyl ring.

The compounds of formula II wherein each of $R^4$ and $R^5$ represents H, V is $CR^6$ and $R^6$ represents a group —$CH_2$—$NR^7R^8$ can be obtained (Scheme 1c) by reducing the compounds of formula I-3 wherein V is $CR^6$ and $R^6$ represents $(C_1-C_3)$alkoxycarbonyl using general reaction technique 5, followed by either sequential activation of the alcohol group of the intermediates of formula Ic-1 using general reaction technique 3 and reaction with the amines of formula $NHR^7R^8$ using general reaction technique 1, or, depending on the nature of $R^7$ and $R^8$, by oxidation of the intermediates of formula Ic-1 using general reaction technique 9 followed by reductive amination using general reaction technique 2. The corresponding compounds of formula II can then be obtained by removal of the protecting group using general reaction technique 4.

The derivatives of formula II wherein each of $R^4$ and $R^5$ represents H, V is $CR^6$ and $R^6$ represents either —$(CH_2)_q$—$NR^7R^8$ or —$(CH_2)_q$—OH wherein q is 2 or 3 can be obtained by similar methods wherein the compounds of formula Ic-1 are oxidized into their corresponding aldehydes and further transformed into their homologous aldehydes by reaction with $Ph_3P$=CH—OMe or $Ph_3P$=CH—CHO followed by hydrolysis or hydrogenolysis respectively. These homologous aldehydes can be further processed affording the desired compounds of formula II wherein q is 2 or 3.

The compounds of formula II wherein n is 0 and each of $R^4$ and $R^5$ represents H can be prepared as described in Scheme 1d hereafter.

Scheme 1d

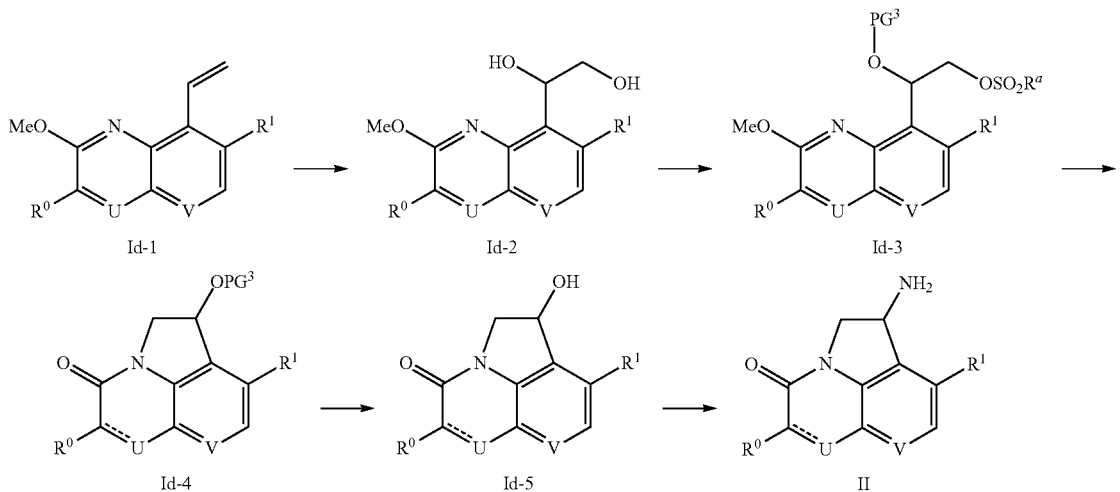

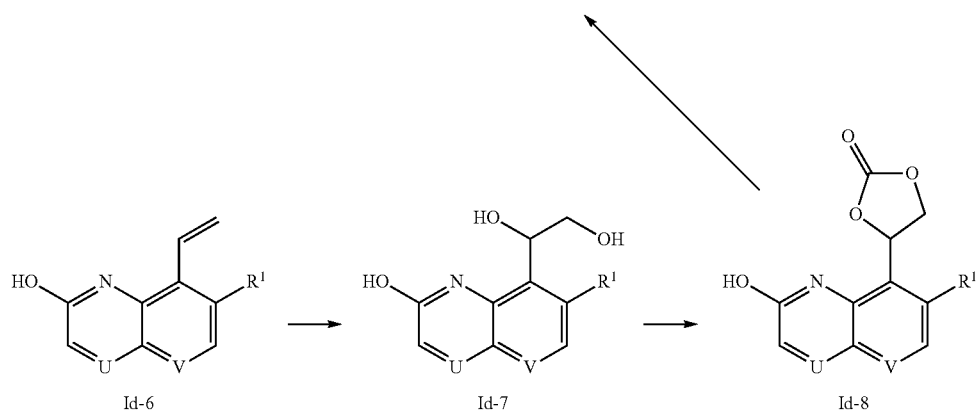

Id-6    Id-7    Id-8

In Scheme 1d, $PG^3$ represents an alcohol protecting group such as TBDMS or TBDPS and $R^a$ represents alkyl, $CF_3$ or tolyl.

The vinylic derivatives of formula Id-1 can be transformed (Scheme 1d) into the corresponding diol derivatives of formula Id-2 using general reaction technique 6. The resulting diols can selectively be transformed into the corresponding monomesylates or monotosylates using general reaction technique 3 and the secondary alcohol function can then be protected using general reaction technique 7, affording the protected derivatives of formula Id-3 which can be cyclised under thermal conditions. The alcohol protecting group in the compounds of formula Id-4 can be removed using general reaction technique 8, affording the free alcohols of formula Id-5. The corresponding compounds of formula II can be obtained after formation of the corresponding azide derivatives (by reaction with DPPA under Mitsunobu conditions; see *Synthesis* (1981), 1) followed by formation of the corresponding amines using general reaction technique 12. The compounds of formula Id-5 wherein $R^0$ is H can also be obtained by dihydroxylation of the vinyl derivatives of formula Id-6 using general reaction technique 6 followed by formation the corresponding carbonate derivatives of formula Id-8 after reaction with CDI or triphosgene and final treatment with a base such as $Cs_2CO_3$. The compounds of formulae Id-4, Id-5 and II wherein "_____" is absent and U represents $CH_2$ or NH can be obtained by hydrogenation of the corresponding compounds of formulae Id-4, Id-5 and II wherein "_____" is a bond and U represents CH or N.

The compounds of formula II wherein $R^1$ represents ethynyl can be prepared as shown in Scheme 1e hereafter.

Scheme 1e

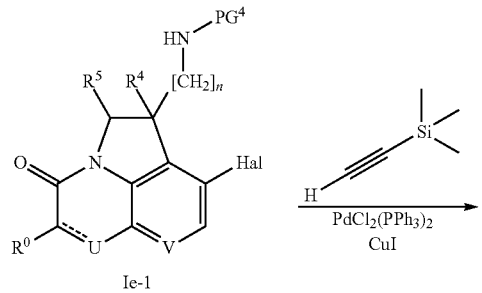

Ie-1

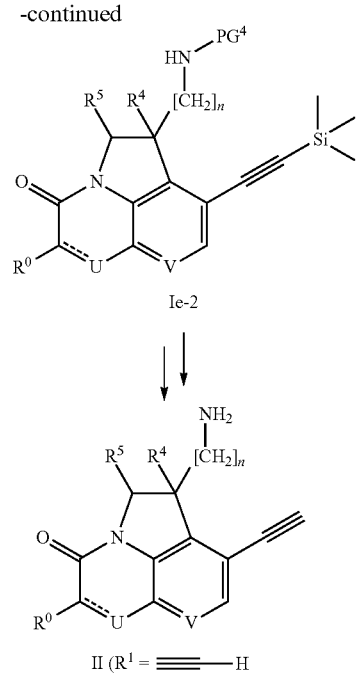

Ie-2

II ($R^1$ = ≡—H)

In Scheme 1e, Hal represents a halogen atom such as bromine and $PG^4$ represents an amino protecting group such as Boc or Fmoc.

The compounds of formula Ie-1 can be treated between +50° C. and +110° C. with ethynyl-trimethylsilane in the presence of $PdCl_2(PPh_3)_2$, CuI and a base like TEA in a solvent like dioxane, affording the compounds of formula Ie-2. The compounds of formula II wherein $R^1$ represents ethynyl can then be obtained from the compounds of formula Ie-2 after removal of the TMS group using TBAF in a solvent like THF and removal of the amino protecting group using general reaction technique 4.

The compounds of formula III wherein p is 1, 2, 3 or 4, the compounds of formula IV wherein A' represents —$(CH_2)_{p-1}$— and p is 3 or 4, the compounds of formula VI wherein p is 1, 2, 3 or 4 and the compounds of formula XV wherein p is 1, 2, 3 or 4 can be obtained as described in Scheme 2 hereafter.

Scheme 2

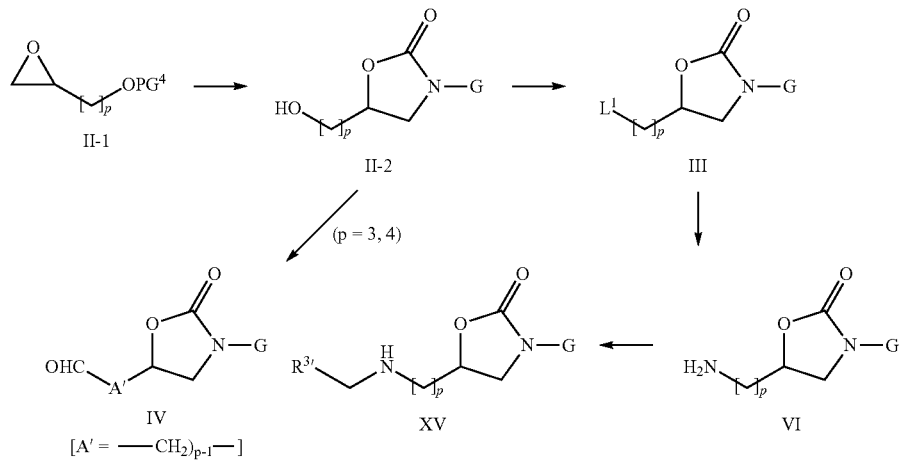

In Scheme 2, PG$^4$ represents —C(O)R$^g$, wherein R$^g$ represents alkyl, or PG$^4$ represents a silyl protecting group such as TBDMS or TBDPS.

The alcohols of formula II-2 can be obtained by reaction of the epoxides of formula II-1 with the anions of the carbamates of formula G-NH—COOR wherein R represents alkyl or benzyl in presence of a base such as KHDMS or lithium tert-butylate, followed by alcohol deprotection as described in general reaction technique 8. The compounds of formula III can then be obtained from the alcohols of formula II-2 using general reaction technique 3. The compounds of formula IV wherein A' represents —(CH$_2$)$_{p-1}$— and p is 3 or 4 can be obtained by oxidation of the corresponding alcohol derivatives of formula II-2 using general reaction technique 9. The compounds of formula VI can be obtained by reaction of the compounds of formula III with sodium azide and subsequent transformation into the corresponding amine following general reaction technique 12. Finally, the compounds of formula XV are obtained by reaction of intermediates of formula VI with an aldehyde of formula R$^{3'}$CHO following general reaction technique 2 or with a derivative of formula R$^{3'}$CH$_2$L$^4$ wherein R$^{3'}$ represents a silylether protected form of the group R$^3$ and L$^4$ represents a halogen such as iodine, bromine or chlorine or a group of the formula OSO$_2$R$^a$ wherein R$^a$ is alkyl, CF$_3$ or tolyl following general reaction technique 1.

The compounds of formula IV wherein A' is —CH$_2$CH(OPG)-, PG being a silyl protecting group such as TBDMS or TBDPS, are prepared as described in Scheme 3 hereafter.

Scheme 3

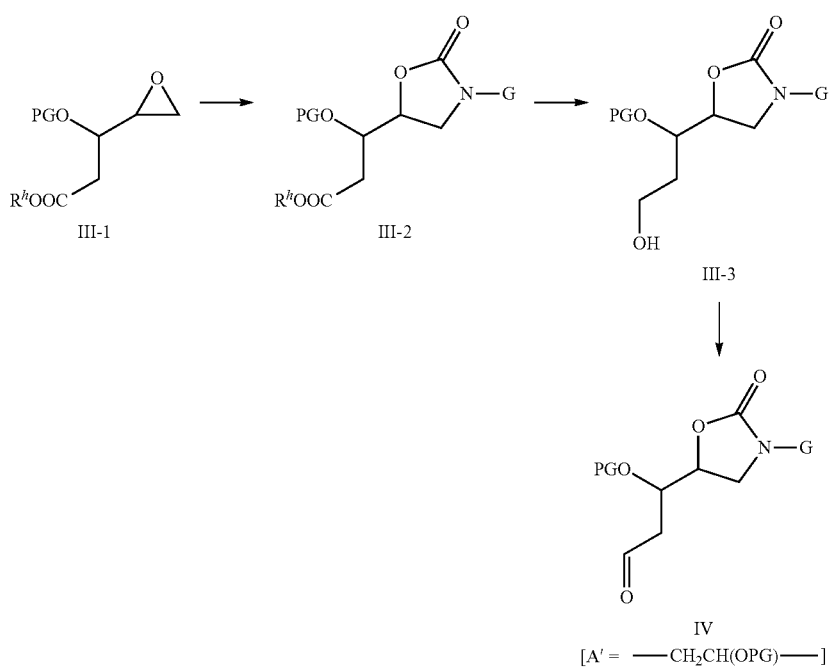

In Scheme 3, $R^h$ represents alkyl (notably tBu) and PG represents an alcohol protecting group such as TBDMS or TBDPS.

The compounds of formula III-1 can be reacted (Scheme 3) with the amines of formula G-NH$_2$ followed by reaction with CDI, affording the oxazolidinones of formula III-2. The corresponding alcohol derivatives of formula III-3 can be obtained after reduction of the ester of formula III-2 using general reaction technique 5. The corresponding aldehydes of formula IV can then be obtained by oxidation of the alcohol derivatives of formula III-3 using general reaction technique 9.

The compounds of formula V wherein each of $R^4$ and $R^5$ represents H and n is 1 or 2 can be prepared as described in Scheme 4 hereafter.

ditions. The resulting esters of formula IV-3 can be reduced using general reaction technique 5, affording the alcohols of formula IV-4, which can be activated using general reaction technique 3, affording the compounds of formula V wherein n is 1. The carbanions of the esters of formula IV-1, generated in the presence of LDA in THF at −78° C., can also be treated with 4-(iodomethyl)-2,2-dimethyl-1,3-dioxolane (commercial), affording the esters of formula IV-5, which can be further transformed into the corresponding alcohols of formula IV-6 using general reaction technique 5. These alcohols can be activated using general reaction technique 3 and cyclised under thermal conditions, affording the tricyclic derivatives of formula IV-7. The acetonide protecting group can be removed under acidic conditions such as aq. acetone in presence of diluted aq. HCl, or an acidic cation exchange resin

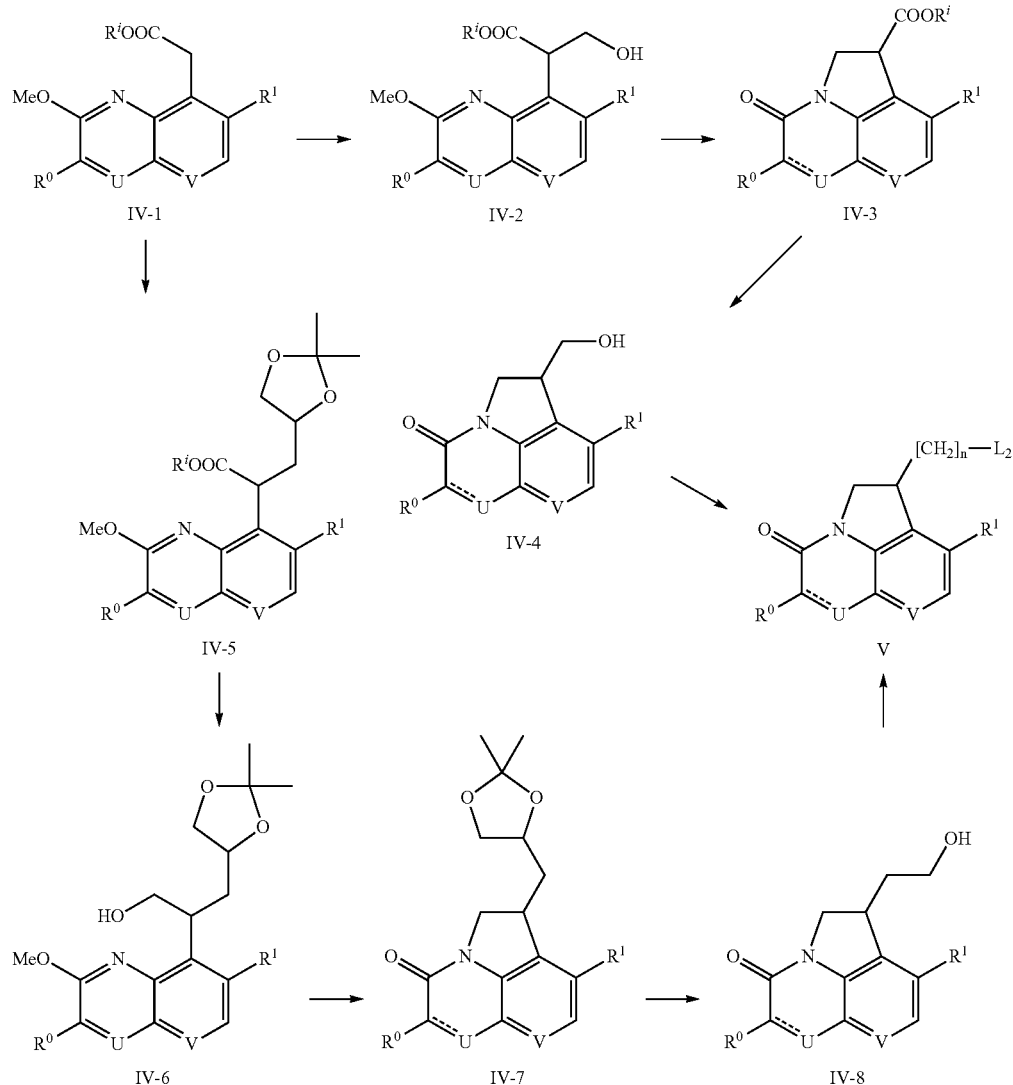

Scheme 4

In Scheme 4, $R^i$ represents alkyl or benzyl and n is 1 or 2.

The esters of formula IV-1 can be treated with paraformaldehyde in the presence of a base such as TEA or K$_2$CO$_3$. The resulting alcohols of formula IV-2 can be activated using general reaction technique 3 and cyclised under thermal consuch as Amberlite® IR120. The corresponding diols can be cleaved in presence of NaIO$_4$ to yield the corresponding aldehydes, which can be reduced into the corresponding alcohols of formula IV-8 by treatment with a hydride reagent such as NaBH$_4$, followed by alcohol activation using general reaction technique 3, affording the compounds of formula V wherein n is 2. The compounds of formulae IV-3, IV-4, IV-7, IV-8 and V wherein "-----" is absent and U represents $CH_2$ or NH can be obtained by hydrogenation of the corresponding compounds of formulae IV-3, IV-4, IV-7, IV-8 and V wherein "-----" is a bond and U represents CH or N. The compounds of formulae IV-4, IV-7, IV-8 and V wherein "-----" is a bond and U represents N can also be reduced into the corresponding compounds wherein "-----" is absent and U represents NH using $NaBH_4$, whereby the transformation of the compounds of formula IV-4 wherein U represents NH into the corresponding compounds of formula V is then preferably performed after transient protection of the NH group.

The compounds of formula V wherein $R^4$ represents OH can be prepared as described in Scheme 4a hereafter.

affording the compounds of formula V wherein $R^4$ is OH and n is 1. The compounds of formula V wherein $R^4$ is OH and n is 2 can be obtained by oxidizing the derivatives of formula Ib-1 using general reaction technique 9, performing a Wittig reaction with methoxymethylene triphenylphosphorane and an acidic hydrolysis of the intermediate of formula IVa-3 and reducing the aldehyde thus obtained into the alcohol derivatives of formula Ib-2 using general reaction technique 5 before activating the alcohol function using general reaction technique 3. The compounds of formula Ib-2 can also be obtained by reaction of the aldehydes of formula IVa-2 with methylenetriphenylphosphorane followed by hydroboration of the intermediate vinyl derivatives of formula IVa-4 with a borane reagent such as 9-BBN, $BH_3.Me_2S$ or $BH_3.THF$ followed by oxidation with $H_2O_2$ in presence of NaOH.

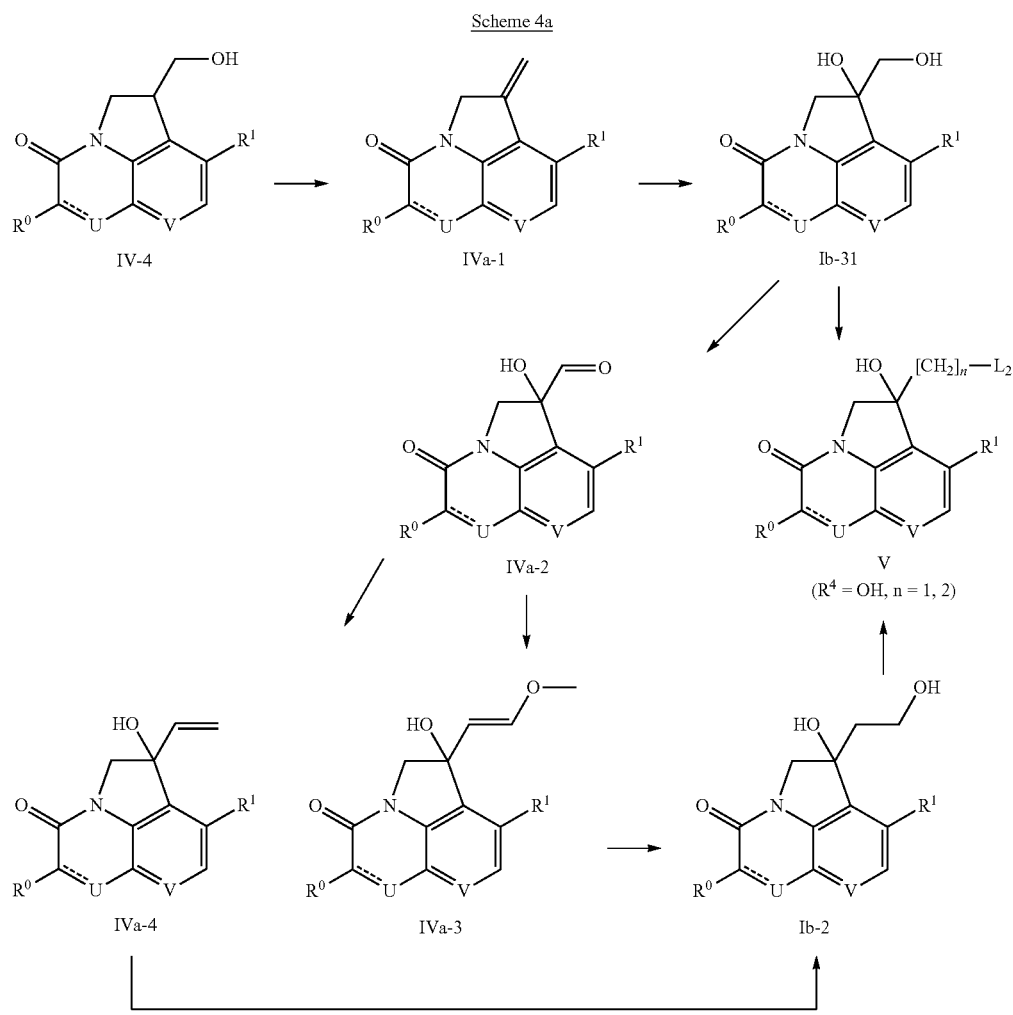

Scheme 4a

The compounds of formula V wherein $R^4$ is OH and n is 1 can be obtained (Scheme 4a) by transforming the compounds of formula IV-4 into the alkene derivatives of formula IVa-1 after activation of the alcohol group using general reaction technique 3 followed by treatment with a base such as DBU. The intermediate alkene derivatives of formula IVa-1 can be dihydroxylated using general reaction technique 6 and the primary alcohol function of the intermediates of formula Ib-1 can then be activated using general reaction technique 3, The compounds of formulae IVa-2 and V wherein "-----" is absent and U represents $CH_2$ or NH can be obtained by hydrogenation of the corresponding compounds wherein "-----" is a bond and U represents CH or N.

The compounds of formula VII can be obtained by oxidation of the corresponding alcohols of formulae Ib-1, Ib-2, IV-4 and IV-8 following general reaction technique 9.

The compounds of formula VIII wherein $R^{20}$ represents $CH_2R^{3'}$, each of $R^4$ and $R^5$ represents H and p is 1, 2 or 3 can be obtained as described in Scheme 5 hereafter.

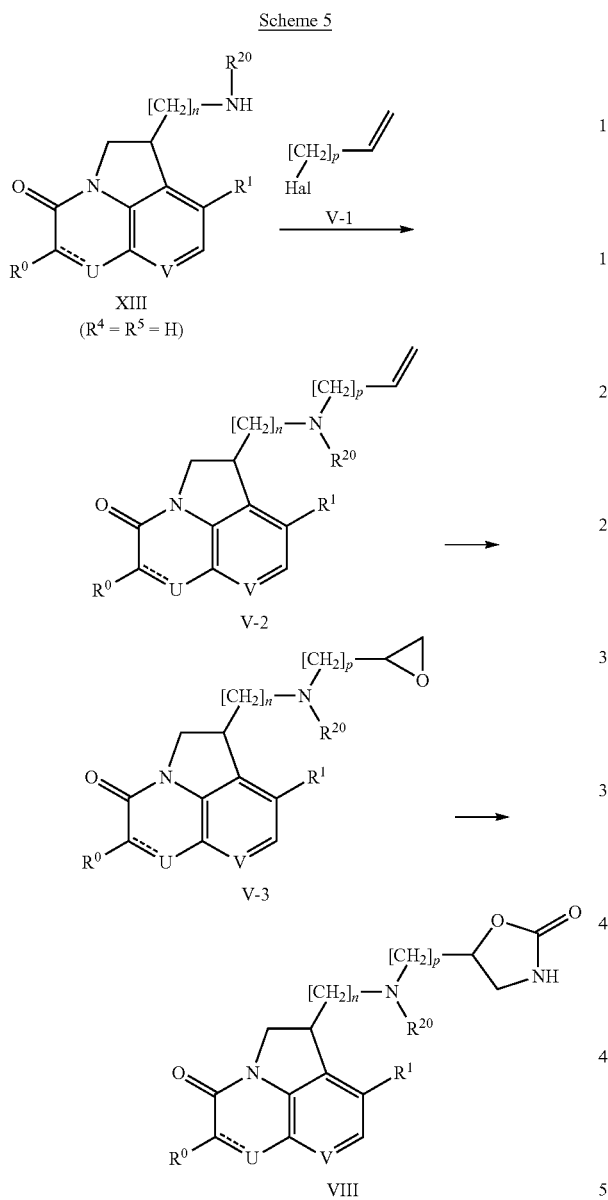

In Scheme 5, Hal represents halogen such as chlorine or bromine, $R^{20}$ represents $CH_2R^{3'}$ and $R^{3'}$ represents hydrogen or $(C_1-C_3)$alkyl or also $R^{3'}$ represents a $(C_1-C_3)$hydroxyalkyl group the hydroxy of which is protected in the form of a silyl ether (e.g. as a TBDMS or TBDPS ether).

The amine derivatives of formula XIII wherein each of $R^4$ and $R^5$ represents H can be reacted with the halogenides of formula V-1 following general reaction technique 1. The resulting derivatives of formula V-2 can be dihydroxylated following general reaction technique 6, the primary alcohol function can be activated following general reaction technique 3 and the epoxide ring can then be formed after treatment with a base such as NaH, $Na_2CO_3$ or TEA. The epoxides of formula V-3 can then be treated with sodium azide followed by formation of the corresponding amines following general reaction technique 12 and subsequently be converted into their corresponding carbamates with CbzCl or $Boc_2O$ following general reaction technique 10. The oxazolidinone ring can then be formed by reaction with NaH. The compounds of formula VIII can also be obtained by reaction of the epoxide derivatives of formula V-3 with a carbamic acid ester in the presence of a salen complex as described in Org. Letters (2004), 6, 3973-3975 or Org. Letters (2005), 7, 1983-1985). The compounds of formula VIII wherein U is $CH_2$ or NH and "____" is absent, can be obtained by hydrogenation of the corresponding compounds of formula VIII wherein "____" is a bond and U represents CH or N. The compounds of formula VIII wherein "____" is a bond and U represents N can also be reduced into the corresponding compounds wherein "____" is absent and U represents NH using $NaBH_4$.

Certain compounds of formula IX are commercially available (e.g. $G=G^1$, Q=O and X=N: CAS 337463-99-7; $G=G^1$, Q=S and X=CH: CAS 6376-70-1; $G=G^1$, Q=O and X=CH: CAS 7652-29-1) or can be obtained according to known literature procedures (e.g. 7-chloro-1,8-naphthyridin-2 (1R)-one: J. Org. Chem. (1990), 4744-59).

The compounds of formula IX wherein $L^3$ is Cl, G is a group $G^1$, X is N and Q is S can be obtained as described in Scheme 6 hereafter.

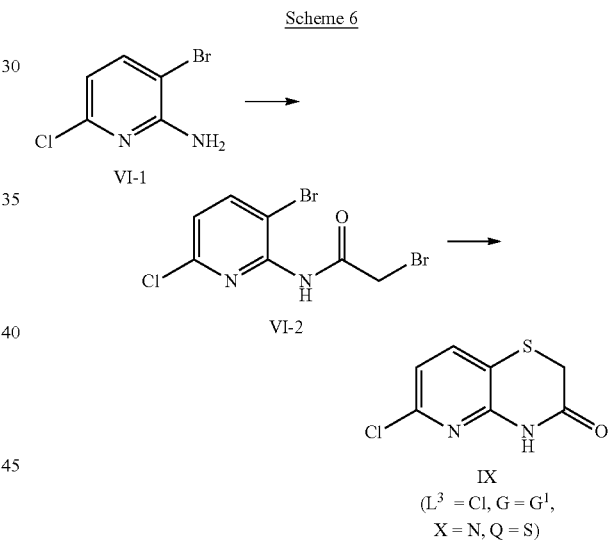

Accordingly, the bromo derivative of formula VI-1 (prepared according to WO 2008/065198) can be reacted with bromoacetyl bromide and the resulting derivative of formula VI-2 can be reacted with sodium thioacetate in presence of NaOMe to afford the compound of formula IX wherein $L^3$=Cl, $G=G^1$, X=N and Q=S.

The compounds of formula X wherein A' represents —$(CH_2)_p$— are compounds of formula I wherein $R^2$ represents H. The compounds of formula X wherein A' represents —$CH_2CH_2CH(OPG)$- can be obtained by reacting compounds of formula II wherein n is 0 with compounds of formula IV wherein A' represents —$CH_2CH(OPG)$-using general reaction technique 2.

The compounds of formula XI can be prepared by activation of the corresponding commercially available alcohol derivatives (e.g. 3-[(tert-butyldimethylsilyl)oxy]-1-propanol or 2-tert-butyldimethylsilyloxyethanol) following general reaction technique 3.

The compounds of formula XII (e.g. (tert-butyldimethyl-silyloxy)acetaldehyde or 3-[(tert-butyldimethylsilyl)oxy] propionaldehyde) and XIIa are commercially available.

The compounds of formula XIII wherein $R^{3'}$ represent H or $(C_1-C_3)$alkyl or also $R^{3'}$ represents a $(C_1-C_3)$hydroxyalkyl group, the hydroxy of which is protected in the form of a silyl ether (e.g. as a TBDMS or TBDPS ether), can be prepared by reductive amination of the aldehydes of formula XII with the amines of formula II following general reaction technique 2. These compounds of formula XIII can also be obtained by alkylation of the amines of formula II with the derivatives of formula XI following general reaction technique 1.

The compounds of formula XIV wherein A' represents —$(CH_2)_{p-1}$— can be prepared by oxidation of the compounds of formula II-2 or IV following general reaction technique 14. The compounds of formula XIV wherein A' represents —$CH_2CH(OPG)$-, PG being a silyl protecting group such as TBDMS or TBDPS, can be prepared by hydrolysis of the corresponding esters of formula III-2 (see Scheme 3) using a base such as LiOH in the case wherein $R^h$ is methyl or ethyl or TFA in the case wherein $R^h$ is tBu.

The compounds of formula XV wherein $R^{3'}$ represents hydrogen or $(C_1-C_3)$alkyl or also $R^{3'}$ represents a $(C_1-C_3)$ hydroxyalkyl group, the hydroxy of which is protected in the form of a silyl ether (e.g. as a TBDMS or TBDPS ether), can be obtained by alkylation of the amines of formula VI with derivatives of formula $R^{3'}$-$CH_2$—X (X being Cl, Br or I) following general reaction technique 1.

The compounds of formula XVI can be obtained from the corresponding compounds of formula I wherein $R^5$ represents $(CH_2)_z$OH following general reaction technique 3.

The compounds of formula XVII can be obtained as described in Scheme 6a hereafter.

In Scheme 6a, $PG^0$ represents an amino protecting group such as Ac, Boc, Cbz or Fmoc and $R^{9'''}$ represents hydrogen or $(C_1-C_2)$alkyl or also $R^{9'''}$ represents a $(C_1-C_2)$hydroxyalkyl group, the hydroxy of which is protected in the form of a silyl ether (e.g. as a TBDMS or TBDPS ether).

The compounds of formula $I_{6a}$ (i.e. the compounds of formula I wherein "_____" is a bond, $R^0$ is H, U is N and $R^2$ is H) can be protected with an amino protecting group $PG^0$ using general reaction technique 10. The resulting compounds of formula 6a-1 can be transformed into the derivatives of formula 6a-2 by reduction over a noble metal catalyst such as Pd/C or reduced with a hydride reagent such as $NaBH_4$. The intermediates of formula 6a-2 can be reacted with the aldehydes of formula 6a-3 following general reaction technique 2, yielding the compounds of formula XVII. Alternatively, the compounds of formula 6a-2 can be transformed into the compounds of formula XVII by reaction with the alkyl halogenides of formula $R^{9'}$-Hal (Hal being a halogen atom).

Preparation of the Intermediates of Formulae I-1, Ia-1, Id-1, Ie-1, II-1, III-1, IV-1 and XIII The compounds of formula I-1 can be obtained from the compounds of formula IV-1 as described in Scheme 7 hereafter.

Scheme 6a

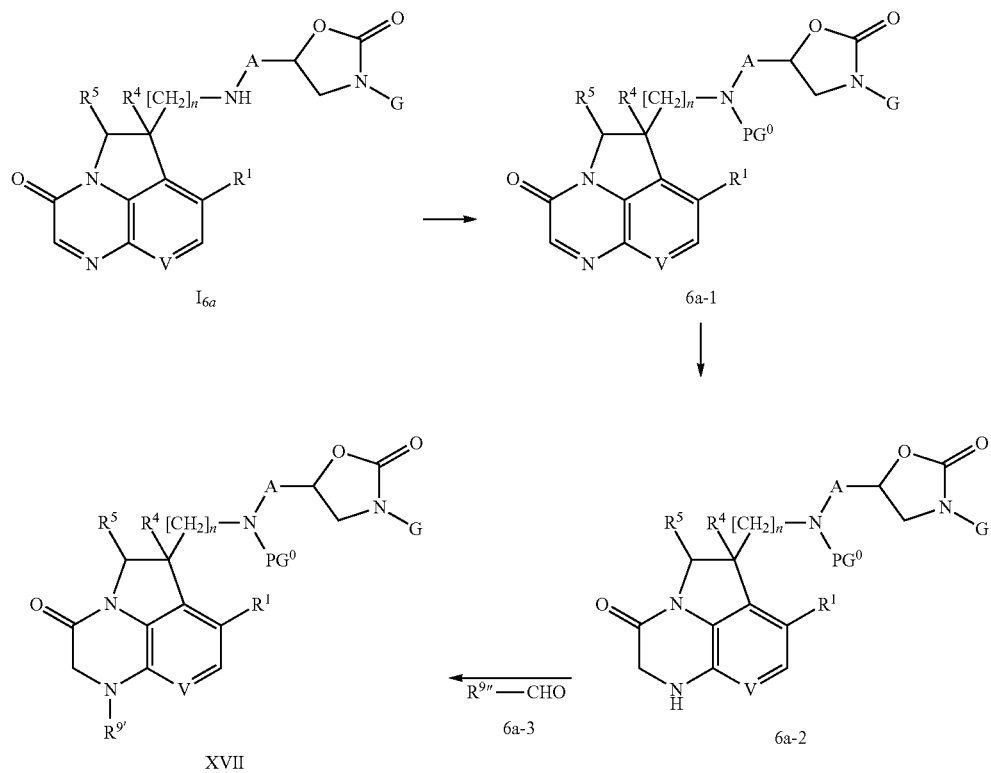

Scheme 7

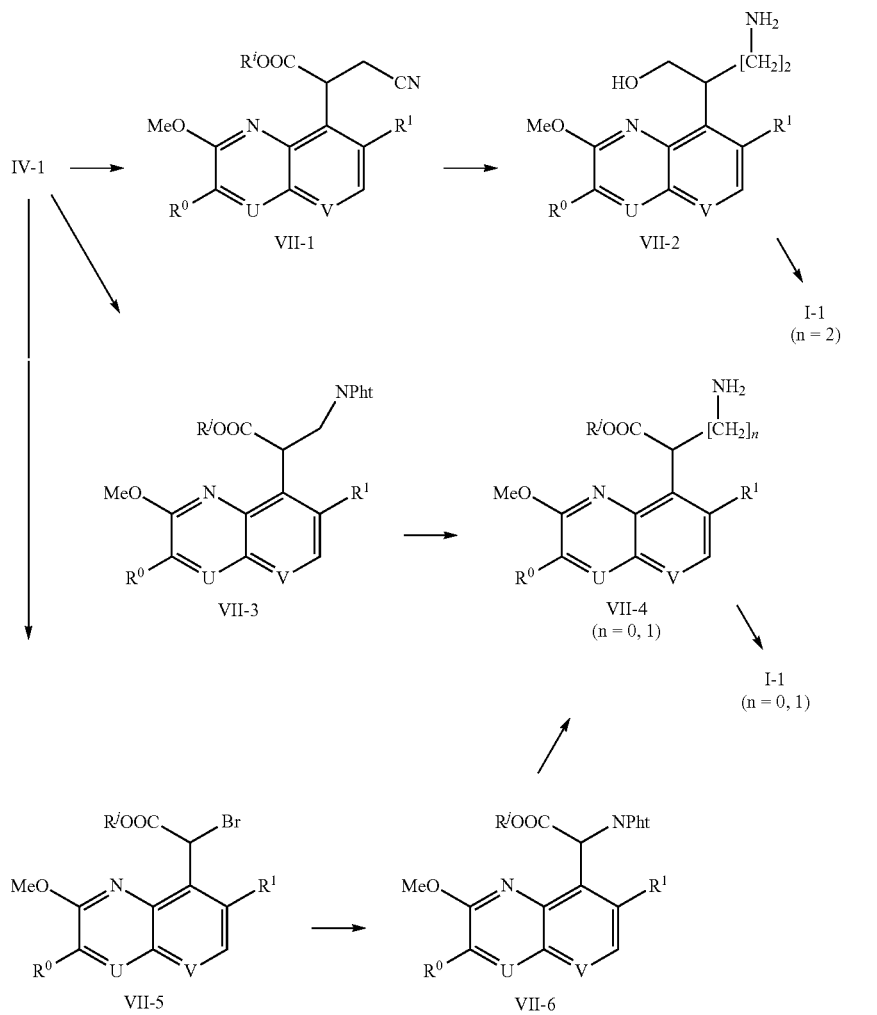

In Scheme 7, $R^j$ is alkyl or benzyl.

The esters of formula IV-1 can be reacted (Scheme 7) with bromoacetonitrile in the presence of a strong base such as LiHMDS in a solvent such as THF between −78° C. and −20° C. The resulting nitrile derivatives of formula VII-1 can be reduced with LAH in a solvent such as THF or ether and the amino group of the resulting compounds of formula VII-2 can be protected according to general reaction technique 10, affording compounds of formula I-1 wherein n is 2. The esters of formula IV-1 can also be reacted with N-(bromomethyl) phthalimide in presence of a strong base such as LiHMDS in a solvent such as THF between −78° C. and −20° C. The resulting phthalimido derivatives of formula VII-3 can then be treated with an hydrazine derivative such as hydrazine hydrate, affording the corresponding primary amine derivatives of formula VII-4 wherein n is 1. The amino group of the derivatives of formula VII-4 can be protected according to general reaction technique 10 and the ester function reduced using general reaction technique 5 to obtain the compounds of formula I-1 wherein n is 1. The esters of formula IV-1 can also be reacted with NBS, affording the corresponding bromides of formula VII-5 which can then be reacted with potassium phthalimide. The resulting phthalimido derivatives of formula VII-6 can be treated with an hydrazine derivative such as hydrazine hydrate to obtain the corresponding primary amine derivatives of formula VII-4 wherein n is 0. The amino group of the derivatives of formula VII-4 can then be protected according to general reaction technique 10 and the ester function reduced using general reaction technique 5, affording compounds of formula I-1 wherein n is 0.

The compounds of formula I-1 wherein n is 0 can furthermore be obtained from the compounds of formula III-2 as described in Scheme 7a hereafter.

Scheme 7a

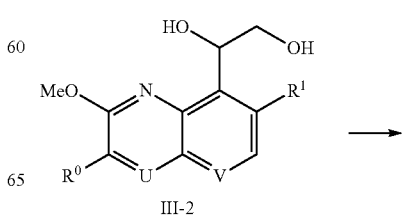

III-2

-continued

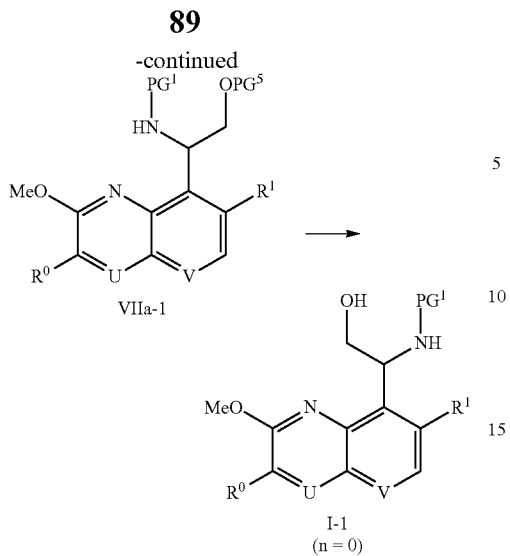

In Scheme 7a, PG$^1$ represents an amino protecting group such as Boc or Fmoc and PG$^5$ represents an alcohol protecting group such as TBDMS or TBDPS.

The compounds of formula I-1 wherein n is 0 can also be obtained (Scheme 7a) from the alkene derivatives of formula III-2. The primary alcohol function of the diols of formula III-2 can be protected using general reaction technique 7 before conversion of the secondary alcohol group into the corresponding azide by activation of the alcohol under Mitsunobu conditions (in the presence of PPh$_3$ and DEAD or DIAD in a solvent such as THF, DMF, DCM or DME between −20° C. and 60° C., as reviewed by O. Mitsunobu in *Synthesis* (1981), 1) reaction with DPPA, formation of the primary amine using general reaction technique 12 and formation of the carbamate using general reaction technique 10, to obtain the compounds of formula VIIa-1. The alcohol protecting group of the intermediates of formula VIIa-1 can then be removed using general reaction technique 8.

The compounds of formula Ia-1 can be obtained from the aldehydes of formula VIII-2

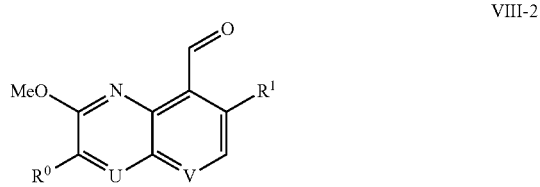

by Wittig reaction with an alkoxycarbonylmethylene triphenylphosphorane.

The compounds of formula Id-1 can be prepared according to WO 02/08224, WO 2004/058144 or WO 2008/126024 or as described in Scheme 8 hereafter.

In Scheme 8, L$^5$ represents halogen (such as bromine) or OTf.

The compounds of formula VIII-1 (see Scheme 8) can be reacted with trivinylboroxin in presence of a palladium catalyst such as tetrakis(triphenylphosphine)palladium, affording the compounds of formula Id-1 wherein R$^0$ represents H. The compounds of formula Id-1 (including those wherein R$^0$ represents (C$_1$-C$_3$)alkoxy) can also be obtained by reacting the aldehydes of formula VIII-2 with methylenetriphenylphosphorane.

The compounds of formula Id-6 can be obtained in analogy to the compounds of formula Id-1 starting from the derivatives of formula VIII-3

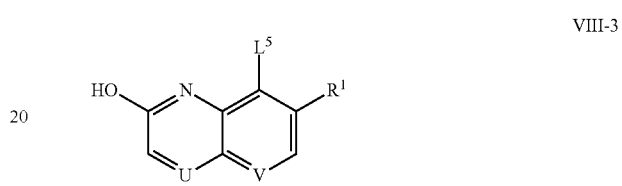

(commercially available or prepared according to WO 2008/148867, WO 2008/003690, WO 2006/125974 or WO 2008/150827).

The compounds of formula Ie-1 can be obtained by protection of the amino group of the corresponding compounds of formula II wherein R$^1$ represents halogen using general reaction technique 10.

The compounds of formula II-1 wherein p is 1 and PG$^4$ is —C(O)R$^g$, R$^g$ being alkyl, are commercially available. The compounds of formula II-1 wherein p is 2 or 3 and PG$^4$ is TBDMS can be prepared according to WO 2007/144423 or EP 518672.

The compounds of formula III-1 wherein PG is TBDMS can be prepared according or in analogy to *Bioorganic & Medicinal Chemistry Letters* (1996), 6 (8), 991-994.

The compounds of formula IV-1 can be prepared as described in WO 2007/122258, WO 2007/115947 and WO 2007/081597.

The compounds of formula VIII-1 wherein R$^1$ is H and L$^5$ is OTf can be prepared according to WO 2004/002490. The compounds of formula VIII-1 wherein R$^1$ is F can be prepared in analogy to the compounds of formula VIII-1 wherein R$^1$ is Cl as described in WO 2006/021448.

The compounds of formula VIII-2 wherein R$^0$ is H or methoxy, R$^1$ is H or F and one of U and V is CH while the other is CH or N can be prepared according to WO 98/17672, WO 2006/046552, WO 2008/126024 or WO 2008/152603.

The compounds of formula VIII-2 wherein U is N, V is N and R$^0$ is H or methoxy can be prepared as described in Scheme 9 hereafter.

Scheme 8

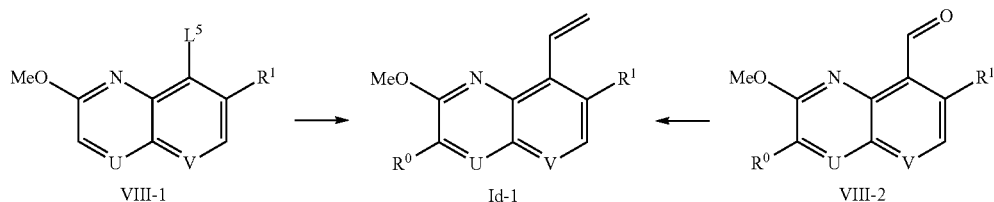

Scheme 9

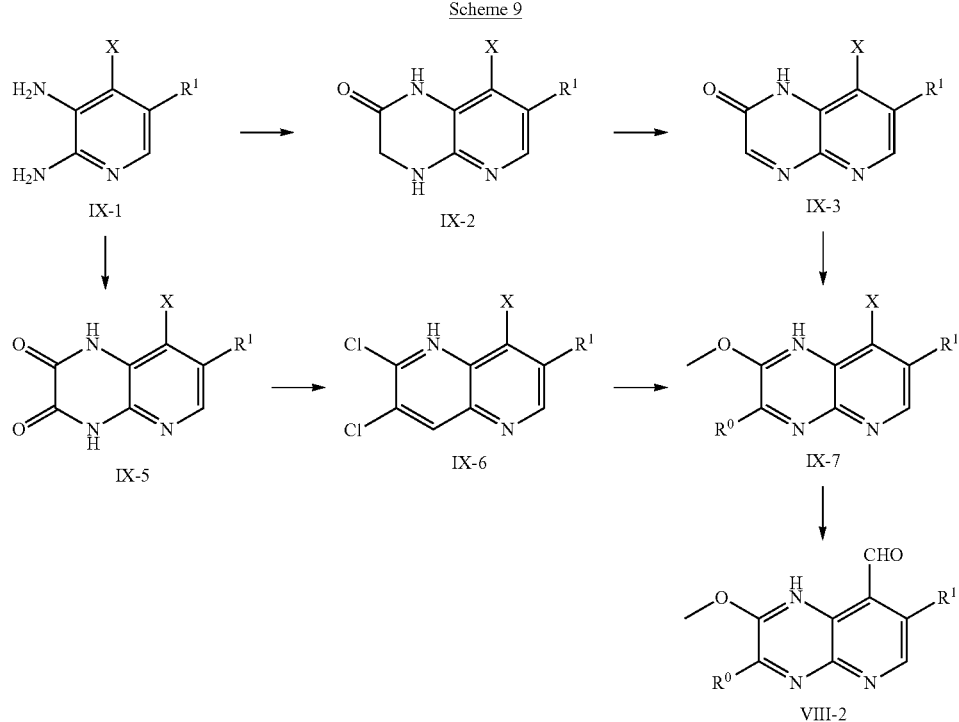

In Scheme 9, X represents halogen such as bromine or chlorine.

The diamino derivatives of formula IX-1 can be reacted with bromoacetic acid, affording the intermediates of formula IX-2 which can then be oxidised using $MnO_2$. The aromatic intermediates of formula IX-3 can be reacted with methyl iodide in the presence of $CsCO_3$, affording the compounds of formula IX-7 wherein $R^0$ is H. The compounds of formula IX-7 wherein $R^0$ is OMe can be obtained by reacting the compounds of formula IX-1 with diethyl glyoxylate, affording the intermediates of formula IX-5 which can further be transformed into the derivatives of formula IX-6 by reaction with $POCl_3$ and the derivatives of formula IX-7 wherein $R^0$ is OMe after reaction with NaOMe in MeOH. The compounds of formula IX-7 can then be transformed into the derivatives of formula VIII-2 after reaction with a strong base such as n-BuLi and trapping the generated intermediates with DMF.

The compounds of formula IX-1 wherein $R^1$ is H can be prepared as described in U.S. Pat. No. 5,298,518. The compound of formula IX-1 wherein X is Br and $R^1$ is F can be obtained as summarised in Scheme 10 hereafter.

Scheme 10

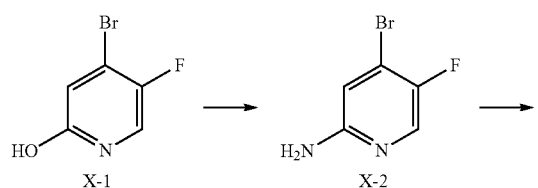

-continued

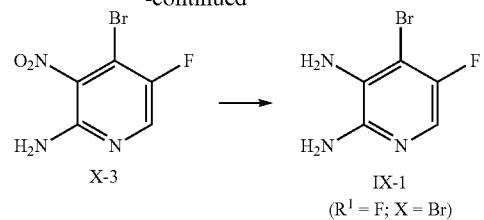

The commercially available pyridine derivative of formula X-1 can be transformed into the corresponding aminopyridine derivative of formula X-2 by reaction with $POCl_3$ followed by ammonia. The intermediate of formula X-2 can then be reacted with $HNO_3/AcOH$ and further reduced (e.g. with Zn/HCl), thus affording the compound of formula IX-1 wherein X is Br and $R^1$ is F.

Particular embodiments of the invention are described in the following Examples, which serve to illustrate the invention in more detail without limiting its scope in any way.

EXAMPLES

All temperatures are stated in ° C. Compounds are characterized by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad, coupling constants are given in Hz. Alternatively compounds are characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point. Compounds are purified by chromatography on Silica gel 60A. $NH_4OH$ as used for CC is 25% aq.

The HPLCs are done over a stationary phase such as a rapid resolution Zorbax SB C18 (1.8 μm) column, or a rapid resolution Zorbax Eclipse Plus C18 (1.8 μm) column. Typical HPLC conditions are a gradient of eluent A (water:MeCN 95:5 with 0.1% of formic acid, in presence or not of 5 mmol/L ammonium formate) and eluent B (MeCN:water 95:5 with 0.1% of formic acid, in the presence or not of 5 mmol/L ammonium formate), at a flow rate of 0.8 to 5 mL/min. Racemates can be separated into their enantiomers as described before. Preferred conditions of chiral HPLC are: ChiralPak AD (4.6×250 mm, 5 μm) column, using an isocratic mixture (e.g. at a ratio of 10/90) of eluent A (EtOH, in presence of diethylamine in an amount of eg. 0.1%) and eluent B (Hex), at rt, at a flow rate of e.g. 0.8 mL/min.

General Procedures:

Procedure A: LAH Reduction of Esters:

To a solution of ester (1 mmol) in THF (15 mL), cooled to −10° C., is added in one portion LAH (3.5 eq.). The mixture is stirred at the same temperature for 0.5 h, then at 0° C./rt until completion of the reaction (1-3 h). Water (0.4 mL) is carefully added, followed by 2M NaOH (0.8 mL) and water (0.4 mL). After stirring for 5 min, $Na_2SO_4$ (1 g) is added and the mixture is stirred for 15 min. The solids are filtered off and thoroughly washed with EA. The filtrate is concentrated under reduced pressure.

Procedure B: Boc Deprotection:

The Boc protected amine (1 mmol) is dissolved in DCM (5 mL) and treated with $Et_3SiH$ (optional; 0.2 mL, 1.1 eq.) and TFA (2 mL). The mixture is stirred at rt for 1 h, concentrated in vacuo and taken up in DCM/aq. $NH_4OH$. The org. layer is washed with water, dried over $MgSO_4$ and concentrated under reduced pressure.

Procedure C: Alkylation of Amines with Mesylates:

A solution of amine (1.0-2.3 mmol), mesylate (1 mmol) and DIPEA (1.1 mmol) in dry DMSO is heated to 70° C. until completion of the reaction (1-5 days). After cooling, water and EA are added and the phases are separated. The aq. layer is extracted two more times with EA and the combined org. layers are washed with water (3×) and brine, dried over $MgSO_4$ and concentrated under reduced pressure. The residue is then purified by CC.

Procedure D: Alkylation of Amines with Iodides:

A solution of amine (1 mmol), iodide (1 mmol) and DIPEA (1.1 mmol) in dry DMSO is heated to 70° C. until completion of the reaction (1-3 days). After cooling, water and EA are added and the phases are separated. The aq. layer is extracted two more times with EA and the combined org. layers are washed with water (3×) and brine, dried over $MgSO_4$ and concentrated under reduced pressure. The residue is then purified by CC.

Procedure E: Reductive Amination:

A solution of amine (1 mmol) and aldehyde (1 mmol) in DCE/MeOH (1-1 to 4-1, 10 mL) is treated with $NaBH(OAc)_3$ (2 mmol). The mixture is stirred at rt until completion of the reaction (1-4 h), diluted with DCM and treated with aq. $NH_4OH$. The phases are separated. The aq. layer is extracted two more times with DCM and the combined org. layers are washed with water and brine, dried over $MgSO_4$ and concentrated under reduced pressure. The residue is then purified by CC.

Procedure F: Hydrogenation:

A solution of unsaturated substrate (1 mmol) in MeOH (20 mL) and AcOH (optional, 20 mL) is hydrogenated over 10% Pd/C (200 mg) for 20 h. The catalyst is filtered off, washed with MeOH/DCM and concentrated. Water and 28% aq. $NH_4OH$ are added and the mixture is extracted with DCM/MeOH 9:1. The org. layer is dried over $MgSO_4$, concentrated and purified by CC.

Procedure G: Boc Protection:

$Boc_2O$ (1.05 eq.) and TEA (1.5 eq.) are added at rt to a solution of the corresponding amine (1.0 eq.) in THF. The reaction mixture is stirred at rt for 1 h, concentrated to dryness and purified by CC.

Procedure H: Mesylate Formation:

TEA or DIPEA (2 eq.) and MsCl (1.2 eq.) are added at 0° C. to a solution of the required alcohol (1 eq.) in DCM or DCE. The reaction is stirred 1 h at this temperature. In the case the resulting mesylate can undergo cyclization to form a tricyclic system, the reaction mixture is further stirred between rt and 45° C. for 6 to 72 h. Sat. aq. $NaHCO_3$ is then added and the mixture is extracted with DCM (3×). The combined org. layers are dried over $MgSO_4$, filtered and concentrated under reduced pressure to afford the desired mesylate which can be used as such in a further step.

Procedure I: Oxazolidinone Formation with CDI:

A solution of the required aminoalcohol (1 eq.) in THF is treated with CDI (1.5 eq.) and heated at 50° C. overnight. The mixture is cooled to rt, diluted with EA and washed with water. The org. layer is washed with 0.5M. HCl (optionally) and water, dried over $MgSO_4$ and concentrated. The residue is either triturated with an org. solvent, crystallized from Hept/EA or purified by CC.

Procedure J: Deprotection of TBDMS Ethers:

A solution of TBDMS ether (1 eq) in THF is treated with TBAF (1M solution in THF, 1.2 eq.) at 0° C. The solution is stirred at 0° C. for 6 h. The mixture is partitioned between water and EA and the aq. phase is extracted with EA (3×). The combined org. layers are washed with water (3×) and brine, dried over $MgSO_4$ and concentrated under reduced pressure. The residue is triturated with an org. solvent or purified by CC.

Procedure K: Finkelstein-Like Iodide Formation:

A suspension of the mesylate (1 eq.) and NaI (3 eq.) in 2-butanone is heated at 85° C. between 3 h and 3 days. After cooling, the mixture is diluted with ether/EA and treated with 10% aq. $Na_2S_2O_3$. After stirring for 10 min, the phases are separated and the aq. layer was washed with EA. The combined org. layers are washed with water (2×), dried over $MgSO_4$ and concentrated under reduced pressure. The residue is triturated with an org. solvent.

Procedure L: Asymmetric Dihydroxylation (*Chem. Rev.* (1994), 94, 2483):

A mixture of olefin (1 mmol) in t-BuOH/$H_2O$ (1:1, 10 mL) at rt is treated with methylsulfonamide (1 eq.) and AD-mix α or β (1.5 g). The mixture is vigorously stirred at rt until completion of reaction, $Na_2S_2O_3$ (1.5 g) is added and the mixture diluted with EA (30 mL). The phases are separated and the aq. phase is extracted once more with EA. The combined org. layers are washed with water and brine, dried over $MgSO_4$ and concentrated. The residue is purified by CC.

Procedure M: TBDMS Protection:

A solution of alcohol (1 eq.) and imidazole (1.1 eq.) in THF (10 mL/mmol) at 0° C. is treated dropwise with a solution of TBDMSCl (1 eq.) in THF. The mixture is stirred at rt until complete conversion. The mixture is diluted with EA, washed with water and brine, dried over $MgSO_4$ and concentrated. The residue is purified by CC.

Procedure N: Mitsunobu Reaction:

To a solution of alcohol (1 eq.) and $PPh_3$ (1.1 eq.) in THF (2 ml/mmol) cooled to 0° C., DPPA (1.1 eq.) and DIAD (1.2 eq.) are added dropwise and the mixture warmed to rt over 1 h and stirred at this temperature until completion of reaction. The mixture is concentrated under reduced pressure and the residue purified by CC.

Procedure N': Mitsunobu Reaction with Staudinger Conditions and Boc Protection:

After performing procedure N with the alcohol (1 eq.) as previously described, the azide is dissolved in THF/water (9:1) and treated with PPh₃ (1.2 eq.) and the resulting solution heated at 50° C. until complete conversion to the amine. The mixture is cooled an treated with Boc₂O (1.5 eq) and stirred at rt overnight. The volatiles are removed under reduced pressure and the residue purified by CC to give the Boc-protected amine.

Preparation A: rac-1-aminomethyl-9-fluoro-1,2-dihydro-pyrrolo[3,2,1-ij]quinolin-4-one A.i. (7-fluoro-2-methoxy-quinolin-8-yl)-acetonitrile To a solution of 8-bromomethyl-7-fluoro-2-methoxy-quinoline (20.0 g, 74 mmol; prepared as in WO 2007/081597) in DMF (530 mL) was added KCN (22.1 g, 339 mmol) and the mixture was stirred at 70° C. overnight. The mixture was concentrated, water and EA were added and the aq. layer was extracted with EA. The combined org layers were washed with brine, dried over MgSO₄ and concentrated to afford the title intermediate as a beige solid (16.13 g, 100% yield).
MS (ESI, m/z): 217.4 [M+H⁺].

A.ii. (7-fluoro-2-methoxy-quinolin-8-yl)-acetic acid methyl ester

To a solution of intermediate A.i (16.1 g, 75 mmol) in MeOH (270 mL) was added TMSCl (32 mL, 3.38 eq) and the solution was stirred at 80° C. for 3 h. The mixture was concentrated under reduced pressure and partitioned between EA and water. The phases were separated and the aq. layer was extracted with EA. The combined org. layers were washed with 2M NaOH, water and brine, dried over MgSO₄, concentrated and purified by CC (DCM) to afford the title intermediate as a colourless solid (8.13 g, 44% yield).
MS (ESI, m/z): 250.2 [M+H⁺].

A.iii. rac-3-(1,3-dioxo-1,3-dihydro-isoindol-2-yl)-2-(7-fluoro-2-methoxy-quinolin-8-yl)-propionic acid methyl ester To a solution of LiHMDS (31.3 mL, 1M in THF) in THF (40 mL) was added at −78° C. a solution of intermediate Aii (6.50 g, 26 mmol) in THF (50 mL) over 10 min. After stirring for 1 h at −78° C., a solution of N-(bromomethyl)phthalimide in THF (50 mL) was added dropwise over 10 min. The mixture was stirred at −78° C. for 1 h and then at rt overnight. The resulting solution was quenched with 1N HCl (260 mL) and extracted with DCM. The combined org. layers were washed with water, dried over MgSO₄, concentrated and purified by CC (Hept/EA 1:1). The resulting solid was triturated with EA to afford the title intermediate as a colourless solid (2.42 g, 23% yield).
MS (ESI, m/z): 409.3 [M+H⁺].

A.iv. rac-3-amino-2-(7-fluoro-2-methoxy-quinolin-8-yl)-propionic acid methyl ester To a suspension of intermediate A.iii (2.40 g, 5.88 mmol) in EtOH (40 mL) was added dropwise hydrazine monohydrate (1.43 mL, 5 eq.) at rt. The mixture was stirred for 2 h at rt and then concentrated. The residue was taken up in EA and 10% citric acid and the layers were separated. The aq. phase was treated another time with EA. The aq. phase was basified with NH₄OH and extracted twice with DCM. The combined DCM phases were dried over MgSO₄ and concentrated to afford the title intermediate as a pale yellow oil (1.62 g, 99% yield).
MS (ESI, m/z): 279.4 [M+H⁺].

A.v. rac-3-tert-butoxycarbonylamino-2-(7-fluoro-2-methoxy-quinolin-8-yl)-propionic acid methyl ester Starting from intermediate A.iv (1.62 g, 5.82 mmol) and using procedure G, the title intermediate was obtained as a colourless solid (1.87 g, 85% yield).
MS (ESI, m/z): 379.2 [M+H⁺].

A.vi. rac-[2-(7-fluoro-2-methoxy-quinolin-8-yl)-3-hydroxy-propyl]-carbamic acid tert-butyl ester Starting from intermediate A.v and using procedure A, the title intermediate was obtained as a colourless solid (1.69 g, 98% yield).
MS (ESI, m/z): 351.3 [M+H⁺].

A.vii. rac-(9-fluoro-4-oxo-1,2-dihydro-4H-pyrrolo[3,2,1-ij]quinolin-1-ylmethyl)-carbamic acid tert-butyl ester Starting from intermediate A.vi (1.68 g, 4.8 mmol) and using procedure H, the title intermediate was obtained as a beige solid (1.56 g, 100% yield).
MS (ESI, m/z): 319.3 [M+H⁺].

A.viii. rac-1-aminomethyl-9-fluoro-1,2-dihydro-pyrrolo[3,2,1-ij]quinolin-4-one

Starting from intermediate A.vii and using procedure B, the title compound was obtained as a pale orange solid (1.08 g, quant.).
¹H NMR (CDCl₃) δ: 7.66 (d, J=9.4 Hz, 1H), 7.40 (dd, J=8.8, 4.7 Hz, 1H), 6.88 (m, 1H), 6.61 (d, J=9.4 Hz, 1H), 4.53 (dd, J=12.9, 9.4 Hz, 1H), 4.36 (dd, J=12.9, 4.7 Hz, 1H), 3.95 (m, 1H), 1.97 (m, 2H), 3.15 (m, 2H).
MS (ESI, m/z): 219.2 [M+H⁺].

Preparation B: rac-1-(2-amino-ethyl)-9-fluoro-1,2-dihydro-pyrrolo[3,2,1-ij]quinolin-4-one B.i. rac-3-cyano-2-(7-fluoro-2-methoxy-quinolin-8-yl)-propionic acid methyl ester LiHMDS (18.4 mL, 1.1 eq., 1M in THF) was added at −78° C. within 15 min to a solution of intermediate Aii (4.17 g, 16.7 mmol) in THF (40 mL). The resulting mixture was stirred at −78° C. for 2 h. Bromoacetonitrile (3.0 g, 1.5 eq.) was added within 20 min and stirring was continued at −78° C. for 2 h. The reaction was quenched with water and extracted with EA (3×). The combined org. phases were washed with brine, dried over MgSO₄, filtered and concentrated. The residue was purified by CC (Hept/EA 2:1 to 1:1) to afford the title intermediate as a yellow solid (3.96 g, 82% yield).
MS (ESI, m/z): 289.4 [M+H⁺].

B.ii. rac-4-amino-2-(7-fluoro-2-methoxy-quinolin-8-yl)-butan-1-ol

To a solution of AlCl₃ (4.0 g, 30 mmol) in ether (150 mL) were added LAH (30 mL, 1M in THF) dropwise within 10 min at −78° C. After stirring for 15 min, a suspension of intermediate B.i (3.94 g, 13.7 mmol) in ether (120 mL) was added within 15 min. The suspension was then stirred at rt for 4 h, cooled to 0° C., quenched with sat. aq. Na$_2$SO$_4$. The mixture was basified with NH$_4$OH and extracted with EA (3×). The combined org. phases were dried over Na$_2$SO$_4$, filtered and concentrated to afford the title intermediate as a yellow oil (3.86 g, quant.) which was used as such in the next step.

MS (ESI, m/z): 265.4 [M+H$^+$].

B.iii. rac-[3-(7-fluoro-2-methoxy-quinolin-8-yl)-4-hydroxy-butyl]-carbamic acid tert-butyl ester Starting from intermediate B.ii (3.85 g, 14.57 mmol) and using procedure G, the title intermediate was obtained as a yellow oil (2.69 g, 51% yield).

MS (ESI, m/z): 365.1 [M+H$^+$].

B.iv. rac-[2-(9-fluoro-4-oxo-1,2-dihydro-4H-pyrrolo[3,2,1-ij]quinolin-1-yl)-ethyl]-carbamic acid tert-butyl ester Starting from intermediate B.iii (2.68 g, 7.4 mmol) and using procedure H, the title intermediate was obtained as a pale orange solid (2.67 g, quant.) which was used as such in the next step.

MS (ESI, m/z): 333.1 [M+H$^+$].

B.v. rac-1-(2-amino-ethyl)-9-fluoro-1,2-dihydro-pyrrolo[3,2,1-ij]quinolin-4-one

Starting from intermediate B.iv and using procedure B, the title compound was obtained after CC (DCM/MeOH/NH$_4$OH 1000:50:4) as a pale orange solid (1.34 g, 72% yield).

$^1$H NMR (CDCl$_3$) δ: 7.68 (d, J=9.3 Hz, 1H), 7.40 (dd, J=8.8, 4.8 Hz, 1H), 6.89 (m, 1H), 6.63 (d, J=9.5 Hz, 1H), 4.56 (dd, J=12.8, 9.3 Hz, 1H), 4.21 (dd, J=12.5, 4.8 Hz, 1H), 4.00 (m, 1H), 2.89 (m, 2H), 2.18 (m, 1H), 1.86 (m, 1H), 1.24 (m, 2H).

MS (ESI, m/z): 233.5 [M+H$^+$].

Preparation C: rac-1-amino-9-fluoro-1,2-dihydro-pyrrolo[3,2,1-ij]quinolin-4-one

C.i. rac-bromo-(7-fluoro-2-methoxy-quinolin-8-yl)-acetic acid methyl ester

NBS (1.6 g) and AIBN (0.1 g) were added to a mixture of intermediate A.ii (1.50 g, 6.0 mmol) in trifluorotoluene (30 mL). The mixture was heated at 80° C. under a sunlamp beam for 5 h. After cooling, the reaction mixture was concentrated. The residue was taken in EA and washed twice with 10% sodium thiosulfate, dried over Na$_2$SO$_4$, filtered and concentrated to dryness. The residue was triturated with Hept/EA to afford the title intermediate as a colourless solid (1.42 g, 72% yield).

MS (ESI, m/z): 328.2 [M+H$^+$].

C.ii. rac-(1,3-dioxo-1,3-dihydro-isoindol-2-yl)-(7-fluoro-2-methoxy-quinolin-8-yl)-acetic acid methyl ester To a solution of intermediate C.i (1.31 g, 4.0 mmol) in dry DMF (25 mL) was added potassium phthalimide (1.24 g, 6.6 mmol) under Ar. The resulting solution was stirred at 120° C. for 1 h. After cooling to rt, water was added and the mixture was extracted with EA. The org. layer was washed with water and brine, dried over MgSO$_4$ and concentrated. The residue was crystallized from Hept/EA to afford the title intermediate as a beige solid (1.04 g, 66% yield).

MS (ESI, m/z): 395.1 [M+H$^+$].

C.iii. rac-amino-(7-fluoro-2-methoxy-quinolin-8-yl)-acetic acid methyl ester

To a solution of intermediate C.ii (714 mg, 1.81 mmol) in EtOH (10 mL) was added dropwise hydrazine monohydrate (0.9 mL, 10 eq.) at rt. The mixture was stirred for 3 h at rt, after which a precipitate had formed, which was filtered off. The filtrate was concentrated under reduced pressure and partitioned between EA and 10% citric acid. The aq. layer was washed once more with EA and then basified using NH$_4$OH. The aq. layer was extracted with DCM and the org. layer was concentrated under reduced pressure to afford the title intermediate as a colourless solid (398 mg, 83% yield).

MS (ESI, m/z): 265.5 [M+H$^+$].

C.iv. rac-tert-butoxycarbonylamino-(7-fluoro-2-methoxy-quinolin-8-yl)-acetic acid methyl ester Starting from intermediate C.iii (380 mg, 1.44 mmol) and using procedure G, the title intermediate was obtained as a colourless solid (560 mg, 100% yield).

MS (ESI, m/z): 365.0 [M+H$^+$].

C.v. rac-[7-(7-fluoro-2-methoxy-quinolin-8-yl)-2-hydroxy-ethyl]-carbamic acid tert-butyl ester Starting from intermediate C.iv and using procedure A, the title intermediate was obtained as a pale yellow solid (473 mg, 92% yield).

MS (ESI, m/z): 337.3 [M+H$^+$].

C.vi. rac-(9-fluoro-4-oxo-1,2-dihydro-4H-pyrrolo[3,2,1-ij]quinolin-1-yl)-carbamic acid tert-butyl ester TEA (0.4 mL, 2 eq.) and MsCl (0.13 mL, 1.2 eq.) were added at 0° C. to a solution of intermediate C.v (470 mg, 1.40 mmol) in DCM (10 mL). The reaction proceeded for 20 min at this temperature. Sodium bicarbonate and DCM were added. The two layers were decanted and the aq. layer was extracted once more with DCM. The combined org. layers were dried over Na$_2$SO$_4$, filtered and concentrated to dryness. The residue was carried on without further purification. A solution of the crude mesylate in toluene (20 mL) was heated at 85° C. overnight. After cooling to rt, water and EA were added and the layers separated. The aq. layer was extracted once more with EA and the combined org. layers were washed with saturated NaHCO$_3$ and concentrated. The residue was triturated with ether/EA to afford the title intermediate as a colourless solid (193 mg, 45% yield).

MS (ESI, m/z): 305.0 [M+H$^+$].

C.vii. rac-1-amino-9-fluoro-1,2-dihydro-pyrrolo[3,2,1-ij]quinolin-4-one

Starting from intermediate C.vi and using procedure B, the title compound was obtained as a beige solid (128 mg, 100% yield).

$^1$H NMR (DMSO-d$_6$) δ: 7.88 (d, J=9.4 Hz, 1H), 7.61 (dd, J=8.5, 5.0 Hz, 1H), 6.99 (dd, J=9.7, 8.8 Hz, 1H), 6.49 (d,

J=9.4 Hz, 1H), 4.92 (dd, J=8.8, 4.4 Hz, 1H), 4.44 (dd, J=12.9, 8.8 Hz, 1H), 3.86 (dd, J=12.6, 3.8 Hz, 1H), 2.29 (s, 2H).
MS (ESI, m/z): 205.1 [M+H$^+$].

Preparation D: (R)-4-amino-4,5-dihydro-pyrrolo[3,2,1-de][1,5]naphthyridin-7-one

D.i. (R)-2-azido-2-(6-methoxy-[1,5]naphthyridin-4-yl)-ethanol and (S)-2-azido-1-(6-methoxy-[1,5]naphthyridin-4-yl)-ethanol A mixture of (S)-2-methoxy-8-oxiranyl-[1,5]naphthyridine (4 g, 20 mmol; prepared as in WO 2006/002047), NH$_4$Cl (2.7 g, 2.5 eq) and NaN$_3$ (3.2 g, 2.5 eq.) in MeOH (100 mL) and water (2 mL) was heated at 65° C. for 4 h, filtered and concentrated in vacuo. The residue was taken up in EA and washed with sat. NaHCO$_3$ and brine, dried over MgSO$_4$ and concentrated. The residue was purified by CC (Hept/EA 1:1, 1:2, EA) to give a 3:2 mixture of regioisomers (5 g, 100% yield) which was used as such in the next step.

D.ii. [(R)-2-hydroxy-1-(6-methoxy-[1,5]naphthyridin-4-yl)-ethyl]-carbamic acid tert-butyl ester A solution of intermediate D.i (mixture of isomers, 5 g, 20.7 mmol) in THF/MeOH 1:1 (200 mL) was hydrogenated over Pd/C (10%, 2.2 g) and 1 bar of H$_2$ for 1 h. The catalyst was filtered off and the filtrate concentrated under reduced pressure. The residue was dissolved in DCM (150 mL) and Boc$_2$O (6.8 g, 1.5 eq.) was added. The mixture was stirred at rt for 2 h, concentrated in vacuo and purified by CC (EA/Hept 2:1, EA, EA/MeOH 9:1) to give the more polar, desired isomer as a colourless foam (2.8 g, 43% yield).
$^1$H NMR (DMSO-d$_6$) δ: 8.72 (d, J=4.4 Hz, 1H), 8.24 (d, J=9.1 Hz, 1H), 7.56 (d, J=4.4 Hz, 1H), 7.33 (d, J=8.5 Hz, 1H), 7.25 (d, J=9.1 Hz, 1H), 5.64 (m, 1H), 3.99 (m, 3H), 3.78 (m, 1H), 3.58 (dd, J=10.8, 7.0 Hz, 1H), 1.35 (s, 9H).

D.iii. ((R)-7-oxo-4,5-dihydro-7H-pyrrolo[3,2,1-de][1,5]naphthyridin-4-yl)-carbamic acid tert-butyl ester Starting from intermediate D.ii (2.8 g, 8.8 mmol) and using procedure H, the title intermediate was obtained as an off-white solid (1.2 g, 47% yield) after CC (EA, EA/MeOH 9:1) and crystallisation from ether/EA.
MS (ESI, m/z): 288.4 [M+H$^+$].

D.iv. (R)-4-amino-4,5-dihydro-pyrrolo[3,2,1-de][1,5]naphthyridin-7-one

A solution of intermediate D.iii (1 g, 3.48 mmol) in dioxane was treated with 4N HCl in dioxane (4 mL). The beige suspension was stirred at rt overnight, filtered and washed with ether and dried to give the dihydrochloride (475 mg, 52% yield). The free base was generated with the use of ion exchange resin (Dowex 50), eluting with methanolic ammonia to give a beige solid (0.3 g).
$^1$H NMR (DMSO-d$_6$) δ: 8.55 (d, J=4.7 Hz, 1H), 7.99 (d, J=9.7 Hz, 1H), 7.65 (dd, J=4.7, 0.9 Hz, 1H), 6.82 (d, J=9.7 Hz, 2H), 5.12 (ddd, J=8.8, 4.1, 0.9 Hz, 1H), 4.53 (dd, J=13.2, 8.8 Hz, 1H), 4.05 (m, 3H).

Preparation E: rac-4-aminomethyl-3-fluoro-4,5-dihydro-pyrrolo[3,2,1-de][1,5]naphthyridin-7-one E.i. 2-(3-fluoro-6-methoxy-[7,5]naphthyridin-4-yl)-malonic acid diethyl ester Diethyl malonate (12.4 mL, 81.7 mmol) was added to a suspension of NaH (3.0 g, 47.9 mmol, 60% in mineral oil) in dioxane (35 mL). The mixture was stirred at rt for 5 min and then heated at 80° C. for 1 h. After cooling to rt, CuBr (1.4 g, 9.6 mmol) and 8-bromo-7-fluoro-2-methoxy-[1,5]naphthyridine (7.0 g, 27.2 mmol, prepared according to WO 2007/122258) were added. The mixture was stirred at 100° C. for 6 h. After cooling to rt, 10% NaHSO$_4$ (100 mL) was added. The mixture was stirred for 30 min at rt. The two layers were decanted and the aq. layer was extracted three times with EA (3×150 mL). The combined org. layers were washed with brine, dried over Na$_2$SO$_4$, filtered and concentrated to dryness. The residue was purified by CC (Hept-EA 3:1 then 1:1) to afford the title intermediate as a yellow oil (8.22 g, 90% yield).
MS (ESI, m/z): 337.3 [M+H$^+$].

E.ii. (3-fluoro-6-methoxy-[7,5]naphthyridin-4-yl)-acetic acid ethyl ester

Water (0.53 mL, 1.2 eq.) and LiCl (2.07 g, 2 eq.) were added to a solution of intermediate E.i (8.22 g, 24.4 mmol) in DMSO (170 mL). The mixture was heated to 110° C. for 16 h and another 2.34 g of LiCl were added. The mixture was further heated at 110° C. for 16 h. The solvent was then evaporated under reduced pressure (bath temperature=70° C., p=0.5 mbar). The residue was partitioned between 10% NaHSO$_4$ (200 mL) and ether (200 mL). The aq. layer was extracted with ether (2×200 mL). The combined org. layers were filtered through a pad of silica gel. The filtrate was concentrated to dryness to afford the title intermediate as a brown oil (5.62 g, 87% yield).
MS (ESI, m/z): 265.3 [M+H$^+$].

E.iii. rac-3-(1,3-dioxo-1,3-dihydro-isoindol-2-yl)-2-(3-fluoro-6-methoxy-[7,5]naphthyridin-4-yl)-propionic acid ethyl ester To a solution of LiHMDS (4.54 mL, 1M in THF) in THF (11 mL) was added at −78° C. a solution of intermediate E.ii (1.0 g, 3.78 mmol) in THF (3 mL) over 10 min. After stirring for 1 h at −78° C. a solution of N-(bromomethyl)phthalimide (1.09 g, 1.2 eq.) in THF (4 mL) was added dropwise over 10 min. The mixture was stirred at −78° C. for 1 h and then at rt overnight. The resulting solution was quenched with 1N HCl and extracted with DCM. The combined org. layers were washed with water, dried over MgSO$_4$, concentrated and purified by CC (Hept/EA 1:1) to afford the title intermediate as an off-white solid (0.361 g, 43% yield).
MS (ESI, m/z): 424.4 [M+H$^+$].

E.iv. rac-3-amino-2-(3-fluoro-6-methoxy-[7,5]naphthyridin-4-yl)-propionic acid ethyl ester To a suspension of intermediate E.iii (368 mg, 0.87 mmol) in EtOH (6 mL) was added dropwise hydrazine monohydrate (0.21 mL, 5 eq.) at rt. The mixture was stirred for 2 h at rt and then concentrated. The residue was taken up in EA and 10% citric acid and the layers were separated. The aq. phase was treated another time with EA. The aq. phase was basified with NH$_4$OH and extracted twice with DCM. The combined DCM phases were dried over MgSO$_4$ and concentrated to afford the title intermediate as a yellow oil (0.21 g, 82% yield).
MS (ESI, m/z): 203.0 [M+H$^+$].

E.v. rac-3-tert-butoxycarbonylamino-2-(3-fluoro-6-methoxy-[7,5]naphthyridin-4-yl)-propionic acid ethyl ester Starting from intermediate E.iv (0.21 g, 0.72 mmol) and using procedure G, the title intermediate was obtained as a pale yellow foam (0.23 g, 83% yield).
MS (ESI, m/z): 394.2[M+H$^+$].

E.vi. rac-[2-(3-fluoro-6-methoxy-[7,5]naphthyridin-4-yl)-3-hydroxy-propyl]-carbamic acid tert-butyl ester Starting from intermediate E.v (0.225 g, 0.57 mmol) and using procedure A, the title intermediate was obtained as a yellow foam (0.20 g, 100% yield).
MS (ESI, m/z): 202.2[M+H$^+$].

E.vii. rac-(3-fluoro-7-oxo-4,5-dihydro-7H-pyrrolo[3,2,1-de][7,5]naphthyridin-4-ylmethyl)-carbamic acid tert-butyl ester Starting from intermediate E.vi (0.20 g, 0.57 mmol) and using procedure H, the title intermediate was obtained as a beige solid (0.204 g, quant.) which was used as such in the next step.
MS (ESI, m/z): 320.2[M+H$^+$].

E.viii. rac-4-aminomethyl-3-fluoro-4,5-dihydro-pyrrolo[3,2,1-de][1,5]naphthyridin-7-one Starting from intermediate E.vii and using procedure B, the title compound was obtained as a brown oil (17 mg, 13% yield).
MS (ESI, m/z): 220.3[M+H$^+$].

Preparation F: rac-4-(2-amino-ethyl)-3-fluoro-4,5-dihydro-pyrrolo[3,2,1-de][1,5]naphthyridin-7-one

F.i. rac-3-cyano-2-(3-fluoro-6-methoxy-[7,5]naphthyridin-4-yl)-propionic acid ethyl ester LiHMDS (4.2 mL, 1.1 eq., 1M in THF) was added at −78° C. within 15 min to a solution of intermediate E.ii (1.5 g, 5.68 mmol) in THF (15 mL). The resulting mixture was stirred at −78° C. for 2 h. Then bromoacetonitrile (1.02 g, 1.5 eq.) was added within 20 min and stirring was continued at −78° C. for 2 h. The reaction was quenched with water and extracted with EA (3×). The combined org. phases were washed with brine, dried over MgSO$_4$, filtered and concentrated. The residue was purified by CC (Hept/EA 1:1) to afford the title intermediate as a yellow oil (1.30 g, 76% yield).
MS (ESI, m/z): 304.2[M+H$^+$].

F.ii. rac-4-amino-2-(3-fluoro-6-methoxy-[7,5]naphthyridin-4-yl)-butan-1-ol

To a solution of AlCl$_3$ (1.3 g, 9.9 mmol) in ether (60 mL) were added LAH (9.9 mL, 1M in THF) dropwise within 10 min at −78° C. After stirring for 15 min a suspension of intermediate F.i (1.36 g, 4.50 mmol) in ether (50 mL) was added within 15 min. The suspension was then stirred for 1 h at −78° C. and for 1 h at −30° C. The mixture was then stirred for 2 h at 0° C., quenched with sat. aq. Na$_2$SO$_4$. The mixture was basified with NH$_4$OH and extracted with EA (3×). The combined org. phases were dried over Na$_2$SO$_4$, filtered and concentrated. The residue was purified by CC (DCM/MeOH/NH$_4$OH 1000:100:8) to afford the title intermediate as a yellow oil (0.30 g, 25% yield).
MS (ESI, m/z): 266.3 [M+H$^+$].

F.iii. rac-[3-(3-fluoro-6-methoxy-[7,5]naphthyridin-4-yl)-4-hydroxy-butyl]-carbamic acid tert-butyl ester Starting from intermediate F.ii (424 mg, 1.60 mmol) and using procedure G, the title intermediate was obtained as a yellow solid (360 mg, 62% yield).
MS (ESI, m/z): 366.2 [M+H$^+$].

F.iv. rac-[2-(3-fluoro-7-oxo-4,5-dihydro-7H-pyrrolo[3,2,1-de][1,5]naphthyridin-4-yl)-ethyl]-carbamic acid tert-butyl ester Starting from intermediate F.iii (360 mg, 0.99 mmol) and using procedure H, the title intermediate was obtained as a brown solid (360 mg, quant.) which was used as such in the next step.
MS (ESI, m/z): 334.1[M+H$^+$].

F.v. rac-4-(2-amino-ethyl)-3-fluoro-4,5-dihydro-pyrrolo[3,2,1-de][1,5]naphthyridin-7-one Starting from intermediate F.iv and using procedure B, the title compound was obtained after CC (DCM/MeOH/NH$_4$OH 1000:100:8) as a yellow solid (130 mg, 49% yield).
MS (ESI, m/z): 234.3[M+H$^+$].

Preparation G: rac-6-amino-5,6-dihydro-pyrrolo[1,2,3-de]quinoxalin-3-one

G.i. rac-2-azido-2-(3-methoxy-quinoxalin-5-yl)-ethanol

A mixture of 2-methoxy-8-oxiranyl-quinoxaline (4.7 g, 23 mmol; prepared as in WO 2004/002490), NH$_4$Cl (2.2 g, 1.8 eq.) and NaN$_3$ (3.8 g, 2.5 eq.) in MeOH (60 mL) was heated at 65° C. for 5 h, filtered and concentrated in vacuo. The residue was taken up in EA and washed with sat. NaHCO$_3$ and brine, dried over MgSO$_4$ and concentrated. The residue was purified by CC (Hept/EA 1:1) to give the desired intermediate as a beige solid (4.4 g, 77% yield).
$^1$H NMR (CDCl$_3$) δ: 8.52 (s, 1H), 8.02 (dd, J=8.5, 1.5 Hz, 1H), 7.77 (dd, J=7.3, 1.5 Hz, 1H), 7.60 (m, 1H), 5.90 (dd, J=7.6, 4.1 Hz, 1H), 4.13 (s, 3H), 4.01 (dd, J=11.4, 3.8 Hz, 1H), 3.87 (dd, J=11.4, 7.9 Hz, 1H).

G.ii. rac-[2-hydroxy-1-(3-methoxy-quinoxalin-5-yl)-ethyl]-carbamic acid tert-butyl ester A solution of intermediate G.i (4.48 g, 18.2 mmol) in THF (100 mL) and water (3.2 mL) was treated with PPh$_3$ (5.3 g, 1.1 eq) and heated at 50° C. for 2 h. The mixture was concentrated to dryness and redissolved in ether/EA. The org. phase was extracted twice with 1M. HCl. The organic phase was discarded and the aqueous phase basified with 6N NaOH and extracted with DCM, dried over MgSO$_4$ and concentrated. The residue was dissolved in DCM (150 mL) and treated with Boc$_2$O (4.8 g, 1.2 eq.). The mixture was stirred at rt for 1 h, concentrated in vacuo and purified by CC (EA/Hept 2:1, EA) to give the desired intermediate as a colourless foam (4.9 g, 84% yield).

$^1$H NMR (DMSO-d$_6$) δ: 8.60 (s, 1H), 7.87 (dd, J=8.2, 1.5 Hz, 1H), 7.70 (m, 1H), 7.58 (m, 1H), 7.26 (m, 1H), 5.64 (td, J=7.6, 4.1 Hz, 1H), 4.76 (t, J=5.9 Hz, 1H), 4.06 (s, 3H), 3.71 (m, 1H), 3.54 (m, 1H), 1.35 (s, 11H).

G.iii. rac-(3-oxo-5,6-dihydro-3H-pyrrolo[1,2,3-de] quinoxalin-6-yl)-carbamic acid tert-butyl ester Starting from intermediate G.ii (4.47 g, 14 mmol) and following procedure H, the reaction mixture was refluxed in DCE (100 mL) for 3 days. The mixture was cooled to rt, diluted with DCM, washed with water, dried over MgSO$_4$ and concentrated. The residue was crystallized from ether/EA to give a mixture of the desired intermediate and the corresponding oxazolidinone as an off-white solid (2.2 g) which was used in the next step without further purification or characterization.

G.iv. rac-6-amino-5,6-dihydro-pyrrolo[1,2,3-de]quinoxalin-3-one

A solution of intermediate G.iii (2.17 g, 3.8 mmol) in DCM (10 mL) was treated with TFA (5 mL). The mixture was stirred at rt for 1 h, concentrated in vacuo and partitioned between DCM and water. The org. phase containing impurities was discarded and the aq. phase basified with NH$_4$OH and extracted several times with DCM/MeOH 9:1. The combined org. phases were dried over MgSO$_4$ and concentrated to give the desired compound as an orange solid (0.36 g, 51% yield).

$^1$H NMR (DMSO-d$_6$) δ: 8.17 (s, 1H), 7.67 (d, J=8.2 Hz, 1H), 7.58 (dt, J=7.3, 0.9 Hz, 1H), 7.32 (dd, J=7.9, 7.3 Hz, 1H), 4.77 (dd, J=8.5, 4.4 Hz, 1H), 4.50 (dd, J=13.2, 8.5 Hz, 1H), 3.86 (dd, J=13.2, 4.4 Hz, 1H).

Preparation H: methanesulfonic acid 2-[(S)-2-oxo-3-(3-oxo-3,4-dihydro-2H-benzo[1,4]oxazin-6-yl)-oxazolidin-5-yl]-ethyl ester

H.i. tert-butyl-dimethyl-[(R)-2-oxiranyl-ethoxy]-silane and (2S)-4-(tert-butyl-dimethyl-silanyloxy)-butane-1,2-diol The title intermediates were prepared in analogy to Kishi et al., *Org. Lett.* (2005), 7, 3997, (intermediate S2-3) via hydrolytic kinetic resolution of (RS)-tert-butyl-dimethyl-(2-oxiranyl-ethoxy)-silane (prepared according to *J. Org. Chem.* (2008), 73, 1093). Two compounds were isolated after CC (Hept/EA 2:1).

First eluting compound: tert-butyl-dimethyl-[(R)-2-oxiranyl-ethoxy]-silane (colourless oil, 25.3 g, 48% yield). $^1$H NMR (CDCl$_3$) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

Second eluting compound: (2S)-4-(tert-butyl-dimethyl-silanyloxy)-butane-1,2-diol (colourless oil, 24.9 g, 43% yield). $^1$H NMR (CDCl$_3$) δ: 3.89 (m, 3H), 3.62 (s, 1H), 3.53 (m, 1H), 3.42 (br. s, 1H), 2.29 (m, 1H), 1.70 (m, 2H), 0.90 (s, 9H), 0.09 (s, 6H).

H.ii. Toluene-4-sulfonic acid (S)-4-(tert-butyl-dimethyl-silanyloxy)-2-hydroxy-butyl ester To a solution of (2S)-4-(tert-butyl-dimethyl-silanyloxy)-butane-1,2-diol (23.9 g, 108 mmol, second eluting compound in H.i and DMAP (2.65 g, 0.2 eq.) in DCM (80 mL) cooled to 0° C. were added TEA (43.8 mL, 2.9 eq.) and a solution of pTsCl (20.7 g, 1.1 eq.) in DCM (15 mL). The mixture was stirred at rt for 5 h, poured into sat. aq. NaHCO$_3$ and extracted with DCM. The org. layer was dried over MgSO$_4$ and concentrated. The residue was purified by CC (Hept/EA 2:1) to afford the title intermediate as a colourless oil (31.3 g, 77% yield).

$^1$H NMR (CDCl$_3$) δ: 7.80 (d, J=7.6 Hz, 2H), 7.34 (d, J=7.6 Hz, 2H), 4.02 (m, 3H), 3.80 (m, 2H), 2.45 (s, 3H), 1.70 (m, 2H), 1.27 (m, 1H), 0.87 (s, 9H), 0.05 (s, 6H).

H.iii. (2S)-tert-butyl-dimethyl-(2-oxiranyl-ethoxy)-silane

2M. NaOH (35 mL) was added to a solution of intermediate H.ii (31.1 g, 83.1 mmol) in THF (350 mL) and the resulting mixture was vigorously stirred at rt for 3 h. The mixture was taken in 1M. NaOH (200 mL) and extracted with TBME (2×). The combined org. layers were washed with water and brine, dried over MgSO$_4$ and concentrated. The resulting oil was purified by Kugelrohr-distillation (ca. 70° C. at 0.1 mbar) to afford the title intermediate as a colourless oil (14.7 g, 87% yield).

$^1$H NMR (CDCl$_3$) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

H.iv. 6-[(S)-4-(tert-butyl-dimethyl-silanyloxy)-2-hydroxy-butylamino]-4H-benzo[1,4]oxazin-3-one A solution of 6-amino-4H-benzo[1,4]oxazin-3-one (5.03 g, 30.6 mmol; commercial) and intermediate H.iii (6.2 g, 1 eq.) in EtOH/H$_2$O (9:1; 180 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure to afford the title intermediate as a brown oil (9.45 g, 84% yield) which was used as such in the next step.

MS (ESI, m/z): 367.2[M+H$^+$].

H.v. 6-{(S)-5-[2-(tert-butyl-dimethyl-silanyloxy)-ethyl]-2-oxo-oxazolidin-3-yl}-4H-benzo[1,4]oxazin-3-one Starting from intermediate H.iv (9.4 g, 25.6 mmol), and using procedure I, the title intermediate was obtained as a beige solid (2.40 g, 24% yield) after CC (DCM/MeOH/NH$_4$OH 1000:50:4).

MS (ESI, m/z): 393.4[M+H$^+$].

H.vi. 6-[(S)-5-(2-hydroxy-ethyl)-2-oxo-oxazolidin-3-yl]-4H-benzo[1,4]oxazin-3-one Starting from intermediate H.v (2.40 g, 6.11 mmol) and using procedure J, the title intermediate was obtained as an off-white solid (0.82 g, 48% yield) after trituration with Et$_2$O/EA.

MS (ESI, m/z): 279.5[M+H$^+$].

H.vii. Methanesulfonic acid 2-[(S)-2-oxo-3-(3-oxo-3,4-dihydro-2H-benzo[1,4]oxazin-6-yl)-oxazolidin-5-yl]-ethyl ester Starting from intermediate H.vi (0.82 g, 2.95 mmol) and using procedure H, the title compound was obtained as a beige solid (0.61 g, 58% yield).

¹H NMR (DMSO-d6) δ: 10.72 (s, 1H), 7.30 (d, J=2.1 Hz, 1H), 6.93 (m, 2H), 4.76 (m, 1H), 4.52 (s, 2H), 4.34 (m, 2H), 4.11 (t, J=8.8 Hz, 1H), 3.72 (m, 1H), 3.20 (s, 3H), 2.17 (m, 2H).

MS (ESI, m/z): 357.3[M+H$^+$].

Preparation I: methanesulfonic acid 2-[(R)-2-oxo-3-(3-oxo-3,4-dihydro-2H-benzo[1,4]oxazin-6-yl)-oxazolidin-5-yl]-ethyl ester I.i. 6-[(R)-4-(tert-butyl-dimethyl-silanyloxy)-2-hydroxy-butylamino]-4H-benzo[1,4]oxazin-3-one A solution of 6-amino-4H-benzo[1,4]oxazin-3-one (commercial; 6.49 g, 39.5 mmol) and tert-butyl-dimethyl-[(R)-2-oxiranyl-ethoxy]-silane (first eluting compound in step H.i; 8.0 g, 39.5 mmol) in EtOH/H$_2$O (9:1; 240 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure and the residue was purified by CC (DCM/MeOH/NH$_4$OH 1000:50:4) to afford the title intermediate as a brown oil (5.82 g, 40% yield).

MS (ESI, m/z): 367.3[M+H$^+$].

I.ii. 6-{(R)-5-[2-(tert-butyl-dimethyl-silanyloxy)-ethyl]-2-oxo-oxazolidin-3-yl}-4H-benzo[1,4]oxazin-3-one Starting from intermediate I.i (5.8 g, 15.8 mmol) and using procedure I, the title intermediate was obtained as a beige solid (2.7 g, 43% yield) after trituration with Et$_2$O/EA/MeOH.

MS (ESI, m/z): 393.5[M+H$^+$].

I.iii. 6-[(R)-5-(2-hydroxy-ethyl)-2-oxo-oxazolidin-3-yl]-4H-benzo[1,4]oxazin-3-one Starting from intermediate I.ii (2.70 g, 6.88 mmol) and using procedure J, the title intermediate was obtained as an off-white solid (1.25 g, 65% yield) after trituration with Et$_2$O/MeOH.

MS (ESI, m/z): 279.5[M+H$^+$].

I.iv. Methanesulfonic acid 2-[(R)-2-oxo-3-(3-oxo-3,4-dihydro-2H-benzo[1,4]oxazin-6-yl)-oxazolidin-5-yl]-ethyl ester Starting from intermediate I.iii (2.1 g, 7.55 mmol) and using procedure H, the title compound was obtained as an off-white solid (1.16 g, 43% yield).

MS (ESI, m/z): 357.2[M+H$^+$].

Preparation J: methanesulfonic acid 2-[(R)-2-oxo-3-(3-oxo-3,4-dihydro-2H-benzo[1,4]thiazin-6-yl)-oxazolidin-5-yl]-ethyl ester J.i. 6-[(R)-4-(tert-butyl-dimethyl-silanyloxy)-2-hydroxy-butylamino]-4H-benzo[1,4]thiazin-3-one A solution of 6-amino-4H-benzo[1,4]thiazin-3-one (10.68 g, 59.3 mmol; commercial) and tert-butyl-dimethyl-[(R)-2-oxiranyl-ethoxy]-silane (first eluting compound in step H.i.; 12.0 g, 59.3 mmol) in EtOH/H$_2$O (9:1; 320 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure to afford the title intermediate as a brown oil (18.8 g, 83% yield) which was used as such in the next step.

MS (ESI, m/z): 383.2[M+H$^+$].

J.ii. 6-{(R)-5-[2-(tert-butyl-dimethyl-silanyloxy)-ethyl]-2-oxo-oxazolidin-3-yl}-4H-benzo[1,4]thiazin-3-one Starting from intermediate J.i (23.5 g, 49.1 mmol) and using procedure I, the title intermediate was obtained as a colourless solid (8.4 g, 42% yield) after CC (DCM/MeOH/NH$_4$OH 1000:50:4).

MS (ESI, m/z): 409.3[M+H$^+$].

J.iii. 6-[(R)-5-(2-hydroxy-ethyl)-2-oxo-oxazolidin-3-yl]-4H-benzo[1,4]thiazin-3-one Starting from intermediate J.ii (8.4 g, 20.6 mmol) and using procedure J, the title intermediate was obtained as an off-white solid (4.79 g, 79% yield) after trituration with Et$_2$O/EA.

MS (ESI, m/z): 295.5[M+H$^+$].

J.iv. Methanesulfonic acid 2-[(R)-2-oxo-3-(3-oxo-3,4-dihydro-2H-benzo[1,4]thiazin-6-yl)-oxazolidin-5-yl]-ethyl ester Starting from intermediate J.iii (4.7 g, 16.0 mmol) and using procedure H, the title compound was obtained as an off-white solid (5.80 g, 98% yield) after CC (DCM/MeOH/NH$_4$OH 1000:50:4).

MS (ESI, m/z): 373.4[M+H$^+$].

Preparation K: 6-[(S)-5-(2-iodo-ethyl)-2-oxo-oxazolidin-3-yl]-4H-benzo[1,4]thiazin-3-one K.i. 6-[(S)-4-(tert-butyl-dimethyl-silanyloxy)-2-hydroxy-butylamino]-4H-benzo[1,4]thiazin-3-one A solution of 6-amino-4H-benzo[1,4]thiazin-3-one (8.0 g, 44.5 mmol; commercial) and intermediate H.iii (9.0 g, 1 eq.) in 9-1EtOH/H$_2$O (250 mL) was heated at 80° C. for 2 days. The mixture was concentrated under reduced pressure. Residual starting aniline could be removed by addition of Et$_2$O/MeOH followed by filtration. The filtrate containing the product was concentrated under reduced pressure to afford the title intermediate as a brown oil (14.58 g, 86% yield) which was used as such in the next step.

MS (ESI, m/z): 383.2[M+H$^+$].

K.ii. 6-{(S)-5-[2-(tert-butyl-dimethyl-silanyloxy)-ethyl]-2-oxo-oxazolidin-3-yl}-4H-benzo[1,4]thiazin-3-one Starting from intermediate K.i (14.5 g, 37.9 mmol) and using procedure I, the title intermediate was obtained as a colourless solid (5.56 g, 36% yield) after CC (DCM/MeOH/NH$_4$OH 1000:50:4).

MS (ESI, m/z): 409.3[M+H$^+$].

K.iii. 6-[(S)-5-(2-hydroxy-ethyl)-2-oxo-oxazolidin-3-yl]-4H-benzo[1,4]thiazin-3-one Starting from intermediate K.ii (5.50 g, 13.6 mmol) and using procedure J, the title intermediate was obtained as an off-white solid (3.08 g, 77% yield) after trituration with Et$_2$O/EA.

MS (ESI, m/z): 295.5[M+H$^+$].

K.iv. Methanesulfonic acid 2-[(S)-2-oxo-3-(3-oxo-3,4-dihydro-2H-benzo[1,4]thiazin-6-A-oxazolidin-5-yl]-ethyl ester Starting from intermediate K.iii (3.0 g, 10.2 mmol) and using procedure H, the title intermediate was obtained as an off-white solid (3.64 g, 96% yield) after trituration with ether.
MS (ESI, m/z): 373.4[M+H$^+$].

K.v. 6-[(S)-5-(2-iodo-ethyl)-2-oxo-oxazolidin-3-yl]-4H-benzo[1,4]thiazin-3-one Starting from intermediate K.iv (2.5 g, 6.7 mmol) and using procedure K, the title compound was obtained as a slightly orange solid (2.11 g, 78% yield) after trituration with Et$_2$O/EA.
$^1$H NMR (DMSO-d6) δ: 10.55 (s, 1H), 7.30 (m, 2H), 7.04 (dd, J=8.5, 2.3 Hz, 1H), 4.68 (m, 1H), 4.10 (t, J=8.8 Hz, 1H), 3.70 (dd, J=8.8, 6.7 Hz, 1H), 3.41 (s, 2H), 3.29 (m, 2H), 2.23 (m, 2H).
MS (ESI, m/z): 405.1[M+H$^+$].

Preparation L: 6-[(R)-5-(2-iodo-ethyl)-2-oxo-oxazolidin-3-yl]-4H-benzo[1,4]thiazin-3-one Starting from intermediate J.iv (3.5 g, 9.4 mmol) and using procedure K, the title compound was obtained as an off-white solid (3.52 g, 93% yield) after trituration with Et$_2$O/EA.
$^1$H NMR (DMSO-d6) δ: 10.55 (s, 1H), 7.30 (m, 2H), 7.04 (dd, J=8.5, 2.3 Hz, 1H), 4.68 (m, 1H), 4.10 (t, J=8.8 Hz, 1H), 3.70 (dd, J=8.8, 6.7 Hz, 1H), 3.41 (s, 2H), 3.29 (m, 2H), 2.23 (m, 2H).
MS (ESI, m/z): 405.0[M+H$^+$].

Preparation M: (RS)-methanesulfonic acid 2-[2-oxo-3-(3-oxo-3,4-dihydro-2H-benzo[1,4]thiazin-6-yl)-oxazolidin-5-yl]-ethyl ester

M.i. (RS)-6-[4-(tert-butyl-dimethyl-silanyloxy)-2-hydroxy-butylamino]-4H-benzo[1,4]thiazin-3-one A solution of 6-amino-4H-benzo[1,4]thiazin-3-one (3.56 g, 19.8 mmol; commercial) and (RS)-tert-butyl-dimethyl-(2-oxiranyl-ethoxy)-silane (prepared according to *J. Org. Chem.* (2008), 73, 1093; 4.0 g, 19.8 mmol) in EtOH/H$_2$O (9:1; 140 mL) was heated at 80° C. for 2 days. The mixture was concentrated under reduced pressure and the residue was purified by CC (DCM/MeOH/NH$_4$OH 1000:50:4) to afford the title intermediate as a brown oil (2.20 g, 29% yield).
MS (ESI, m/z): 383.2[M+H$^+$].

M.ii. (RS)-6-{5-[2-(tert-butyl-dimethyl-silanyloxy)-ethyl]-2-oxo-oxazolidin-3-yl}-4H-benzo[1,4]thiazin-3-one Starting from intermediate M.i (2.20 g, 5.75 mmol) and using procedure I, the title intermediate was obtained as a pale orange solid (1.53 g, 65% yield) after CC (DCM/MeOH/NH$_4$OH 1000:50:4).
MS (ESI, m/z): 409.4[M+H$^+$].

M.iii. (RS)-6-[5-(2-hydroxy-ethyl)-2-oxo-oxazolidin-3-yl]-4H-benzo[1,4]thiazin-3-one Starting from intermediate M.ii (1.50 g, 3.67 mmol) and using procedure J, the title intermediate was obtained as an off-white solid (0.73 g, 68% yield) after trituration with Et$_2$O/EA.
MS (ESI, m/z): 295.1[M+H$^+$].

M.iv. (RS)-methanesulfonic acid 2-[2-oxo-3-(3-oxo-3,4-dihydro-2H-benzo[1,4]thiazin-6-yl)-oxazolidin-5-yl]-ethyl ester Starting from intermediate M.iii (0.70 g, 2.38 mmol) and using procedure H, the title compound was obtained as a beige solid (0.80 g, 90% yield) after CC (DCM/MeOH/NH$_4$OH 1000:50:4).
MS (ESI, m/z): 373.1[M+H$^+$].

Preparation N: 6-((S)-5-iodomethyl-2-oxo-oxazolidin-3-yl)-4H-benzo[1,4]thiazin-3-one

N.i. 6-((S)-3-chloro-2-hydroxy-propylamino)-4H-benzo[1,4]thiazin-3-one

A suspension of 6-amino-4H-benzo[1,4]thiazin-3-one (18.0 g, 100 mmol; commercial) and Ca(OTf)$_2$ (0.5 eq.) in MeCN (800 mL) was heated at 50° for 1 h. (S)-epichlorohydrin (18.5 g, 200 mmol) was added and the mixture was stirred at rt for 72 h and at 45° C. for 24 h. The volatiles were removed under reduced pressure. After aqueous workup and extraction with EA, the title intermediate crystallised from EA to afford a beige solid (17.38 g, 64% yield).
MS (ESI, m/z): 273.2[M+H$^+$].

N.ii. 6-((S)-5-chloromethyl-2-oxo-oxazolidin-3-yl)-4H-benzo[1,4]thiazin-3-one Starting from intermediate N.i (39.3 g, 144 mmol.) and using procedure I, the title intermediate was obtained as a beige solid (34.2 g, 79% yield) after CC (EA/Hept 2:1, EA).
MS (ESI, m/z): 299.1[M+H$^+$].

N.iii. 6-((S)-5-iodomethyl-2-oxo-oxazolidin-3-yl)-4H-benzo[1,4]thiazin-3-one Starting from intermediate N.ii (14.0 g, 46.9 mmol) and using procedure K, the title compound was obtained as a pale beige solid (15.0 g, 82% yield).
$^1$H NMR (DMSO-d6) δ: 10.56 (s, 1H), 7.31 (m, 2H), 7.12 (dd, J=8.5, 2.3 Hz, 1H), 4.71 (m, 1H), 4.14 (t, J=9.1 Hz, 1H), 3.59 (m, 3H), 3.31 (s, 2H).
MS (ESI, m/z): 391.4 [M+H$^+$].

Preparation O: 6-((R)-5-iodomethyl-2-oxo-oxazolidin-3-yl)-4H-benzo[1,4]thiazin-3-one

O.i. 6-((R)-3-chloro-2-hydroxy-propylamino)-4H-benzo[1,4]thiazin-3-one

A solution of 6-amino-4H-benzo[1,4]thiazin-3-one (18.39 g, 102 mmol; commercial) and (R)-epichlorohydrin (8.0 mL, 1 eq.) in EtOH/H$_2$O (9:1; 450 mL) was heated at 80° C. overnight. The mixture was concentrated under reduced pressure. Residual starting aniline could be removed by addition of Et$_2$O/EA followed by filtration. The filtrate containing the product was concentrated under reduced pressure to afford the title intermediate as a beige solid (22.52 g, 81% yield) which was used as such in the next step.
MS (ESI, m/z): 273.2[M+H$^+$].

O.ii. 6-((R)-5-chloromethyl-2-oxo-oxazolidin-3-yl)-4H-benzo[1,4]thiazin-3-one Starting from intermediate O.i (22.0 g, 81.0 mmol) and using procedure I, the title intermediate was obtained as a yellow solid (8.79 g, 36% yield) after trituration with DCM/MeOH.

MS (ESI, m/z): 299.1[M+H$^+$].

O.iii 6-((R)-5-iodomethyl-2-oxo-oxazolidin-3-yl)-4H-benzo[1,4]thiazin-3-one

Starting from intermediate O.ii (8.75 g, 29 mmol) and using procedure K, the title compound was obtained as an off-white solid (9.27 g, 81% yield) after trituration with Et$_2$O/EA.

$^1$H NMR (DMSO-d6) δ: 10.56 (s, 1H), 7.31 (m, 2H), 7.12 (dd, J=8.5, 2.3 Hz, 1H), 4.71 (m, 1H), 4.14 (t, J=9.1 Hz, 1H), 3.59 (m, 3H), 3.31 (s, 2H).

MS (ESI, m/z): 390.9[M+H$^+$].

Preparation P: (S)-3-(2,3-dihydro-benzo[1,4]dioxin-6-yl)-5-iodomethyl-oxazolidin-2-one

P.i. (S)-3-(2,3-dihydro-benzo[1,4]dioxin-6-yl)-5-hydroxymethyl-oxazolidin-2-one A solution of (2,3-dihydro-benzo[1,4]dioxin-6-yl)-carbamic acid benzyl ester (13.0 g, 45.6 mmol) in THF (220 mL) was cooled to −78° C. before the dropwise addition of n-BuLi (29.5 mL of a 2.3M solution in Hex, 1.1 eq.). The mixture was stirred at −78° C. for 1 h and then warmed to −15° C. and treated dropwise with (S)-glycidyl butyrate (7.37 g, 1.1 eq.). The mixture was stirred at rt overnight. Cs$_2$CO$_3$ (tip of a spatula) was added and the mixture heated at 40° C. until complete conversion. The mixture was diluted with EA and washed with a sat. aq. NH$_4$Cl and water. The org. layer was dried over MgSO$_4$ and concentrated. The residue was purified by CC (Hex/EA 2:1, 1:1) to afford the title intermediate as a grey solid (7.04 g, 62% yield).

$^1$H NMR (DMSO-d6) δ: 7.13 (d, J=2.5 Hz, 1H), 6.96 (dd, J=2.5, 8.9 Hz, 1H), 6.86 (d, J=8.9 Hz, 1H), 5.16 (t, J=5.8 Hz, 1H), 4.70-4.50 (m, 1H), 4.30-4.10 (m, 4H), 4.10-3.90 (m, 1H), 4.80-4.70 (m, 1H), 4.70-4.60 (m, 1H), 4.60-4.50 (m, 1H).

P.ii. Methanesulfonic acid (S)-3-(2,3-dihydro-benzo[1,4]dioxin-6-yl)-2-oxo-oxazolidin-5-ylmethyl ester Starting from intermediate P.i (7.0 g, 27.9 mmol) and using procedure H, the title intermediate was obtained as a colourless solid (9.0 g, 98% yield).

MS (ESI, m/z): 330.3 [M+H$^+$].

P.iii. (S)-3-(2,3-dihydro-benzo[1,4]dioxin-6-yl)-5-iodomethyl-oxazolidin-2-one Starting from intermediate P.ii (9.0 g, 27.3 mmol) and using procedure K, the title compound was obtained as an off-white solid (6.91 g, 70% yield) after trituration with Et$_2$O/EA.

$^1$H NMR (CDCl$_3$) δ: 7.07 (d, J=2.6 Hz, 1H), 6.98 (dd, J=9.1, 2.6 Hz, 1H), 6.85 (d, J=8.9 Hz, 1H), 4.68 (m, 1H), 4.24 (s, 4H), 4.10 (t, J=9.1 Hz, 1H), 3.72 (dd, J=9.1, 5.9 Hz, 1H), 3.46 (m, 1H), 3.33 (m, 1H).

MS (ESI, m/z): 362.2[M+H$^+$].

Preparation Q: methanesulfonic acid (S)-2-oxo-3-(3-oxo-3,4-dihydro-2H-benzo[1,4]oxazin-6-yl)-oxazolidin-5-ylmethyl ester

Q.i. 6-[(S)-3-(tert-butyl-dimethyl-silanyloxy)-2-hydroxy-propylamino]-4H-benzo[1,4]oxazin-3-one LiClO$_4$ (7.20 g, 3 eq.) was added to a solution of tert-butyl-dimethyl-((S)-1-oxiranylmethoxy)-silane (commercial; 4.25 g, 22.6 mmol) in MeCN (70 mL). 6-amino-4H-benzo[1,4]oxazin-3-one (commercial; 3.70 g, 1 eq.) was then added and the mixture was stirred at 50° C. for 6 h. The solvent was removed under reduced pressure and the residue was purified by CC (DCM/MeOH/NH$_4$OH 1000/25/2) to afford the title intermediate as a pale brown foam (5.25 g, 66% yield).

MS (ESI, m/z): 353.3[M+H$^+$].

Q.ii. 6-[(S)-5-(tert-butyl-dimethyl-silanyloxymethyl)-2-oxo-oxazolidin-3-yl]-4H-benzo[1,4]oxazin-3-one Starting from intermediate Q.i (10.24 g, 29 mmol) and using procedure I, the title intermediate was obtained as a pale yellow solid (6.30 g, 57% yield) after trituration with ether.

MS (ESI, m/z): 379.2[M+H$^+$].

Q.iii. 6-((S)-5-hydroxymethyl-2-oxo-oxazolidin-3-yl)-4H-benzo[1,4]oxazin-3-one Starting from intermediate Q.ii (6.30 g, 16.6 mmol) and using procedure J, the title intermediate was obtained as a colourless solid (3.49 g, 79% yield) after trituration with EA.

MS (ESI, m/z): 265.5[M+H$^+$].

Q.iv. Methanesulfonic acid (S)-2-oxo-3-(3-oxo-3,4-dihydro-2H-benzo[1,4]oxazin-6-yl)-oxazolidin-5-ylmethyl ester A suspension of intermediate Q.iii (4.93 g, 18.7 mmol) in anhydrous DCM (110 mL) was treated with DIPEA (12.0 mL, 3.75 eq.) and the mixture was cooled to 0° C. Ms$_2$O (4.88 g, 1.5 eq.) was added portionwise. The resulting mixture was stirred at 0° C. for 15 min. Water was added and stirring was continued for 15 min at rt. The precipitated product was filtered, washed with water and DCM. The thus obtained solid was triturated with DCM/MeOH/NH$_4$OH (1000:25:2) to give the title intermediate as a colourless solid (3.785 g, 60% yield).

$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 2H), 3.23 (s, 3H).

MS (ESI, m/z): 343.3[M+H$^+$].

Preparation R: (S)-3-(3-fluoro-4-methyl-phenyl)-5-iodomethyl-oxazolidin-2-one

R.i. (S)-3-(3-fluoro-4-methyl-phenyl)-5-hydroxymethyl-oxazolidin-2-one

A mixture of 3-fluoro-4-methyl-aniline (commercial; 1.25 g, 10 mmol), sat. aq. NaHCO$_3$ (10 mL) and acetone (10 mL) was treated dropwise with benzyl chloroformate (1.70 g, 1.41 mL, 1 eq.). After CO$_2$ evolution ceased, the mixture was partitioned between EA and sat. aq. NaHCO$_3$, the org. layer was dried over MgSO$_4$ and concentrated under reduced pressure. The resulting benzyl carbamate was dissolved in THF (50 mL) and cooled under argon to −78° C. n-BuLi (2.5M in Hex, 6.45 mL, 1.1 eq.) was added dropwise, and the resulting solution was stirred for 1 h at that temperature. The reaction was then allowed to warm to −15° C. at which (S)-glycidyl butyrate (1.69 mL, 1.1 eq.) was added dropwise. The mixture was stirred at rt overnight. A tip of a spatula of $Cs_2CO_3$ was added, and the mixture was stirred at rt for 3 h. $NH_4Cl$ and EA were added and the phases were separated. The aq. phase was extracted once more with EA and the combined org. extracts were washed several times with sat. aq. $NH_4Cl$, then with brine, dried over $Na_2SO_4$ and concentrated. The orange solid obtained was triturated with EA to afford the title intermediate as a pale yellow solid (1.18 g, 53% yield).
MS (ESI, m/z): 226.3[M+H$^+$].

R.ii. Methanesulfonic acid (S)-3-(3-fluoro-4-methyl-phenyl)-2-oxo-oxazolidin-5-ylmethyl ester Starting from intermediate R.i (4.70 g, 20.9 mmol) and following procedure H the title intermediate was obtained as a yellow solid (6.37 g, 100% yield) after trituration in ether.
$^1$H NMR (CDCl$_3$) δ: 7.36 (dd, J=11.7, 2.3 Hz, 1H), 7.13 (m, 2H), 4.91 (m, 1H), 4.46 (m, 2H), 4.13 (t, J=9.1 Hz, 1H), 3.92 (dd, J=9.1, 6.2 Hz, 1H), 3.10 (s, 3H), 2.25 (d, J=1.8 Hz, 3H).
MS (ESI, m/z): 330.3[M+H$^+$].

R.iii. (S)-3-(3-fluoro-4-methyl-phenyl)-5-iodomethyl-oxazolidin-2-one

Starting from intermediate R.ii (6.30 g, 20.8 mmol) and using procedure K, the title compound was obtained as a slightly pink solid (6.3 g, 91% yield) after trituration with Et$_2$O/EA.
$^1$H NMR (CDCl$_3$) δ: 7.36 (dd, J=12.0, 2.1 Hz, 1H), 7.16 (m, 2H), 4.73 (m, 1H), 4.14 (m, 1H), 3.76 (dd, J=9.4, 6.2 Hz, 1H), 3.48 (m, 1H), 3.35 (dd, J=10.3, 8.2 Hz, 1H), 2.25 (d, J=1.8 Hz, 3H).
MS (ESI, m/z): 335.8 [M+H$^+$].

Preparation S: (RS)-methanesulfonic acid 2-[3-(3-fluoro-4-methyl-phenyl)-2-oxo-oxazolidin-5-yl]-ethyl ester S.i. (RS)-4-(tert-butyl-dimethyl-silanyloxy)-1-(3-fluoro-4-methyl-phenylamino)-butan-2-ol To a solution of (RS)-tert-butyl-dimethyl-(2-oxiranyl-ethoxy)-silane (4.4 g, 200 mmol; prepared as in *J. Org. Chem.* (2008), 73, 1093) in MeCN (60 mL) was added LiClO$_4$ (6.31 g, 3 eq.). 3-fluoro-4-methylaniline (commercial; 2.28 g, 0.92 eq.) was added and the mixture was stirred at 50° C. for 5 h. The solvent was removed under reduced pressure and the residue was purified by CC (DCM/MeOH/NH$_4$OH 1000:25:2) to afford the title intermediate as a brown oil (5.56 g, 86% yield).
MS (ESI, m/z): 328.4[M+H$^+$].

S.ii. (RS)-5-[2-(tert-butyl-dimethyl-silanyloxy)-ethyl]-3-(3-fluoro-4-methyl-phenyl)-oxazolidin-2-one Starting from intermediate S.i (2.50 g, 7.63 mmol) and using procedure I, the title intermediate was obtained as an off-white solid (1.22 g, 45% yield) after trituration with ether/EA.
MS (ESI, m/z): 354.2[M+H$^+$].

S.iii. (RS)-3-(3-fluoro-4-methyl-phenyl)-5-(2-hydroxy-ethyl)-oxazolidin-2-one

Starting from intermediate S.ii (1.20 g, 3.40 mmol) and using procedure J, the title intermediate was obtained as a colourless solid (0.478 g, 59% yield) after trituration with Et$_2$O/EA/DCM.
MS (ESI, m/z): 240.1[M+H$^+$].

S.iv. (RS)-methanesulfonic acid 2-[3-(3-fluoro-4-methyl-phenyl)-2-oxo-oxazolidin-5-yl]-ethyl ester Starting from intermediate S.iii (470 mg, 2.0 mmol) and using procedure H, the title compound was obtained as an off-white solid (0.60 g, 96% yield) after CC (DCM/MeOH/NH$_4$OH 1000:50:4).
MS (ESI, m/z): 318.2[M+H$^+$].

Preparation T: 3-[(R)-2-oxo-3-(3-oxo-3,4-dihydro-2H-benzo[1,4]oxazin-6-yl)-oxazolidin-5-yl]-propionaldehyde T.i. 6-[(R)-5-(tert-butyl-dimethyl-silanyloxy)-2-hydroxy-pentylamino]-4H-benzo[1,4]oxazin-3-one A mixture of (R)-tert-butyl-dimethyl-(3-oxiranyl-propoxy)-silane (13 g, 60 mmol; prepared according to *Org. Lett.* (2005), 7, 3997) and 6-amino-4H-benzo[1,4]oxazin-3-one (9.9 g) in EtOH/H$_2$O (9:1, 325 mL) was heated at reflux overnight. The volatiles were removed under reduced pressure and the residue purified by CC (Hept/EA 1:1) to give the desired intermediate as a brown oil (8.9 g, 39% yield).
MS (ESI, m/z): 318.2[M+H$^+$].

T.ii. 6-{(R)-5-[3-(tert-butyl-dimethyl-silanyloxy)-propyl]-2-oxo-oxazolidin-3-yl}-4H-benzo[1,4]oxazin-3-one Starting from intermediate T.i (8.8 g, 23 mmol) and using procedure I, the title intermediate was obtained as an orange solid (9.8 g, quant.) after crystallisation from Hept/EA.
MS (ESI, m/z): 407.6[M+H$^+$].

T.iii. 6-[(R)-5-(3-hydroxy-propyl)-2-oxo-oxazolidin-3-yl]-4H-benzo[1,4]thiazin-3-one Starting from intermediate T.ii (9.8 g, 24 mmol) and using procedure J, the title intermediate was obtained as a yellowish solid (5.0 g, 71% yield) after CC (EA, EA/MeOH 9:1) followed by crystallisation from ether/EA.
MS (ESI, m/z): 293.3[M+H$^+$].

T.iv. 3-[(R)-2-oxo-3-(3-oxo-3,4-dihydro-2H-benzo[1,4]oxazin-6-yl)-oxazolidin-5-yl]-propionaldehyde To a solution of intermediate T.iii (292 mg, 1 mmol) and DIPEA (0.5 mL, 3 eq.) in DCM (5 mL) at rt was added dropwise a solution of SO$_3$.pyridine complex (318 mg, 2 eq.) in DMSO (1 mL) over 10 min. The mixture was stirred at rt for 2 h, diluted with DCM and washed with water. The org. phase was washed several times with water, dried over MgSO$_4$ and concentrated to give the desired aldehyde as a beige solid (260 mg, 90% yield).
$^1$H NMR (DMSO-d6) δ: 10.71 (s, 1H) 9.68 (d, J=0.9 Hz, 1H), 7.31 (s, 1H), 6.92 (m, 2H), 4.64 (m, 1H), 4.52 (d, J=1.2 Hz, 2H), 4.07 (m, 1H), 3.66 (m, 1H), 2.60 (m, 2H), 1.98 (m, 2H).

Preparation U: 3-[(R)-2-oxo-3-(3-oxo-3,4-dihydro-2H-benzo[1,4]thiazin-6-yl)-oxazolidin-5-yl]-propionaldehyde

U.i. 6-[(R)-5-(tert-butyl-dimethyl-silanyloxy)-2-hydroxy-pentylamino]-4H-benzo[1,4]thiazin-3-one A mixture of (R)-tert-butyl-dimethyl-(3-oxiranyl-propoxy)-silane (13 g, 60 mmol; prepared as in *Org. Lett.* (2005), 7, 3997) and 6-amino-4H-benzo[1,4]thiazin-3-one (10.8 g) in EtOH/H$_2$O (9:1, 325 mL) was heated at reflux overnight. The volatiles were removed under reduced pressure and the residue purified by CC (Hept/EA 1:1) to give the desired intermediate as a brown oil (6.8 g, 28% yield).
MS (ESI, m/z): 397.1 [M+H$^+$].

U.ii. 6-{(R)-5-[3-(tert-butyl-dimethyl-silanyloxy)-propyl]-2-oxo-oxazolidin-3-yl}-4H-benzo[1,4]thiazin-3-one Starting from intermediate U.i (6.7 g, 17 mmol) and using procedure I, the title intermediate was obtained as an orange solid (7.8 g, quant.) after crystallisation from Hept/EA.
MS (ESI, m/z): 423.4[M+H$^+$].

U.iii. 6-[(R)-5-(3-hydroxy-propyl)-2-oxo-oxazolidin-3-yl]-4H-benzo[1,4]thiazin-3-one Starting from intermediate U.ii (7.1 g, 16.8 mmol) and using procedure J, the title intermediate was obtained as a yellowish solid (3.1 g, 60% yield) after CC (EA. EA/MeOH 9:1).
MS (ESI, m/z): 309.1[M+H$^+$].

U.iv. 3-[(R)-2-oxo-3-(3-oxo-3,4-dihydro-2H-benzo[1,4]thiazin-6-yl)-oxazolidin-5-yl]-propionaldehyde To a solution of intermediate U.iii (500 mg, 1.6 mmol) and DIPEA (0.83 mL, 3 eq.) in DCM (7 mL) at rt was added dropwise a solution of SO$_3$.pyridine complex (516 mg, 2 eq.) in DMSO (1.7 mL) over 10 min. The mixture was stirred at rt for 2 h, diluted with DCM and washed with water. The org. phase was washed several times with water, dried over MgSO$_4$ and concentrated to give the desired aldehyde after trituration with ether/EA as a beige solid (440 mg, 88% yield).
MS (ESI, m/z): 307.5[M+H$^+$].

Preparation V: (R)-4-aminomethyl-4,5-dihydro-pyrrolo[3,2,1-de][1,5]naphthyridin-7-one

V.i. 2-(6-methoxy-[1,5]naphthyridin-4-yl)-propane-1,3-diol

A mixture of 2-methoxy-8-methyl-[1,5]naphthyridine (2.90 g, 16.6 mmol; prepared according to WO 00/21948) and formaldehyde (37% in water, 7.8 mL) was heated at 100° C. for 3 days and at 110° C. for 2 days. After cooling to rt, the mixture was concentrated, taken up in MeOH and concentrated again. The residue was purified by CC (DCM/MeOH/NH$_4$OH 1000:100:8) to afford the title intermediate as a pale beige solid (2.78 g, 71% yield).
$^1$H NMR (DMSO-d$_6$) δ: 8.67 (d, J=4.4 Hz, 1H), 8.22 (d, J=9.1 Hz, 1H), 7.51 (d, J=4.4 Hz, 1H), 7.22 (d, J=9.1 Hz, 1H), 4.56 (m, 2H), 4.00 (s, 3H), 3.84 (m, 3H).

V.ii. Acetic acid (S)-3-hydroxy-2-(6-methoxy-[1,5]naphthyridin-4-yl)-propyl ester A 0.5M solution of intermediate V.i (5.45 g, 23.3 mmol) in vinyl acetate (60 mL) was treated with powdered 3 Å molecular sieves (350 mg) and stirred at rt for 15 min under a nitrogen atmosphere. Lipase from *Candida antarctica* (2.69 g, bound to acrylic resin) was added and stirring was continued for 4 h at rt. The mixture was filtered; the filter cake was washed with EA and the filtrate was concentrated. The residue was purified by CC (DCM/MeOH/NH$_4$OH 1000:25:2) to afford the title intermediate as a colourless oil (2.70 g, 42% yield). The corresponding diacetate (3.81 g, 51% yield) was then afterwards cleaved back to the diol and used again as substrate.
$^1$H NMR (CDCl$_3$) δ: 8.72 (d, J=4.4 Hz, 1H), 8.23 (d, J=9.1 Hz, 1H), 7.46 (d, J=4.4 Hz, 1H), 7.14 (d, J=9.1 Hz, 1H), 4.65 (m, 2H), 4.22 (m, 1H), 4.07 (m, 4H), 2.96 (m, 1H), 2.04 (s, 1H).
MS (ESI, m/z): 277.3[M+H$^+$].
Alternative α:

V.iii. Acetic acid (S)-7-oxo-4,5-dihydro-7H-pyrrolo[3,2,1-de][1,5]naphthyridin-4-ylmethyl ester TEA (2.1 mL, 2 eq.) and MsCl (0.70 mL, 1.2 eq.) were added at 0° C. to a solution of intermediate V.ii (2.05 g, 7.41 mmol) in DCM (40 mL). The reaction was stirred for 20 min at this temperature. DCE (40 mL) was added and the solution was slowly warmed to 60° C. and let stir at this temperature for 4 h. After cooling to rt, water was added and the two layers were decanted and the aq. layer was extracted once more with DCM. The combined org. layers were concentrated to dryness. The residue was triturated with TBME to afford the title intermediate as a grey solid (1.40 g, 77% yield).
$^1$H NMR (CDCl$_3$) δ: 8.52 (d, J=4.7 Hz, 1H), 7.93 (d, J=9.7 Hz, 1H), 7.34 (d, J=4.7 Hz, 1H), 6.89 (d, J=9.7 Hz, 1H), 4.56 (dd, J=12.9, 9.4 Hz, 1H), 4.36 (m, 2H), 4.27 (dd, J=13.2, 5.0 Hz, 1H), 4.10 (m, 1H), 2.06 (s, 3H).
MS (ESI, m/z): 245.2[M+H$^+$].

V.iv. (S)-4-hydroxymethyl-4,5-dihydro-pyrrolo[3,2,1-de][1,5]naphthyridin-7-one K$_2$CO$_3$ (0.40 g, 0.5 eq.) was added to a solution of intermediate V.iii (1.40 g, 5.73 mmol) cooled to 0° C. and the resulting mixture was vigorously stirred at 0° C. for 30 min. The mixture was concentrated and the residue was purified by CC (DCM/MeOH/NH$_4$OH 1000:100:8). The product was triturated with EA/TBME to afford the title intermediate as a grey solid (0.98 g, 85% yield).
MS (ESI, m/z): 203.0[M+H$^+$].

V.v. Methanesulfonic acid (S)-7-oxo-4,5-dihydro-7H-pyrrolo[3,2,1-de][1,5]naphthyridin-4-ylmethyl ester A solution of intermediate V.iv (0.33 g, 1.63 mmol) and TEA (0.57 mL, 2.5 eq.) in anhydrous DCM (15 mL) was cooled to 0° C. and treated dropwise with MsCl (0.19 mL, 1.5 eq.). The resulting mixture was stirred at 0° C. for 1 h. Water and DCM were added and the phases separated. The org. layer was dried over MgSO$_4$ and concentrated under reduced pressure to afford the title intermediate as a colourless gum (0.40 g, 88% yield) which was used in the next step without further purification.
MS (ESI, m/z): 281.3[M+H$^+$].

V.vi. (R)-4-aminomethyl-4,5-dihydro-pyrrolo[3,2,1-de][1,5]naphthyridin-7-one A solution of intermediate V.v (0.35 g, 1.24 mmol) in DMF (12 mL) was treated with sodium azide (0.65 g, 8 eq.) and stirred at 50° C. for 1.5 h. After cooling to rt, water was added and the mixture was extracted with DCM. The org. layer was dried over MgSO$_4$ and concentrated under reduced pressure to give a yellow oil (crude azide) which was taken up in THF (1.5 mL). PPh$_3$ (390 mg) and water (0.13 mL) were added and the mixture was heated at 50° C. for 3 h. The reaction mixture was concentrated to dryness and the residue was purified by CC (DCM/MeOH/NH$_4$OH 1000:100:8) to afford the title intermediate as a yellow oil (30 mg, 12% yield).
MS (ESI, m/z): 202.2[M+H$^+$].
Alternative β:

V.ii. Acetic acid (R)-3-(tert-butyl-dimethyl-silanyloxy)-2-(6-methoxy-[1,5]naphthyridin-4-yl)-propyl ester To a solution of intermediate V.ii (1.66 g) in DCM (50 mL) were added imidazole (1 eq.) and TBDMSCl (1 eq.). The mixture was stirred at rt for 3 h. Another eq. of each reagent was added and the reaction was complete after 15 min. Water was added and the mixture was extracted with DCM. The org. layer was dried over MgSO$_4$ and concentrated to afford the title intermediate as a colourless oil (2.36 g, 100% yield).
MS (ESI, m/z): 391.5[M+H$^+$].

V.iii. (R)-3-(tert-butyl-dimethyl-silanyloxy)-2-(6-methoxy-[1,5]naphthyridin-4-yl)-propan-1-ol A suspension of intermediate V.vii (2.36 g) and K$_2$CO$_3$ (3.34 g) in MeOH (50 mL) was vigorously stirred at rt for 30 min. Water and DCM were added. The two layers were decanted and the aq. layer was extracted once more with DCM. The combined org. layers were dried over MgSO$_4$, filtered and concentrated to dryness to afford the title intermediate as a colourless oil (2.1 g, 100% yield).
MS (ESI, m/z): 349.1[M+H$^+$].

V.ix. 8-[(R)-2-azido-1-(tert-butyl-dimethyl-silanyloxymethyl)-ethyl]-2-methoxy-[1,5]naphthyridine Starting from intermediate V.viii (2.09 g) and following procedure N, the title intermediate was isolated as a colourless oil (1.79 g, 80% yield).
MS (ESI, m/z): 374.1[M+H$^+$].

V.x. [(R)-3-(tert-butyl-dimethyl-silanyloxy)-2-(6-methoxy-[1,5]naphthyridin-4-yl)-propyl]-carbamic acid tert-butyl ester Starting from intermediate V.ix (1.79 g) and using procedure F and procedure G, the title intermediate was obtained as a dark oil (2.14 g, 100% yield).
MS (ESI, m/z): 448.2[M+H$^+$].

V.xi. [(R)-3-hydroxy-2-(6-methoxy-[1,5]naphthyridin-4-yl)-propyl]-carbamic acid tert-butyl ester Starting from intermediate V.x (2.14 g) and using procedure J, the title intermediate was obtained as a colourless solid (1.14 g, 72% yield).
MS (ESI, m/z): 334.2[M+H$^+$].

V.xii. ((R)-7-oxo-4,5-dihydro-7H-pyrrolo[3,2,1-de][1,5]naphthyridin-4-ylmethyl)-carbamic acid tert-butyl ester Starting from intermediate V.xi (1.14 g) and using procedure H followed by heating at 60° C. for 2 h in DCE, the title intermediate was obtained as a colourless solid (0.91 g, 88% yield).
MS (ESI, m/z): 302.2[M+H$^+$].

V.xiii. (R)-4-aminomethyl-4,5-dihydro-pyrrolo[3,2,1-de][1,5]naphthyridin-7-one Starting from intermediate V.xi (0.91 g) and using procedure B, the title intermediate was obtained as a pale yellow solid (0.496 g, 82% yield).
MS (ESI, m/z): 202.1[M+H$^+$].

Preparation W: (RS)-methanesulfonic acid 7-oxo-4,5-dihydro-7H-pyrrolo[3,2,1-de][1,5]naphthyridin-4-ylmethyl ester

W.i. 3-(tert-butyl-dimethyl-silanyloxy)-2-(6-methoxy-[1,5]naphthyridin-4-yl)-propan-1-ol A solution of the intermediate V.i (1.10 g) in THF (55 mL) was treated at 0° C. with imidazole (351 mg) and a solution of TBDMSCl (707 mg) in THF (10 mL). After stirring at rt for 2 days, the reaction mixture was diluted with EA and extracted with water and brine. The org phase was dried over MgSO$_4$ and purified by CC (Hept/EA 1.1 to 0:1), affording a colourless oil (570 mg; 35% yield).
MS (ESI, m/z): 349.2[M+H$^+$].

W.ii. Methanesulfonic acid 3-(tert-butyl-dimethyl-silanyloxy)-2-(6-methoxy-[1,5]naphthyridin-4-yl)-propyl ester Starting from intermediate W.i (1.4 g) and MsCl (0.374 mL) and using procedure H, the title compound was obtained as a yellow oil (1.4 g, 81% yield).
$^1$H NMR (CDCl$_3$) δ: 8.72 (d, J=4.4 Hz, 1H) 8.23 (d, J=9.1 Hz, 1H), 7.50 (d, J=4.7 Hz, 1H), 7.15 (d, J=9.1 Hz, 1H), 4.78 (m, 2H), 4.44 (m, 1H), 4.05 (m, 5H), 2.90 (s, 3H), 0.87 (m, 12H), −0.02 (d, J=8.5 Hz, 6H).

W.iii. 4-(tert-butyl-dimethyl-silanyloxymethyl)-4,5-dihydro-pyrrolo[3,2,1-de][1,5]naphthyridin-7-one A solution of intermediate W.ii (1.4 g) in DCE (20 mL) was heated at 85° C. overnight. The reaction mixture was evaporated under reduced pressure. The residue was purified by CC (EA to EA/MeOH 9:1), affording a colourless oil (340 mg; 33% yield).
MS (ESI, m/z): 317.1[M+H$^+$].

W.iv. 4-hydroxymethyl-4,5-dihydro-pyrrolo[3,2,1-de][1,5]naphthyridin-7-one

Starting from intermediate W.iii (330 mg) and using procedure J, the title compound was obtained as a colourless solid (90 mg, 43% yield).
MS (ESI, m/z): 203.2[M+H$^+$].

W.v. (RS)-methanesulfonic acid 7-oxo-4,5-dihydro-7H-pyrrolo[3,2,1-de][1,5]naphthyridin-4-ylmethyl ester Starting from intermediate W.iv (90 mg) and using procedure H, the title compound was obtained as a yellow solid (90 mg, 72% yield).

Analytical data identical to the (S)-enantiomer (intermediate V.v).

Preparation X: rac-1-amino-1,2-dihydro-pyrrolo[3,2,1-ij]quinolin-4-one

X.i. 2-azido-2-(2-methoxy-quinolin-8-yl)-ethanol

A solution of 2-methoxy-8-(2-oxiranyl)-quinoline (900 mg; prepared according to WO 2006/046552) in dioxane/water (5:1; 60 mL) was reacted with $NaN_3$ at 90° C. for 5 h. The solvents were removed under reduced pressure and the residue was purified by CC (Hex/EA 2:1 to 1:1), affording a yellow oil (480 mg; 44% yield).
MS (ESI, m/z): 245.0[M+H$^+$].

X.ii. rac-2-amino-2-(2-methoxy-quinolin-8-yl)-ethanol

Starting from intermediate X.i (470 mg) and using procedure F, the title compound was obtained as a yellow oil (450 mg; 100% yield).
MS (ESI, m/z): 219.1[M+H$^+$].

X.iii. rac-[2-hydroxy-1-(2-methoxy-quinolin-8-yl)-ethyl]-carbamic acid tert-butyl ester Starting from intermediate X.ii (430 mg) and using procedure G, the title compound was obtained as a yellow oil (720 mg; quant.)
MS (ESI, m/z): 319.1[M+H$^+$].

X.iv. rac-methanesulfonic acid 2-tert-butoxycarbonylamino-2-(2-methoxy-quinolin-8-yl)-ethyl ester Starting from intermediate X.iii (700 mg) and using procedure H, the title compound was obtained as a yellow oil (900 mg, quant.).
MS (ESI, m/z): 397.0 [M+H$^+$].

X.v. rac-(4-oxo-1,2-dihydro-4H-pyrrolo[3,2,1-ij]quinolin-1-yl)-carbamic acid tert-butyl ester A solution of intermediate X.iv (850 mg) in DCE (10 mL) was heated at 85° C. overnight. The solvent was evaporated under reduced pressure, affording a brown oil (780 mg; quant.) which was used without further purification in the next step.
MS (ESI, m/z): 287.1[M+H$^+$].

X.vi. rac-1-amino-1,2-dihydro-pyrrolo[3,2,1-ij]quinolin-4-one

Starting from intermediate X.v (572 mg) and using procedure B, the title compound was obtained as a beige solid (230 mg; 62% yield).
MS (ESI, m/z): 187.0[M+H$^+$].

Preparation Y: (S)-4-amino-4,5-dihydro-pyrrolo[3,2,1-de][1,5]naphthyridin-7-one

Y.i. (S)-2-azido-2-(6-methoxy-[1,5]naphthyridin-4-yl)-ethanol

This compound was prepared in analogy to Preparation X, step Xi, but starting from 2-methoxy-8-[(2R)-2-oxiranyl]-1,5-naphthyridine (prepared according to WO 02/08224).

The compound was purified by CC (Hept/EA 1:1 to 2:1 to 0:1), affording a yellow solid (3.9 g (87%; contaminated by its region isomer).
MS (ESI, m/z): 246.3[M+H$^+$].

Y.ii. (S)-2-amino-2-(6-methoxy-[1,5]naphthyridin-4-yl)-ethanol

Starting from intermediate Y.i (3.90 g) and using procedure F, the title compound was obtained as a yellow oil (2.80 g, 80% yield).
MS (ESI, m/z): 220.0[M+H$^+$].

Y.iii. (S)-[2-hydroxy-1-(6-methoxy-[1,5]naphthyridin-4-yl)-ethyl]-carbamic acid tert-butyl ester Starting from intermediate Y.ii (2.90 g) and using procedure G, the title compound was obtained as a colourless foam (1.40 g, 33% yield).
MS (ESI, m/z): 320.1[M+H$^+$].

Y.iv. ((S)-7-oxo-4,5-dihydro-7H-pyrrolo[3,2,1-de][1,5]naphthyridin-4-yl)-carbamic acid tert-butyl ester Starting from the intermediate Y.iii (1.40 g) and using procedure H followed by heating at 80° C. for 7 h, the title compound was obtained as a beige solid (570 mg, 45% yield).
MS (ESI, m/z): 288.4[M+H$^+$].

Y.v. (S)-4-amino-4,5-dihydro-pyrrolo[3,2,1-de][1,5]naphthyridin-7-one

Starting from intermediate Y.iv (570 mg) and using procedure B, the title compound was obtained as a beige solid (470 mg, quant.).
$^1$H NMR (CDCl$_3$) δ: 8.43 (d, J=4.7 Hz, 1H), 7.79 (d, J=9.7 Hz, 1H), 7.43 (dd, J=4.7, 0.9 Hz, 1H), 6.74 (d, J=10.0 Hz, 1H), 4.91 (m, 1H), 4.52 (dd, J=13.2, 8.5 Hz, 1H), 4.02 (dd, J=13.5, 4.7 Hz, 1H).

Preparation Z: (S)-6-amino-5,6-dihydro-pyrrolo[1,2,3-de]quinoxalin-3-one

Z.i. 2-methoxy-8-vinyl-quinoxaline

A suspension of methyltriphenylphosphonium bromide (22.78 g) in THF (200 mL) was treated with tBuOK (7.15 g) and further stirred at rt for 1 h. The mixture was cooled to 0° C. and treated with a solution of 3-methoxy-5-quinoxalinecarboxaldehyde (10.0 g; prepared according to WO 2006/021448) in THF (100 mL). The mixture was further stirred at rt for 3 h, diluted with ether and washed with water and an aq. sat. NH$_4$Cl solution. The org. phase was dried over MgSO$_4$ and concentrated under reduced pressure. The residue was crystallized from ether and the crystals were filtered off. The mother liquor was purified by CC (Hex/EA 1:1), affording a light orange solid (8.70 g; 88% yield).

¹H NMR (CDCl₃) δ: 8.48 (s, 1H), 7.92 (m, 2H), 7.78 (dd, J=17.9, 11.1 Hz, 1H), 7.54 (m, 1H), 6.03 (dd, J=17.9, 1.5 Hz, 1H), 5.48 (dd, J=11.4, 1.5 Hz, 1H), 4.12 (s, 3H).

Z.ii. (R)-1-(3-methoxy-quinoxalin-5-yl)-ethane-1,2-diol

Starting from intermediate Z.i (8.70 g) and using procedure L with AD-mix β, the title compound was obtained as a beige solid (7.60 g, 74% yield) after crystallization from ether/EA.
MS (ESI, m/z): 221.1[M+H⁺].

Z.iii. (R)-2-(tert-butyl-dimethyl-silanyloxy)-1-(3-methoxy-quinoxalin-5-yl)-ethanol Starting from intermediate Z.ii (7.60 g) and using procedure M, the title compound was obtained as a yellow oil (8.80 g, 76% yield).
MS (ESI, m/z): 335.0[M+H⁺].

Z.iv. (S)-2-amino-2-(3-methoxy-quinoxalin-5-yl)-ethanol

Starting from intermediate Z.iii (8.80 g) and using procedure N, the desired azide (20 g) was obtained, which was used without further purification in the next reaction. A solution of this azide (20 g, contaminated with PPh₃O) in THF (228 mL) was then treated with PPh₃ (7.50 g) and water (4.68 mL). The reaction mixture was further stirred at 50° C. for 2 days, and then extracted with 3M. HCl. The aq. phase was basified with aq. NaOH solution and extracted with EA. The org layer was dried over MgSO₄ and evaporated under reduced pressure, affording a yellow oil (6.10 g; title compound contaminated with traces of PPh₃O).
MS (ESI, m/z): 220.0[M+H⁺].

Z.v. [(S)-2-hydroxy-1-(3-methoxy-quinoxalin-5-yl)-ethyl]-carbamic acid tert-butyl ester Starting from intermediate Z.iv (6.00 g) and using procedure G, the title compound was obtained as a yellowish foam (5.90 g, 67% yield).
MS (ESI, m/z): 320.1[M+H⁺].

Z.vi. ((S)-3-oxo-5,6-dihydro-3H-pyrrolo[1,2,3-de]quinoxalin-6-yl)-carbamic acid tert-butyl ester A solution of intermediate Z.v (5.80 g) and TEA (3.0 mL) in DCE (45 mL) was treated dropwise at 0° C. with MsCl (1.55 mL). The reaction mixture was further refluxed overnight. The reaction mixture was diluted with DCM, washed with water and brine, dried over MgSO₄ and evaporated under reduced pressure affording, after crystallization from ether/EA, a beige solid (3.50 g; 67% yield) consisting of an inseparable 2:1 mixture of the desired product and 4-(3-methoxy-quinoxalin-5-yl)-oxazolidin-2-one which was used as such in the next step.
MS (ESI, m/z): 288.0 and 246.0[M+H⁺].

Z.vii. (S)-6-amino-5,6-dihydro-pyrrolo[1,2,3-de]quinoxalin-3-one

Starting from intermediate Z.vi (3.50 g) and using procedure B, the title compound was obtained as a beige solid (780 mg, 34% yield). The side product from cyclisation was removed by acid/base extraction.
MS (ESI, m/z): 188.1[M+H⁺].

Preparation AA: (R)-6-amino-5,6-dihydro-pyrrolo[1,2,3-de]quinoxalin-3-one

The title compound was prepared in analogy to Preparation Z, using AD-mix α in the second step.
The analytical data are identical to those of the compound of Preparation Z.

Preparation AB: rac-methanesulfonic acid 4-oxo-1,2-dihydro-4H-pyrrolo[3,2,1-ij]quinolin-1-ylmethyl ester

AB.i. 2-(2-methoxy-quinolin-8-yl)-malonic acid dimethyl ester

A mixture of 8-bromo-2-methoxy-quinoline (4.76 g; prepared according to WO 2008/125594) and dimethylmalonate (36 mL) in was degassed by bubbling N₂ through for 10 min and treated with CuBr (3.47 g) and NaOMe (2.6 g). The mixture was heated at 100° C. for 20 h and then partitioned between EA and water. The org. phase was washed with brine, dried over MgSO₄ and the excess dimethylmalonate was removed by distillation. The residue was purified by CC (Hept/EA 4:1, 2:1), affording an oil (2.80 g; 48% yield).
¹H NMR (CDCl₃) δ: 7.98 (d, J=8.8 Hz, 1H), 7.71 (dd, J=8.2, 1.5 Hz, 1H), 7.66 (m, 1H), 7.39 (m, 1H), 6.92 (d, J=8.8 Hz, 1H), 6.00 (s, 1H), 4.03 (s, 3H), 3.76 (s, 3H).

AB.ii. 2-(2-methoxy-quinolin-8-yl)-propane-1,3-diol

Starting from intermediate AB.i (5.80 g) and using procedure A, the title compound was obtained as a light yellow oil (1.06 g, 23% yield).
MS (ESI, m/z): 234.2[M+H⁺].

AB.iii. rac-methanesulfonic acid 4-oxo-1,2-dihydro-4H-pyrrolo[3,2,1-ij]quinolin-1-ylmethyl ester Starting from intermediate AB.ii (840 mg) and using procedure H, but using 3 eq. of methansulfonyl anhydride instead of MSCl and 4 eq. of Pyr as a base, the intermediate dimesylate was further stirred at 70° C. for 1 h. The reaction mixture was diluted with 2N HCl and extracted with DCM. The org. phase was dried over MgSO₄ and evaporated under reduced pressure affording, after purification by CC (EE/MeOH 9:1), a beige foam (1.10 g; 76% yield).
MS (ESI, m/z): 280.4[M+H⁺].

Preparation AC: rac-6-aminomethyl-5,6-dihydro-pyrrolo[1,2,3-de]quinoxalin-3-one

AC.i. (3-methoxy-quinoxalin-5-yl)-acetic acid methyl ester

TBDMSCl (2.4 mL) was added dropwise to a solution of 3-methoxy-5-quinoxalineacetonitrile (1.08 g, prepared according to WO 2008/126024) in dry MeOH (20 mL). The solution was stirred at reflux overnight. TBDMSCl (2.4 mL) was added and the reaction mixture was further stirred for 8 h. TBDMSCl (2.4 mL) was added and the reaction mixture was further stirred at reflux overnight. The mixture was concentrated under reduced pressure and partitioned between EA and water. The org. layer was washed with 2M. NaOH, water and brine, dried over MgSO₄, concentrated under reduced pressure and purified by CC (Hept/EtOAc 1:1), affording a yellow oil (520 mg; 41% yield).
MS (ESI, m/z): 233.3[M+H⁺].

AC.ii. rac-3-(1,3-dioxo-1,3-dihydro-isoindol-2-yl)-2-(3-methoxy-quinoxalin-5-yl)-propionic acid methyl ester A solution of intermediate AC.i (2.03 g) in THF (19 mL) was added dropwise at −78° C. to a solution of LiHMDS (1M in THF; 10.5 mL) in THF (10 mL). The solution was further stirred at −78° C. stirred for 1 h and treated dropwise with a solution of N-(bromomethyl)phthalimide (2.6 g) in THF (19 mL). The reaction mixture was further stirred at −78° C. for 1 h and at rt overnight. The solution was quenched with 1N HCl (30 mL) and extracted with EA. The org. layer was washed with water and brine, dried over MgSO$_4$, concentrated under reduced pressure and purified by CC (Hept/EA 1:1), affording, after crystallization from EA, a beige solid (2.28 g; 66% yield).
MS (ESI, m/z): 392.3[M+H$^+$].

AC.iii. rac-3-amino-2-(3-methoxy-quinoxalin-5-yl)-propionic acid methyl ester Hydrazine monohydrate (1.42 mL) was added dropwise at rt to a suspension of intermediate AC.ii (2.28 g) in EtOH (38 mL). After stirring at rt for 2 h the solvent was evaporated under reduced pressure and the residue was taken up in EA and aq. citric acid (10%). The aq. layer was washed with NH$_4$OH and extracted with DCM. The org. layer was dried over MgSO$_4$ and evaporated under reduced pressure affording a yellow oil (1.16 g; 77% yield) which was further used without any further purification.
MS (ESI, m/z): 262.3[M+H$^+$].

AC.iv. rac-3-tert-butoxycarbonylamino-2-(3-methoxy-quinoxalin-5-yl)-propionic acid methyl ester Starting from intermediate AC.iii (1.16 g) and using procedure G, the title compound was obtained as a colourless solid (1.34 g, 83% yield).
MS (ESI, m/z): 362.0[M+H$^+$].

AC.v. rac-[3-hydroxy-2-(3-methoxy-1,2-dihydro-quinoxalin-5-yl)-propyl]-carbamic acid tert-butyl ester Starting from intermediate AC.iv (701 mg) and using procedure A, the compound was obtained as a colourless foam (554 mg, 85% yield).
MS (ESI, m/z): 336.2[M+H$^+$].

AC.vi. rac-[3-hydroxy-2-(3-methoxy-quinoxalin-5-yl)-propyl]-carbamic acid tert-butyl ester A solution of intermediate AC.v (553 mg) in DCM (30 mL) was treated with MnO$_2$ (1.35 g). The mixture was stirred at rt for 2 h, filtered and concentrated in vacuo to give the desired intermediate as a slightly orange foam (489 mg, 89% yield).
MS (ESI, m/z): 334.1[M+H$^+$].

AC.vii. rac-(3-oxo-5,6-dihydro-3H-pyrrolo[1,2,3-de]quinoxalin-6-ylmethyl)-carbamic acid tert-butyl ester Starting from intermediate AC.vi (486 mg) and using procedure H, the title compound was obtained as a beige solid (393 mg, 89% yield).
MS (ESI, m/z): 302.1[M+H$^+$].

AC.viii. rac-6-aminomethyl-5,6-dihydro-pyrrolo[1,2,3-de]quinoxalin-3-one

Starting from intermediate AC.viii (388 mg) and using procedure B, the title compound was obtained as a yellow solid (172 mg, 66% yield).
MS (ESI, m/z): 202.3[M+H$^+$].

Preparation AD: (S)-6-amino-7-fluoro-5,6-dihydro-pyrrolo[1,2,3-de]quinoxalin-3-one

AD.i. (R)-1-(6-fluoro-3-methoxy-quinoxalin-5-yl)-ethane-1,2-diol

Starting from 7-fluoro-2-methoxy-8-(2-propen-1-yl)-quinoxaline (3.24 g; prepared according to WO 2008/003690) and using procedure L with AD-mix β, the title compound was obtained, after purification by CC (Hept/EA 1:1 then 0:1), as a beige solid (3.39 g, 90% yield).
$^1$H NMR (DMSO d6) δ: 8.57 (s, 1H), 7.96 (dd, J=9.1, 5.6 Hz, 1H), 7.48 (dd, J=10.3, 9.1 Hz, 1H), 5.64 (d, J=6.7 Hz, 1H), 5.26 (d, J=6.4 Hz, 1H), 4.75 (m, 1H), 4.05 (s, 3H), 3.88 (m, 1H), 3.73 (m, 1H).

AD.ii. (R)-2-(tert-butyl-dimethyl-silanyloxy)-1-(6-fluoro-3-methoxy-quinoxalin-5-yl)-ethanol Starting from intermediate AD.i (3.39 g) and using procedure M, the title compound was obtained as a colourless oil (4.83 g, 96% yield).
$^1$H NMR (CDCl$_3$) δ: 8.47 (s, 1H), 7.95 (m, 1H), 7.35 (m, 1H), 5.5 (m, 1H), 4.09 (s, 3H), 4.03 (m, 2H), 0.76 (s, 9H), −0.12 (d, J=5.0 Hz, 6H).

AD.iii. (S)-[2-(tert-butyl-dimethyl-silanyloxy)-1-(6-fluoro-3-methoxy-quinoxalin-5-yl)-ethyl]-carbamic acid tert-butyl ester Starting from intermediate AD.ii (4.73 g) and using procedure N', the title compound was obtained, after purification by CC (Hept/EA 4:1), as a colourless foam (3.48 g; 84% yield).
$^1$H NMR (CDCl$_3$) δ: 8.45 (s, 1H), 7.93 (dd, J=9.1, 5.6 Hz, 1H), 7.30 (m, 1H), 6.60 (m, 1H), 5.85 (m, 1H), 4.12 (s, 4H), 3.94 (m, 2H), 1.43 (s, 9H), 0.75 (s, 9H), −0.08 (s, 3H), −0.12 (s, 3H).

AD.iv. (S)-[1-(6-fluoro-3-methoxy-quinoxalin-5-yl)-2-hydroxy-ethyl]-carbamic acid tert-butyl ester Starting from intermediate AD.iii (5.54 g) and using procedure J, the title compound was obtained as a colourless foam (3.48 g, 84% yield).
$^1$H NMR (CDCl$_3$) δ: 8.45 (s, 1H), 7.95 (dd, J=9.4, 5.9 Hz, 1H), 7.34 (m, 1H), 6.60 (m, 1H), 5.85 (m, 1H), 4.11 (s, 3H), 3.92 (m, 2H), 1.42 (s, 9H).

AD.v. (S)-(7-fluoro-3-oxo-5,6-dihydro-3H-pyrrolo[1,2,3-de]quinoxalin-6-yl)-carbamic acid tert-butyl ester Starting from intermediate AD.iv (3.45 g) and using procedure H followed by heating at reflux for 12 h, a foam (2.64 g) was obtained which contained the desired product in a 1:1 mixture with (S)-4-(6-fluoro-3-methoxy-quinoxalin-5-yl)-oxazolidin-2-one. It was used as such in the next step.

AD.vi. (S)-6-amino-7-fluoro-5,6-dihydro-pyrrolo[1,2,3-de]quinoxalin-3-one

Starting from the mixture obtained at step AD.v (2.64 g, purity 50%) and using procedure B followed by acid/base extraction, the title compound was obtained as an orange solid (550 mg, 60% yield).

$^1$H NMR (DMSO d6) δ: 8.12 (s, 1H), 7.74 (dd, J=8.8, 4.4 Hz, 1H), 7.11 (m, 1H), 4.94 (dd, J=8.5, 3.8 Hz, 1H), 4.50 (dd, J=13.2, 8.5 Hz, 1H), 3.90 (dd, J=13.2, 3.8 Hz, 1H), 2.32 (br., 2H).

Preparation AE: rac-1-aminomethyl-1,2-dihydro-pyrrolo[3,2,1-ij]quinolin-4-one

AE.i. rac-1-azidomethyl-1,2-dihydro-pyrrolo[3,2,1-ij]quinolin-4-one

A solution of the compound of Preparation AB (1.00 g) in DMF (16 mL) was heated at 60° C. for 3 h in presence of NaN$_3$ (2.80 g). The reaction mixture was diluted with water and extracted with EA. The org. layer was washed with water and brine, dried over MgSO$_4$ and evaporated affording a yellow powder (800 mg; 99% yield).

$^1$H NMR (CDCl$_3$) δ: 7.72 (d, J=9.4 Hz, 1H), 7.45 (m, 2H), 7.19 (m, 1H), 6.69 (d, J=9.4 Hz, 1H), 4.55 (dd, J=13.2, 9.4 Hz, 1H), 4.26 (dd, J=13.2, 4.7 Hz, 1H), 3.91 (m, 1H), 3.67 (m, 2H).

AE.ii. rac-1-aminomethyl-1,2-dihydro-pyrrolo[3,2,1-ij]quinolin-4-one

Starting from intermediate AE.i (800 mg) and using procedure F, the title compound was obtained as a yellow oil (310 mg, 44% yield).

$^1$H NMR (CDCl$_3$) δ: 7.70 (d, J=9.4 Hz, 1H), 7.41 (m, 2H), 7.17 (t, J=7.6 Hz, 1H), 6.67 (d, J=9.4 Hz, 1H), 4.54 (dd, J=13.2, 9.7 Hz, 1H), 4.32 (dd, J=12.6, 4.7 Hz, 1H), 3.80 (m, 1H), 3.10 (d, J=6.2 Hz, 2H).

Preparation AF: 6-[(R)-5-(2-amino-ethyl)-2-oxo-oxazolidin-3-yl]-4H-benzo[1,4]thiazin-3-one

AF.i. 6-[(R)-5-(2-azido-ethyl)-2-oxo-oxazolidin-3-yl]-4H-benzo[1,4]thiazin-3-one A solution of the compound of Preparation J (2.5 g) and NaN$_3$ (523 mg) in DMF (12 mL) was heated at 80° C. overnight. The reaction mixture was diluted with EA and extracted with water and brine. The org. layer was dried over MgSO$_4$ and evaporated under reduced pressure. The residue was stirred in ether/MeOH, affording a beige solid (1.9 g; 89% yield).

MS (ESI, m/z): 320.2[M+H$^+$].

AF.ii. 6-[(R)-5-(2-amino-ethyl)-2-oxo-oxazolidin-3-yl]-4H-benzo[1,4]thiazin-3-one Starting from intermediate AF.i (1.8 g) and using procedure F, the title compound was obtained as a colourless solid (1.40 g, 85% yield).

MS (ESI, m/z): 294.4[M+H$^+$].

Preparation AG: methanesulfonic acid (S)-2-oxo-3-(4-propyl-phenyl)-oxazolidin-5-ylmethyl ester

AG.i. (S)-5-hydroxymethyl-3-(4-propyl-phenyl)-oxazolidin-2-one

Starting from 4-propyl-aniline and following the procedure described for the preparation of intermediate R.i., the title compound was obtained as a yellow solid (4.3 g; 63% yield)

MS (ESI, m/z): 235.9[M+H$^+$].

AG.ii. Methanesulfonic acid (S)-2-oxo-3-(4-propyl-phenyl)-oxazolidin-5-ylmethyl ester Starting from intermediate AG.i (4.25 g) and using procedure H (with however 1.5 eq. Ms$_2$O instead of MsCl), the title compound was obtained as an off-white solid (4.30 g, 76% yield).

MS (ESI, m/z): 314.1[M+H$^+$].

Preparation AH: methanesulfonic acid (S)-3-(4-butyl-phenyl)-2-oxo-oxazolidin-5-ylmethyl ester

AH.i. (S)-5-hydroxymethyl-3-(4-butyl-butyl)-oxazolidin-2-one

Starting from 4-butyl-aniline and following the procedure described for the preparation of intermediate R.i, the title compound was obtained as a yellow solid (2.99 g; 58% yield).

$^1$H NMR (CDCl$_3$) δ: 7.43 (d, J=8.8 Hz, 2H), 7.17 (d, J=8.8 Hz, 2H), 4.73 (m, 1H), 3.99 (m, 3H), 3.76 (m, 1H), 2.58 (m, 2H), 2.00 (br. s, 1H), 1.57 (m, 2H), 1.34 (m, 2H), 0.92 (t, J=7.0 Hz, 3H).

AH.ii. Methanesulfonic acid (S)-3-(4-butyl-phenyl)-2-oxo-oxazolidin-5-ylmethyl ester Starting from intermediate AH.i (2.90 g) and using procedure H (with however 1.5 eq. of Ms$_2$O instead of MsCl), the title compound was obtained as an off-white solid (2.48 g, 65% yield).

MS (ESI, m/z): 328.3[M+H$^+$].

Preparation AI: methanesulfonic acid 2-[(S)-2-oxo-3-(3-oxo-3,4-dihydro-2H-benzo[1,4]thiazin-6-yl)-oxazolidin-5-yl]-ethyl ester The title compound was prepared in analogy to Preparation J, using however tert-butyl-dimethyl-[(S)-2-oxiranyl-ethoxy]-silane.

The analytical data were identical with those of the compound of Preparation J.

Preparation AJ: methanesulfonic acid 2-[(S)-2-oxo-3-(3-oxo-3,4-dihydro-2H-benzo[1,4]thiazin-6-yl)-oxazolidin-5-yl]-ethyl ester

AJ.i. (2,3-dihydro-[1,4]dioxino[2,3-c]pyridin-7-yl)-carbamic acid tert-butyl ester A suspension of 2,3-dihydro-1,4-dioxino[2,3-c]pyridine-7-carboxylic acid (3.20 g; prepared according to WO 2007/016610) in tBuOH (100 mL) was treated with DPPA (4.60 mL) and TEA (3.0 mL) and heated at 80° C. overnight. The solvent was evaporated under reduced pressure and the residue as partitioned between water and EA. The org. layer was washed with brine, dried over MgSO$_4$ and evaporated under reduced pressure. The residue was stirred in ether, affording a beige solid (2.90 g; 65% yield).
$^1$H NMR (CDCl$_3$) δ: 7.84 (s, 1H), 7.49 (s, 1H), 4.31 (m, 2H), 4.23 (m, 2H), 1.52 (s, 11H).

AJ.ii. rac-5-[2-(tert-butyl-dimethyl-silanyloxy)-ethyl]-3-(2,3-dihydro-[1,4]dioxino[2,3-c]pyridin-7-yl)-oxazolidin-2-one A solution of intermediate AJ.i (3.30 g) and 2-[2-[[(tert-butyl)dimethylsilyl]oxy]ethyl]-oxirane (2.65 g; prepared according to *J. Org. Chem.* (2008), 73 (3), 1093-1098) in DMF (42 mL) was cooled to 0° C. and treated with tBuOLi (18 mL; 2.2M in THF). The reaction mixture was allowed to reach rt and further stirred at 80° C. for 2 days. The reaction mixture was diluted with EA and washed with water and brine. The org. layer was dried over MgSO$_4$ and purified by CC (Hex/EA1:1), affording a yellow oil (2.70 g; 54% yield).
MS (ESI, m/z): 381.0[M+H$^+$].

AJ.iii. rac-3-(2,3-dihydro-[1,4]dioxino[2,3-c]pyridin-7-yl)-5-(2-hydroxy-ethyl)-oxazolidin-2-one Starting from intermediate AJ.ii and using procedure J, the title compound was obtained as a yellow solid (1.10 g, 58% yield).
MS (ESI, m/z): 267.1[M+H$^+$].

AJ.iv. Methanesulfonic acid 2-[(S)-2-oxo-3-(3-oxo-3,4-dihydro-2H-benzo[1,4]thiazin-6-yl)-oxazolidin-5-yl]-ethyl ester Starting from intermediate AJ.iii and using procedure H, the title compound was obtained as a beige solid (1.30 g, 100% yield).
MS (ESI, m/z): 345.2[M+H$^+$].

Preparation AK: rac-methanesulfonic acid 2-[3-(2,3-dihydro-[1,4]dioxino[2,3-b]pyridin-6-yl)-2-oxo-oxazolidin-5-yl]-ethyl ester AK.i. (2,3-dihydro-[1,4]dioxino[2,3-b]pyridin-6-yl)-carbamic acid benzyl ester A solution of 2,3-dihydro-1,4-dioxino[2,3-b]pyridin-6-amine (commercial; 2.70 g) in acetone/water 1:1 (40 mL) was treated at 0° C. with 1M. NaHCO$_3$ (35 mL) and CbzCl (2.63 mL). The reaction mixture was stirred at rt for 3 h, the org. solvent was evaporated under reduced pressure and the residue was partitioned between water and ether/EA. The org layer was dried over MgSO$_4$ and evaporated under reduced pressure, affording a beige solid (5.3 g; 100% yield).
$^1$H NMR (CDCl$_3$) δ: 7.50 (d, J=8.5 Hz, 1H), 7.36 (m, 5H), 7.20 (d, J=8.8 Hz, 1H), 7.15 (br., 1H), 4.37 (m, 2H), 4.19 (m, 2H).

AK.ii. rac-5-[2-(tert-butyl-dimethyl-silanyloxy)-ethyl]-3-(2,3-dihydro-[7,4]dioxino[2,3-b]pyridin-6-yl)-oxazolidin-2-one Starting from intermediate AK.i and 2-[2-[[(tert-butyl)dimethylsilyl]oxy]ethyl]-oxirane, the compound was prepared in analogy to Preparation AJ, step AJ.ii. The product was purified by CC (Hex/EA 1:1), affording a brown oil (2.90 g; 73% yield).
MS (ESI, m/z): 381.2[M+H$^+$].

AK.iii. rac-3-(2,3-dihydro-[1,4]dioxino[2,3-b]pyridin-6-yl)-5-(2-hydroxy-ethyl)-oxazolidin-2-one Starting from intermediate AK.ii and using procedure J, the title compound was obtained as a yellow solid (1.10 g, 56% yield).
MS (ESI, m/z): 266.8[M+H$^+$].

AK.iv. rac-methanesulfonic acid 2-[3-(2,3-dihydro-[1,4]dioxino[2,3-b]pyridin-6-yl)-2-oxo-oxazolidin-5-yl]-ethyl ester Starting from intermediate AK.iii and using procedure H, the title compound was obtained as a beige solid (1.24 g, 96% yield).
$^1$H NMR (CDCl$_3$) δ: 7.71 (d, J=8.8 Hz, 1H), 7.24 (m, 1H), 4.79 (m, 1H), 4.43 (m, 4H), 4.33 (m, 1H), 4.23 (m, 2H), 3.89 (dd, J=10.3, 6.7 Hz, 1H), 3.04 (s, 3H), 2.20 (m, 2H).

Preparation AL: methanesulfonic acid 2-[(R)-3-(4-ethoxy-phenyl)-2-oxo-oxazolidin-5-yl]-ethyl ester AL.i. (R)-4-(tert-butyl-dimethyl-silanyloxy)-1-(4-ethoxy-phenylamino)-butan-2-ol A solution of 4-ethoxy-aniline (commercial; 3.2 mL) in EtOH/water (9:1; 150 mL) was reacted with (2R)-2-[2-[[(tert-butyl)dimethylsilyl]oxy]ethyl]-oxirane (prepared according to WO 2007/144423) and further heated at 80° C. overnight. The solvents were removed under reduced pressure and the residue was purified by CC (EA/Hept 1:1), affording a brown oil (5.22 g; 62% yield).
MS (ESI, m/z): 340.2[M+H$^+$].

AL.ii. (R)-5-[2-(tert-butyl-dimethyl-silanyloxy)-ethyl]-3-(4-ethoxy-phenyl)-oxazolidin-2-one Starting from intermediate AL.i and using procedure I, the title compound was obtained as an off-white solid (4.30 g, 76% yield).
MS (ESI, m/z): 366.1[M+H$^+$].

AL.iii. (R)-3-(4-ethoxy-phenyl)-5-(2-hydroxy-ethyl)-oxazolidin-2-one

Starting from intermediate AL.ii and using procedure J, the title compound was obtained as an off-white solid (1.53 g, 52% yield).
MS (ESI, m/z): 251.9[M+H$^+$].

AL.iv. Methanesulfonic acid 2-[(R)-3-(4-ethoxy-phenyl)-2-oxo-oxazolidin-5-yl]-ethyl ester Starting from intermediate AL.iii and using procedure H, the title compound was obtained as an off-white solid (1.89 g, 96% yield).
MS (ESI, m/z): 330.0 [M+H$^+$].

Preparation AM: methanesulfonic acid 2-[(R)-2-oxo-3-(4-propyl-phenyl)-oxazolidin-5-yl]-ethyl ester AM.i. (R)-4-(tert-butyl-dimethyl-silanyloxy)-1-(4-propyl-phenylamino)-butan-2-ol Starting from 4-propyl-aniline, the title compound was prepared in analogy to Preparation AL, step AL.i. A brown oil (6.99 g; 84% yield) was obtained.
MS (ESI, m/z): 338.2[M+H$^+$].

AM.ii. (R)-5-[2-(tert-butyl-dimethyl-silanyloxy)-ethyl]-3-(4-propyl-phenyl)-oxazolidin-2-one Starting from intermediate AM.i and using procedure I, the title compound was obtained as a brown oil (4.50 g, 60% yield).
MS (ESI, m/z): 364.1[M+H$^+$].

AM.iii. (R)-5-(2-hydroxy-ethyl)-3-(4-propyl-phenyl)-oxazolidin-2-one

Starting from intermediate AM.ii and using procedure J, the title compound was obtained as a yellowish solid (1.76 g, 57% yield).
MS (ESI, m/z): 249.9[M+H$^+$].

AM.iv. Methanesulfonic acid 2-[(R)-2-oxo-3-(4-propyl-phenyl)-oxazolidin-5-yl]-ethyl ester Starting from intermediate AM.iii and using procedure H, the title compound was obtained as an off-white solid (2.13 g, 93% yield).
MS (ESI, m/z): 328.4[M+H$^+$].

Preparation AN: methanesulfonic acid 2-[(R)-3-(2,3-dihydro-benzo[1,4]dioxin-6-yl)-2-oxo-oxazolidin-5-yl]-ethyl ester

AN.i. (R)-4-(tert-butyl-dimethyl-silanyloxy)-1-(2,3-dihydro-benzo[1,4]dioxin-6-ylamino)-butan-2-ol Starting from 2,3-dihydro-1,4-benzodioxin-6-amine (commercial), the title compound was prepared in analogy to Preparation AL, step AL.i. A brown oil (4.50 g; 51% yield) was obtained.
MS (ESI, m/z): 354.3[M+H$^+$].

AN.ii. (R)-5-[2-(tert-butyl-dimethyl-silanyloxy)-ethyl]-3-(2,3-dihydro-benzo[1,4]dioxin-6-yl)-oxazolidin-2-one Starting from intermediate AN.i and using procedure I, the title compound was obtained as a yellow solid (3.42 g, 71% yield).
MS (ESI, m/z): 380.2[M+H$^+$].

AN.iii. (R)-3-(2,3-dihydro-benzo[1,4]dioxin-6-yl)-5-(2-hydroxy-ethyl)-oxazolidin-2-one Starting from intermediate AN.ii and using procedure J, the title compound was obtained as an off-white solid (1.72 g, 72% yield).
$^1$H NMR (CDCl$_3$) δ: 7.06 (d, J=2.6 Hz, 1H), 6.97 (dd, J=8.8, 2.6 Hz, 1H), 6.84 (m, 1H), 4.81 (m, 1H), 4.24 (m, 4H), 4.06 (t, J=8.8 Hz, 1H), 3.88 (m, 2H), 3.69 (dd, J=8.8, 7.3 Hz, 1H), 2.03 (m, 2H), 1.82 (br. s, 1H).

AN.iv. Methanesulfonic acid 2-[(R)-3-(2,3-dihydro-benzo[1,4]dioxin-6-yl)-2-oxo-oxazolidin-5-yl]-ethyl ester Starting from intermediate AN.iii and using procedure H, the title compound was obtained as an off-white solid (2.03 g, 92% yield).
MS (ESI, m/z): 344.2[M+H$^+$].

Preparation AO: rac-methanesulfonic acid 2-{3-[4-(4-methoxy-benzyl)-3-oxo-3,4-dihydro-2H-pyrido[3,2-b][1,4]oxazin-6-yl]-2-oxo-oxazolidin-5-yl}-ethyl ester

AO.i. 6-bromo-4-(4-methoxy-benzyl)-4H-pyrido[3,2-b][1,4]oxazin-3-one

A suspension of 6-bromo-2H-pyrido[3,2-b]-1,4-oxazin-3(4H)-one (2.0 g; prepared according to WO 01/30782) in DMF (40 mL) was treated with 4-methoxybenzyl chloride (1.18 mL) and Cs$_2$CO$_3$ (8.5 g) and stirred at rt for 2 h. The solvent was evaporated under reduced pressure and the residue was partitioned between EA and water. The org. layer was washed with brine, dried over MgSO$_4$ and evaporated under reduced pressure. The residue was triturated with Hept, affording a beige solid (2.8 g; 92% yield).
$^1$H NMR (CDCl$_3$) δ: 7.49 (d, J=8.8 Hz, 2H), 7.05 (s, 2H), 6.83 (d, J=8.8 Hz, 2H), 6.83 (d, J=8.8 Hz, 2H), 6.83 (d, J=8.8 Hz, 2H), 4.67 (s, 2H), 3.77 (s, 3H).

AO.ii. rac-1-azido-4-(tert-butyl-dimethyl-silanyloxy)-butan-2-ol

A solution of 2-[2-[[(tert-butyl)dimethylsilyl]oxy]ethyl]-oxirane (5.0 g; prepared according to WO 2007/144423) in MeOH (150 mL) was reacted with NaN$_3$ (3.95 g) and NH$_4$Cl (2.37 g). The reaction mixture was further stirred at 80° C. overnight. The solvent was evaporated under reduced pressure and the residue was partitioned between EA and water. The org. layer was washed with brine, dried over Na$_2$SO$_4$ and evaporated under reduced pressure, affording a yellow oil (4.9 g; 81% yield).
$^1$H NMR (CDCl$_3$) δ: 4.01 (m, 1H), 3.87 (m, 2H), 3.30 (m, 2H), 1.72 (m, 2H), 0.90 (m, 9H), 0.06 (m, 6H).

AO.iii. rac-1-amino-4-(tert-butyl-dimethyl-silanyloxy)-butan-2-ol

A solution of intermediate AO.ii (4.85 g) in THF (100 mL) was hydrogenated for 3 h over 10% Pd/C (1.0 g). The catalyst was filtered off and the filtrate was evaporated under reduced pressure, affording a yellow oil (4.1 g; 94.5% yield).
MS (ESI, m/z): 219.8[M+H$^+$].

AO.iv. rac-5-[2-(tert-butyl-dimethyl-silanyloxy)-ethyl]-oxazolidin-2-one

Starting from intermediate AO.iii (4.0 g) and using procedure I, the title compound was obtained as a light yellow oil (3.3 g; 74% yield).
$^1$H NMR (CDCl$_3$) δ: 5.22 (br., 1H), 4.80 (m, 1H), 3.74 (m, 3H), 3.33 (m, 1H), 1.93 (m, 2H), 0.89 (m, 9H), 0.07 (m, 6H).

AO.v. rac-6-{5-[2-(tert-butyl-dimethyl-silanyloxy)-ethyl]-2-oxo-oxazolidin-3-yl}-4-(4-methoxy-benzyl)-4H-pyrido[3,2-b][1,4]oxazin-3-one Intermediates AO.iv (1.97 g) and AO.i (2.8 g), CuI (305 mg) and K$_2$CO$_3$ (2.2 g) were placed in a round bottom flask which was then flushed with argon. Trans-1,2-diaminocyclohexane (1.2 mL) and dioxane (60 mL) were added to the mixture and the reaction flask was again flushed with argon. The reaction mixture was stirred at 100° C. for 2 days and partitioned between EA and water. The org. layer was washed with brine, dried over MgSO$_4$ and evaporated under reduced pressure. The residue was purified by CC (DCM/MeOH 19:1), affording, after crystallisation from Hept, a colourless solid (1.7 g; 41% yield).

$^1$H NMR (CDCl$_3$) δ: 7.81 (d, J=8.8 Hz, 1H), 7.28 (m, 3H), 6.81 (m, 2H), 5.20 (s, 2H), 4.82 (m, 1H), 4.28 (m, 1H), 3.85 (m, 3H), 3.77 (s, 3H), 2.00 (m, 2H), 0.89 (s, 9H), 0.07 (s, 6H).

AO.vi. rac-6-[5-(2-hydroxy-ethyl)-2-oxo-oxazolidin-3-yl]-4-(4-methoxy-benzyl)-4H-pyrido[3,2-b][1,4]oxazin-3-one Starting from intermediate AO.v (1.7 g) and using procedure J, the title compound was obtained, after purification by CC (EA then EA/MeOH 9:1), as a yellow oil (1.4 g; 100% yield).

MS (ESI, m/z): 400.0[M+H$^+$].

AO.vii. rac-methanesulfonic acid 2-{3-[4-(4-methoxy-benzyl)-3-oxo-3,4-dihydro-2H-pyrido[3,2-b][1,4]oxazin-6-yl]-2-oxo-oxazolidin-5-yl}-ethyl ester Starting from intermediate AO.vi (1.32 g) and using procedure H, the title compound was obtained as a colourless foam (1.3 g; 82.5% yield)

MS (ESI, m/z): 477.8[M+H$^+$].

Preparation AP: 6-[(S)-5-(2-amino-ethyl)-2-oxo-oxazolidin-3-yl]-4H-benzo[1,4]thiazin-3-one

AP.i. 6-[(S)-5-(2-azido-ethyl)-2-oxo-oxazolidin-3-yl]-4H-benzo[1,4]thiazin-3-one A solution of intermediate L (1.90 g) in DMF (8 mL) was treated with NaN$_3$ (400 mg) and stirred at 80° C. overnight. The reaction mixture was diluted with water and extracted with EA. The org. layer was washed with water and brine, dried over MgSO$_4$ and evaporated under reduced pressure. The residue was stirred in ether/MeOH, affording a beige solid (1.30 g; 80% yield).

MS (ESI, m/z): 320.3[M+H$^+$].

AP.ii. 6-[(S)-5-(2-amino-ethyl)-2-oxo-oxazolidin-3-yl]-4H-benzo[1,4]thiazin-3-one Starting from intermediate AP.i and using procedure F, the title compound was obtained as a beige solid (0.90 g, 82% yield).

MS (ESI, m/z): 294.4[M+H$^+$].

Preparation AQ: methanesulfonic acid 2-[(S)-3-(2,3-dihydro-benzo[1,4]dioxin-6-yl)-2-oxo-oxazolidin-5-yl]-ethyl ester Starting from (2S)-2-[2-[[(tert-butyl)dimethylsilyl]oxy]ethyl]-oxirane, the title compound was prepared in analogy to Preparation AN.

The analytical data were identical with those of the compound of Preparation AN.

Preparation AR: 3-[(R)-2-oxo-3-(3-oxo-3,4-dihydro-2H-pyrido[3,2-b][1,4]oxazin-6-yl)-oxazolidin-5-yl]-propionaldehyde

AR.i. (R)-1-azido-5-(tert-butyl-dimethyl-silanyloxy)-pentan-2-ol

Starting from (R)-2-[2-[[(tert-butyl)dimethylsilyl]oxy]propyl]-oxirane (5.0 g; prepared according to *Organic Letters* (2005), 7 (18), 3997-4000) and NaN$_3$, the title compound was prepared in analogy to Preparation AO, step AO.ii. It was obtained as an oil (5.17 g; 86% yield).

$^1$H NMR (CDCl$_3$) δ: 3.79 (m, 1H), 3.68 (m, 2H), 3.29 (m, 2H), 1.66 (m, 4H), 0.90 (m, 9H), 0.07 (m, 6H).

AR.ii. (R)-5-[2-(tert-butyl-dimethyl-silanyloxy)-propyl]-oxazolidin-2-one

The title compound was prepared in analogy to Preparation AO, steps AO.iii and AO.iv by hydrogenation of intermediate AR.ii using procedure F and reaction with CDI using procedure I. It was obtained as a colourless solid (3.48 g; 67% yield).

$^1$H NMR (CDCl$_3$) δ: 5.22 (br., 1H), 4.68 (m, 1H), 3.66 (m, 3H), 3.25 (t, J=7.6 Hz, 1H), 1.72 (m, 4H), 0.89 (m, 9H), 0.05 (m, 6H).

AR.iii. (R)-6-{5-[2-(tert-butyl-dimethyl-silanyloxy)-propyl]-2-oxo-oxazolidin-3-yl}-4-(4-methoxy-benzyl)-4H-pyrido[3,2-b][1,4]oxazin-3-one Starting from intermediates AO.i (1.97 g) and AR.ii, the title compound was prepared in analogy to Preparation AO, step AO.v. It was obtained as a colourless foam (4.43 g; 70% yield).

$^1$H NMR (CDCl$_3$) δ: 7.80 (d, J=8.5 Hz, 1H), 7.28 (m, 3H), 6.81 (d, J=8.8 Hz, 2H), 5.20 (s, 2H), 4.67 (m, 3H), 4.22 (dd, J=10.0, 8.5 Hz, 1H), 3.77 (s, 3H), 3.70 (m, 2H), 1.78 (m, 4H), 0.90 (m, 9H), 0.06 (s, 6H).

AR.iv. (R)-6-[5-(2-hydroxy-propyl)-2-oxo-oxazolidin-3-yl]-4-(4-methoxy-benzyl)-4H-pyrido[3,2-b][1,4]oxazin-3-one The title compound was prepared in analogy to Preparation AO, step AO.vi, starting from intermediate AR.iii. It was obtained as a colourless solid (640 mg; 38% yield).

$^1$H NMR (DMSO d6) δ: 11.16 (s, 1H), 7.57 (m, 1H), 7.40 (d, J=8.8 Hz, 1H), 4.68 (s, 1H), 4.59 (s, 2H), 4.47 (t, J=5.0 Hz, 1H), 4.19 (m, 1H), 3.69 (dd, J=10.0, 7.0 Hz, 1H), 3.43 (q, J=6.2 Hz, 2H), 1.73 (m, 2H), 1.51 (dd, J=9.7, 6.7 Hz, 2H).

AR.v. 3-[(R)-2-oxo-3-(3-oxo-3,4-dihydro-2H-pyrido[3,2-b][1,4]oxazin-6-yl)-oxazolidin-5-yl]-propionaldehyde A solution of SO$_3$.Pyr complex (900 mg) in DMSO (3 mL) was added dropwise at rt over 10 min to a suspension of intermediate AR.iv (830 mg) and DIPEA (1.45 mL) in DCM/DMSO (1:1; 5 mL). The mixture was further stirred at rt for 1 h, diluted with water and extracted with DCM. The org. layer was successively washed with water and brine, dried over MgSO$_4$, concentrated under reduced pressure and crystallized from ether/EA, affording a colourless solid (618 mg; 75% yield).

$^1$H NMR (DMSO d6) δ: 11.17 (s, 1H), 9.68 (s, 1H), 7.57 (m, 1H), 7.40 (d, J=8.8 Hz, 1H), 4.66 (m, 1H), 4.59 (s, 2H), 4.20 (m, 1H), 3.70 (dd, J=10.0, 7.0 Hz, 1H), 2.59 (m, 2H), 1.98 (m, 2H).

Preparation AS: (S)-1-amino-1,2-dihydro-pyrrolo[3,2,1-ij]quinolin-4-one

AS.i. 2-methoxy-8-vinyl-quinoline (PPh$_3$)$_4$Pd (578 mg) was added at rt to a solution of vinylboronic anhydride pyridine complex (1.2 g) in DME (80 mL).

The solution was degassed by bubbling N₂ through for 20 min. K₂CO₃ (1.38 g), water (24 mL) and trifluoro-methane-sulfonic acid 2-methoxy-quinolin-8-yl ester (3.07 g) were added. The mixture was refluxed overnight, cooled to rt and partitioned between water and ether. The aq. phase was washed with ether and the combined org. phases were washed with water and brine, dried over MgSO₄, concentrated under reduced pressure and purified by CC (Hept/EA 4:1), affording a yellow liquid (1.18 g; 64% yield).

$^1$H NMR (CDCl₃) δ: 7.97 (d, J=8.8 Hz, 1H), 7.88 (m, 2H), 7.64 (dd, J=7.9, 1.5 Hz, 1H), 7.36 (t, J=7.6 Hz, 1H), 6.91 (d, J=8.8 Hz, 1H), 6.02 (dd, J=17.9, 1.8 Hz, 1H), 5.45 (dd, J=11.1, 1.8 Hz, 1H), 4.10 (s, 3H).

AS.ii. (R)-1-(2-methoxy-quinolin-8-yl)-ethane-1,2-diol

Starting from intermediate AS.i and AD-mix p and using procedure L, the title compound was obtained as a beige solid (3.22 g, quant).

MS (ESI, m/z): 279.3[M+H⁺].

AS.iii. (R)-2-(tert-butyl-dimethyl-silanyloxy)-1-(2-methoxy-quinolin-8-yl)-ethanol Starting from intermediate AS.ii and using procedure M, the title compound was obtained as a yellow oil (4.16 g, quant.).

MS (ESI, m/z): 334.0[M+H⁺].

AS.iv. [(S)-2-(tert-butyl-dimethyl-silanyloxy)-1-(2-methoxy-quinolin-8-yl)-ethyl]-carbamic acid tert-butyl ester Starting from intermediate AS.iii (4.70 g), the title compound was prepared in analogy to Preparation Z, steps Z.iv (Mitsunobu reaction followed by azide reduction) and Z.v. (Boc protection using procedure G). It was obtained as a slightly yellow oil (8.4 g; quant.; contaminated by Boc₂O).

MS (ESI, m/z): 359.3[M+H⁺].

AS.v. [(S)-2-hydroxy-1-(2-methoxy-quinolin-8-yl)-ethyl]-carbamic acid tert-butyl ester Starting from intermediate AS.iv (6.48 g) and using procedure J, the title compound was obtained as a colourless foam (2.99 g; 63% yield).

MS (ESI, m/z): 319.0[M+H⁺].

AS.vi. ((S)-4-oxo-1,2-dihydro-4H-pyrrolo[3,2,1-ij]quinolin-1-yl)-carbamic acid tert-butyl ester Starting from intermediate AS.v (3.34 g) and using procedure H (but heating the reaction mixture at 50° C.), the title compound was obtained as a colourless solid (2.64 g; 88% yield).

MS (ESI, m/z): 287.1[M+H⁺].

AS.vii. (S)-1-amino-1,2-dihydro-pyrrolo[3,2,1-ij]quinolin-4-one

Starting from intermediate AS.vi (2.63 g) and using procedure B, the title compound was obtained as a colourless solid (1.58 g; 93% yield).

MS (ESI, m/z): 187.1[M+H⁺].

Preparation AT: (S)-4-aminomethyl-4,5-dihydro-pyrrolo[3,2,1-de][1,5]naphthyridin-7-one AT.i. Acetic acid (S)-3-azido-2-(6-methoxy-[1,5]naphthyridin-4-yl)-propyl ester Starting from intermediate V.ii (1.65 g) and using the same procedure as for the preparation of intermediate Z.iv, the title compound was obtained as a colourless oil (1.63 g; 90% yield).

MS (ESI, m/z): 302.0[M+H⁺].

AT.ii. Acetic acid (S)-3-tert-butoxycarbonylamino-2-(6-methoxy-[1,5]naphthyridin-4-yl)-propyl ester Starting from intermediate AT.i (1.63 g) and using successively procedures F and G, the title compound was obtained as pale yellow oil (2.04 g; 100% yield).

MS (ESI, m/z): 376.2[M+H⁺].

AT.iii. [(S)-3-hydroxy-2-(6-methoxy-[1,5]naphthyridin-4-yl)-propyl]-carbamic acid tert-butyl ester A suspension of intermediate AT.ii (2.05 g) and K₂CO₃ (3.02 g) in MeOH (72 mL) was stirred at rt for 30 min. The solvent was removed under reduced pressure and the residue was taken up in DCM/water. The org. layer was washed with brine, dried over MgSO₄, concentrated and purified by CC (DCM/MeOH/NH₄OH 1000:50:4), affording a colourless foam (1.28 g; 70% yield).

MS (ESI, m/z): 334.2[M+H⁺].

AT.iv. ((S)-7-oxo-4,5-dihydro-7H-pyrrolo[3,2,1-de][1,5]naphthyridin-4-ylmethyl)-carbamic acid tert-butyl ester Starting from intermediate AT.iii (1.28 g) and using procedure H for the formation of the mesylate, followed by heating of the reaction mixture for 2 h at 60° C. to complete the cyclisation, the title compound was obtained as a colourless foam (985 mg; 85% yield).

MS (ESI, m/z): 302.2[M+H⁺].

AT.v. (S)-4-aminomethyl-4,5-dihydro-pyrrolo[3,2,1-de][1,5]-naphthyridin-7-one

Starting from intermediate AT.iv (980 mg) and using procedure B, the title compound was obtained as pale yellow solid (522 mg; 80% yield).

MS (ESI, m/z): 202.2[M+H⁺].

Preparation AU: 3-[(S)-2-oxo-3-(3-oxo-3,4-dihydro-2H-benzo[1,4]thiazin-6-yl)-oxazolidin-5-yl]-propionaldehyde Starting from (S)-tert-butyl-dimethyl-(3-oxiranyl-propoxy)-silane (prepared according to *Org. Lett.* (2005), 7 (19), 4083-4086), the title compound (obtained as a pink solid) was prepared in analogy to Preparation U in 4 steps (epoxide opening: 50% yield; oxazolidinone formation: 100% yield; alcohol deprotection: 71% yield; aldehyde formation: 91% yield).

The analytical data were identical with those of the compound of Preparation U.

Preparation AV: 3-[(S)-2-oxo-3-(3-oxo-3,4-dihydro-2H-benzo[1,4]oxazin-6-yl)-oxazolidin-5-yl]-propionaldehyde Starting from (S)-tert-butyl-dimethyl-(3-oxiranyl-propoxy)-silane (prepared according to *Org. Lett.* (2005), 7 (19), 4083-4086), the title compound (obtained as a beige solid) was prepared in analogy to Preparation T in 4 steps (epoxide opening: 45% yield, oxazolidinone formation: 100% yield, alcohol deprotection: 65% yield, aldehyde formation: 87% yield).

The analytical data were identical with those of the compound of Preparation T.

Preparation AW: methanesulfonic acid 3-[(S)-2-oxo-3-(3-oxo-3,4-dihydro-2H-benzo[1,4]thiazin-6-yl)-oxazolidin-5-yl]-propyl ester AW.i. 6-[(S)-5-(tert-butyl-dimethyl-silanyloxy)-2-hydroxy-pentylamino]-4H-benzo[1,4]thiazin-3-one A mixture of (S)-tert-butyl-dimethyl-(3-oxiranyl-propoxy)-silane (28.3 g, prepared according to *Org. Lett.* (2005), 7, 3997) and 6-amino-4H-benzo[1,4]thiazin-3-one (23.6 g) in MeCN (390 mL) was treated with LiClO$_4$ (41.8 g) and heated at 60° C. for 4 h. The volatiles were removed under reduced pressure and the residue partitioned between EA and brine. The org. phase was dried over MgSO$_4$ and concentrated. The residue was purified by CC (Hept/EA 1:1, EA) to give the desired intermediate as a yellowish foam (8.4 g; 16% yield).
MS (ESI, m/z): 397.1 [M+H$^+$].

AW.ii. 6-{(S)-5-[3-(tert-butyl-dimethyl-silanyloxy)-propyl]-2-oxo-oxazolidin-3-yl}-4H-benzo[1,4]thiazin-3-one A solution of intermediate AW.i (8.0 g) in THF (500 mL) was treated with CDI (4.9 g) and heated at 50° C. overnight. The mixture was cooled to rt, diluted with EA and washed with water and brine, dried over MgSO$_4$ and concentrated. The product was crystallized from Hept/EA to give the desired oxazolidinone as a beige solid (4.5 g; 53% yield).
MS (ESI, m/z): 423.4[M+H$^+$].

AW.iii. 6-[(S)-5-(3-hydroxy-propyl)-2-oxo-oxazolidin-3-yl]-4H-benzo[1,4]thiazin-3-one A suspension of intermediate AW.ii (4.5 g) in THF (42 mL) was treated with 1M. TBAF solution in THF (1 eq.). The brown solution was stirred at rt for 4 h, diluted with EA and washed with water and brine, dried over MgSO$_4$ and concentrated. The residue was purified by CC (EA then EA/MeOH 9:1) to give the desired alcohol as a yellowish foam (3.6 g; 100% yield).
MS (ESI, m/z): 309.3[M+H$^+$].

AW.iv. Methanesulfonic acid 3-[(S)-2-oxo-3-(3-oxo-3,4-dihydro-2H-benzo[1,4]thiazin-6-yl)-oxazolidin-5-yl]-propyl ester A suspension of intermediate AW.iii (3.0 g) in DCM was treated with TEA (2.8 mL) and dropwise with MsCl (1.37 g). The mixture was stirred at rt for 2 h, diluted with DCM, washed with water, dried over MgSO$_4$ and concentrated. The residue was crystallized from ether/EA to give the desired mesylate as a beige solid (3.6 g; 93% yield).
MS (ESI, m/z): 387.2[M+H$^+$].

Preparation AX: rac-4-amino-3-fluoro-4,5-dihydropyrrolo[3,2,1-de][1,5]naphthyridin-7-one AX.i. 7-fluoro-2-methoxy-8-vinyl-[1,5]naphthyridine To a solution of 8-bromo-7-fluoro-2-methoxy-1,5-naphthyridine (5.0 g; commercial) in 1,2-DME (150 mL) was added tetrakis-(PPh$_3$)Pd (1.1 g) and the mixture was purged with N$_2$ for 20 min. K$_2$CO$_3$ (2.69 g), water (50 mL) and vinylboronic anhydride pyridine complex (2.34 g) were added. The mixture was stirred at reflux for 3 h. After cooling to rt, water was added and the mixture was extracted with EA. The combined org. phases were washed with brine, dried over MgSO$_4$, concentrated and purified by CC (EA/Hept 1:1), affording the title intermediate as a brown oil (3.12 g, 79% yield).
MS (ESI, m/z): 205.0[M+H$^+$].

AX.ii. (R)-1-(3-fluoro-6-methoxy-[1,5]naphthyridin-4-yl)-ethane-1,2-diol

Starting from intermediate AX.i (3.12 g) and using procedure L with AD-mix (3, the title compound was obtained as an off-white solid (4 g, quant.).
MS (ESI, m/z): 239.0[M+H$^+$].

AX.iii. (R)-2-(tert-butyl-dimethyl-silanyloxy)-1-(3-fluoro-6-methoxy-[7,5]naphthyridin-4-yl)-ethanol To a solution of intermediate AX.ii (3.96 g) in DCM (160 mL) were added imidazole (1.05 eq.), TBDMSCl (1.05 eq.) and DMAP (0.1 eq.). The mixture was stirred at rt for 1 h. Water was added and the mixture was extracted with DCM. The org. layer was dried over MgSO$_4$ and concentrated to afford the title intermediate as a yellow oil (4.52 g, 77%).
MS (ESI, m/z): 353.2 [M+H$^+$].

AX.iv. [(S)-2-(tert-butyl-dimethyl-silanyloxy)-1-(3-fluoro-6-methoxy-[7,5]naphthyridin-4-yl)-ethyl]-carbamic acid tert-butyl ester Starting from intermediate AX.iii (4.52 g) and using procedure N', the title intermediate was obtained as a light yellow oil (6.76 g, quant.).
MS (ESI, m/z): 452.2[M+H$^+$].

AX.v. [(S)-1-(3-fluoro-6-methoxy-[7,5]naphthyridin-4-yl)-2-hydroxy-ethyl]-carbamic acid tert-butyl ester Starting from intermediate AX.iv (6.76 g) and using procedure J, the title intermediate was obtained as a yellow oil (3.96 g, 78% yield).
MS (ESI, m/z): 338.2[M+H$^+$].

AX.vi. ((S)-3-fluoro-7-oxo-4,5-dihydro-7H-pyrrolo[3,2,1-de][1,5]naphthyridin-4-yl)-carbamic acid tert-butyl ester Starting from intermediate AX.v (3.46 g) and using procedure H followed by heating at 80° C. for 18 h in DCE, the title intermediate was obtained as a yellow oil (0.90 g, 28% yield).
MS (ESI, m/z): 306.2[M+H$^+$].

AX.vii. rac-4-amino-3-fluoro-4,5-dihydro-pyrrolo[3,2,1-de][1,5]naphthyridin-7-one Starting from intermediate AX.vi (0.875 g) and using procedure B, the title intermediate was obtained as a pale yellow solid (0.42 g, 71% yield). An analysis of the ee-value indicated that the product was present as a racemate. Since no ee-determinations in previous steps have been made, a racemisation at an earlier stage in the synthetic sequence cannot be excluded.

MS (ESI, m/z): 206.1[M+H$^+$].

Preparation AY: methanesulfonic acid 2-[(S)-2-oxo-3-(3-oxo-3,4-dihydro-2H-benzo[1,4]oxazin-6-yl)-oxazolidin-5-yl]-ethyl ester Starting from tert-butyl-dimethyl-[(S)-2-oxiranyl-ethoxy]-silane, the title compound was prepared in analogy to Preparation I.

The analytical data were identical with those of the compound of Preparation I.

Preparation AZ: (R)-6-amino-7-fluoro-5,6-dihydro-pyrrolo[1,2,3-de]quinoxalin-3-one The title compound was prepared as described in Preparation AD, using however AD-mix α in the first step.

The analytical data were identical with those of the compound of Preparation AD.

Preparation BA: 6-{5-[(1RS)-1-(tert-butyl-dimethyl-silanyloxy)-3-hydroxy-propyl]-((5RS)-2-oxo-oxazolidin-3-yl)}-4H-benzo[1,4]thiazin-3-one

BA.i. (3RS)-3-(tert-butyl-dimethyl-silanyloxy)-3-((2RS)-oxiran-2-A-propionic acid tert-butyl ester A solution of 3-[[(tert-butyl-dimethylsilyl]oxy]-4-pentenoic acid tert-butyl ester (3.60 g; prepared according to *J. Org. Chem.* (1994), 59, 4760-4764) in DCM (100 mL) was reacted with MCPBA (3.96 g) for 2 days. The reaction mixture was partitioned between DCM and an aq. solution containing Na$_2$S$_2$O$_3$ (10%) and NaHCO$_3$ (sat.). The org. phase was separated, dried over MgSO$_4$, evaporated under reduced pressure and purified by CC (Hept/EA 9:1 to 4:1), affording a colourless liquid (2.55 g; 67% yield; 3:2 mixture of diastereomers).

$^1$H NMR (CDCl$_3$) δ: 4.02 (m, 1H, diast. B), 3.76 (d, J=6.4 Hz, 1H, diast. A), 3.02 (m, 1H, diast. A), 2.99 (m, 1H, diast. B), 2.8-2.4 (m, 4H, diast. A and B), 1.45 (s, 9H, diast. A and B), 0.88 (m, 9H, diast. A and B), 0.10 (m, 6H, diast. A and B).

BA.ii. (3RS)-3-(tert-butyl-dimethyl-silanyloxy)-(4RS)-4-hydroxy-5-(3-oxo-3,4-dihydro-2H-benzo[1,4]thiazin-6-ylamino)-pentanoic acid tert-butyl ester A solution of intermediate BA.i (6.05 g) and 6-amino-4H-benzo[1,4]thiazin-3-one (3.60 g) in EtOH/water (9:1; 100 mL) was refluxed for 30 h. The org. solvent was removed under reduced pressure and the residue was taken up in EA (20 mL) and filtered. The filtrate was concentrated under reduced pressure and purified by CC (Hept/EA 1:1 to 1:2), affording after trituration in EA/ether, a colourless solid (3.26 g; 34% yield).

MS (ESI, m/z): 483.2[M+H$^+$].

BA.iii. (3RS)-3-(tert-butyl-dimethyl-silanyloxy)-3-[((5RS)-2-oxo-3-(3-oxo-3,4-dihydro-2H-benzo[1,4]thiazin-6-yl))-oxazolidin-5-yl]-propionic acid tert-butyl ester Starting from intermediate BA.ii (3.25 g) and following procedure I, the title compound was obtained as a colourless solid (3.27 g; 95% yield).

MS (ESI, m/z): 509.1[M+H$^+$].

BA.iv. 6-{5-[(1RS)-1-(tert-butyl-dimethyl-silanyloxy)-3-hydroxy-propyl]-((5RS)-2-oxo-oxazolidin-3-yl)}-4H-benzo[1,4]thiazin-3-one Starting from intermediate BA.iii (1.01 g) and following procedure A, the title compound was obtained, after CC (Hept/EA 2:1 then 0:1), as a colourless foam (205 mg; 23% yield).

MS (ESI, m/z): 439.1[M+H$^+$].

Preparation BB: (R)-6-amino-7-fluoro-2-methoxy-5,6-dihydro-pyrrolo[1,2,3-de]quinoxalin-3-one

BB.i. 6-fluoro-2,3-dimethoxy-quinoxaline-5-carbaldehyde

A solution of tetramethylpiperidine (16.4 mL) in dry THF (100 mL) was cooled to −78° C. and treated dropwise with n-BuLi (2.5M in Hex; 39 mL). The solution was further stirred at −78° C. for 30 min. A solution of 6-fluoro-2,3-dimethoxy-quinoxaline (15.6 g; prepared from the commercially available 2,3-dichloro-6-fluoroquinoxaline according to *Egyptian Journal of Chemistry* (1980), Volume Date 1977, 20, 427-39) in dry THF (450 mL) was cooled to −78° C., treated dropwise with the first solution and further stirred at −78° C. for 30 min. The resulting reaction mixture was treated with DMF (11.56 mL) and further stirred at −78° C. for 15 min. The reaction mixture was poured onto a mixture of a sat. NH$_4$Cl solution and ice and extracted with ether. The org. layer was washed with brine, dried over MgSO$_4$, evaporated under reduced pressure and crystallised from Hex/EA affording a light yellow solid (12.5 g; 71% yield).

$^1$H NMR (CDCl$_3$) δ: 11.10 (d, J=0.6 Hz, 1H), 7.96 (dd, J=9.1, 5.3 Hz, 1H), 7.30 (m, 1H), 4.19 (m, 3H), 4.15 (m, 3H).

BB.ii. 6-fluoro-2,3-dimethoxy-5-vinyl-quinoxaline

A suspension of methyltriphenylphosphonium bromide (18.15 g) in THF (200 mL) was treated with tBuOK (5.7 g). After stirring for 1 h, the solution was cooled to 0° C. and treated with a solution of intermediate BB.i (10.0 g) in THF (100 mL). The reaction mixture was further stirred at rt for 3 h and sequentially washed with water and with a sat. NH$_4$Cl solution. The org. layer was dried over MgSO$_4$, evaporated and purified by CC (Hex/EA 4:1 to 2:1), affording a colourless solid (8.80 g; 89% yield).

$^1$H NMR (CDCl$_3$) δ: 7.62 (dd, J=8.8, 5.3 Hz, 1H), 7.46 (m, 1H), 7.25 (m, 1H), 6.34 (m, 1H), 5.69 (m, 1H), 4.17 (s, 3H), 4.13 (s, 3H).

BB.iii. (S)-1-(6-fluoro-2,3-dimethoxy-quinoxalin-5-yl)-ethane-1,2-diol

Starting from intermediate BB.ii (8.70 g) and using procedure L with AD-mix α, the title compound was obtained as a beige solid (5.60 g; 56% yield) after crystallization from ether.

¹H NMR (DMSO d6) δ: 7.67 (dd, J=9.1, 5.6 Hz, 1H), 7.35 (dd, J=10.3, 9.1 Hz, 1H), 5.56 (m, 1H), 5.20 (d, J=6.4 Hz, 1H), 4.73 (t, J=6.2 Hz, 1H), 4.05 (s, 3H), 4.01 (s, 3H), 3.87 (m, 1H), 3.69 (m, 1H).

BB.iv. (S)-2-(tert-butyl-dimethyl-silanyloxy)-1-(6-fluoro-2,3-dimethoxy-quinoxalin-5-yl)-ethanol Starting from intermediate BB.iii (5.50 g) and using procedure M, the title compound was obtained, after purification by CC (Hept/EA 2:1), as a yellow oil (7.40 g; 94% yield).
MS (ESI, m/z): 383.2[M+H⁺].

BB.v. [(R)-2-(tert-butyl-dimethyl-silanyloxy)-1-(6-fluoro-2,3-dimethoxy-quinoxalin-5-yl)-ethyl]-carbamic acid tert-butyl ester Starting from intermediate BB.iv (7.30 g) and using procedure N', the title compound was obtained, after purification by CC (Hept/EA 9:1 t 4:1), as a yellow oil (6.7 g, 73% yield).
¹H NMR (CDCl₃) δ: 7.66 (dd, J=9.1, 5.6 Hz, 1H), 7.23 (m, 1H), 6.50 (m, 1H), 4.17 (s, 3H), 4.13 (s, 3H), 3.92 (d, J=6.4 Hz, 2H), 1.42 (s, 9H), 0.76 (s, 9H), −0.09 (s, 3H), −0.14 (s, 3H).

BB.vi. [(R)-1-(6-fluoro-2,3-dimethoxy-quinoxalin-5-yl)-2-hydroxy-ethyl]-carbamic acid tert-butyl ester Starting from intermediate BB.v (6.70 g) and using procedure J, the title compound was obtained, after crystallization from Hept/EA 1:1, as a colourless solid (3.60 g; 70% yield).
¹H NMR (CDCl₃) δ: 7.69 (dd, J=9.1, 5.6 Hz, 1H) 7.26 (m, 1H), 6.60 (m, 1H), 5.80 (m, 1H), 4.17 (s, 3H), 4.13 (s, 3H), 3.95 (m, 2H), 1.43 (s, 9H).

BB.vii. ((R)-7-fluoro-2-methoxy-3-oxo-5,6-dihydro-3H-pyrrolo[1,2,3-de]quinoxalin-6-yl)-carbamic acid tert-butyl ester Starting from intermediate BB.vi (3.50 g) and using procedure H, the intermediate mesylate was formed. The reaction mixture was further stirred at reflux for 12 h, cooled to rt, washed with water. The org. layer was dried over MgSO₄ and concentrated under reduced pressure affording a crude solid (2.70 g, 84% yield) containing the title compound in a 3:2 mixture with (R)-4-(6-fluoro-2,3-dimethoxy-quinoxalin-5-yl)-oxazolidin-2-one. The mixture was used without any further purification in the next step.

BB.viii. (R)-6-amino-7-fluoro-2-methoxy-5,6-dihydro-pyrrolo[1,2,3-de]quinoxalin-3-one Starting from intermediate BB.vii (2.70 g) and using procedure B, the title compound was obtained after purification by CC (EA/MeOH 9:1 containing 1% NH₄OH) as a colourless solid (469 mg; 25% yield).
MS (ESI, m/z): 236.2[M+H⁺].

Preparation BC: (R)-1-amino-1,2-dihydro-pyrrolo[3,2,1-ij]quinolin-4-one

The title compound was prepared in analogy to Preparation AS, using however AD-mix a in the second step.
The analytical data were identical with those of the compound of Preparation AS.

Preparation BD: toluene-4-sulfonic acid (R)-4-hydroxy-7-oxo-4,5-dihydro-7H-pyrrolo[3,2,1-de][1,5]naphthyridin-4-ylmethyl ester BD.i. 2-(6-methoxy-[1,5]naphthyridin-4-yl)-propane-1,3-diol A solution of 2-methoxy-8-methyl-1,5-naphthyridine (2.90 g; prepared according to WO 00/21948) in aq. formaldehyde (37%; 7.8 mL) was heated at 100° C. for 3 days. After cooling to rt, the reaction mixture was concentrated to dryness and the residue was taken up in MeOH (10 mL) and concentrated again. The residue was purified by CC (DCM/MeOH/NH₄OH 1000:100:8) to give a colourless solid (2.78 g; 71% yield).
¹H NMR (DMSO-d₆) δ: 8.67 (d, J=4.4 Hz, 1H), 8.22 (d, J=9.1 Hz, 1H), 7.51 (d, J=4.4 Hz, 1H), 7.22 (d, J=9.1 Hz, 1H), 4.56 (m, 2H), 4.00 (m, 4H), 3.84 (m, 4H).

BD.ii. Acetic acid (S)-3-hydroxy-2-(6-methoxy-[1,5]naphthyridin-4-yl)-propyl ester A solution of intermediate BD.i (1.34 g) in vinyl acetate (10 mL) was treated with powdered 3 Å molecular sieves (78 mg) and stirred at rt for 15 min under an atmosphere of nitrogen. Lipase acrylic resin from *Candida antarctica* (600 mg, Sigma L4777) was added and stirring was continued for 4 h at rt. The polymer bound enzyme was filtered off, the filter cake was rinsed with THF and the filtrate was concentrated. The residue was purified by CC (DCM/MeOH/NH₄OH 1000:25:2), affording a colourless oil (0.688 g; 44% yield).
¹H NMR (CDCl₃) δ: 8.72 (d, J=4.7 Hz, 1H), 8.23 (d, J=9.1 Hz, 1H), 7.46 (d, J=4.7 Hz, 1H), 7.15 (d, J=9.1 Hz, 1H), 4.64 (m, 2H), 4.24 (m, 1H), 4.08 (m, 5H), 2.05 (s, 3H).

BD.iii. Acetic acid (S)-7-oxo-4,5-dihydro-7H-pyrrolo[3,2,1-de][1,5]naphthyridin-4-ylmethyl ester A solution of intermediate BD.ii (2.05 g) in DCM (40 mL) was transformed into the corresponding mesylate using procedure H. After full consumption of the alcohol, DCE (40 mL) was added and the solution was further stirred at 60° C. for 4 h. After cooling to rt, water was added and the two layers were decanted and the aq. layer was extracted once more with DCM. The combined org. layers were concentrated to dryness. The residue was triturated with TBME, affording a grey solid (1.40 g; 77% yield).
¹H NMR (CDCl₃) δ: 8.53 (d, J=4.7 Hz, 1H), 7.93 (d, J=9.7 Hz, 1H), 7.34 (dd, J=4.7, 0.9 Hz, 1H), 6.90 (d, J=9.7 Hz, 1H), 4.57 (dd, J=12.9, 9.4 Hz, 1H), 4.37 (d, J=6.4 Hz, 2H), 4.27 (dd, J=13.2, 5.0 Hz, 1H), 4.09 (m, 1H), 2.06 (s, 3H).

BD.iv. (S)-4-hydroxymethyl-4,5-dihydro-pyrrolo[3,2,1-de][1,5]naphthyridin-7-one

To a solution of intermediate BD.iii (1.11 g) in MeOH (30 mL), cooled to −10° C., K₂CO₃ (313 mg, 0.5 eq.) was added and the mixture was vigorously stirred at 0° C. for 20 min. The mixture was concentrated and the residue was purified by CC (DCM/MeOH/NH₄OH 1000:100:8), affording a colourless solid (773 mg; 84% yield).
MS (ESI, m/z): 203.0[M+H⁺].

BD.v. Methanesulfonic acid (S)-7-oxo-4,5-dihydro-7H-pyrrolo[3,2,1-de][1,5]naphthyridin-4-ylmethyl ester A solution of intermediate BD.iv (600 mg) in DCM (30 mL) was transformed into the corresponding mesylate using procedure H. The crude material (1.03 g) was used in the next step without any further purification.
MS (ESI, m/z): 281.2[M+H$^+$].

BD.vi. 4-methylene-4,5-dihydro-pyrrolo[3,2,1-de][1,5]naphthyridin-7-one

A solution of intermediate BD.v (1.03 g) in DMF (10 mL) was stirred at rt in the presence of DBU (1.12 mL) for 2 h. The reaction mixture was diluted with EA and water. The aq. layer was extracted with EA (2×100 mL) and DCM/MeOH (3×50 mL; 9:1). The combined org. layers were sequentially washed with water and brine and dried over MgSO$_4$. The solvent was evaporated under reduced pressure, affording a yellow solid (490 mg; 72% yield).
$^1$H NMR (CDCl$_3$) δ: 8.55 (d, J=5.0 Hz, 1H), 7.96 (d, J=9.7 Hz, 1H), 7.44 (d, J=5.0 Hz, 1H), 6.92 (d, J=9.7 Hz, 1H), 6.00 (td, J=2.9, 0.9 Hz, 1H), 5.65 (td, J=2.6, 0.9 Hz, 1H), 5.02 (t, J=2.6 Hz, 2H).

BD.vii. (R)-4-hydroxy-4-hydroxymethyl-4,5-dihydro-pyrrolo[3,2,1-de][1,5]naphthyridin-7-one A solution of intermediate BD.vi (240 mg) was dihydroxylated in presence of AD-mix a using procedure L. The crude yellow solid (216 mg; 76% yield) was used in the next step without any further purification.
$^1$H NMR (CDCl$_3$) δ: 8.55 (d, J=4.7 Hz, 1H), 7.90 (m, 1H), 7.53 (d, J=4.7 Hz, 1H), 6.81 (m, 1H), 4.35 (m, 2H), 3.89 (m, 3H).

BD.viii. Toluene-4-sulfonic acid (R)-4-hydroxy-7-oxo-4,5-dihydro-7H-pyrrolo[3,2,1-de][1,5]naphthyridin-4-ylmethyl ester A solution of intermediate BD.vii (210 mg) was stirred at rt overnight in presence of TEA (0.20 mL), TsCl (185 mg) and dibutyltin oxide (12 mg). The reaction mixture was diluted with water (3 mL). The org. layer was washed with sat. NaHCO$_3$ and brine and dried over MgSO$_4$. The solvent was evaporated under reduced pressure, affording an off-white solid (172 mg; 48% yield).
MS (ESI, m/z): 373.0[M+H$^+$].

Preparation BE: rac-1-amino-9-bromo-1,2-dihydro-pyrrolo[3,2,1-ij]quinolin-4-one

BE.i. (7-bromo-2-methoxy-quinolin-8-yl)-methanol

A suspension of 7-bromo-8-bromomethyl-2-(methyloxy) quinoline (35.2 g; prepared according to WO 2007/081597; containing 20% of debrominated compound) in acetone/water (1:1; 860 mL) was refluxed for 6 h in presence of NaHCO$_3$ (14.63 g). The org. solvent was removed under reduced pressure and the residue was extracted with EA. The org. layer was washed with brine and dried over Na$_2$SO$_4$. The solvent was then evaporated and the residue was crystallized from TBDME, affording an off-white solid (16.0 g; 56% yield).
MS (ESI, m/z): 268.0[M+H$^+$].

BE.ii. 7-bromo-2-methoxy-quinoline-8-carbaldehyde

A solution of oxalyl chloride (9.47 mL) in DCM (200 mL) was cooled to −78° C. and treated dropwise with a solution of DMSO (9.52 mL) in DCM (80 mL). After stirring for 15 min, the solution was treated with a solution of intermediate BE.i (10.0 g) in DCM (80 mL). After further stirring at −78° C. for 3 h, the reaction mixture was treated dropwise with a solution of TEA (39.0 mL) in DCM (80 mL) over 1 h. The reaction mixture was further stirred for 40 min and allowed to reach rt. The reaction mixture was than treated with a sat. NaHCO$_3$ solution. The org. layer was separated and washed with brine, dried over Na$_2$SO$_4$. The solvent was evaporated and the residue was dissolved in EA and filtered through a pad of silica gel, affording a pale yellow solid (3.74 g; 38% yield).
$^1$H NMR (DMSO-d$_6$) δ: 11.06 (s, 1H), 8.36 (d, J=8.8 Hz, 1H), 8.04 (d, J=8.8 Hz, 1H), 7.74 (m, 1H), 7.17 (d, J=8.8 Hz, 1H), 4.01 (s, 4H).

BE.iii. 7-bromo-2-methoxy-8-vinyl-quinoline

To a solution of methyltriphenylphosphonium bromide (1.00 g) in THF (8 mL) cooled to −78° C. was added n-BuLi (2.5M in Hex, 1.09 mL, 1.5 eq.). The mixture was stirred 15 min at this temperature and then 45 min at 0° C. before cooling again to −78° C. A solution of intermediate BE.ii (500 mg) in THF (8 mL) was quickly added. The reaction proceeded overnight with gradual warming to rt. MeOH was added to quench the reaction and the mixture was concentrated under reduced pressure. The residue was purified by CC (Hept/EA 4:1 to 2:1), affording the title compound as a yellowish oil (411 mg; 83% yield).
MS (ESI, m/z): 264.3 [M+H$^+$].

BE.iv. rac-1-(7-bromo-2-methoxy-quinolin-8-yl)-ethane-1,2-diol

Starting from intermediate BE.iii (5.50 g) and proceeding in analogy to Preparation AX, step AX.ii, using however K$_2$OsO$_4$/NMO instead of AD-mix β and omitting the use of methylsulfonamide, the title compound was obtained as a beige solid (5.75 g, 93% yield) after crystallization from TBDME.
$^1$H NMR (CDCl$_3$) δ: 8.01 (d, J=9.1 Hz, 1H), 7.58 (m, 1H), 7.50 (m, 1H), 6.97 (m, 1H), 5.53 (m, 1H), 4.07 (s, 3H), 3.91 (m, 2H).

BE.v. rac-1-(7-bromo-2-methoxy-quinolin-8-yl)-2-(tert-butyl-dimethyl-silanyloxy)-ethanol Starting from intermediate BE.iv (5.70 g) and using procedure M, the title compound was obtained as a brown oil (7.79 g, 99% yield).
$^1$H NMR (CDCl$_3$) δ: 7.97 (d, J=8.8 Hz, 1H), 7.55 (m, 1H), 7.45 (m, 1H), 6.93 (d, J=8.8 Hz, 1H), 5.54 (t, J=5.6 Hz, 1H), 4.12 (m, 1H), 4.04 (s, 3H), 3.98 (m, 1H), 0.75 (m, 9H), −0.14 (d, J=0.9 Hz, 6H).

BE.vi. rac-1-(7-bromo-2-methoxy-quinolin-8-yl)-2-(tert-butyl-dimethyl-silanyloxy)-ethylamine Starting from intermediate BE.v (7.75 g), the title compound was prepared in analogy to Preparation Z, step Z.iv. A yellow oil (2.6 g; 33% yield) was obtained.
MS (ESI, m/z): 411.3[M+H$^+$].

BE.vii. rac-[1-(7-bromo-2-methoxy-quinolin-8-yl)-2-(tert-butyl-dimethyl-silanyloxy)-ethyl]-carbamic acid tert-butyl ester Starting from intermediate BE.vi (2.60 g) and using procedure G, the title compound was obtained as a yellow oil (3.20 g, 99% yield).

¹H NMR (CDCl₃) δ: 7.95 (d, J=9.1 Hz, 1H), 7.55 (m, 1H), 7.44 (m, 1H), 6.92 (d, J=9.1 Hz, 1H), 6.35 (m, 1H), 4.97 (m, 1H), 4.06 (m, 3H), 4.03 (m, 1H), 3.74 (m, 1H), 1.25 (m, 9H), 0.75 (s, 9H), −0.11 (s, 6H).

BE.viii. rac-[7-(7-bromo-2-methoxy-quinolin-8-yl)-2-hydroxy-ethyl]-carbamic acid tert-butyl ester Starting from intermediate BE.vii (3.20 g) and using procedure J, the title compound was obtained as an off-white solid (1.70 g, 68% yield).
¹H NMR (CDCl₃) δ: 7.98 (d, J=9.1 Hz, 1H), 7.60 (m, 1H), 7.49 (m, 1H), 6.96 (d, J=8.8 Hz, 1H), 5.92 (m, 1H), 4.08 (m, 4H), 4.03 (m, 2H), 1.44 (s, 9H).

BE.ix. rac-(9-bromo-4-oxo-1,2-dihydro-4H-pyrrolo[3,2,1-ij]quinolin-1-yl)-carbamic acid tert-butyl ester Starting from intermediate BE.viii (400 mg) and using the same procedure as for the preparation of intermediate Z.vi, the title compound was obtained as a yellow solid (372 mg, 100% yield).
¹H NMR (CDCl₃) δ: 7.67 (d, J=9.4 Hz, 1H), 7.32 (m, 2H), 6.68 (m, 1H), 5.58 (m, 1H), 4.97 (m, 1H), 4.64 (m, 1H), 4.32 (m, 1H), 1.24 (m, 9H).
MS (ESI, m/z): 365.3[M+H⁺].

BE.x. rac-1-amino-9-bromo-1,2-dihydro-pyrrolo[3,2,1-ij]quinolin-4-one

Starting from intermediate BE.ix (100 mg) and using procedure B, the title compound was obtained as an off-white solid (52 mg, 72% yield).
¹H NMR (CDCl₃) δ: 7.67 (d, J=9.7 Hz, 1H), 7.33 (m, 2H), 6.68 (d, J=9.7 Hz, 1H), 4.89 (dd, J=8.8, 3.5 Hz, 1H), 4.62 (dd, J=13.5, 8.5 Hz, 1H), 4.17 (dd, J=13.5, 3.8 Hz, 1H), 1.80 (m, 2H).

Preparation BF: (R)-1-amino-4-oxo-1,2-dihydro-4H-pyrrolo[3,2,1-ij]quinoline-7-carboxylic acid ethyl ester BF.i. 2-methoxy-8-vinyl-quinoline-5-carboxylic acid ethyl ester A solution of vinylboronic anhydride pyridine complex (1:1; 3.81 g) in DMF (240 mL) was treated with tetrakis(triphenylphosphine)palladium(0) (731 mg) and stirred under nitrogen for 20 min. The reaction mixture was sequentially treated with K₂CO₃ (4.372 g) water (73 mL) and 2-methoxy-8-[[(trifluoromethyl)sulfonyl]oxy]-5-quinoline carboxylic acid ethyl ester (12.0 g; prepared in analogy to the corresponding n-butyl ester described in WO 2006/046552) and further stirred at 85° C. overnight. The reaction mixture was diluted with water and extracted with ether. The org. layer was dried over MgSO₄, concentrated to dryness and purified by CC (Hex/EA, 4:1), affording a yellow oil (5.40 g; 66% yield).
¹H NMR (CDCl₃) δ: 9.20 (d, J=9.1 Hz, 1H), 8.08 (dd, J=7.9, 0.6 Hz, 1H), 7.96 (dd, J=18.2, 11.1 Hz, 1H), 7.86 (d, J=7.9 Hz, 1H), 7.02 (d, J=9.4 Hz, 1H), 6.05 (dd, J=18.2, 1.5 Hz, 1H), 5.54 (dd, J=11.1, 1.5 Hz, 1H), 4.45 (q, J=7.3 Hz, 2H), 4.10 (s, 3H), 1.45 (t, J=7.0 Hz, 3H).

BF.ii. 8-((S)-1,2-dihydroxy-ethyl)-2-methoxy-quinoline-5-carboxylic acid ethyl ester A solution of intermediate BF.i (5.40 g) was dihydroxylated in the presence of AD-mix a using procedure L. After crystallization from ether, the product was obtained as a white solid (4.30 g; 70% yield; enantiomeric excess not checked, assumed 100%).
¹H NMR (DMSO d6) δ: 9.05 (d, J=9.4 Hz, 1H), 8.04 (m, 1H), 7.87 (d, J=7.9 Hz, 1H), 7.15 (d, J=9.4 Hz, 1H), 5.66 (m, 1H), 5.35 (m, 1H), 4.67 (m, 1H), 4.37 (q, J=7.0 Hz, 2H), 4.00 (s, 3H), 3.79 (m, 1H), 3.43 (m, 1H), 1.35 (t, J=7.3 Hz, 3H)

BF.iii. 8-[(S)-2-(tert-butyl-dimethyl-silanyloxy)-1-hydroxy-ethyl]-2-methoxy-quinoline-5-carboxylic acid ethyl ester Starting from intermediate BF.ii (4.20 g) and using procedure M, the title intermediate was obtained as a yellow oil (5.48 g; 94% yield).
MS (ESI, m/z): 406.2[M+H⁺].

BF.iv. 8-[(R)-1-tert-butoxycarbonylamino-2-(tert-butyl-dimethyl-silanyloxy)-ethyl]-2-methoxy-quinoline-5-carboxylic acid ethyl ester A solution of intermediate BF.iii (5.30 g) and PPh₃ (4.11 g) in THF (130 mL) was cooled to 0° C. and treated dropwise with DPPA (3.4 mL) and DIAD (3.36 mL). The reaction mixture was stirred at 0° C. for 15 min than at rt for 1.5 h. The reaction mixture was evaporated to dryness and purified by CC (Hept/EA 2:1), affording the intermediate azide as a yellow oil (6.0 g). The latter was dissolved in THF/water (9:1; 50 mL), treated with PPh₃ (4.1 g) and stirred at 50° C. for 1.5 h. The reaction mixture was then reacted with Boc₂O (5.7 g) and further stirred at rt over the weekend. The reaction mixture was concentrated under reduced pressure and purified by CC (Hept/EA 9:1 to 4:1), affording a yellow oil (9.20 g; contaminated by remaining Boc₂O).
¹H NMR (CDCl₃) δ: 9.21 (d, J=9.4 Hz, 1H), 8.05 (d, J=7.9 Hz, 1H), 7.59 (d, J=7.6 Hz, 1H), 7.01 (d, J=9.4 Hz, 1H), 5.64 (t, J=4.7 Hz, 1H), 4.44 (q, J=7.0 Hz, 2H), 4.07 (m, 5H), 1.50 (m, 3H), 1.44 (s, 9H), 0.76 (s, 9H), −0.23 (m, 6H).

BF.v. 8-((R)-1-tert-butoxycarbonylamino-2-hydroxy-ethyl)-2-methoxy-quinoline-5-carboxylic acid ethyl ester Starting from intermediate BF.iv (6.56 g) and using procedure J, the title intermediate was obtained as a colourless solid (2.60 g; 51% yield).
¹H NMR (CDCl₃) δ: 9.22 (d, J=9.4 Hz, 1H), 8.06 (d, J=7.6 Hz, 1H), 7.62 (d, J=7.9 Hz, 1H), 7.04 (d, J=9.4 Hz, 1H), 5.55 (m, 1H), 4.44 (q, J=7.3 Hz, 2H), 4.03 (m, 5H), 1.44 (s, 9H).

BF.vi. (R)-1-tert-butoxycarbonylamino-4-oxo-1,2-dihydro-4H-pyrrolo[3,2,1-ij]quinoline-7-carboxylic acid ethyl ester Starting from intermediate BF.v (2.40 g) and using procedure H, the title intermediate was obtained as a colourless solid after trituration in ether (2.10 g; 95% yield).
MS (ESI, m/z): 359.2 [M+H⁺].

BF.vii. (R)-1-amino-4-oxo-1,2-dihydro-4H-pyrrolo[3,2,1-ij]quinoline-7-carboxylic acid ethyl ester Starting from intermediate BF.vi (1.00 g) and using procedure B, the title compound was obtained as a beige solid (690 mg; 96% yield).
MS (ESI, m/z): 259.2[M+H⁺].

Preparation BG: (R)-1-amino-7-hydroxymethyl-1,2-dihydro-pyrrolo[3,2,1-ij]quinolin-4-one

BG.i. ((R)-7-hydroxymethyl-4-oxo-1,2-dihydro-4H-pyrrolo[3,2,1-ij]quinolin-1-yl)-carbamic acid tert-butyl ester Starting from intermediate BF.vi (250 mg) and using procedure A, the title intermediate was obtained as a yellowish solid after trituration in ether (190 mg; 86% yield).
MS (ESI, m/z): 317.2[M+H⁺].

BG.ii. (R)-1-αAmino-7-hydroxymethyl-1,2-dihydro-pyrrolo[3,2,1-ij]quinolin-4-one Starting from intermediate BG.i (180 mg) and using procedure B, the title compound was isolated from the water phase after evaporation to dryness and suspension in DCM/MeOH (9:1), affording 400 mg of a beige solid (contaminated by inorganic salts). The material was used without any further purification in the next steps.
$^1$H NMR (DMSO d6) δ: 8.10 (d, J=9.7 Hz, 1H), 7.65 (d, J=7.6 Hz, 1H), 7.27 (d, J=7.6 Hz, 1H), 6.61 (d, J=9.7 Hz, 1H), 5.41 (m, 1H), 5.19 (m, 1H), 4.79 (m, 2H), 4.55 (dd, J=13.5, 8.5 Hz, 1H), 4.22 (dd, J=13.5, 3.2 Hz, 1H), 4.07 (ddd, J=3.2, 2.1, 0.9 Hz, 1H).

Preparation BH: (R)-1-amino-7-dimethylaminomethyl-1,2-dihydro-pyrrolo[3,2,1-ij]quinolin-4-one

BH.i. ((R)-7-formyl-4-oxo-1,2-dihydro-4H-pyrrolo[3,2,1-ij]quinolin-1-yl)-carbamic acid tert-butyl ester A solution of intermediate BG.i (640 mg) in DCM/THF (40 mL; 2:1) was stirred in the presence of MnO₂ (3.75 g) for 30 min. The reaction mixture was filtered through Celite® and the filtrate was evaporated to dryness. The residue was triturated in ether/Hept, affording a yellow solid (480 mg; 75% yield).
$^1$H NMR (CDCl₃) δ: 10.19 (s, 1H), 8.84 (d, J=9.7 Hz, 1H), 7.69 (m, 2H), 6.81 (d, J=9.7 Hz, 1H), 5.66 (m, 1H), 5.11 (m, 1H), 4.74 (dd, J=13.8, 9.1 Hz, 1H), 4.25 (m, 1H), 1.45 (m, 9H).

BH.ii. ((R)-7-dimethylaminomethyl-4-oxo-1,2-dihydro-4H-pyrrolo[3,2,1-ij]quinolin-1-yl)-carbamic acid tert-butyl ester Starting from intermediate BH.i (200 mg) and NHMe₂ (0.11 mL; 5.6M in EtOH) and using procedure E, the title intermediate was obtained as a yellow solid (140 mg; 64% yield).
MS (ESI, m/z): 344.6[M+H⁺].

BH.iii. (R)-1-amino-7-dimethylaminomethyl-1,2-dihydro-pyrrolo[3,2,1-ij]quinolin-4-one Starting from intermediate BH.ii (140 mg) and using procedure B, the title compound was obtained as an orange oil (74 mg; 76% yield).
MS (ESI, m/z): 244.3[M+H⁺].

Preparation BI: (R)-1-amino-7-pyrrolidin-1-ylmethyl-1,2-dihydro-pyrrolo[3,2,1-ij]quinolin-4-one

BI.i. ((R)-4-oxo-7-pyrrolidin-1-ylmethyl-1,2-dihydro-4H-pyrrolo[3,2,1-ij]quinolin-1-yl)-carbamic acid tert-butyl ester Starting from intermediate BH.i (200 mg) and pyrrolidine (52 µL) and using procedure E, the title intermediate was obtained as a yellow solid (190 mg; 80% yield).
MS (ESI, m/z): 370.4[M+H⁺].

BI.ii. (R)-1-amino-7-pyrrolidin-1-ylmethyl-1,2-dihydro-pyrrolo[3,2,1-ij]quinolin-4-one Starting from intermediate BI.i (190 mg) and using procedure B, the title compound was obtained as an orange oil (100 mg; 72% yield).
MS (ESI, m/z): 269.9[M+H⁺].

Preparation BJ: 3-[(S)-2-oxo-3-(3-oxo-3,4-dihydro-2H-pyrido[3,2-b][1,4]oxazin-6-yl)-oxazolidin-5-yl]-propionaldehyde The title compound was prepared in analogy to Preparation AR, starting however from (S)-2-[2-[[(tert-butyl)dimethylsilyl]oxy]propyl]-oxirane. The yields were similar and the analytical data (MS, $^1$H NMR) were identical.

Preparation BK: 3-[(R)-2-oxo-3-(3-oxo-3,4-dihydro-2H-pyrido[3,2-b][1,4]thiazin-6-yl)-oxazolidin-5-yl]-propionaldehyde

BK.i. (2-tert-butoxycarbonylamino-6-chloro-pyridin-3-ylsulfanyl)-acetic acid ethyl ester A solution of TMEDA (1.677 mL) in THF (20 mL) was cooled to −20° C. and treated dropwise with 2.3M n-BuLi (4.75 mL). After stirring at this temperature for 20 min, the solution was cooled to −78° C. and treated dropwise with a solution of 2-tert-butoxycarbonylamino-6-chloropyridine (1.14 g; commercial) in THF (7.5 mL). The solution was further stirred at this temperature for 1 h and treated with sulfur (S8). After further stirring at this temperature for 20 min the reaction mixture was treated with ethyl bromoacetate (0.86 mL). After further stirring for 2 h at −78° C., the temperature was allowed to reach −45° C. and quenched by the addition of EA and water. The org phase was sequentially washed with 1N HCl, conc. NH₄Cl solution and brine. The org. phase was dried over MgSO₄ and the solvents were evaporated. The residue was purified by CC (Hept/EA 4:1 to 2:1), affording a colourless oil (1.05 g; 60% yield).
$^1$H NMR (CDCl₃) δ: 8.01 (s, 1H), 7.79 (d, J=8.2 Hz, 1H), 6.98 (d, J=8.2 Hz, 1H), 4.14 (q, J=7.0 Hz, 3H), 3.47 (s, 2H), 1.54 (s, 12H), 1.22 (t, J=7.0 Hz, 3H).

BK.ii. 6-chloro-4H-pyrido[3,2-b][1,4]thiazin-3-one

A solution of intermediate BK.i (1.0 g) in DCM (6 mL) was stirred at rt overnight in the presence of TFA (6 mL). The reaction mixture was evaporated to dryness and the residue was dissolved in EtOH and refluxed for 2 days. The reaction mixture was evaporated to dryness and the residue was taken up in EA and a sat. aq. NaHCO₃ solution. The org. layer was washed with brine, dried over MgSO₄, concentrated under reduced pressure and crystallized from ether/Hept, affording a yellow solid (400 mg; 69% yield).

¹H NMR (CDCl₃) δ: 8.28 (d, J=1.5 Hz, 1H), 7.57 (dd, J=8.2, 0.6 Hz, 1H), 6.98 (d, J=8.2 Hz, 1H), 3.50 (m, 2H).

BK.iii. 6-{(R)-5-[3-(tert-butyl-dimethyl-silanyloxy)-propyl]-2-oxo-oxazolidin-3-yl}-4H-pyrido[3,2-b][1,4]thiazin-3-one A vial was charged with intermediate BK.ii (2 g), palladium(II)acetate (224 mg), DPEphos (1.08 g), potassium phosphate tribasic (powdered; 4.33 g) and intermediate AR.ii (3.1 g). Dioxane (dry, over molecular sieves, 50 mL) was then added using a syringe and the resulting suspension was sparged with argon for 5 min. The mixture was then heated in a sealed flask at 80° C. overnight. The residue was extracted with EA/water. The org. layer was washed with brine, dried over MgSO₄ and concentrated. The residue was purified by CC (Hept/EA 2:1, 1:1) affording a yellowish solid (3.58 g; 84% yield).
¹H NMR (DMSO d6) δ: 10.81 (s, 1H), 7.77 (m, 1H), 7.66 (m, 1H), 4.71 (m, 1H), 4.20 (m, 1H), 3.69 (dd, J=10.5, 7.3 Hz, 1H), 3.62 (t, J=6.4 Hz, 2H), 3.51 (s, 2H), 1.74 (m, 2H), 1.56 (dd, J=9.4, 7.3 Hz, 2H), 0.85 (m, 9H), 0.02 (s, 6H).

BK.iv. 6-[(R)-5-(3-hydroxy-propyl)-2-oxo-oxazolidin-3-yl]-4H-pyrido[3,2-b][1,4]thiazin-3-one Starting from intermediate BK.iii (3.58 g) and using procedure J, the title intermediate was obtained as a colourless solid (2.0 g; 76% yield).
¹H NMR (DMSO d6) δ: 10.83 (s, 1H), 7.77 (m, 1H), 7.66 (m, 1H), 4.70 (m, 1H), 4.48 (t, J=5.3 Hz, 1H), 4.20 (m, 1H), 3.70 (dd, J=10.3, 7.0 Hz, 1H), 3.51 (s, 2H), 3.43 (q, J=6.2 Hz, 2H), 3.28 (s, 3H), 1.75 (m, 2H), 1.51 (m, 2H).

BK.v. 3-[(R)-2-oxo-3-(3-oxo-3,4-dihydro-2H-pyrido[3,2-b][1,4]thiazin-6-yl)-oxazolidin-5-yl]-propionaldehyde Starting from intermediate BK.iv (250 mg) and using the procedure of Preparation U, step U.iv, the title compound was obtained as a colourless solid (200 mg; 80% yield).
MS (ESI, m/z): 308.3[M+H⁺].

Preparation BL: 3-[(S)-2-oxo-3-(3-oxo-3,4-dihydro-2H-pyrido[3,2-b][1,4]thiazin-6-yl)-oxazolidin-5-yl]-propionaldehyde The title compound was prepared in analogy to Preparation BK, starting however from (S)-2-[2-[[(tert-butyl)dimethylsilyl]oxy]propyl]-oxirane. The yields were similar and the analytical data (MS, ¹H NMR) were identical.

Preparation BM: (R)-4-amino-3-fluoro-4,5-dihydro-pyrrolo[3,2,1-de][1,5]naphthyridin-7-one

BM.i. rac-1-(3-fluoro-6-methoxy-[7,5]naphthyridin-4-yl)-ethane-1,2-diol

Starting from intermediate Ax.i (12.75 g) and proceeding in analogy to Preparation AX, step AX.ii, using however K₂OsO₄/NMO instead of AD-mix p and omitting the use of methylsulfonamide, the title compound was isolated as a light brown solid (9.80 g; 66% yield).
MS (ESI, m/z)1: 238.4[M+H⁺].

BM.ii. rac-2-(tert-butyl-dimethyl-silanyloxy)-1-(3-fluoro-6-methoxy-[7,5]naphthyridin-4-yl)-ethanol Starting from intermediate BM.i (12.35 g) and using procedure M, the title intermediate was obtained as a brown oil (18.85 g; 100% yield).
MS (ESI, m/z): 353.4[M+H⁺].

BM.iii. rac-8-[7-azido-2-(tert-butyl-dimethyl-silanyloxy)-ethyl]-7-fluoro-2-methoxy-[1,5]naphthyridine Starting from intermediate BM.ii (18.85 g) and using procedure N, the title intermediate was obtained as an orange oil (22.2 g; contaminated with PPh₃O).
¹H NMR (CDCl₃) δ: 8.66 (d, J=1.5 Hz, 1H), 8.20 (d, J=9.1 Hz, 1H), 7.11 (d, J=9.1 Hz, 1H), 5.85 (m, 1H), 4.36 (m, 1H), 4.11 (m, 3H), 4.04 (m, 1H), 0.87 (s, 9H), 0.06 (d, J=8.8 Hz, 6H).

BM.iv. rac-2-azido-2-(3-fluoro-6-methoxy-[7,5]naphthyridin-4-yl)-ethanol

Starting from intermediate BM.iii (20.0 g) and using procedure J, the title intermediate was obtained as a yellowish solid (13.76 g; 99% yield).
¹H NMR (CDCl₃) δ: 8.69 (m, 1H), 8.23 (dd, J=9.1, 0.9 Hz, 1H), 7.13 (d, J=9.1 Hz, 1H), 5.92 (dd, J=7.9, 4.7 Hz, 1H), 4.29 (m, 1H), 4.11 (m, 3H), 4.06 (d, J=4.4 Hz, 1H), 1.25 (m, 1H).

BM.v. rac-4-azido-3-fluoro-4,5-dihydro-pyrrolo[3,2,1-de][1,5]naphthyridin-7-one Starting from intermediate BM.iv (17.75 g) and using procedure H, the title intermediate was obtained as an orange solid (7.94 g; 51% yield).
¹H NMR (CDCl₃) δ: 8.45 (m, 1H), 7.88 (m, 1H), 6.84 (m, 1H), 5.66 (dd, J=8.5, 3.5 Hz, 1H), 4.62 (dd, J=13.8, 8.5 Hz, 1H), 4.35 (dd, J=13.8, 3.5 Hz, 1H).

BM.vi. (R)-4-amino-3-fluoro-4,5-dihydro-pyrrolo[3,2,1-de][1,5]naphthyridin-7-one A solution of intermediate BM.v (7.93 g) in THF (140 mL) was stirred at 60° C. for 3 h in the presence of PPh₃ (9.90 g) and water (6.17 mL). The reaction mixture was concentrated to dryness and the residue was purified by CC (DCM/MeOH/NH₄OH 1000:50:4 to 1000:100:8) affording, after stirring in TBME, (RS)-4-amino-3-fluoro-4,5-dihydro-pyrrolo[3,2,1-de][1,5]naphthyridin-7-one (6.37 g; 91% yield). This racemic material (6.22 g) was separated by preparative chiral HPLC using a 5 μm (R,R)-Whelk-01 column (50×250 mm) eluting with 4:1 MeCN-EtOH containing 0.1% of diethylamine, with t_R=5.21 min for the title compound (compound of Preparation BM) and t_R=6.13 min for the optical antipode (compound of Preparation BN). The recovery was 3.00 g (first eluting enantiomer, compound of Preparation BM, 100% ee) and 2.92 g (second eluting enantiomer, compound of Preparation BN, 100% ee).
The absolute configuration of the title molecule was determined by X-ray analysis of the corresponding carboxamide obtained from (S)-mandelic acid.
MS (ESI, m/z): 206.1[M+H⁺]

Preparation BN: (S)-4-amino-3-fluoro-4,5-dihydro-pyrrolo[3,2,1-de][1,5]naphthyridin-7-one The title compound was obtained as the second eluting enantiomer (t_R=6.13 min) at Preparation BM, step BM.vi.
MS (ESI, m/z): 206.1[M+H⁺].

Preparation BO: rac-1-amino-9-methyl-1,2-dihydro-pyrrolo[3,2,1-ij]quinolin-4-one

BO.i. (7-bromo-2-methoxy-quinolin-8-yl)-methanol

A suspension of 7-bromo-8-bromomethyl-2-methoxyquinoline (35.2 g; prepared according to WO 2007/081597) and NaHCO$_3$ (14.63 g) in acetone (430 mL) and water (430 mL) was refluxed for 6 h. The org. solvent was removed under reduced pressure and the aq. layer was extracted twice with EA. The combined org. layers were sequentially washed with water and brine and dried over Na$_2$SO$_4$. The solvent was removed under reduced pressure and the residue was crystallized from TBDME, affording an off-white solid (16.01 g; 56% yield).
MS (ESI, m/z): 268.0[M+H$^+$].

BO.ii. 7-bromo-2-methoxy-quinoline-8-carbaldehyde

A solution of oxalyl chloride (5.68 mL) in DCM (265 mL) was cooled to −78° C. and treated dropwise with a solution of DMSO (5.71 mL) in DCM (50 mL). The resulting solution was treated with a solution of intermediate BO.i (6.00 g) in DCM (50 mL). After stirring for 1 h at −78° C., the reaction mixture was treated with TEA (23.4 mL) in DCM (50 mL) and gradually allowed to reach rt. The reaction mixture was treated with sat. aq. NaHCO$_3$ (300 mL) and the org. layer was separated and dried over Na$_2$SO$_4$. The solvent was evaporated under reduced pressure and the crude material was stirred in TBME, affording a yellow solid (4.68 g; 79% yield; contaminated by traces of starting material).
MS (ESI, m/z): 266.0[M+H$^+$].

BO.iii. 7-bromo-2-methoxy-8-vinyl-quinoline

Starting from intermediate BO.ii (500 mg) and methyltriphenylphosphonium bromide (1.01 g) and proceeding in analogy to Preparation Z, step Z.i, the title compound was obtained a colourless solid (411 mg; 83% yield).
MS (ESI, m/z): 264.3[M+H$^+$].

BO.iv. rac-1-(7-bromo-2-methoxy-quinolin-8-yl)-ethane-1,2-diol

Starting from intermediate BO.iii (5.50 g) and proceeding in analogy to Preparation AX, step AX.ii, using however K$_2$OsO$_4$/NMO instead of AD-mix β and omitting the use of methylsulfonamide, the title compound was obtained as a beige solid (5.75 g; 93% yield).
$^1$H NMR (CDCl3) δ: 8.01 (d, J=9.1 Hz, 1H), 7.58 (m, 1H), 7.50 (m, 1H), 6.97 (m, 1H), 5.53 (m, 1H), 4.07 (m, 3H), 3.91 (m, 2H).

BO.v. rac-1-(7-bromo-2-methoxy-quinolin-8-yl)-2-(tert-butyl-dimethyl-silanyloxy)-ethanol Starting from intermediate BO.iv (5.71 g) and using procedure M, the title compound was obtained as a brown oil (7.79 g; 99% yield).
$^1$H NMR (CDCl$_3$) δ: 7.97 (d, J=8.8 Hz, 1H), 7.55 (m, 1H), 7.45 (m, 1H), 6.93 (d, J=8.8 Hz, 1H), 5.54 (t, J=5.6 Hz, 1H), 4.12 (m, 1H), 4.04 (s, 3H), 3.98 (m, 1H), 0.75 (m, 9H), −0.14 (d, J=0.9 Hz, 6H).

BO.vi. rac-8-[1-azido-2-(tert-butyl-dimethyl-silanyloxy)-ethyl]-7-bromo-2-methoxy-quinoline Starting from intermediate BO.v (7.75 g) and using Procedure N, the title intermediate was obtained as a yellow oil (8.47 g; 100% yield).
MS (ESI, m/z): 437.2[M+H$^+$].

BO.vii. rac-1-(7-bromo-2-methoxy-quinolin-8-yl)-2-(tert-butyl-dimethyl-silanyloxy)-ethylamine Starting from intermediate BO.vi. (8.45 g) and proceeding in analogy to Preparation BM, step BM.vi, the title intermediate was obtained as a yellow oil (2.60 g; 33% yield).
MS (ESI, m/z): 411.3[M+H$^+$].

BO.viii. rac-[7-(7-bromo-2-methoxy-quinolin-8-yl)-2-(tert-butyl-dimethyl-silanyloxy)-ethyl]-carbamic acid tert-butyl ester Starting from intermediate BO.vii (2.60 g) and using procedure G, the title intermediate was obtained as a yellow oil (3.20 g; 99% yield).
$^1$H NMR (CDCl$_3$) δ: 7.95 (d, J=9.1 Hz, 1H), 7.55 (m, 1H), 7.44 (m, 1H), 6.92 (d, J=9.1 Hz, 1H), 6.35 (m, 1H), 4.97 (m, 1H), 4.06 (m, 3H), 4.03 (m, 1H), 3.74 (m, 1H), 1.25 (m, 9H), 0.75 (s, 9H), −0.11 (s, 6H).

BO.ix. rac-[1-(7-bromo-2-methoxy-quinolin-8-yl)-2-hydroxy-ethyl]-carbamic acid tert-butyl ester Starting from intermediate BO.viii (3.20 g) and using procedure J, the title intermediate was obtained as an off-white solid (1.70 g; 68% yield).
MS (ESI, m/z): 396.9[M+H$^+$].

BO.x. rac-(9-bromo-4-oxo-1,2-dihydro-4H-pyrrolo[3,2,1-ij]quinolin-1-yl)-carbamic acid tert-butyl ester Starting from intermediate BO.ix (400 mg) and using procedure H, the title intermediate was obtained as a yellow solid (372 mg; 100% yield).
MS (ESI, m/z): 365.3[M+H$^+$].

BO.xi. rac-(9-methyl-4-oxo-1,2-dihydro-4H-pyrrolo[3,2,1-ij]quinolin-1-yl)-carbamic acid tert-butyl ester A solution of intermediate BO.x (90 mg) in DME (1.5 mL) was treated with tetrakis-(triphenylphosphine)palladium and the solution was purged with N$_2$. The solution was treated with K$_2$CO$_3$ (34 mg), water (0.5 mL) and trimethylboroxine (25 mg) and further stirred at 80° C. overnight. The reaction mixture was diluted with water and extracted with EA. The org. layer was sequentially washed with water, brine and dried over MgSO$_4$. The solvent was removed under reduced pressure and the residue was purified by CC (EA), affording a colourless solid (82 mg; 100% yield).
MS (ESI, m/z): 301.2[M+H$^+$].

BO.xii. rac-1-amino-9-methyl-1,2-dihydro-pyrrolo[3,2,1-ij]quinolin-4-one

Starting from intermediate BO.xi. (81 mg) and using procedure B, the title compound was obtained as a grey solid (34 mg; 79% yield).
MS (ESI, m/z): 201.5[M+H$^+$].

Preparation BP: rac-4-[2-oxo-3-(3-oxo-3,4-dihydro-2H-benzo[1,4]thiazin-6-yl)-oxazolidin-5-yl]-butyraldehyde

BP.i. rac-6-[6-(tert-butyl-dimethyl-silanyloxy)-2-hydroxy-hexylamino]-4H-benzo[1,4]thiazin-3-one A solution of 2-[4-[(tert-butyl)dimethylsiloxy]butyl]oxirane (10.0 g) and 6-amino-4H-benzo[1,4]thiazin-3-one (7.81 g; commercial) in EtOH/water (300 mL; 9:1) was refluxed for 2 days. The solvents were removed under reduced pressure and the residue was taken up in EA/Hex (1:1; 100 mL) and filtered. The filtrate was concentrated under reduced pressure and purified by CC (EA/Hex; 1:1), affording an orange solid (7.40 g; 42% yield).
MS (ESI, m/z): 411.3 [M+H$^+$]

BP.ii. rac-6-{5-[4-(tert-Butyl-dimethyl-silanyloxy)-butyl]-2-oxo-oxazolidin-3-yl}-4H-benzo[1,4]thiazin-3-one Starting from intermediate BP.i (7.30 g) and using procedure I, the title intermediate was obtained as a colourless solid (4.40 g; 79% yield).
MS (ESI, m/z): 437.4[M+H$^+$].

BP.iii. rac-6-[5-(4-hydroxy-butyl)-2-oxo-oxazolidin-3-yl]-4H-benzo[1,4]thiazin-3-one Starting from intermediate BP.ii (4.40 g) and using procedure J, the title intermediate was obtained as a colourless solid (3.00 g; 92% yield).
MS (ESI, m/z): 323.4[M+H$^+$].

BP.iv. rac-4-[2-oxo-3-(3-oxo-3,4-dihydro-2H-benzo[1,4]thiazin-6-yl)-oxazolidin-5-yl]-butyraldehyde Starting from intermediate BP.iii (3.0 g) and using the procedure of Preparation U, step U.iv, the title intermediate was obtained as a colourless solid (2.30 g; 77% yield).
MS (ESI, m/z): 321.3[M+H$^+$].

Preparation BQ: rac-(1R*,2R*)-1-amino-4-oxo-1,2-dihydro-4H-pyrrolo[3,2,1-ij]quinoline-2-carboxylic acid methyl ester

BQ.i. (E)-3-(2-methoxy-quinolin-8-yl)-acrylic acid methyl ester

A solution of 8-bromo-2-methyloxyquinoline (10.0 g), Pd(OAc)$_2$ (311 mg), P(o-Tol)$_3$ (1.28 g) in DMF (100 mL) was treated with TEA (17.6 mL) and methyl acrylate (18.93 mL). The solution was purged 3 times with nitrogen and stirred at 120° C. for 1 h. The reaction mixture was diluted with water (200 mL) and extracted with ether/EA. The org. layer was washed with water (3×200 mL) and brine and dried over MgSO$_4$. The solvent was removed under reduced pressure and the residue was purified by CC (Hept/EA 4:1), affording a pale yellow solid (9.34 g; 91% yield).
$^1$H NMR (CDCl$_3$) δ: 8.00 (d, J=9.1 Hz, 1H), 7.66 (dd, J=7.9, 1.5 Hz, 1H), 7.57 (d, J=6.7 Hz, 1H), 7.36 (m, 1H), 6.92 (d, J=8.8 Hz, 1H), 6.24-6.05 (m, 2H), 4.84 (m, 1H), 4.10 (s, 3H), 3.89 (d, J=5.0 Hz, 1H), 3.78 (s, 3H), 1.43 (m, 9H).

BQ.ii. (2S*3R*)-3-tert-butoxycarbonylamino-2-hydroxy-3-(2-methoxy-quinolin-8-yl)-propionic acid methyl ester A solution of tert-butyl carbamate (7.06 g) in n-propanol (120 mL) was sequentially treated with 0.4M. NaOH (218 mL) and tert-butyl hypochlorite (10.6 mL; freshly prepared as described in *Org. Lett.* (2003), 5 (12), 2123-2126 (S-2)). The reaction mixture was treated with a solution of (DHQD)$_2$PHAL (565 mg) and (DHQ)$_2$PHAL (565 mg) in n-propanol (100 mL) and after 5 min cooled to 10° C. and sequentially treated with a suspension of intermediate BQ.i. (7.07 g) in water/n-propanol (1:1; 140 mL) and potassium osmate(VI) dihydrate (428 mg). After stirring at +10° C. for 20 min the reaction mixture was treated with Na$_2$SO$_3$ (15 g) and further stirred at rt for 10 min. The reaction mixture was extracted with EA and the org. layer was sequentially washed with 5% aq. K$_2$CO$_3$, sat. aq. NaHCO$_3$ and brine. After drying over MgSO$_4$ and evaporation of the solvent, the residue was purified by CC (DCM/MeOH 10-1 containing 1% NH$_4$OH), affording a pale yellow foam (6.85 g; 63% yield).
MS (ESI, m/z): 377.6[M+H$^+$].

BQ.iii. rac-(1R*,2R*)-1-tert-butoxycarbonylamino-4-oxo-1,2-dihydro-4H-pyrrolo[3,2,1-ij]quinoline-2-carboxylic acid methyl ester Starting from intermediate BQ.ii (7.80 g) and using procedure H, the title intermediate was obtained as a colourless solid (6.24 g; 87% yield).
MS (ESI, m/z): 345.5[M+H$^+$].

BQ.iv. rac-(1R*,2R*)-1-amino-4-oxo-1,2-dihydro-4H-pyrrolo[3,2,1-ij]quinoline-2-carboxylic acid methyl ester Starting from intermediate BQ.iii. (1.00 g) and using procedure B, the title compound was obtained as a colourless solid (684 mg; 96% yield).
MS (ESI, m/z): 245.2[M+H$^+$].

Preparation BR: rac-(1R*,2R*)-1-amino-2-hydroxymethyl-1,2-dihydro-pyrrolo[3,2,1-ij]quinolin-4-one

BR.i. rac-(1R*,2R*)-2-hydroxymethyl-4-oxo-1,2-dihydro-4H-pyrrolo[3,2,1-ij]quinolin-1-yl)-carbamic acid tert-butyl ester Starting from intermediate BQ.iii (3.20 g) and using procedure A, the title intermediate was obtained as a colourless solid (2.67 g; 91% yield).
MS (ESI, m/z): 317.3[M+H$^+$].

BR.ii. rac-(1R*,2R*)-1-amino-2-hydroxymethyl-1,2-dihydro-pyrrolo[3,2,1-ij]quinolin-4-one Starting from intermediate BR.i (600 mg) and using procedure B, the title compound was obtained as a colourless oil (400 mg; 98% yield).
MS (ESI, m/z): 217.3[M+H$^+$].

151

Preparation BS: rac-(1R*,2R*)-1-amino-2-methoxymethyl-1,2-dihydro-pyrrolo[3,2,1-ij]quinolin-4-one BS.i. rac-((1R*,2R*)-2-methoxymethyl-4-oxo-1,2-dihydro-4H-pyrrolo[3,2,1-i]quinolin-1-yl)-carbamic acid tert-butyl ester A solution of intermediate BR.i (400 mg) in THF (anhydrous; 4 mL) was treated at 0° C. with NaH (60% dispersion in oil; 51 mg). After a few min the reaction mixture was treated with MeI (83 µL) and further stirred at rt for 30 min. The reaction mixture was treated with sat. aq. NH$_4$Cl and extracted with EA. The org. layer was washed with water and brine and dried over MgSO$_4$. The solvent was evaporated under reduced pressure and the residue was purified by CC (DCM/MeOH/NH$_4$OH 1000:50:4), affording a pale yellow solid (42 mg; 10% yield).
MS (ESI, m/z): 331.2[M+H$^+$].

BS.ii. rac-(1R*,2R*)-1-amino-2-methoxymethyl-1,2-dihydro-pyrrolo[3,2,1-ij]quinolin-4-one Starting from intermediate BS.i (42 mg) and using procedure B, the title compound was obtained as a pale yellow oil (28 mg; 96% yield).
MS (ESI, m/z): 231.2[M+H$^+$].

Preparation BT: rac-(1R*,2S*)-1-amino-2-methyl-1,2-dihydro-pyrrolo[3,2,1-ij]quinolin-4-one BT.i. rac-((1R*2S*)-2-methyl-4-oxo-1,2-dihydro-4H-pyrrolo[3,2,1-ij]quinolin-1-yl)-carbamic acid tert-butyl ester Starting from intermediate BR.i (800 mg) and using procedure H, the intermediate mesylate was formed and further reacted after usual work up. It was dissolved in DME (45 mL) and refluxed in presence of NaI (1.21 g). After 1.5 h the reaction mixture was treated with Bu$_3$SnH (3 mL) and further refluxed for 3 h. The reaction mixture was diluted in ether and stirred in presence of 8% aq. KF for 16 h. The mixture was filtered. The two phases were separated and the aq. layer was extracted with EA. The combined org. layers were washed with water and brine and dried over MgSO$_4$. The solvents were removed under reduced pressure and the residue was purified by CC (Hept/EA 1:1), affording a colourless solid (476 mg; 63% yield).
MS (ESI, m/z): 301.3[M+H$^+$].

BT.ii. rac-(1R*2S*)-1-amino-2-methyl-1,2-dihydro-pyrrolo[3,2,1-ij]quinolin-4-one Starting from intermediate BT.i (467 mg) and using procedure B, the title compound was obtained as a yellow oil (274 mg; 88% yield).
MS (ESI, m/z): 201.3[M+H$^+$].

Preparation BU: rac-(1R*,2R*)-1-amino-2-(1-hydroxy-1-methyl-ethyl)-1,2-dihydro-pyrrolo[3,2,1-ij]quinolin-4-one BU.i. rac-[(1R*,2R*)-2-(1-hydroxy-1-methyl-ethyl)-4-oxo-1,2-dihydro-4H-pyrrolo[3,2,1-ij]quinolin-1-yl]-carbamic acid tert-butyl ester A solution BQ.iii (422 mg) in THF (anhydrous; 8 mL) was treated dropwise at 0° C. with MeMgBr (1.4M in toluene/

152

THF 3:1; 3.1 mL). After stirring 2 h at 0° C., the reaction mixture was allowed to reach rt and treated with MeMgBr (1.4M in toluene/THF 3:1; 5 mL). The reaction mixture was further stirred at rt overnight, quenched by the addition of sat. NH$_4$Cl solution and extracted with EA. The org. layer was sequentially washed with water and brine and dried over MgSO$_4$. The solvents were evaporated under reduced pressure and the residue was purified by CC (DCM/MeOH/NH$_4$OH 1000:50:4), affording a pale yellow foam (74 mg; 17% yield).
MS (ESI, m/z): 345.5[M+H$^+$].

BU.ii. rac-(1R*,2R*)-1-amino-2-(1-hydroxy-1-methyl-ethyl)-1,2-dihydro-pyrrolo[3,2,1-ij]quinolin-4-one Starting from intermediate BU.i (74 mg) and using procedure B, the title compound was obtained as a brown oil (22 mg; 42% yield).
MS (ESI, m/z): 245.3[M+H$^+$].

Preparation BV: rac-1-amino-4-oxo-1,2-dihydro-4H-pyrrolo[3,2,1-ij]quinoline-9-carbonitrile BV.i. rac-(9-cyano-4-oxo-1,2-dihydro-4H-pyrrolo[3,2,1-ij]quinolin-1-yl)-carbamic acid tert-butyl ester A mixture of intermediate BE.ix (135 mg), Zn(CN)$_2$ (52 mg) and Pd(PPh$_3$)$_4$ (21 mg) in DMF (2 mL) was heated at 110° C. overnight under argon in a sealed flask. After cooling to rt, the reaction mixture was diluted with water and extracted with EA. The org. layer was washed with water and brine and dried over MgSO$_4$. The solvent was removed under reduced pressure and the residue was triturated in TBME, affording a pinkish solid (88 mg; 76% yield).
MS (ESI, m/z): 312.3[M+H$^+$].

BV.ii. rac-1-amino-4-oxo-1,2-dihydro-4H-pyrrolo[3,2,1-ij]quinoline-9-carbonitrile Starting from intermediate BV.i (88 mg) and using procedure B, the title compound was obtained as a colourless solid (57 mg, 95% yield).
MS (ESI, m/z): 212.1[M+H$^+$].

Preparation BW: methanesulfonic acid (R)-2-oxo-3-(3-oxo-3,4-dihydro-2H-pyrido[3,2-b][1,4]thiazin-6-yl)-oxazolidin-5-ylmethyl ester BW.i. 6-[(R)-5-(tert-butyl-dimethyl-silanyloxymethyl)-2-oxo-oxazolidin-3-yl]-4H-pyrido[3,2-b][1,4]thiazin-3-one Starting from (5R)-5-[[[tert-butyldimethylsilyl]oxy]methyl]-2-oxazolidinone (1.20 g; prepared in according to Org. Letters (2005), 7, 1983-1985) and intermediate BK.ii (867 mg), the title compound was prepared in analogy to the preparation of intermediate BK.iii. After work-up and CC (Hept/EA 1:1), a beige solid (1.20 g; 70% yield) was obtained.
$^1$H NMR (CDCl$_3$) δ: 7.90 (d, J=8.5 Hz, 1H), 7.80 (s, 1H), 7.60 (d, J=8.5 Hz, 1H), 4.67 (m, 1H), 4.11 (m, 2H), 3.90 (m, 1H), 3.78 (m, 1H), 3.48 (s, 2H), 0.84 (s, 9H), 0.07 (s, 6H).

BW.ii. 64 (R)-5-hydroxymethyl-2-oxo-oxazolidin-3-yl)-4H-pyrido[3,2-b][1,4]thiazin-3-one Starting from intermediate BW.i (1.20 g) and using procedure J, the title compound was obtained as a beige solid (880 mg; 100% yield).
MS (ESI, m/z):282.3[M+H$^+$].

BW.iii. Methanesulfonic acid (R)-2-oxo-3-(3-oxo-3,4-dihydro-2H-pyrido[3,2-b][1,4]thiazin-6-yl)-oxazolidin-5-ylmethyl ester Starting from intermediate BW.ii (850 mg) and using procedure H, the title compound was obtained as a beige solid (850 mg; 78% yield).
$^1$H NMR (DMSO-$d_6$) δ: 10.88 (s, 1H), 7.79 (m, 1H), 7.66 (m, 1H), 5.00 (m, 1H), 4.50 (m, 2H), 4.21 (m, 1H), 3.86 (dd, J=10.5, 6.2 Hz, 1H), 3.51 (s, 2H), 3.23 (s, 3H).

Preparation BX: methanesulfonic acid 2-[(S)-2-oxo-3-(3-oxo-3,4-dihydro-2H-pyrido[3,2-b][1,4]thiazin-6-yl)-oxazolidin-5-yl]-ethyl ester

BX.i. (S)-5-[2-(tert-butyl-dimethyl-silanyloxy)-ethyl]-oxazolidin-2-one

Starting from 2-[2-[[(tert-butyl)dimethylsilyl]oxy]ethyl]-oxirane, (7.00 g; prepared according to WO 2007/144423), carbamic acid ethyl ester (1.46 g), 4-nitrobenzoic acid (347 mg), (R,R)-(salen)Co$^{II}$ complex (626 mg) and NaH (1.676 g) and proceeding in analogy to *Org. Letters* (2005), 7, 1983-1985, the title compound was obtained as a dark orange solid (880 mg; 11% yield).
$^1$H NMR (DMSO-$d_6$) δ: 7.39 (s, 1H), 4.59 (m, 1H), 3.67 (m, 2H), 3.53 (m, 1H), 3.13 (m, 1H), 1.79 (m, 2H), 0.85 (s, 9H), 0.02 (s, 6H).

BX.ii. 6-{(S)-5-[2-(tert-butyl-dimethyl-silanyloxy)-ethyl]-2-oxo-oxazolidin-3-yl}-4H-pyrido[3,2-b][1,4]thiazin-3-one Starting from intermediate BX.i (880 mg) and intermediate BK.ii (720 mg), the title compound was prepared in analogy to the preparation of intermediate BK.iii. After work-up and CC (Hept/EA 1:1), a beige solid (1.00 g; 68% yield) was obtained.
MS (ESI, m/z): 410.4[M+H$^+$].

BX.iii. 6-[(S)-5-(2-hydroxy-ethyl)-2-oxo-oxazolidin-3-yl]-4H-pyrido[3,2-b][1,4]thiazin-3-one Starting from intermediate BX.ii (1.00 g) and using procedure J, the title compound was obtained as a colourless solid (640 mg; 89% yield).
MS (ESI, m/z): 296.4.3[M+H$^+$].

BX.iv. Methanesulfonic acid 2-[(S)-2-oxo-3-(3-oxo-3,4-dihydro-2H-pyrido[3,2-b][1,4]thiazin-6-yl)-oxazolidin-5-yl]-ethyl ester Starting from intermediate BX.iii (600 mg) and using procedure H, the title compound was obtained as a beige solid (649 mg; 81% yield).
MS (ESI, m/z): 374.4 [M+H$^+$].

Preparation BY: rac-1-amino-9-chloro-1,2-dihydro-pyrrolo[3,2,1-ij]quinolin-4-one

BY.i. rac-(9-chloro-4-oxo-1,2-dihydro-4H-pyrrolo[3,2,1-ij]quinolin-1-yl)-carbamic acid tert-butyl ester A suspension of intermediate BE.ix (140 mg), CuCl (152 mg) and pyridine (0.5 mL) in dry DMSO was heated at 120° C. for 1 h. After cooling to rt, the mixture was partitioned between 1M. HCl and EA. The aq. layer was extracted with EA and the combined org. layers were sequentially washed with water, NH$_4$Cl, NaHCO$_3$, dried over MgSO$_4$ and concentrated under reduced pressure. The residue was purified by CC (DCM/MeOH/NH$_4$OH 1000:50:4), affording a pale orange solid (104 mg; 85% yield).
MS (ESI, m/z): 321.5[M+H$^+$].

BY.ii. rac-1-amino-9-chloro-1,2-dihydro-pyrrolo[3,2,1-ij]quinolin-4-one

Starting from intermediate BY.i (90 mg) and using procedure B, the title compound was obtained as an off-white solid (55 mg, 89% yield).
MS (ESI, m/z): 221.1[M+H$^+$].

Preparation BZ: rac-1-amino-9-ethyl-1,2-dihydro-pyrrolo[3,2,1-ij]quinolin-4-one

BZ.i. rac-(4-oxo-9-trimethylsilanylethynyl-1,2-dihydro-4H-pyrrolo[3,2,1-ij]quinolin-1-yl)-carbamic acid tert-butyl ester PdCl$_2$ (PPh$_3$)$_2$ (23 mg) and CuI (7.8 mg) were added to a suspension of intermediate BE.ix (300 mg) in TEA-dioxane (3 mL; 4:1). The reaction mixture was heated to 70° C. and ethynyl-trimethyl-silane (0.14 mL) was added in one portion and the reaction mixture was further heated in a sealed glass vial at 100° C. for 2 days. After cooling to rt, the mixture was partitioned between 1M. HCl and DCM. The org. layer was sequentially washed with water, NH$_4$Cl, and NaHCO$_3$, dried over MgSO$_4$ and concentrated under reduced pressure. The residue was purified by CC (DCM/MeOH/NH$_4$OH 1000:50.4), affording a beige solid (132 mg; 42% yield).
MS (ESI, m/z): 383.4[M+H$^+$].

BZ.ii. rac-(9-ethynyl-4-oxo-1,2-dihydro-4H-pyrrolo[3,2,1-ij]quinolin-1-yl)-carbamic acid tert-butyl ester A solution of intermediate BZ.i (115 mg) in THF (2 mL) was treated with TBAF (1M in THF; 0.33 mL) at rt. After 15 min, the mixture was concentrated, water was added and the mixture was extracted with DCM. The org. layer was dried over MgSO$_4$, filtered and concentrated. The residue was purified by CC (DCM/MeOH/NH$_4$OH 1000:50:4), affording a yellow solid (82 mg; 88% yield).
MS (ESI, m/z): 311.6 [M+H$^+$].

BZ.iii. rac-(9-ethyl-4-oxo-1,2-dihydro-4H-pyrrolo[3,2,1-ij]quinolin-1-yl)-carbamic acid tert-butyl ester A solution of intermediate BZ.ii (40 mg) in MeOH (1 mL) was hydrogenated over Pd/C for 2 h. The suspension was filtered using a glass fiber filter. The filter cake was washed with DCM/MeOH and the filtrate was concentrated under reduced pressure, affording a pale yellow solid (37 mg; 91% yield).
MS (ESI, m/z): 315.3[M+H$^+$].

BZ.iv. rac-1-amino-9-ethyl-1,2-dihydro-pyrrolo[3,2,1-ij]quinolin-4-one

Starting from intermediate BZ.iii. (30 mg) and using procedure B, the title compound was obtained as a colourless solid (13 mg, 64% yield).
MS (ESI, m/z): 215.5[M+H$^+$].

Preparation CA: rac-1-amino-9-ethynyl-1,2-dihydro-pyrrolo[3,2,1-ij]quinolin-4-one Starting from intermediate BZ.ii (40 mg) and using procedure B, the title compound was obtained as a beige solid (20 mg, 74% yield).
MS (ESI, m/z): 211.3[M+H$^+$].

Preparation CB: rac-(1R*,2R*)-1-amino-9-fluoro-4-oxo-1,2-dihydro-4H-pyrrolo[3,2,1-ij]quinoline-2-carboxylic acid methyl ester

CB.i. (2S*3R*)-3-tert-butoxycarbonylamino-2-hydroxy-3-(7-fluoro-2-methoxy-quinolin-8-yl)-propionic acid methyl ester Starting from (E)-3-(7-fluoro-2-methoxy-quinolin-8-yl)-acrylic acid methyl ester (7.07 g; prepared in analogy to the corresponding n-butyl ester described in WO 2008/128953) and proceeding in analogy to the preparation of intermediate BQ.ii, the title compound was obtained as a light yellow semi-solid material (7.621 g; 84% yield).
MS (ESI, m/z): 395.4[M+H$^+$].

CB.ii. rac-(1R*,2R*)-1-tert-butoxycarbonylamino-9-fluoro-4-oxo-1,2-dihydro-4H-pyrrolo[3,2,1-ij]quinoline-2-carboxylic acid methyl ester Starting from intermediate CB.i (4.60 g) and using procedure H, the title intermediate was obtained as a beige solid (81 mg; 19% yield).
MS (ESI, m/z): 363.4[M+H$^+$].

CB.iii. rac-(1R*,2R*)-1-amino-9-fluoro-4-oxo-1,2-dihydro-4H-pyrrolo[3,2,1-ij]quinoline-2-carboxylic acid methyl ester Starting from intermediate CB.ii. (100 mg) and using procedure B, the title compound was obtained as a colourless solid (58 mg; 80% yield).
$^1$H NMR (CDCl$_3$) δ: 7.71 (dd, J=9.4, 0.9 Hz, 1H), 7.49 (m, 1H), 6.92 (m, 1H), 6.63 (d, J=9.4 Hz, 1H), 5.02 (m, 2H), 3.83 (d, J=1.2 Hz, 3H).

Preparation CC: rac-(1R*,2R*)-1-amino-9-fluoro-2-hydroxymethyl-1,2-dihydro-pyrrolo[3,2,1-ij]quinolin-4-one

CC.i. rac-(1R*,2R*)-9-fluoro-2-hydroxymethyl-9-fluoro-4-oxo-1,2-dihydro-4H-pyrrolo[3,2,1-ij]quinolin-1-yl)-carbamic acid tert-butyl ester Starting from intermediate CB.ii (200 mg) and using procedure A, the title intermediate was obtained as a colourless solid (112 mg; 61% yield).
MS (ESI, m/z): 335.4[M+H$^+$].

CC.ii. rac-(1R*,2R*)-1-amino-9-fluoro-2-hydroxymethyl-1,2-dihydro-pyrrolo[3,2,1-ij]quinolin-4-one Starting from intermediate CC.i (104 mg) and using procedure B, the title compound was obtained as a colourless solid (60 mg; 82% yield).
MS (ESI, m/z): 235.1[M+H$^+$].

Preparation CD: rac-(1R*,2S*)-1-amino-9-fluoro-2-methyl-1,2-dihydro-pyrrolo[3,2,1-ij]quinolin-4-one

CD.i. rac-((1R*,2S*)-9-fluoro-2-methyl-4-oxo-1,2-dihydro-4H-pyrrolo[3,2,1-ij]quinolin-1-yl)-carbamic acid tert-butyl ester Starting from intermediate CC.i (495 mg) and using procedure H, the intermediate mesylate was formed and further reacted after usual work-up. It was dissolved in DME (25 mL) and refluxed in presence of NaI (710 mg). After 1.5 h, the reaction mixture was treated with Bu$_3$SnH (0.96 mL) and further refluxed for 3 h. The reaction mixture was diluted in ether and stirred in presence of 8% aq. KF for 16 h. The mixture was filtered. The two phases were separated and the aq. layer was extracted with EA. The combined org. layers were washed with water and brine and dried over MgSO$_4$. The solvents were removed under reduced pressure and the residue was purified by CC (Hept/EA 1:1 to 0:1), affording a colourless solid (374 mg; 79% yield).
MS (ESI, m/z): 319.3[M+H$^+$].

CD.ii. rac-(1R*,2S*)-1-amino-9-fluoro-2-methyl-1,2-dihydro-pyrrolo[3,2,1-ij]quinolin-4-one Starting from intermediate CD.i (370 mg) and using procedure B, the title compound was obtained as a colourless solid (198 mg; 78% yield).
MS (ESI, m/z): 218.9[M+H$^+$].

Preparation CE: rac-(1R*,2R*)-methanesulfonic acid 1-amino-9-fluoro-4-oxo-1,2-dihydro-4H-pyrrolo[3,2,1-ij]quinolin-2-ylmethyl ester

CE.i. rac-(1R*,2R*)-methanesulfonic acid 1-tert-butoxycarbonylamino-9-fluoro-4-oxo-1,2-dihydro-4H-pyrrolo[3,2,1-ij]quinolin-2-ylmethyl ester Starting from intermediate CC.i (200 mg) and using procedure H, the title compound was obtained as a yellow foam (285 mg; 100% yield).
MS (ESI, m/z): 413.3[M+H$^+$].

CE.ii. rac-(1R*,2R*)-methanesulfonic acid 1-amino-9-fluoro-4-oxo-1,2-dihydro-4H-pyrrolo[3,2,1-ij]quinolin-2-ylmethyl ester Starting from intermediate CE.i (280 mg) and using procedure B, the title compound was obtained as a beige foam (140 mg; 77% yield).
MS (ESI, m/z): 313.5[M+H$^+$].

Preparation CF: (S)-1-amino-9-fluoro-1,2-dihydro-pyrrolo[3,2,1-ij]quinolin-4-one Intermediate C was separated by chiral prep. HPLC (Column: Daicel, ChiralPak IA, 20×250 mm; eluent: 5% EtOH in MeCN+0.1% DEA; flow: 16.00 mL/min). The title compound was obtained as the first eluting compound (t$_R$=7.36 min). The absolute stereochemistry was assigned based on the NMR of the corresponding Mosher amide.
MS (ESI, m/z): 205.2[M+H$^+$].

Preparation CG: (R)-1-amino-9-fluoro-1,2-dihydro-pyrrolo[3,2,1-ij]quinolin-4-one Intermediate C was separated by chiral prep. HPLC (Column: Daicel, ChiralPak IA, 20×250 mm; eluent: 5% EtOH in MeCN+0.1% DEA; flow: 16.00 mL/min). The title compound was obtained as the second eluting compound ($t_R$=8.94 min). The absolute stereochemistry was assigned based on the NMR of the corresponding Mosher amide.

MS (ESI, m/z): 205.2[M+H$^+$].

Preparation CH: methanesulfonic acid 2-[(R)-2-oxo-3-(3-oxo-3,4-dihydro-2H-pyrido[3,2-b][1,4]thiazin-6-yl)-oxazolidin-5-yl]-ethyl ester This intermediate was prepared in analogy to Preparation BX, steps BX.i to BX.iii, using however the (S,S)-(salen)Co$^{II}$ complex.

The analytical data were identical with those of the compound of Preparation BX.

Preparation CI: (RS)-6-amino-7-fluoro-5,6-dihydro-pyrrolo[1,2,3-de]quinoxalin-3-one The title compound was prepared as described in Preparation AD, using however NMO and $K_2OsO_4$ as dehydroxylating agent (Cha, J. K., *Chem. Rev.* (1995), 95, 1761-1795) in the first step.

The analytical data were identical with those of the compound of Preparation AD.

Example 1

(1RS)-9-fluoro-1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one Starting from the compounds of Preparations A and H and using procedure C, the title compound was obtained as a pale yellow solid (39 mg; 18% yield).

$^1$H NMR (DMSO-d$_6$) δ: 10.71 (s, 1H), 7.89 (d, J=9.4 Hz, 1H), 7.58 (m, 1H), 7.32 (m, 1H), 6.94 (m, 3H), 6.50 (d, J=9.4 Hz, 1H), 4.67 (m, 1H), 4.53 (s, 2H), 4.36 (m, 2H), 4.00 (m, 2H), 3.67 (m, 1H), 3.02 (m, 1H), 2.74 (m, 3H), 2.04 (m, 1H), 1.81 (m, 2H).

MS (ESI, m/z): 479.3[M+H$^+$].

Example 2

(1RS)-9-fluoro-1-({2-[(R)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one Starting from the compounds of Preparations A and I and using procedure C, the title compound was obtained as a pale yellow solid (35 mg; 16% yield).

$^1$H NMR (DMSO-d$_6$) δ: 10.71 (s, 1H), 7.88 (d, J=9.4 Hz, 1H), 7.59 (dd, J=8.8, 4.7 Hz, 1H), 7.32 (m, 1H), 6.96 (m, 3H), 6.50 (d, J=9.4 Hz, 1H), 4.68 (m, 1H), 4.53 (s, 2H), 4.32 (m, 2H), 4.00 (m, 2H), 3.65 (m, 1H), 3.02 (m, 1H), 2.74 (m, 3H), 2.04 (m, 1H), 1.83 (m, 2H).

MS (ESI, m/z): 479.3[M+H$^+$].

Example 3

(1RS)-9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one Starting from the compounds of Preparations A and J and using procedure C, the title compound was obtained as an off-white solid (34 mg; 15% yield).

$^1$H NMR (DMSO-d$_6$) δ: 10.56 (s, 1H), 7.88 (d, J=9.4 Hz, 1H), 7.59 (m, 1H), 7.32 (m, 2H), 7.01 (m, 2H), 6.50 (dd, J=9.7, 0.9 Hz, 1H), 4.69 (m, 1H), 4.32 (m, 2H), 4.02 (m, 2H), 3.66 (m, 1H), 3.43 (s, 2H), 3.02 (m, 1H), 2.74 (m, 3H), 1.90 (m, 3H).

MS (ESI, m/z): 495.3[M+H$^+$].

Example 4

(1RS)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one Starting from the compounds of Preparations A and K and using procedure D, the title compound was obtained as an off-white solid (79 mg; 35% yield).

$^1$H NMR (DMSO-d$_6$) δ: 10.55 (s, 1H), 7.88 (d, J=9.7 Hz, 1H), 7.57 (m, 1H), 7.32 (m, 2H), 7.01 (m, 2H), 6.50 (dd, J=9.4, 0.6 Hz, 1H), 4.69 (m, 1H), 4.34 (m, 2H), 4.03 (m, 2H), 3.66 (m, 1H), 3.42 (s, 2H), 3.02 (s, 1H), 2.72 (m, 3H), 1.99 (m, 1H), 1.84 (m, 2H).

MS (ESI, m/z): 495.3[M+H$^+$].

Example 5

(1RS)-9-fluoro-1-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one Starting from the compounds of Preparations A and N and using procedure D, the title compound was obtained as a yellow solid (31 mg; 37% yield).

MS (ESI, m/z): 481.1[M+H$^+$].

Example 6

(1RS)-9-fluoro-1-({2-[(RS)-3-(3-fluoro-4-methyl-phenyl)-2-oxo-oxazolidin-5-yl]-ethylamino}-methyl)-1,2-dihydro-pyrrolo[3,2,1-ij]quinolin-4-one Starting from the compounds of Preparations A and S and using procedure C, the title compound was obtained as a yellow solid (94 mg; 47% yield).

MS (ESI, m/z): 440.5[M+H$^+$].

Example 7

(1RS)-1-(2-{[(R)-3-(2,3-dihydro-benzo[1,4]dioxin-6-yl)-2-oxo-oxazolidin-5-ylmethyl]-amino}-ethyl)-9-fluoro-1,2-dihydro-pyrrolo[3,2,1-ij]quinolin-4-one Starting from the compounds of Preparations B and P and using procedure D, the title compound was obtained as a pale yellow solid (45 mg; 28% yield).

MS (ESI, m/z): 466.2[M+H$^+$].

Example 8

(1RS)-9-fluoro-1-(2-{[(S)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one Starting from the compounds of Preparations B and O and using procedure D, the title compound was obtained as a yellow solid (50 mg; 29% yield).

MS (ESI, m/z): 495.1[M+H$^+$].

Example 9

(1RS)-9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2-dihydro-pyrrolo[3,2,1-ij]quinolin-4-one Starting from the compounds of Preparations B and Q and using procedure C, the title compound was obtained as a pale yellow solid (47 mg; 20% yield).
MS (ESI, m/z): 479.2[M+H$^+$].

Example 10

(1RS)-9-fluoro-1-(2-{[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one Starting from the compounds of Preparations B and N and using procedure D, the title compound was obtained as a pale yellow solid (38 mg; 16% yield).
MS (ESI, m/z): 494.9[M+H$^+$].

Example 11

(1RS)-9-fluoro-1-(2-{[(R)-3-(3-fluoro-4-methyl-phenyl)-2-oxo-oxazolidin-5-ylmethyl]-amino}-ethyl)-1,2-dihydro-pyrrolo[3,2,1-ij]quinolin-4-one Starting from the compounds of Preparations B and R and using procedure D, the title compound was obtained as a yellow solid (29 mg; 19% yield).
MS (ESI, m/z): 440.5[M+H$^+$].

Example 12

(1RS)-9-fluoro-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one Starting from the compounds of Preparations C and T and using procedure E, the title compound was obtained as a colourless solid (42 mg; 45% yield).
$^1$H NMR (CDCl$_3$) δ: 7.70 (d, J=9.4 Hz, 1H), 7.47 (m, 1H), 7.32 (m, 1H), 6.92 (m, 2H), 6.76 (m, 1H), 6.62 (d, J=9.4 Hz, 1H), 4.96 (m, 1H), 4.64 (m, 1H), 4.50 (m, 3H), 4.26 (m, 1H), 4.04 (m, 1H), 3.60 (m, 1H), 3.42 (m, 2H), 2.73 (m, 2H), 1.76 (m, 4H).
MS (ESI, m/z): 479.2[M+H$^+$].

Example 13

(1RS)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations C and U and using procedure E, the title compound was obtained as a pale beige solid (48 mg; 50% yield).
$^1$H NMR (CDCl$_3$) δ: 7.69 (d, J=9.7 Hz, 1H), 7.47 (dd, J=8.5, 4.7 Hz, 1H), 7.35 (d, J=2.3 Hz, 1H), 7.24 (m, 2H), 6.91 (m, 2H), 6.61 (d, J=9.4 Hz, 1H), 4.95 (dd, J=8.2, 3.2 Hz, 1H), 4.65 (m, 1H), 4.49 (dd, J=13.5, 8.2 Hz, 1H), 4.26 (dd, J=13.2, 3.5 Hz, 1H), 4.06 (m, 1H), 3.60 (m, 1H), 3.36 (s, 2H), 2.73 (m, 2H), 1.77 (m, 5H).
MS (ESI, m/z): 495.0[M+H$^+$].

Example 14

(1RS)-9-fluoro-1-{2-[(RS)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one Starting from the compounds of Preparations C and M and using procedure C, the title compound was isolated as a pale yellow solid (13 mg; 12% yield).
$^1$H NMR (CDCl$_3$) δ: 8.76 (m, 1H), 7.66 (d, J=9.4 Hz, 1H), 7.44 (m, 2H), 7.24 (m, 1H), 6.91 (m, 2H), 6.61 (d, J=9.7 Hz, 1H), 4.96 (m, 1H), 4.80 (m, 1H), 4.50 (m, 1H), 4.28 (m, 1H), 4.08 (m, 1H), 3.68 (m, 1H), 3.38 (s, 2H), 2.94 (m, 2H), 1.97 (m, 3H).
MS (ESI, m/z): 481.1[M+H$^+$].

Example 15

(4R)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compounds of Preparations V and J and using procedure C, the title compound was obtained as a colourless solid (9 mg; 12% yield).
MS (ESI, m/z): 478.0[M+H$^+$].

Example 16

(4RS)-3-fluoro-4-(2-{[(S)-2-oxo-3-(3-oxo-3,4-dihydro-2H-benzo[1,4]thiazin-6-yl)-oxazolidin-5-ylmethyl]-amino}-ethyl)-4,5-dihydro-pyrrolo[3,2,1-de][1,5]naphthyridin-7-one Starting from the compounds of Preparations F and O and using procedure D, the title compound was obtained as a yellow solid (6 mg; 7% yield).
MS (ESI, m/z): 496.3[M+H$^+$].

Example 17

(4RS)-3-fluoro-4-(2-{[(R)-2-oxo-3-(3-oxo-3,4-dihydro-2H-benzo[1,4]thiazin-6-yl)-oxazolidin-5-ylmethyl]-amino}-ethyl)-4,5-dihydro-pyrrolo[3,2,1-de][1,5]naphthyridin-7-one Starting from the compounds of Preparations F and N and using procedure D, the title compound was obtained as a yellow solid (8 mg; 9% yield).
MS (ESI, m/z): 496.4[M+H$^+$].

Example 18

(4R)-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the dihydrochloride salt of the compound of Preparation D (112 mg) and the compound of Preparation U (153 mg) and using procedure E, the title compound was obtained as an orange solid (27 mg; 11% yield).
MS (ESI, m/z): 478.1[M+H$^+$].

Example 19

(4R)-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the dihydrochloride salt of the compound of Preparation D (78 mg) and the compound of Preparation T (101 mg) and using procedure E, the title compound was obtained as an orange solid (17 mg; 11% yield).
MS (ESI, m/z): 462.1[M+H$^+$].

Example 20

(6RS)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one Starting from the compounds of Preparations G (93 mg) and U (153 mg) and using procedure E, the title compound was obtained as a yellow solid (210 mg; 88% yield).
MS (ESI, m/z): 478.0[M+H$^+$].

Example 21

(6RS)-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one Starting from the compounds of Preparations G and T and using procedure E, the title compound was obtained as a yellow solid (276 mg; 70% yield).
MS (ESI, m/z): 462.1[M+H$^+$].

Example 22

(1RS)-9-fluoro-1-(2-{[(S)-2-oxo-3-(3-oxo-3,4-dihydro-2H-benzo[1,4]thiazin-6-yl)-oxazolidin-5-ylmethyl]-amino}-ethyl)-1,2,5,6-tetrahydro-pyrrolo[3,2,1-ij]quinolin-4-one The compound of Example 8 was hydrogenated according to procedure F, affording a colourless solid (10 mg; 23% yield).
MS (ESI, m/z): 497.3[M+H$^+$].

Example 23

(1RS)-9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2,5,6-tetrahydro-pyrrolo[3,2,1-ij]quinolin-4-one 23.i. rac-(9-fluoro-4-oxo-1,2,5,6-tetrahydro-4H-pyrrolo[3,2,1-ij]quinolin-1-ylmethyl)-carbamic acid tert-butyl ester A solution of intermediate A.vii of Preparation A (47 mg, 0.15 mmol) in MeOH (5 mL) was hydrogenated over 10% Pd/C (31 mg) for 2 h. The catalyst was filtered off and washed with MeOH. The filtrate was concentrated to afford the title intermediate as a colourless solid (48 mg; 100% yield).
MS (ESI, m/z): 321.3[M+H$^+$].

23.ii. rac-1-aminomethyl-9-fluoro-1,2,5,6-tetrahydro-pyrrolo[3,2,1-ij]quinolin-4-one Starting from intermediate 23.i and using procedure B, the title intermediate was obtained as a yellow solid (29 mg; 88% yield).
MS (ESI, m/z): 221.2[M+H$^+$].

23.iii. (1RS)-9-fluoro-1-({2-[(R)-2-oxo-3-(3-oxo-3,4-dihydro-2H-benzo[1,4]thiazin-6-yl)-oxazolidin-5-yl]-ethylamino}-methyl)-1,2,5,6-tetrahydro-pyrrolo[3,2,1-ij]quinolin-4-one Starting from intermediate 23.ii and the compound of Preparation L and using procedure D, the title compound was obtained as a pale brown solid (8 mg; 14% yield).
MS (ESI, m/z): 497.4[M+H$^+$].

Example 24

(1RS)-9-fluoro-1-(2-{[(R)-2-oxo-3-(3-oxo-3,4-dihydro-2H-benzo[1,4]thiazin-6-yl)-oxazolidin-5-ylmethyl]-amino}-ethyl)-1,2,5,6-tetrahydro-pyrrolo[3,2,1-ij]quinolin-4-one The compound of Example 10 was hydrogenated using procedure F, affording the title compound as an off-white solid (8 mg; 16% yield).
MS (ESI, m/z): 497.2[M+H$^+$].

Example 25

(1RS)-9-fluoro-1-(2-{[(R)-2-oxo-3-(3-oxo-3,4-dihydro-2H-benzo[1,4]oxazin-6-yl)-oxazolidin-5-ylmethyl]-amino}-ethyl)-1,2,5,6-tetrahydro-pyrrolo[3,2,1-ij]quinolin-4-one The compound of Example 9 was hydrogenated using procedure F, affording the title compound as a colourless solid (12 mg; 32% yield).
MS (ESI, m/z): 481.2[M+H$^+$].

Example 26

(1RS)-1-(2-{[(R)-3-(2,3-dihydro-benzo[1,4]dioxin-6-yl)-2-oxo-oxazolidin-5-ylmethyl]-amino}-ethyl)-9-fluoro-1,2,5,6-tetrahydro-pyrrolo[3,2,1-ij]quinolin-4-one The compound of Example 7 was hydrogenated using procedure F, affording the title compound as an off-white solid (21 mg; 52% yield).
MS (ESI, m/z): 468.2[M+H$^+$].

Example 27

(1RS)-9-fluoro-1-(2-{[(R)-3-(3-fluoro-4-methyl-phenyl)-2-oxo-oxazolidin-5-ylmethyl]-amino}-ethyl)-1,2,5,6-tetrahydro-pyrrolo[3,2,1-ij]quinolin-4-one The compound of Example 11 was hydrogenated using procedure F, affording the title compound as an off-white solid (17 mg; 74% yield).
MS (ESI, m/z): 442.2[M+H$^+$].

Example 28

(4RS)-3-fluoro-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compounds of Preparations E and L and using procedure D, the title compound was obtained as a yellow solid (7 mg; 18% yield).
MS (ESI, m/z): 496.2[M+H$^+$].

Example 29

(1RS)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2,5,6-tetrahydro-pyrrolo[3,2,1-ij]quinolin-4-one The compound of Example 4 was hydrogenated using procedure F, affording the title compound as a colourless solid (17 mg; 39% yield).
MS (ESI, m/z): 497.2[M+H$^+$].

Example 30

(1RS)-9-fluoro-1-({[(S)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one Starting from the compounds of Preparations A and O and using procedure D, the title compound was obtained as a yellow solid (49 mg; 37% yield).
MS (ESI, m/z): 481.2[M+H$^+$].

Example 31

(1RS)-1-({[(R)-3-(2,3-dihydro-benzo[1,4]dioxin-6-yl)-2-oxo-oxazolidin-5-ylmethyl]-amino}-methyl)-9-fluoro-1,2-dihydro-pyrrolo[3,2,1-ij]quinolin-4-one Starting from the compounds of Preparations A and P and using procedure D, the title compound was obtained as a yellow solid (33 mg; 27% yield).
MS (ESI, m/z): 452.2[M+H$^+$].

Example 32

(1RS)-9-fluoro-1-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one Starting from the compounds of Preparations A and Q and using procedure C, the title compound was obtained as a yellow solid (35 mg; 27% yield).
MS (ESI, m/z): 465.2[M+H$^+$].

Example 33

(1RS)-9-fluoro-1-({[(R)-3-(3-fluoro-4-methyl-phenyl)-2-oxo-oxazolidin-5-ylmethyl]-amino}-methyl)-1,2-dihydro-pyrrolo[3,2,1-ij]quinolin-4-one Starting from the compounds of Preparations A and R and using procedure D, the title compound was obtained as a yellow solid (17 mg; 15% yield).
MS (ESI, m/z): 426.2[M+H$^+$].

Example 34

(RS)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compound of Preparations W and AF and using procedure C, the title compound was obtained as a beige solid (13 mg; 8% yield).
MS (ESI, m/z): 478.0[M+H$^+$].

Example 35

(RS)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations X and U and using procedure E, the title compound was obtained as a beige solid (30 mg; 24% yield).
MS (ESI, m/z): 476.9[M+H$^+$].

Example 36

(RS)-1-({[(R)-3-(4-ethoxy-phenyl)-2-oxo-oxazolidin-5-ylmethyl]-amino}-methyl)-9-fluoro-1,2-dihydro-pyrrolo[3,2,1-ij]quinolin-4-one Starting from the compound of Preparation A and (5S)-3-(4-ethoxyphenyl)-5-[[(methylsulfonyl)oxy]methyl]-2-oxazolidinone (prepared according to WO 2008/126034) and using procedure C, the title compound was obtained as a yellow solid (44 mg; 27% yield).
MS (ESI, m/z): 472.3[M+H$^+$].

Example 37

(RS)-9-fluoro-1-({[(R)-2-oxo-3-(4-propyl-phenyl)-oxazolidin-5-ylmethyl]-amino}-methyl)-1,2-dihydro-pyrrolo[3,2,1-ij]quinolin-4-one Starting from the compounds of Preparations A and AG and using procedure C, the title compound was obtained as a yellow solid (46 mg; 29% yield).
MS (ESI, m/z): 436.1[M+H$^+$].

Example 38

(RS)-1-({[(R)-3-(4-butyl-phenyl)-2-oxo-oxazolidin-5-ylmethyl]-amino}-methyl)-9-fluoro-1,2-dihydro-pyrrolo[3,2,1-ij]quinolin-4-one Starting from the compounds of Preparations A and AH and using procedure C, the title compound was obtained as a yellow solid (36 mg; 22% yield).
MS (ESI, m/z): 450.1[M+H$^+$].

Example 39

(S)-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the compounds of Preparations Y and U and using procedure E, the title compound was obtained as a beige solid (90 mg; 23% yield).
MS (ESI, m/z): 477.9[M+H$^+$].

Example 40

(S)-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the compounds of Preparations Y and T and using procedure E, the title compound was obtained as a beige foam (55 mg; 15% yield).
MS (ESI, m/z): 461.9[M+H$^+$].

Example 41

(S)-4-{2-[(S)-2-oxo-3-(3-oxo-3,4-dihydro-2H-benzo[1,4]thiazin-6-yl)-oxazolidin-5-yl]-ethylamino}-4,5-dihydro-pyrrolo[3,2,1-de][1,5]naphthyridin-7-one Starting from the compounds of Preparations Y and AI and using procedure C, the title compound was obtained as a yellow solid (10 mg; 2% yield).
MS (ESI, m/z): 464.1[M+H$^+$].

Example 42

(RS)-1-({2-[(RS)-3-(2,3-dihydro-[1,4]dioxino[2,3-e]pyridin-7-yl)-2-oxo-oxazolidin-5-yl]-ethylamino}-methyl)-9-fluoro-1,2-dihydro-pyrrolo[3,2,1-ij]quinolin-4-one Starting from the compounds of Preparations A and AJ and using procedure C, the title compound was obtained as a yellow solid (48 mg; 34% yield).
MS (ESI, m/z): 467.1[M+H$^+$].

Example 43

(RS)-1-({2-[(RS)-3-(2,3-dihydro-[1,4]dioxino[2,3-b]pyridin-6-yl)-2-oxo-oxazolidin-5-yl]-ethylamino}-methyl)-9-fluoro-1,2-dihydro-pyrrolo[3,2,1-ij]quinolin-4-one Starting from the compounds of Preparations A and AK and using procedure C, the title compound was obtained as a yellow foam (42 mg; 30% yield).
MS (ESI, m/z): 467.1[M+H$^+$].

Example 44

(RS)-1-({2-[(R)-3-(4-ethoxy-phenyl)-2-oxo-oxazolidin-5-yl]-ethylamino}-methyl)-9-fluoro-1,2-dihydro-pyrrolo[3,2,1-ij]quinolin-4-one Starting from the compounds of Preparations A and AL and using procedure C, the title compound was obtained as a yellow foam (20 mg; 14% yield).
$^1$H NMR (CDCl$_3$) δ: 7.65 (dd, J=9.4, 1.5 Hz, 1H), 7.38 (m, 3H), 6.87 (m, 3H), 6.60 (d, J=9.7 Hz, 1H), 4.70 (m, 1H), 4.44 (m, 2H), 4.01 (m, 4H), 3.61 (td, J=9.1, 7.3 Hz, 1H), 3.14 (m, 1H), 2.90 (m, 3H), 1.92 (m, 2H), 1.39 (t, J=6.7 Hz, 3H).
MS (ESI, m/z): 452.1[M+H$^+$].

Example 45

(RS)-9-fluoro-1-({2-[(R)-2-oxo-3-(4-propyl-phenyl)-oxazolidin-5-yl]-ethylamino}-methyl)-1,2-dihydro-pyrrolo[3,2,1-ij]quinolin-4-one Starting from the compounds of Preparations A and AM and using procedure C, the title compound was obtained as a yellow foam (24 mg; 17% yield).
$^1$H NMR (CDCl$_3$) δ: 7.65 (dd, J=9.7, 1.5 Hz, 1H), 7.39 (m, 3H), 7.16 (d, J=8.5 Hz, 2H), 6.87 (td, J=9.1, 1.8 Hz, 1H), 6.60 (d, J=9.4 Hz, 1H), 4.72 (m, 1H), 4.44 (m, 2H), 4.02 (m, 2H), 3.64 (m, 1H), 3.14 (m, 1H), 2.90 (m, 3H), 2.55 (m, 2H), 1.91 (m, 2H), 1.61 (m, 2H), 0.92 (t, J=7.3 Hz, 3H).
MS (ESI, m/z): 450.1[M+H$^+$].

Example 46

(RS)-1-({2-[(R)-3-(2,3-dihydro-benzo[1,4]dioxin-6-yl)-2-oxo-oxazolidin-5-yl]-ethylamino}-methyl)-9-fluoro-1,2-dihydro-pyrrolo[3,2,1-ij]quinolin-4-one Starting from the compounds of Preparations A and AN and using procedure C, the title compound was obtained as an off-white solid (32 mg; 21% yield).
$^1$H NMR (CDCl$_3$) δ: 7.64 (dd, J=9.4, 1.2 Hz, 1H), 7.38 (dd, J=8.8, 4.7 Hz, 1H), 7.03 (t, J=2.3 Hz, 1H), 6.89 (m, 3H), 6.58 (d, J=9.4 Hz, 1H), 4.68 (m, 1H), 4.48 (m, 1H), 4.36 (m, 1H), 4.22 (m, 4H), 3.97 (m, 2H), 3.56 (m, 1H), 3.12 (m, 1H), 2.88 (m, 3H), 1.90 (m, 2H).
MS (ESI, m/z): 466.0[M+H$^+$].

Example 47

(RS)-9-fluoro-1-({2-[(RS)-2-oxo-3-(3-oxo-3,4-dihydro-2H-pyrido[3,2-b][1,4]oxazin-6-yl)-oxazolidin-5-yl]-ethylamino}-methyl)-1,2-dihydro-pyrrolo[3,2,1-ij]quinolin-4-one Starting from the compounds of Preparations A and AO and using procedure C, the intermediate (RS)-9-fluoro-1-[(2-{3-[(RS)-4-(4-methoxy-benzyl)-3-oxo-3,4-dihydro-2H-pyrido[3,2-b][1,4]oxazin-6-yl]-2-oxo-oxazolidin-5-yl}-ethylamino)-methyl]-1,2-dihydro-pyrrolo[3,2,1-ij]quinolin-4-one was obtained as a yellowish foam (148 mg, 36% yield). Said intermediate was further treated with TFA (4 mL) at reflux for 3 days. The solvent was removed under reduced pressure and the residue was partitioned between DCM and aq. NH$_4$OH. The org. phase was washed with water and brine and dried over MgSO$_4$. The residue was purified by CC (EA/MeOH 9:1 containing 1% NH$_4$OH), affording, after trituration in ether/MeOH, a beige solid (55 mg; 17% yield).
MS (ESI, m/z): 480.0[M+H$^+$].

Example 48

(S)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one Starting from the compounds of Preparations Z and U and using procedure E, the title compound was obtained as a beige solid (135 mg; 53% yield).
$^1$H NMR (DMSO d6) δ: 10.54 (s, 1H), 8.17 (s, 1H), 7.70 (d, J=7.9 Hz, 1H), 7.60 (d, J=7.3 Hz, 1H), 7.31 (m, 3H), 7.06 (dd, J=8.5, 2.3 Hz, 1H), 4.70 (m, 2H), 4.44 (m, 1H), 4.07 (m, 2H), 3.62 (dd, J=8.8, 7.3 Hz, 1H), 3.41 (s, 2H), 2.63 (m, 2H), 1.76 (m, 2H), 1.53 (m, 2H).

Examples 49 and 50

(S)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one and (R)-9-fluoro-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one Starting from the compounds of Preparations A and AI and using procedure C, the title compounds were obtained as a light yellow solid (466 mg, 26%, mixture of diastereoisomers; MS (ESI, m/z): 495.1 [M+H$^+$]). This mixture (75 mg) was separated on a chiral HPLC column (ChiralPak IA, 4.6×250 mm, 5 μm; eluents: MeCN and EtOH containing 0.1% of DEA) affording the corresponding diastereoisomers:

First eluting compound (27 mg): $^1$H NMR (CDCl$_3$) δ: 7.69 (d, J=9.4 Hz, 1H), 7.41 (dd, J=8.5, 4.4 Hz, 1H), 7.23 (m, 1H), 7.12 (m, 2H), 6.89 (t, J=9.1 Hz, 1H), 6.62 (d, J=9.7 Hz, 1H), 4.71 (m, 1H), 4.45 (m, 2H), 4.03 (m, 2H), 3.62 (m, 2H), 3.34 (s, 2H), 2.95 (m, 3H), 2.00 (m, 1H), 1.78 (m, 1H).

Second eluting compound (20 mg): $^1$H NMR (CDCl$_3$) δ: 7.69 (d, J=9.4 Hz, 1H), 7.41 (dd, J=8.8, 4.4 Hz, 1H), 7.22 (m, 2H), 7.08 (dd, J=8.5, 2.3 Hz, 1H), 6.89 (t, J=9.1 Hz, 1H), 6.60 (d, J=9.4 Hz, 1H), 4.62 (m, 1H), 4.48 (m, 1H), 4.35 (m, 1H), 3.96 (m, 2H), 3.71 (m, 1H), 3.34 (s, 2H), 3.10 (dd, J=12.0, 4.4 Hz, 1H), 2.88 (m, 3H), 1.91 (m, 2H).

Example 51

(RS)-9-fluoro-1-({3-[(R)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one Starting from the compounds of Preparations A and U and using procedure E, the title compound was obtained as a light yellow foam (69 mg; 59% yield).
MS (ESI, m/z): 509.2[M+H$^+$].

Example 52

(RS)-9-fluoro-1-({3-[(R)-2-oxo-3-(3-oxo-3,4-dihydro-2H-benzo[1,4]oxazin-6-yl)-oxazolidin-5-yl]-propylamino}-methyl)-1,2-dihydro-pyrrolo[3,2,1-ij]quinolin-4-one Starting from the compounds of Preparations A and T and using procedure E, the title compound was obtained as a light yellow foam (60 mg; 53% yield).
MS (ESI, m/z): 493.2[M+H$^+$].

Example 53

(RS)-1-({2-[(R)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one Starting from the compounds of Preparations AB and AF and using procedure C, the title compound was obtained as a light yellow foam (10 mg; 8% yield).
MS (ESI, m/z): 476.9[M+H$^+$].

Example 54

(S)-6-{2-[(R)-2-oxo-3-(3-oxo-3,4-dihydro-2H-benzo[1,4]thiazin-6-yl)-oxazolidin-5-yl]-ethylamino}-5,6-dihydro-pyrrolo[1,2,3-de]quinoxalin-3-one Starting from the compounds of Preparations Z and J and using procedure C, the title compound was obtained as an orange solid (30 mg, 14% yield).
MS (ESI, m/z): 464.1[M+H$^+$].

Example 55

(S)-6-{2-[(S)-2-oxo-3-(3-oxo-3,4-dihydro-2H-benzo[1,4]thiazin-6-yl)-oxazolidin-5-yl]-ethylamino}-5,6-dihydro-pyrrolo[1,2,3-de]quinoxalin-3-one Starting from the compounds of Preparation Z and intermediate K.iv and using procedure C, the title compound was obtained as an orange solid (50 mg; 20% yield).
MS (ESI, m/z): 464.3[M+H$^+$].

Example 56

(RS)-6-({2-[(S)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one Starting from the compounds of Preparations AC and AI and using procedure C, the title compound was obtained as a yellow foam (98 mg; 28% yield).
MS (ESI, m/z): 477.9[M+H$^+$].

Example 57

(S)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one Starting from the compounds of Preparations AD and T and using procedure E, the title compound was obtained as a colourless solid (70 mg; 29% yield).
MS (ESI, m/z): 480.1[M+H$^+$].

Example 58

(S)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one Starting from the compounds of Preparations AD and U and using procedure E, the title compound was obtained as a colourless solid (85 mg; 34% yield).
MS (ESI, m/z): 469.1[M+H$^+$].

Example 59

(RS)-9-fluoro-1-{2-[(R)-2-oxo-3-(4-propyl-phenyl)-oxazolidin-5-yl]-ethylamino}-1,2-dihydro-pyrrolo[3,2,1-ij]quinolin-4-one Starting from the compounds of Preparations C and AM and using procedure C, the title compound was obtained as a yellow solid (46 mg; 31% yield).

¹H NMR (CDCl₃) δ: 7.68 (dd, J=9.4, 0.9 Hz, 1H), 7.45 (m, 3H), 7.17 (d, J=8.2 Hz, 2H), 6.92 (t, J=8.8 Hz, 1H), 6.61 (d, J=9.4 Hz, 1H), 4.99 (m, 1H), 4.78 (m, 1H), 4.52 (m, 1H), 4.31 (dd, J=13.2, 3.2 Hz, 1H), 4.10 (t, J=8.5 Hz, 1H), 3.69 (m, 1H), 2.95 (m, 2H), 2.56 (m, 2H), 2.02 (m, 2H), 1.62 (m, 2H), 0.92 (t, J=7.3 Hz, 3H).
MS (ESI, m/z): 436.2[M+H⁺].

Example 60

(RS)-1-({2-[(S)-3-(2,3-dihydro-benzo[1,4]dioxin-6-yl)-2-oxo-oxazolidin-5-yl]-ethylamino}-methyl)-9-fluoro-1,2-dihydro-pyrrolo[3,2,1-ij]quinolin-4-one Starting from the compounds of Preparations A and AQ and using procedure C, the title compound was obtained as a yellow foam (29 mg; 34% yield).
¹H NMR (CDCl₃) δ: 7.65 (dd, J=9.7, 0.9 Hz, 1H), 7.39 (dd, J=8.8, 4.7 Hz, 1H), 7.02 (t, J=2.1 Hz, 1H), 6.87 (m, 3H), 6.58 (d, J=9.4 Hz, 1H), 4.70 (m, 1H), 4.44 (m, 2H), 4.22 (m, 4H), 3.98 (m, 2H), 3.58 (m, 2H), 3.15 (m, 1H), 2.91 (m, 3H), 1.92 (m, 2H).
MS (ESI, m/z): 466.2[M+H⁺].

Example 61

(RS)-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one Starting from the compounds of Preparations AE and AI and using procedure C, the title compound was obtained as a beige solid (110 mg; 46% yield).
¹H NMR (DMSO d6) δ: 10.58 (s, 1H), 7.90 (d, J=9.7 Hz, 1H), 7.54 (m, 2H), 7.32 (m, 2H), 7.18 (t, J=7.9 Hz, 1H), 7.08 (m, 1H), 6.55 (d, J=9.7 Hz, 1H), 4.81 (m, 1H), 4.39 (m, 2H), 4.08 (m, 3H), 3.72 (m, 1H), 3.42 (s, 3H), 3.05 (m, 4H), 2.12 (m, 2H).
MS (ESI, m/z): 476.8[M+H⁺].

Example 62

(RS)-1-({2-[(S)-2-oxo-3-(3-oxo-3,4-dihydro-2H-benzo[1,4]oxazin-6-yl)-oxazolidin-5-yl]-ethylamino}-methyl)-1,2-dihydro-pyrrolo[3,2,1-ij]quinolin-4-one Starting from the compounds of Preparations AE and H and using procedure C, the title compound was obtained as a beige solid (90 mg; 39% yield).
MS (ESI, m/z): 460.9[M+H⁺].

Example 63

(RS)-1-({[(R)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one Starting from the compounds of Preparations AE and N and using procedure D, the title compound was obtained as a beige solid (44 mg; 19% yield).
MS (ESI, m/z): 462.9[M+H⁺].

Example 64

(R)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one Starting from the compounds of Preparations AA and U and using procedure E, the title compound was obtained as an orange solid (100 mg; 42% yield).
MS (ESI, m/z): 477.8[M+H⁺].

Example 65

(R)-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one Starting from the compounds of Preparations AA and T and using procedure E, the title compound was obtained as an orange solid (140 mg; 61% yield).
MS (ESI, m/z): 461.9[M+H⁺].

Example 66

(S)-7-fluoro-6-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-5,6-dihydro-pyrrolo[1,2,3-de]quinoxalin-3-one Starting from the compound of Example 58 and (tert-butyldimethylsilyloxy)-acetaldehyde and using procedure E, followed by treatment of the intermediate thus obtained with aq. TFA (50%; 2 mL), the title compound was obtained as a colourless foam (45 mg; 40% yield).
MS (ESI, m/z): 539.9[M+H⁺].

Example 67

(S)-7-fluoro-6-((2-hydroxy-ethyl)-{3-[(R)-2-oxo-3-(3-oxo-3,4-dihydro-2H-benzo[1,4]oxazin-6-yl)-oxazolidin-5-yl]-propyl}-amino)-5,6-dihydro-pyrrolo[1,2,3-de]quinoxalin-3-one Starting from the compound of Example 57 and (tert-butyldimethylsilyloxy)-acetaldehyde and using procedure E, followed by treatment of the intermediate thus obtained with aq. TFA (50%; 2 mL), the title compound was obtained as a colourless foam (80 mg; 45% yield).
MS (ESI, m/z): 523.9[M+H⁺].

Example 68

(RS)-9-fluoro-1-(2-{(3-hydroxy-propyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one 68.i. (RS)-1-(2-{[3-(tert-butyl-dimethyl-silanyloxy)-propyl]-[2-oxo-3-(3-oxo-3,4-dihydro-2H-benzo[1,4]thiazin-6-yl)-oxazolidin-5-ylmethyl]-amino}-ethyl)-9-fluoro-1,2-dihydro-pyrrolo[3,2,1-ij]quinolin-4-one Starting from the compound of Example 10 and 3-(tert-butyldimethylsilyloxy)-propionaldehyde and using procedure E, the title compound was obtained as a colourless solid (101 mg; 75% yield).
MS (ESI, m/z): 667.4[M+H⁺].

68.ii. (RS)-9-fluoro-1-(2-{(3-hydroxy-propyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one Starting from intermediate 68.i and using procedure J, the title compound was obtained as an off-white solid (70 mg; 87% yield).
MS (ESI, m/z): 553.2[M+H$^+$].

Example 69

(RS)-9-fluoro-1-(2-{(2-hydroxy-ethyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one 69.i. (RS)-1-(2-{[2-(tert-butyl-dimethyl-silanyloxy)-ethyl]-[2-oxo-3-(3-oxo-3,4-dihydro-2H-benzo[1,4]thiazin-6-yl)-oxazolidin-5-ylmethyl]-amino}-ethyl)-9-fluoro-1,2-dihydro-pyrrolo[3,2,1-ij]quinolin-4-one Starting from the compound of Example 10 and tert-butyldimethylsilyloxy-acetaldehyde and using procedure E, the title compound was obtained as a colourless solid (100 mg; 76% yield).
MS (ESI, m/z): 653.4[M+H$^+$].

69.ii. (RS)-9-fluoro-1-(2-{(2-hydroxy-ethyl)-[(R)-2-oxo-3-(3-oxo-3,4-dihydro-2H-benzo[1,4]thiazin-6-yl)-oxazolidin-5-ylmethyl]-amino}-ethyl)-1,2-dihydro-pyrrolo[3,2,1-ij]quinolin-4-one Starting from intermediate 69.i and using procedure J, the title compound was obtained as an off-white solid (54 mg; 69% yield).
MS (ESI, m/z): 539.2[M+H$^+$].

Example 70

(RS)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations C and AR and using procedure E, the title compound was obtained as a colourless solid (175 mg; 73% yield).
MS (ESI, m/z): 480.0[M+H$^+$].

Example 71

(S)-7-fluoro-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one Starting from the compounds of Preparations AD and AR and using procedure E, the title compound was obtained as a colourless solid (87 mg; 36% yield).
MS (ESI, m/z): 481.1[M+H$^+$].

Example 72

(S)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations AS and U and using procedure E, the title compound was obtained as a colourless solid (223 mg; 72% yield).
MS (ESI, m/z): 477.2[M+H$^+$].

Example 73

(S)-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one Starting from the compounds of Preparations AS and T and using procedure E, the title compound was obtained as a colourless solid (259 mg; 87% yield).
MS (ESI, m/z): 461.2[M+H$^+$].

Example 74

(S)-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations AS and AR and using procedure E, the title compound was obtained as a colourless solid (190 mg; 83% yield).
MS (ESI, m/z): 462.2[M+H$^+$].

Example 75

(R)-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one Starting from the compounds of Preparations AA and AR and using procedure E, the title compound was obtained as an orange solid (54 mg; 23% yield).
MS (ESI, m/z): 463.0[M+H$^+$].

Example 76

(S)-4-({2-[(R)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compounds of Preparations AT and J and using procedure C, the title compound was obtained as a pale yellow solid (24 mg; 7% yield).
$^1$H NMR (DMSO-d$_6$) δ: 10.54 (s, 1H), 8.44 (d, J=4.4 Hz, 1H), 7.94 (d, J=9.7 Hz, 1H), 7.52 (dd, J=4.4, 0.6 Hz, 1H), 7.31 (m, 2H), 7.04 (m, 1H), 6.77 (d, J=9.7 Hz, 1H), 4.74 (m, 1H), 4.38 (m, 1H), 4.10 (m, 2H), 3.90 (m, 1H), 3.66 (m, 1H), 3.42 (s, 2H), 2.90 (m, 2H), 2.69 (m, 2H), 1.86 (m, 2H).
MS (ESI, m/z): 478.2[M+H$^+$].

Example 77

(S)-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compounds of Preparations AT and K and using procedure D, the title compound was obtained as a beige solid (25 mg; 7% yield).
MS (ESI, m/z): 478.2[M+H$^+$].

Example 78

(R)-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compounds of Preparations V and K and using procedure D, the title compound was obtained as a pale yellow solid (150 mg; 42% yield).
MS (ESI, m/z): 478.2[M+H$^+$].

Example 79

(S)-7-fluoro-6-{3-[(S)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one Starting from the compounds of Preparations AD and AU and using procedure E, the title compound was obtained as a pale yellow foam (195 mg; 79% yield).
$^1$H NMR (DMSO-d$_6$) δ: 10.53 (s, 1H), 8.13 (m, 1H), 7.76 (dd, J=8.8, 4.1 Hz, 1H), 7.34 (d, J=2.3 Hz, 1H), 7.29 (d, J=8.5 Hz, 1H), 7.10 (m, 2H), 4.87 (m, 1H), 4.65 (m, 1H), 4.44 (dd, J=12.9, 8.2 Hz, 1H), 4.08 (m, 2H), 3.62 (dd, J=8.8, 7.0 Hz, 1H), 3.41 (s, 2H), 2.60 (m, 2H), 1.74 (m, 2H), 1.74 (m, 2H).

Example 80

(S)-7-fluoro-6-{3-[(S)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one Starting from the compounds of Preparations AD and AV and using procedure E, the title compound was obtained as a pale yellow solid (215 mg; 90% yield).
$^1$H NMR (DMSO-d$_6$) δ: 10.69 (s, 1H), 8.13 (s, 1H), 7.76 (dd, J=8.8, 4.4 Hz, 1H), 7.31 (d, J=2.3 Hz, 1H), 7.13 (t, J=9.1 Hz, 1H), 6.91 (m, 2H), 4.51 (s, 2H), 4.43 (m, 1H), 4.07 (m, 2H), 2.60 (m, 2H), 1.75 (m, 2H), 1.55 (m, 2H).

Example 81

(RS)-1-({[(S)-2-oxo-3-(3-oxo-3,4-dihydro-2H-benzo[1,4]thiazin-6-yl)-oxazolidin-5-ylmethyl]-amino}-methyl)-1,2-dihydro-pyrrolo[3,2,1-ij]quinolin-4-one Starting from the compounds of Preparations AE and O and using procedure D, the title compound was obtained as a pale yellow solid (42 mg; 18% yield).
MS (ESI, m/z): 463.2[M+H$^+$].

Example 82

(RS)-1-({[(R)-2-oxo-3-(3-oxo-3,4-dihydro-2H-benzo[1,4]oxazin-6-yl)-oxazolidin-5-ylmethyl]-amino}-methyl)-1,2-dihydro-pyrrolo[3,2,1-ij]quinolin-4-one Starting from the compounds of Preparations AE and Q and using procedure C, the title compound was obtained as a beige solid (65 mg; 29% yield).
MS (ESI, m/z): 447.3[M+H$^+$].

Example 83

(RS)-1-({3-[(RS)-2-oxo-3-(3-oxo-3,4-dihydro-2H-benzo[1,4]thiazin-6-yl)-oxazolidin-5-yl]-propylamino}-methyl)-1,2-dihydro-pyrrolo[3,2,1-ij]quinolin-4-one Starting from the compounds of Preparations AE and AW and using procedure C, the title compound was obtained as a beige solid (40 mg; 16% yield).
MS (ESI, m/z): 490.9[M+H$^+$].

Example 84

(RS)-3-fluoro-4-{2-[(S)-2-oxo-3-(3-oxo-3,4-dihydro-2H-benzo[1,4]thiazin-6-yl)-oxazolidin-5-yl]-ethylamino}-4,5-dihydro-pyrrolo[3,2,1-de][1,5]naphthyridin-7-one Starting from the compound of Preparation AX and intermediate K iv and using procedure C, the title compound was obtained as a light brown solid (4 mg; 3% yield).
MS (ESI, m/z): 482.2[M+H$^+$].

Example 85

(S)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations AS and AU and using procedure E, the title compound was obtained as an off-white solid (182 mg; 77% yield).
MS (ESI, m/z): 476.9[M+H$^+$].

Example 86

(S)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one Starting from the compounds of Preparations AS and AV and using procedure E, the title compound was obtained as an off-white solid (167 mg; 72% yield).
MS (ESI, m/z): 460.9[M+H$^+$].

Example 87

(S)-1-{2-[(R)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one Starting from the compounds of Preparations AS and J and using procedure C, the title compound was obtained as a light brown solid (82 mg; 27% yield).
MS (ESI, m/z): 462.9[M+H$^+$].

Example 88

(S)-1-{2-[(S)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one Starting from the compound of Preparation AS and intermediate K.iv and using procedure C, the title compound was obtained as a light brown solid (99 mg; 33% yield).
MS (ESI, m/z): 463.0[M+H$^+$].

Example 89

(S)-1-{2-[(S)-2-oxo-3-(3-oxo-3,4-dihydro-2H-benzo[1,4]oxazin-6-yl)-oxazolidin-5-yl]-ethylamino}-1,2-dihydro-pyrrolo[3,2,1-ij]quinolin-4-one Starting from the compounds of Preparations AS and AY and using procedure C, the title compound was obtained as a light brown solid (76 mg; 26% yield).
MS (ESI, m/z): 447.0[M+H$^+$].

Example 90

(RS)-9-fluoro-1-[((3-hydroxy-propyl)-{2-[(S)-2-oxo-3-(3-oxo-3,4-dihydro-2H-benzo[1,4]thiazin-6-yl)-oxazolidin-5-yl]ethyl}-amino)-methyl]-1,2-dihydro-pyrrolo[3,2,1-ij]quinolin-4-one 90.i. (RS)-1-[([3-(tert-butyl-dimethyl-silanyloxy)-propyl]-{2-[(S)-2-oxo-3-(3-oxo-3,4-dihydro-2H-benzo[1,4]thiazin-6-yl)-oxazolidin-5-yl]-ethyl}-amino)-methyl]-9-fluoro-1,2-dihydro-pyrrolo[3,2,1-ij]quinolin-4-one Starting from the compound of Example 4 and 3-(tert-butyldimethylsilyloxy)-propionaldehyde and using procedure E, the title compound was obtained as a yellow foam (82 mg; 87% yield).
MS (ESI, m/z): 667.4[M+H$^+$].

90.ii. (RS)-9-fluoro-1-[((3-hydroxy-propyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one Starting from intermediate 90.i and using procedure J, the title compound was obtained as a light yellow foam (46 mg; 68% yield).
MS (ESI, m/z): 553.2[M+H$^+$].

Example 91

(RS)-9-fluoro-1-[((2-hydroxy-ethyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one 91.i. (RS)-1-[([2-(tert-butyl-dimethyl-silanyloxy)-ethyl]-{2-[(S)-2-oxo-3-(3-oxo-3,4-dihydro-2H-benzo[1,4]thiazin-6-yl)-oxazolidin-5-yl]-ethyl}-amino)-methyl]-9-fluoro-1,2-dihydro-pyrrolo[3,2,1-ij]quinolin-4-one Starting from the compound of Example 4 and tert-butyldimethylsilyloxy-acetaldehyde and using procedure E, the title compound was obtained as a yellow foam (55 mg; 59% yield).
MS (ESI, m/z): 653.4[M+H$^+$].

91.ii. (RS)-9-fluoro-1-[((2-hydroxy-ethyl)-{2-[(S)-2-oxo-3-(3-oxo-3,4-dihydro-2H-benzo[1,4]thiazin-6-yl)-oxazolidin-5-yl]-ethyl}-amino)-methyl]-1,2-dihydro-pyrrolo[3,2,1-ij]quinolin-4-one Starting from intermediate 91.i and using procedure J, the title compound was obtained as an off-white foam (25 mg; 55% yield).
MS (ESI, m/z): 539.2[M+H$^+$].

Example 92

(RS)-9-fluoro-1-((3-hydroxy-propyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one 92.i. (RS)-1-([3-(tert-butyl-dimethyl-silanyloxy)-propyl]-{3-[(R)-2-oxo-3-(3-oxo-3,4-dihydro-2H-benzo[1,4]thiazin-6-yl)-oxazolidin-5-yl]-propyl}-amino)-9-fluoro-1,2-dihydro-pyrrolo[3,2,1-n]quinolin-4-one Starting from the compound of Example 13 and 3-(tert-butyldimethylsilyloxy)-propionaldehyde and using procedure E, the title compound was obtained as a yellow foam (62 mg; 46% yield).
MS (ESI, m/z): 667.4[M+H$^+$].

92.ii. (RS)-9-fluoro-((3-hydroxy-propyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one Starting from intermediate 92.i and using procedure J, the title compound was obtained as an off-white foam (20 mg; 39% yield).
MS (ESI, m/z): 553.2[M+H$^+$].

Example 93

(RS)-9-fluoro-1-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one 93.i. (RS)-1-([2-(tert-butyl-dimethyl-silanyloxy)-ethyl]-{3-[(R)-2-oxo-3-(3-oxo-3,4-dihydro-2H-benzo[1,4]thiazin-6-yl)-oxazolidin-5-yl]-propyl}-amino)-9-fluoro-1,2-dihydro-pyrrolo[3,2,1-n]quinolin-4-one Starting from the compound of Example 13 and tert-butyldimethylsilyloxy-acetaldehyde and using procedure E, the title compound was obtained as a yellow foam (57 mg; 43% yield).
MS (ESI, m/z): 653.4[M+H$^+$].

93.ii. (RS)-9-fluoro-1-((2-hydroxy-ethyl)-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one Starting from intermediate 93.i and using procedure J, the title compound was obtained as a yellowish foam (15 mg; 32% yield).
MS (ESI, m/z): 539.2[M+H$^+$].

Example 94

(RS)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the compounds of Preparations AX and U and using procedure E, the title compound was obtained as a light yellow solid (44 mg; 36% yield).

MS (ESI, m/z): 496.2[M+H$^+$].

Example 95

(RS)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the compounds of Preparations AX and T and using procedure E, the title compound was obtained as a light yellow foam (43 mg; 37% yield).

MS (ESI, m/z): 480.2[M+H$^+$].

Example 96

(RS)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the compounds of Preparations AX and AU and using procedure E, the title compound was obtained as an off-white foam (53 mg; 44% yield).

MS (ESI, m/z): 496.2[M+H$^+$].

Example 97

(RS)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the compounds of Preparations AX and AV and using procedure E, the title compound was obtained as a light yellow foam (44 mg; 38% yield).

MS (ESI, m/z): 480.2[M+H$^+$].

Example 98

(RS)-3-fluoro-4-({[(R)-2-oxo-3-(3-oxo-3,4-dihydro-2H-benzo[1,4]oxazin-6-yl)-oxazolidin-5-ylmethyl]-amino}-methyl)-4,5-dihydro-pyrrolo[3,2,1-de][1,5]naphthyridin-7-one Starting from the compounds of Preparations E and S and using procedure C, the title compound was obtained as a yellow foam (12 mg; 6% yield).

MS (ESI, m/z): 466.2[M+H$^+$].

Example 99

(RS)-3-fluoro-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one Starting from the compounds of Preparations E and AI and using procedure C, the title compound was obtained as a yellow solid (48 mg; 21% yield).

MS (ESI, m/z): 496.2[M+H$^+$].

Example 100

(RS)-3-fluoro-4-({[(R)-2-oxo-3-(3-oxo-3,4-dihydro-2H-benzo[1,4]thiazin-6-yl)-oxazolidin-5-ylmethyl]-amino}-methyl)-4,5-dihydro-pyrrolo[3,2,1-de][1,5]naphthyridin-7-one Starting from the compounds of Preparations E and N and using procedure D, the title compound was obtained as a yellow foam (27 mg; 12% yield).

MS (ESI, m/z): 482.2[M+H$^+$].

Example 101

(RS)-3-fluoro-4-({[(S)-2-oxo-3-(3-oxo-3,4-dihydro-2H-benzo[1,4]thiazin-6-yl)-oxazolidin-5-ylmethyl]-amino}-methyl)-4,5-dihydro-pyrrolo[3,2,1-de][1,5]naphthyridin-7-one Starting from the compounds of Preparations E and O and using procedure D, the title compound was obtained as a yellow foam (19 mg; 9% yield).

MS (ESI, m/z): 482.2[M+H$^+$].

Example 102

(RS)-3-fluoro-4-({2-[(S)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one Starting from the compounds of Preparations E and H and using procedure C, the title compound was obtained as a yellow foam (15 mg; 7% yield).

MS (ESI, m/z): 480.2[M+H$^+$].

Example 103

(RS)-3-fluoro-4-({2-[(R)-2-oxo-3-(3-oxo-3,4-dihydro-2H-benzo[1,4]oxazin-6-yl)-oxazolidin-5-yl]-ethylamino}-methyl)-4,5-dihydro-pyrrolo[3,2,1-de][1,5]naphthyridin-7-one Starting from the compounds of Preparations E and I and using procedure C, the title compound was obtained as a yellow solid (16 mg; 11% yield).

MS (ESI, m/z): 480.2[M+H$^+$].

Example 104

(R)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one Starting from the compounds of Preparations AZ and T and using procedure E, the title compound was obtained as a beige solid (97 mg; 40% yield).
MS (ESI, m/z): 480.2[M+H$^+$].

Example 105

(R)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one Starting from the compounds of Preparations AZ and U and using procedure E, the title compound was obtained as a beige solid (81 mg; 32% yield).
MS (ESI, m/z): 496.2[M+H$^+$].

Example 106

(RS)-6-({[(S)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one Starting from the compounds of Preparations AC and O and using procedure D, the title compound was obtained as a beige solid (158 mg; 31% yield).
MS (ESI, m/z): 464.2[M+H$^+$].

Example 107

(RS)-1-{2-[(S)-3-(2,3-dihydro-benzo[1,4]dioxin-6-yl)-2-oxo-oxazolidin-5-yl]-ethylamino}-9-fluoro-1,2-dihydro-pyrrolo[3,2,1-ij]quinolin-4-one Starting from the compounds of Preparations C and AQ and using procedure C, the title compound was obtained as a light brown solid (20 mg; 23% yield).
MS (ESI, m/z): 452.2[M+H$^+$].

Example 108

(RS)-N-((S)-9-fluoro-4-oxo-1,2-dihydro-4H-pyrrolo[3,2,1-ij]quinolin-1-yl)-3-hydroxy-3-[(RS)-2-oxo-3-(3-oxo-3,4-dihydro-2H-benzo[1,4]thiazin-6-yl)-oxazolidin-5-yl]-propionamide 108.i. (RS)-3-(tert-butyl-dimethyl-silanyloxy)-(3RS)-[2-oxo-3-(3-oxo-3,4-dihydro-2H-benzo[1,4]thiazin-6-yl)-oxazolidin-5-yl]-propionic acid Starting from a solution of intermediate BA.iii (400 mg; see Preparation B) in DCM and treating with TFA, the title intermediate was obtained, after aqueous workup and trituration with ether, as a colourless solid (0.2 g, 56% yield).
MS (ESI, m/z): 453.0[M+H$^+$].

108.ii. (RS)-N-((S)-9-fluoro-4-oxo-1,2-dihydro-4H-pyrrolo[3,2,1-ij]quinolin-1-yl)-3-hydroxy-3-[(RS)-2-oxo-3-(3-oxo-3,4-dihydro-2H-benzo[1,4]thiazin-6-yl)-oxazolidin-5-yl]-propionamide A propylphosphonic anhydride solution (50% in EA, 0.31 ml) was added dropwise to a solution of the compound of Preparation C (0.1 g), intermediate 108.i (0.22 g) and DIPEA (0.26 mL) in DMF (4 mL). The mixture was stirred at rt for 1 h and partitioned between water and EA. The org. phase was washed with dilute HCl and brine, dried over MgSO$_4$ and concentrated. Purification of the crude using CC (EA/MeOH 19:1) gave a mixture of diastereomeric compounds (ratio and relative stereochemistry was not elucidated) as a colourless solid (245 mg). This intermediate was treated with HCl in MeOH (1.25/14), stirred at rt for 1 h, concentrated in vacuo, partitioned between EA and a bicarbonate solution. The product precipitated out of this mixture, was filtered off and dried under HV to give the title compound as a colourless solid (20 mg, mixture of diastereomers).
MS (ESI, m/z): 525.1[M+H$^+$].

Example 109

(R)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BC and U and using procedure E, the title compound was obtained as a colourless solid (96 mg; 67% yield).
MS (ESI, m/z): 477.2[M+H$^+$].

Example 110

(RS)-6-({[(R)-2-oxo-3-(3-oxo-3,4-dihydro-2H-benzo[1,4]thiazin-6-yl)-oxazolidin-5-ylmethyl]-amino}-methyl)-5,6-dihydro-pyrrolo[1,2,3-de]quinoxalin-3-one Starting from the compounds of Preparations AC and N and using procedure D, the title compound was obtained as a colourless solid (15 mg; 3% yield).
MS (ESI, m/z): 464.2[M+H$^+$].

Example 111

(R)-7-fluoro-2-methoxy-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one Starting from the compounds of Preparations BB and T and using procedure E, the title compound was obtained as a colourless solid (100 mg; 39% yield).
MS (ESI, m/z): 510.2[M+H$^+$].

Example 112

(R)-7-fluoro-2-methoxy-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one Starting from the compounds of Preparations BB and U and using procedure E, the title compound was obtained as a colourless solid (75 mg; 28% yield).
MS (ESI, m/z): 526.2[M+H$^+$].

Example 113

(1RS)-9-fluoro-1-{(3RS)-3-hydroxy-3-[(5RS)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one

113.i. 3-(tert-butyl-dimethyl-silanyloxy)-3-[2-oxo-3-(3-oxo-3,4-dihydro-2H-benzo[1,4]thiazin-6-yl)-oxazolidin-5-yl]-propionaldehyde (mixture of diastereomers)

To a solution of the compound of Preparation BA (0.2 g) and DIPEA (0.23 mL) in DCM (5 mL) at rt was added dropwise a solution of $SO_3$.Pyr complex (0.145 g) in DMSO (0.5 mL) over 2 min. The mixture was stirred at rt for 1.5 h and partitioned between water and DCM. The org. phase was washed several times with water, dried over $MgSO_4$ and concentrated. The crude product was used as such in the next step (yield assumed to be quantitative).

MS (ESI, m/z): 437.1[M+H$^+$].

113.ii. (1RS)-9-fluoro-1-{(3RS)-3-hydroxy-3-[(5RS)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compound of Preparation C and intermediate 113.i and using procedure E followed by TBDMS cleavage using procedure J, the title compound was obtained as a yellowish solid (21 mg; 9% yield).

MS (ESI, m/z): 510.6[M+H$^+$].

Example 114

(S)-6-{3-[(R)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one A solution of the compound of Example 48 (33 mg) in MeOH/DCE (5 mL; 4:1) was treated with $NaBH_4$ (3 mg) for 30 min then quenched with 1M. HCl (1 mL) and partitioned between DCM and an aq. $NH_4OH$ solution. The org. layer was washed with water and brine, dried over $MgSO_4$ and purified by CC (EA/MeOH 19:1 to 9:1 containing 1% $NH_4OH$) affording a colourless solid (26 mg; 78% yield).

MS (ESI, m/z): 480.4[M+H$^+$].

Example 115

(RS)-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one Starting from the compounds of Preparations G and BK and using procedure E, the title compound was obtained as an orange solid (95 mg, 40% yield).

$^1$H NMR (DMSO-$d_6$) δ: 10.82 (s, 1H), 8.17 (s, 1H), 7.77 (m, 1H), 7.68 (m, 2H), 7.60 (d, J=7.3 Hz, 1H), 7.31 (dd, J=7.9, 7.3 Hz, 1H), 4.71 (m, 2H), 4.44 (m, 1H), 4.19 (m, 1H), 4.05 (dd, J=12.9, 3.8 Hz, 1H), 3.69 (dd, J=10.3, 7.0 Hz, 1H), 3.51 (s, 2H), 2.64 (m, 2H), 1.76 (m, 2H), 1.50 (m, 2H).

MS (ESI, m/z): 479.4[M+H$^+$].

Example 116

(RS)-9-bromo-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BE and U and using procedure E, the title compound was obtained as a colourless solid (10 mg, 9% yield).

MS (ESI, m/z): 555.2[M+H$^+$].

Example 117

(RS)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-9-carbonitrile Starting from the compounds of Preparations BV and U and using procedure E, the title compound was obtained as a colourless solid (14 mg, 21% yield).

MS (ESI, m/z): 502.5 [M+H$^+$]

Example 118

(RS)-4-oxo-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-4H-pyrrolo[3,2,1-ij]quinoline-9-carbonitrile Starting from the compounds of Preparations BV and BK and using procedure E, the title compound was obtained as a colourless solid (15 mg, 22% yield).

$^1$H NMR (CDCl$_3$) δ: 7.83 (dd, J=8.5, 1.2 Hz, 1H), 7.75 (d, J=9.4 Hz, 1H), 7.58 (m, 2H), 7.41 (d, J=7.9 Hz, 1H), 6.81 (d, J=9.4 Hz, 1H), 5.02 (m, 1H), 4.69 (m, 1H), 4.53 (m, 1H), 4.28 (m, 2H), 3.76 (dd, J=10.5, 7.3 Hz, 1H), 3.43 (s, 2H), 2.75 (m, 2H), 1.92 (m, 5H).

MS (ESI, m/z): 503.6[M+H$^+$].

Example 119

(R)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-7-carboxylic acid ethyl ester Starting from the compounds of Preparations BF and AU and using procedure E, the title compound was obtained as a colourless solid (910 mg, 66% yield).

MS (ESI, m/z): 549.2[M+H$^+$]

Example 120

(R)-7-hydroxymethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BG and AU and using procedure E, the title compound was obtained as a beige solid (40 mg, 16% yield).

MS (ESI, m/z): 507.2[M+H$^+$].

Example 121

(R)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-7-carboxylic acid hydrochloride A suspension of the compound of Example 119 (100 mg) in 6M. HCl (0.6 mL) was stirred at 90° C. for 6 h. The reaction mixture was evaporated under reduced pressure and the residue was taken up in MeOH and collected by filtration, affording a beige solid (37 mg; 36% yield).
MS (ESI, m/z): 521.5[M+H$^+$].

Example 122

(R)-7-dimethylaminomethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BH and AU and using procedure E, the title compound was obtained as a beige solid (39 mg; 30% yield).
MS (ESI, m/z): 534.5[M+H$^+$].

Example 123

(R)-1-{3-[(S)-2-oxo-3-(3-oxo-3,4-dihydro-2H-benzo[1,4]thiazin-6-yl)-oxazolidin-5-yl]-propylamino}-7-pyrrolidin-1-ylmethyl-1,2-dihydro-pyrrolo[3,2,1-ij]quinolin-4-one Starting from the compounds of Preparations BI and AU and using procedure E, the title compound was obtained as a beige foam (50 mg, 27% yield).
MS (ESI, m/z): 560.6[M+H$^+$].

Example 124

(RS)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations C and BJ and using procedure E, the title compound was obtained as a colourless foam (87 mg, 60% yield).
MS (ESI, m/z): 480.5[M+H$^+$].

Example 125

(RS)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations C and BK and using procedure E, the title compound was obtained as a colourless solid (84 mg, 49% yield).
$^1$H NMR (CDCl$_3$) δ: 8.04 (m, 1H), 7.88 (dd, J=8.5, 2.9 Hz, 1H), 7.68 (dd, J=9.4, 1.2 Hz, 1H), 7.60 (dd, J=8.5, 1.5 Hz, 1H), 7.47 (dd, J=8.8, 4.7 Hz, 1H), 6.91 (t, J=9.1 Hz, 1H), 6.63 (d, J=9.4 Hz, 1H), 5.00 (m, 1H), 4.66 (m, 1H), 4.51 (m, 1H), 4.27 (m, 2H), 3.77 (dt, J=10.3, 6.7 Hz, 1H), 3.47 (s, 2H), 2.77 (m, 2H), 1.80 (m, 4H).
MS (ESI, m/z): 496.6[M+H$^+$].

Example 126

(RS)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations C and BL and using procedure E, the title compound was obtained as a colourless solid (54 mg, 32% yield).
$^1$H NMR (CDCl$_3$) δ: 8.03 (m, 1H), 7.88 (dd, J=8.8, 2.9 Hz, 1H), 7.68 (dd, J=9.4, 0.9 Hz, 1H), 7.60 (dd, J=8.5, 1.5 Hz, 1H), 7.47 (dd, J=8.8, 4.7 Hz, 1H), 6.91 (t, J=9.1 Hz, 1H), 6.63 (d, J=9.4 Hz, 1H), 5.00 (m, 1H), 4.66 (m, 1H), 4.51 (m, 1H), 4.28 (m, 2H), 3.77 (dt, J=10.5, 7.0 Hz, 1H), 3.47 (s, 2H), 2.77 (m, 2H), 1.80 (m, 4H).
MS (ESI, m/z): 496.6[M+H$^+$].

Examples 127 and 128

(R)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (S)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one The product of Example 13 was separated by preparative chiral HPLC using a 5 μm (R,R)-Whelk-01 column (21.1× 250 mm) eluting with 1:1 MeCN-EtOH containing 0.1% of diethylamine with t$_R$=7.25 min (compound of Example 127, 100% ee) and t$_R$=10.26 min (compound of Example 128, 100% ee).
Data obtained for the compound of Example 127:
$^1$H NMR (CDCl$_3$) δ: 7.69 (d, J=9.7 Hz, 1H), 7.47 (dd, J=8.8, 4.7 Hz, 1H), 7.31 (d, J=2.3 Hz, 1H), 7.22 (d, J=8.5 Hz, 1H), 6.91 (m, 2H), 6.60 (d, J=9.4 Hz, 1H), 4.95 (dd, J=8.2, 3.5 Hz, 1H), 4.64 (m, 1H), 4.48 (m, 1H), 4.26 (dd, J=13.5, 3.5 Hz, 1H), 4.04 (t, J=8.8 Hz, 1H), 3.59 (dd, J=8.8, 7.0 Hz, 1H), 3.34 (s, 2H), 2.73 (m, 2H), 1.76 (m, 4H).
MS (ESI, m/z): 495.3 [M+H$^+$].
Data obtained for the compound of Example 128:
$^1$H NMR (CDCl$_3$) δ: 7.68 (d, J=9.4 Hz, 1H), 7.46 (dd, J=8.5, 4.7 Hz, 1H), 7.31 (d, J=2.3 Hz, 1H), 7.21 (d, J=8.5 Hz, 1H), 6.90 (m, 2H), 6.59 (d, J=9.4 Hz, 1H), 4.94 (dd, J=8.2, 2.9 Hz, 1H), 4.62 (m, 1H), 4.47 (dd, J=13.2, 8.2 Hz, 1H), 4.24 (dd, J=13.5, 3.5 Hz, 1H), 4.02 (t, J=8.5 Hz, 1H), 3.60 (m, 1H), 3.33 (s, 2H), 2.72 (m, 2H), 1.74 (m, 4H).
MS (ESI, m/z): 495.3[M+H$^+$].

Examples 129 and 130

(R)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (S)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one First Step:
Starting from the compound of Example 4 and 3-(tert-butyldimethylsilyloxy)-propionaldehyde and using procedure E, the title compound was obtained as a yellow foam (82 mg; 87% yield).
MS (ESI, m/z): 667.4[M+H$^+$].

Second Step:

The product from the first step was separated by preparative chiral HPLC using a 5 μm (R,R)-Whelk-01 column (21.1×250 mm) eluting with 1:1 MeCN-EtOH containing 0.1% of diethylamine with $t_R$=7.41 min (compound of Example 129, 100% ee) and $t_R$=10.35 min (compound of Example 130, 100% ee).

Data obtained for the compound of Example 129:
$^1$H NMR (CDCl$_3$) δ: 7.68 (d, J=9.4 Hz, 1H), 7.46 (dd, J=8.8, 4.7 Hz, 1H), 7.30 (d, J=2.1 Hz, 1H), 7.20 (d, J=8.5 Hz, 1H), 6.90 (m, 2H), 6.58 (d, J=9.4 Hz, 1H), 4.94 (dd, J=8.2, 3.2 Hz, 1H), 4.63 (m, 1H), 4.46 (dd, J=13.5, 8.5 Hz, 1H), 4.23 (dd, J=13.5, 3.5 Hz, 1H), 4.02 (t, J=8.5 Hz, 1H), 3.58 (dd, J=7.9, 7.0 Hz, 1H), 3.33 (s, 2H), 2.72 (m, 2H), 1.74 (m, 4H).
MS (ESI, m/z): 495.4[M+H$^+$].

Data obtained for the compound of Example 130:
$^1$H NMR (CDCl$_3$) δ: 7.68 (d, J=9.4 Hz, 1H), 7.46 (dd, J=8.8, 4.7 Hz, 1H), 7.30 (d, J=2.3 Hz, 1H), 7.21 (d, J=8.5 Hz, 1H), 6.90 (m, 2H), 6.59 (d, J=9.4 Hz, 1H), 4.94 (dd, J=8.5, 3.5 Hz, 1H), 4.64 (m, 1H), 4.47 (m, 1H), 4.24 (dd, J=13.2, 3.5 Hz, 1H), 4.03 (t, J=8.5 Hz, 1H), 3.59 (dd, J=8.8, 7.0 Hz, 1H), 3.33 (s, 2H), 2.71 (m, 2H), 1.75 (m, 4H).
MS (ESI, m/z): 495.4[M+H$^+$].

Example 131

(R)-7-fluoro-6-{3-[(S)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one Starting from the compounds of Preparations AA and BJ and using procedure E, the title compound was obtained as a yellowish solid (61 mg, 42% yield).
$^1$H NMR (DMSO-d6) δ: 11.14 (s, 1H), 8.13 (s, 1H), 7.76 (dd, J=8.8, 4.4 Hz, 1H), 7.56 (m, 1H), 7.39 (d, J=8.8 Hz, 1H), 7.13 (t, J=9.1 Hz, 1H), 4.66 (s, 1H), 4.58 (s, 3H), 4.44 (m, 1H), 4.18 (m, 1H), 4.08 (dd, J=13.2, 3.2 Hz, 1H), 3.67 (dd, J=10.0, 7.0 Hz, 1H), 2.60 (m, 2H), 1.74 (m, 2H), 1.49 (m, 2H).
MS (ESI, m/z): 481.4[M+H$^+$].

Example 132

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one Starting from the compounds of Preparations AA and BK and using procedure E, the title compound was obtained as a colourless solid (50 mg, 50% yield).
$^1$H NMR (DMSO-d6) δ: 10.81 (s, 1H), 8.13 (s, 1H), 7.77 (m, 2H), 7.66 (m, 1H), 7.13 (t, J=9.1 Hz, 1H), 4.90 (m, 1H), 4.69 (m, 1H), 4.44 (dd, J=12.9, 8.2 Hz, 1H), 4.19 (m, 1H), 4.08 (m, 1H), 3.68 (dd, J=10.0, 7.0 Hz, 1H), 3.51 (s, 2H), 2.60 (dd, J=1.2, 0.6 Hz, 2H), 1.75 (m, 2H), 1.50 (m, 2H).

Example 133

(R)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BC and AU and using procedure E, the title compound was obtained as a yellow solid (54 mg, 45% yield).
MS (ESI, m/z): 477.2[M+H$^+$].

Example 134

(R)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one Starting from the compounds of Preparations BC and AV and using procedure E, the title compound was obtained as a colourless solid (80 mg, 69% yield).
MS (ESI, m/z): 461.2[M+H$^+$].

Example 135

(R)-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations BC and BJ and using procedure E, the title compound was obtained as an off-white solid (75 mg, 65% yield).
MS (ESI, m/z): 462.1[M+H$^+$].

Example 136

(S)-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations AS and BL and using procedure E, the title compound was obtained as a beige solid (31 mg, 33% yield).
$^1$H NMR (DMSO-d6) δ: 10.82 (s, 1H), 7.89 (d, J=9.7 Hz, 1H), 7.77 (m, 1H), 7.66 (m, 1H), 7.55 (m, 2H), 7.18 (t, J=7.6 Hz, 1H), 6.54 (d, J=9.4 Hz, 1H), 4.70 (m, 2H), 4.37 (m, 1H), 4.19 (m, 1H), 4.00 (m, 1H), 3.69 (m, 1H), 3.51 (s, 2H), 2.64 (m, 2H), 1.76 (m, 2H), 1.52 (m, 2H).
MS (ESI, m/z): 478.2[M+H$^+$].

Example 137

(S)-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations AS and BK and using procedure E, the title compound was obtained as an off-white foam (143 mg, 60% yield).
MS (ESI, m/z): 478.2[M+H$^+$].

Example 138

(R)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the compounds of Preparations BM and U and using procedure E, the title compound was obtained as an off-white foam (17 mg, 14% yield).
$^1$H NMR (CDCl$_3$) δ: 9.04 (s, 1H), 8.36 (s, 1H), 7.87 (m, 1H), 7.41 (d, J=2.1 Hz, 1H), 7.23 (m, 1H), 6.84 (m, 2H), 5.04 (dd, J=8.5, 3.8 Hz, 1H), 4.59 (m, 2H), 4.28 (dd, J=13.5, 3.8 Hz, 1H), 4.04 (t, J=8.8 Hz, 1H), 3.59 (m, 1H), 3.36 (s, 2H), 2.80 (m, 2H), 1.83 (m, 5H).
MS (ESI, m/z): 496.3[M+H$^+$].

Example 139

(R)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the compounds of Preparations BM and AU and using procedure E, the title compound was obtained as a yellowish foam (10 mg, 8% yield).
$^1$H NMR (CDCl$_3$) δ: 8.37 (s, 1H), 7.90 (m, 1H), 7.32 (d, J=2.6 Hz, 1H), 7.24 (m, 2H), 6.90 (m, 1H), 6.82 (d, J=9.7 Hz, 1H), 5.06 (m, 1H), 4.60 (m, 2H), 4.30 (m, 1H), 4.05 (t, J=8.8 Hz, 1H), 3.61 (m, 1H), 3.35 (s, 2H), 2.81 (m, 2H), 1.79 (m, 4H).
MS (ESI, m/z): 496.6[M+H$^+$].

Example 140

(R)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the compounds of Preparations BM and T and using procedure E, the title compound was obtained as yellowish foam (6 mg, 5%).
$^1$H NMR (CDCl$_3$) δ: 8.36 (d, J=1.2 Hz, 1H), 7.89 (d, J=9.7 Hz, 1H), 7.30 (d, J=2.6 Hz, 1H), 6.81 (m, 3H), 5.03 (m, 1H), 4.59 (m, 4H), 4.26 (dd, J=13.2, 3.8 Hz, 1H), 4.03 (t, J=8.5 Hz, 1H), 3.58 (m, 1H), 2.77 (m, 2H), 1.77 (m, 5H).
MS (ESI, m/z): 480.6[M+H$^+$].

Example 141

(R)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the compounds of Preparations BM and AV and using procedure E, the title compound was obtained as a yellowish foam (8 mg, 7% yield).
$^1$H NMR (CDCl$_3$) δ: 8.37 (d, J=1.5 Hz, 1H), 7.90 (d, J=9.7 Hz, 1H), 7.36 (d, J=2.3 Hz, 1H), 6.90 (m, 1H), 6.83 (d, J=9.4 Hz, 1H), 6.73 (dd, J=8.8, 2.6 Hz, 1H), 5.03 (m, 1H), 4.59 (m, 4H), 4.25 (dd, J=13.2, 3.8 Hz, 1H), 4.04 (t, J=8.5 Hz, 1H), 3.59 (m, 1H), 2.76 (m, 2H), 1.78 (m, 5H).
MS (ESI, m/z): 480.6[M+H$^+$].

Example 142

(R)-3-fluoro-4-{3-[(R)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one Starting from the compounds of Preparations BM and BK and using procedure E, the title compound was obtained as a yellowish solid (24 mg, 20% yield).
$^1$H NMR (DMSO-d$_6$) δ: 10.81 (s, 1H), 8.45 (d, J=0.9 Hz, 1H), 7.96 (d, J=9.7 Hz, 1H), 7.77 (m, 1H), 7.66 (m, 1H), 6.75 (d, J=9.7 Hz, 1H), 4.95 (m, 1H), 4.70 (m, 1H), 4.44 (dd, J=12.9, 8.5 Hz, 1H), 4.19 (m, 1H), 4.04 (dd, J=12.9, 3.5 Hz, 1H), 3.69 (dd, J=10.3, 7.0 Hz, 1H), 3.51 (s, 2H), 2.67 (m, 3H), 1.75 (m, 2H), 1.51 (m, 2H).
MS (ESI, m/z): 497.4[M+H$^+$].

Example 143

(R)-3-fluoro-4-{3-[(S)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one Starting from the compounds of Preparations BM and BL and using procedure E, the title compound was obtained as an off-white solid (26 mg, 21% yield).
$^1$H NMR (DMSO-d$_6$) δ: 10.81 (s, 1H), 8.45 (d, J=0.6 Hz, 1H), 7.96 (dd, J=9.7, 0.6 Hz, 1H), 7.77 (m, 1H), 7.66 (m, 1H), 6.75 (d, J=9.7 Hz, 1H), 4.95 (m, 1H), 4.70 (m, 1H), 4.44 (m, 1H), 4.19 (m, 1H), 4.04 (dd, J=12.6, 3.5 Hz, 1H), 3.69 (m, 1H), 3.51 (s, 3H), 2.67 (m, 3H), 1.76 (m, 2H), 1.52 (m, 2H).
MS (ESI, m/z): 497.3[M+H$^+$].

Example 144

(R)-3-fluoro-4-{3-[(S)-2-oxo-3-(3-oxo-3,4-dihydro-2H-pyrido[3,2-b][1,4]oxazin-6-yl)-oxazolidin-5-yl]-propylamino}-4,5-dihydro-pyrrolo[3,2,1-de][1,5]naphthyridin-7-one Starting from the compounds of Preparations BM and BJ and using procedure E, the title compound was obtained as a colourless solid (20 mg, 17% yield).
$^1$H NMR (DMSO-d$_6$) δ: 11.15 (s, 1H), 8.45 (d, J=1.5 Hz, 1H), 7.96 (d, J=9.7 Hz, 1H), 7.57 (m, 1H), 7.40 (m, 1H), 6.75 (d, J=9.7 Hz, 1H), 4.95 (m, 1H), 4.67 (m, 1H), 4.58 (s, 2H), 4.44 (dd, J=12.9, 8.5 Hz, 1H), 4.18 (m, 1H), 4.04 (dd, J=12.6, 3.5 Hz, 1H), 3.69 (m, 1H), 2.68 (m, 3H), 1.75 (m, 2H), 1.52 (m, 2H).
MS (ESI, m/z): 481.5[M+H$^+$].

Example 145

(S)-3-fluoro-4-{3-[(R)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the compounds of Preparations BN and U and using procedure E, the title compound was obtained as a yellowish foam (16 mg, 13% yield).
$^1$H NMR (CDCl$_3$) δ: 8.37 (d, J=1.2 Hz, 1H), 7.89 (d, J=9.7 Hz, 1H), 7.31 (d, J=2.3 Hz, 1H), 7.22 (d, J=8.5 Hz, 1H), 6.91 (dd, J=8.5, 2.3 Hz, 1H), 6.81 (d, J=9.7 Hz, 1H), 5.08 (m, 1H), 4.60 (m, 2H), 4.32 (m, 1H), 4.05 (m, 1H), 3.60 (m, 1H), 3.34 (s, 2H), 2.83 (m, 2H), 1.85 (m, 4H).
MS (ESI, m/z): 496.5[M+H$^+$].

Example 146

(S)-3-fluoro-4-{3-[(R)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the compounds of Preparations BN and T and using procedure E, the title compound was obtained as a yellow foam (7 mg, 6% yield).
MS (ESI, m/z): 480.6[M+H$^+$].

Example 147

(S)-3-fluoro-4-{3-[(R)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one Starting from the compounds of Preparations BN and BK and using procedure E, the title compound was obtained as a colourless solid (13 mg, 11% yield).
$^1$H NMR (DMSO-d$_6$) δ: 10.82 (s, 1H), 8.45 (s, 1H), 7.96 (d, J=10.0 Hz, 1H), 7.77 (m, 1H), 7.66 (m, 1H), 6.75 (d, J=10.0 Hz, 1H), 4.96 (m, 1H), 4.69 (m, 1H), 4.44 (m, 1H), 4.19 (m, 1H), 4.04 (m, 1H), 3.69 (m, 1H), 3.50 (s, 2H), 2.66 (m, 2H), 1.75 (m, 2H), 1.51 (m, 2H).
MS (ESI, m/z): 497.6[M+H$^+$].

Example 148

(S)-3-fluoro-4-{3-[(S)-2-oxo-3-(3-oxo-3,4-dihydro-2H-benzo[1,4]thiazin-6-yl)-oxazolidin-5-yl]-propylamino}-4,5-dihydro-pyrrolo[3,2,1-de][1,5]naphthyridin-7-one Starting from the compounds of Preparations BN and AU and using procedure E, the title compound was obtained as a yellowish foam (30 mg, 25% yield).
$^1$H NMR (CDCl$_3$) δ: 8.36 (d, J=1.5 Hz, 1H), 7.89 (d, J=10.0 Hz, 1H), 7.32 (d, J=2.3 Hz, 1H), 7.22 (d, J=8.5 Hz, 1H), 6.90 (dd, J=8.5, 2.3 Hz, 1H), 6.81 (d, J=9.7 Hz, 1H), 5.04 (ddd, J=8.5, 4.1, 0.6 Hz, 1H), 4.59 (m, 2H), 4.27 (dd, J=13.2, 3.8 Hz, 1H), 4.05 (m, 1H), 3.60 (dd, J=9.1, 7.3 Hz, 1H), 3.35 (s, 2H), 2.79 (m, 2H), 1.78 (m, 5H).
MS (ESI, m/z): 496.6[M+H$^+$].

Example 149

(S)-3-fluoro-4-{3-[(S)-2-oxo-3-(3-oxo-3,4-dihydro-2H-benzo[1,4]oxazin-6-yl)-oxazolidin-5-yl]-propylamino}-4,5-dihydro-pyrrolo[3,2,1-de][1,5]naphthyridin-7-one Starting from the compounds of Preparations BN and AV and using procedure E, the title compound was obtained as a yellow foam (8 mg, 7% yield).
MS (ESI, m/z): 480.5[M+H$^+$].

Example 150

(S)-3-fluoro-4-{3-[(S)-2-oxo-3-(3-oxo-3,4-dihydro-2H-pyrido[3,2-b][1,4]thiazin-6-yl)-oxazolidin-5-yl]-propylamino}-4,5-dihydro-pyrrolo[3,2,1-de][1,5]naphthyridin-7-one Starting from the compounds of Preparations BN and BL and using procedure E, the title compound was obtained as an orange foam (6 mg, 5% yield).
MS (ESI, m/z): 497.4[M+H$^+$]

Example 151

(S)-3-fluoro-4-{3-[(S)-2-oxo-3-(3-oxo-3,4-dihydro-2H-pyrido[3,2-b][1,4]oxazin-6-yl)-oxazolidin-5-yl]-propylamino}-4,5-dihydro-pyrrolo[3,2,1-de][1,5]naphthyridin-7-one Starting from the compounds of Preparations BN and BJ and using procedure E, the title compound was obtained as a yellowish solid (11 mg, 9% yield).
$^1$H NMR (DMSO-d$_6$) δ: 11.15 (s, 1H), 8.45 (s, 1H), 7.96 (d, J=9.7 Hz, 1H), 7.57 (m, 1H), 7.40 (m, 1H), 6.75 (d, J=10.0 Hz, 1H), 4.96 (m, 1H), 4.67 (m, 1H), 4.58 (s, 2H), 4.44 (m, 1H), 4.19 (m, 1H), 4.05 (m, 1H), 3.68 (m, 1H), 2.66 (m, 2H), 1.76 (m, 2H), 1.51 (m, 3H).
MS (ESI, m/z): 481.5[M+H$^+$].

Example 152

(RS)-9-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BO and U and using procedure E, the title compound was obtained as a colourless solid (32 mg, 38% yield).
MS (ESI, m/z): 491.2[M+H$^+$].

Example 153

(RS)-9-fluoro-1-(methyl-{3-[(R)-2-oxo-3-(3-oxo-3,4-dihydro-2H-benzo[1,4]thiazin-6-yl)-oxazolidin-5-yl]-propyl}-amino)-1,2-dihydro-pyrrolo[3,2,1-ij]quinolin-4-one A suspension of the compound of Example 152 (20 mg) in MeOH (2 mL) was treated with an aq. formaldehyde solution (37%; 16 μL) for 10 min, then treated with NaBH$_3$CN (2.5 mg). After 3 h stirring at rt, the reaction mixture was taken up in water and extracted with EA. The org. layer was washed with water, brine and dried over MgSO$_4$. The org. layer was filtrated and evaporated under reduced pressure and the residue was purified by CC (DCM/MeOH/NH$_4$OH 100:50:4), affording a colourless foam (9 mg; 44% yield).
$^1$H NMR (CDCl$_3$) δ: 8.50 (s, 1H), 7.70 (d, J=9.7 Hz, 1H), 7.48 (dd, J=8.5, 4.4 Hz, 1H), 7.40 (d, J=2.1 Hz, 1H), 7.27 (m, 1H), 6.94 (m, 2H), 6.64 (d, J=9.4 Hz, 1H), 5.03 (t, J=6.4 Hz, 1H), 4.67 (m, 1H), 4.38 (d, J=6.4 Hz, 2H), 4.08 (m, 1H), 3.62 (m, 1H), 3.40 (s, 2H), 2.50 (m, 2H), 2.22 (d, J=4.1 Hz, 3H), 1.77 (m, 4H).
MS (ESI, m/z): 509.3[M+H$^+$].

Example 154

(RS)-6-({2-[(S)-2-oxo-3-(3-oxo-3,4-dihydro-2H-benzo[1,4]oxazin-6-yl)-oxazolidin-5-yl]-ethylamino}-methyl)-5,6-dihydro-pyrrolo[1,2,3-de]quinoxalin-3-one Starting from the compounds of Preparations AC and H and using procedure C, the title compound was obtained as a yellowish foam (82 mg, 35% yield).
MS (ESI, m/z): 462.1 [M+H$^+$]

Example 155

(RS)-6-({2-[(R)-2-oxo-3-(3-oxo-3,4-dihydro-2H-benzo[1,4]oxazin-6-yl)-oxazolidin-5-yl]-ethylamino}-methyl)-5,6-dihydro-pyrrolo[1,2,3-de]quinoxalin-3-one Starting from the compounds of Preparations AC and I and using procedure C, the title compound was obtained as yellow foam (90 mg, 39% yield).
MS (ESI, m/z): 462.1[M+H$^+$].

Example 156

(RS)-6-({2-[(R)-2-oxo-3-(3-oxo-3,4-dihydro-2H-benzo[1,4]thiazin-6-yl)-oxazolidin-5-yl]-ethylamino}-methyl)-5,6-dihydro-pyrrolo[1,2,3-de]quinoxalin-3-one Starting from the compounds of Preparations AC and J and using procedure C, the title compound was obtained as a brown foam (270 mg, 37% yield).
MS (ESI, m/z): 478.2[M+H$^+$].

Example 157

(R)-1-{2-[(S)-2-oxo-3-(3-oxo-3,4-dihydro-2H-benzo[1,4]oxazin-6-yl)-oxazolidin-5-yl]-ethylamino}-1,2-dihydro-pyrrolo[3,2,1-ij]quinolin-4-one Starting from the compounds of Preparations BC and H and using procedure C, the title compound was obtained as a yellowish foam (59 mg, 26% yield).
MS (ESI, m/z): 447.2[M+H$^+$].

Example 158

(R)-1-{2-[(R)-2-oxo-3-(3-oxo-3,4-dihydro-2H-benzo[1,4]thiazin-6-yl)-oxazolidin-5-yl]-ethylamino}-1,2-dihydro-pyrrolo[3,2,1-ij]quinolin-4-one Starting from the compounds of Preparations BC and J and using procedure C, the title compound was obtained as a brown foam (81 mg, 35% yield).
MS (ESI, m/z): 463.2[M+H$^+$].

Example 159

(RS)-9-fluoro-1-{4-[(RS)-2-oxo-3-(3-oxo-3,4-dihydro-2H-benzo[1,4]thiazin-6-yl)-oxazolidin-5-yl]-butylamino}-1,2-dihydro-pyrrolo[3,2,1-ij]quinolin-4-one Starting from the compounds of Preparations C and BP and using procedure E, the title compound was obtained as a colourless foam (84 mg, 55% yield).
MS (ESI, m/z): 509.1[M+H$^+$].

Example 160

(S)-7-fluoro-6-{3-[(S)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one A solution of the compound of Example 79 (42 mg) in DCM/MeOH (2:1; 6 mL) was treated with NaBH$_4$ (3.2 mg). After 30 min stirring at rt, the reaction mixture was quenched with 1M. HCl (1 mL) and partitioned between DCM and aq. NH$_4$OH. The org. layer was washed with water, dried over MgSO$_4$, concentrated under reduced pressure and purified by CC (EA/MeOH 19:1 to 9:1), affording a beige solid (29 mg; 69% yield).
MS (ESI, m/z): 498.2 [M+H$^+$].

Example 161

(1R,2R)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester and (1S,2S)-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester Starting from the compounds of Preparations BQ and U and using procedure E, a mixture of the title compounds was obtained as a yellowish solid (46 mg, 23% yield).
MS (ESI, m/z): 535.6[M+H$^+$].

Example 162

(1R,2R)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester and (1S,2S)-4-oxo-1-{3-[(S)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester Starting from the compounds of Preparations BQ and AU and using procedure E, a mixture of the title compounds was obtained as a colourless solid (67 mg, 32% yield).
MS (ESI, m/z): 535.7[M+H$^+$].

Example 163

(1R,2R)-2-hydroxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (1S,2S)-2-hydroxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BR and U and using procedure E, a mixture of the title compounds was obtained as a colourless solid (99 mg, 54% yield).
MS (ESI, m/z): 507.2[M+H$^+$].

Example 164

(1R,2R)-2-hydroxymethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (1S,2S)-2-hydroxymethyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BR and AU and using procedure E, a mixture of the title compounds was obtained as a colourless solid (110 mg, 60% yield).
MS (ESI, m/z): 507.2[M+H$^+$].

Example 165

(1R,2R)-2-methoxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (1S,2S)-2-methoxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BS and U and using procedure E, a mixture of the title compounds was obtained as a colourless solid (20 mg, 32% yield).
MS (ESI, m/z): 521.6[M+H$^+$].

Example 166

(1R,2S)-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (1S,2R)-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BT and U and using procedure E, a mixture of the title compounds was obtained as a colourless solid (56 mg, 38% yield).
$^1$H NMR (CDCl$_3$) δ: 8.57 (s, 1H), 7.71 (dd, J=9.4, 0.6 Hz, 1H), 7.52 (m, 2H), 7.33 (m, 1H), 7.23 (m, 2H), 6.99 (m, 1H), 6.69 (dd, J=9.4, 1.5 Hz, 1H), 4.82 (d, J=6.4 Hz, 1H), 4.65 (m, 1H), 4.26 (s, 1H), 4.05 (td, J=8.5, 6.2 Hz, 1H), 3.63 (m, 1H), 3.39 (s, 2H), 2.80 (m, 2H), 1.87 (m, 5H), 1.56 (d, J=6.7 Hz, 3H).
MS (ESI, m/z): 491.3[M+H$^+$].

Example 167

(1R,2S)-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (1S,2R)-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BT and AU and using procedure E, a mixture of the title compounds was obtained as a colourless solid (59 mg, 40% yield).
$^1$H NMR (CDCl$_3$) δ: 8.60 (dd, J=2.3, 0.6 Hz, 1H), 7.71 (dd, J=9.4, 0.9 Hz, 1H), 7.51 (m, 2H), 7.33 (dd, J=14.4, 2.3 Hz, 1H), 7.24 (m, 2H), 6.98 (td, J=8.2, 2.3 Hz, 1H), 6.69 (dd, J=9.4, 1.8 Hz, 1H), 4.80 (dt, J=6.4, 1.8 Hz, 1H), 4.64 (m, 1H), 4.24 (s, 1H), 4.05 (td, J=8.5, 5.9 Hz, 1H), 3.61 (dd, J=8.8, 7.0 Hz, 1H), 3.39 (s, 2H), 2.80 (m, 2H), 1.79 (m, 5H), 1.55 (d, J=6.4 Hz, 3H).
MS (ESI, m/z): 491.3[M+H$^+$].

Example 168

(1R,2S)-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one and (1S,2R)-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations BT and BK and using procedure E, a mixture of the title compounds was obtained as a colourless solid (42 mg, 24% yield).
$^1$H NMR (CDCl$_3$) δ: 8.50 (s, 1H), 7.81 (m, 1H), 7.68 (dd, J=9.4, 5.6 Hz, 1H), 7.51 (m, 3H), 7.19 (m, 1H), 6.63 (dd, J=9.4, 5.0 Hz, 1H), 4.76 (m, 1H), 4.62 (d, J=7.9 Hz, 1H), 4.18 (m, 2H), 3.72 (m, 1H), 3.43 (s, 2H), 2.76 (m, 2H), 1.77 (m, 5H), 1.53 (d, J=6.4 Hz, 3H).
MS (ESI, m/z): 492.3[M+H$^+$].

Example 169

(1R,2S)-2-methyl-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one and (1S,2R)-2-methyl-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations BT and BL and using procedure E, a mixture of the title compounds was obtained as a colourless solid (43 mg, 24% yield).
$^1$H NMR (CDCl$_3$) δ: 8.10 (m, 1H), 7.86 (dd, J=8.8, 3.8 Hz, 1H), 7.71 (dd, J=9.4, 1.5 Hz, 1H), 7.55 (m, 3H), 7.22 (m, 1H), 6.67 (d, J=9.4 Hz, 1H), 4.83 (m, 1H), 4.64 (m, 1H), 4.22 (m, 2H), 3.75 (dt, J=10.5, 7.3 Hz, 1H), 3.46 (s, 2H), 2.79 (m, 2H), 1.87 (m, 5H), 1.57 (dd, J=6.4, 1.2 Hz, 3H).
MS (ESI, m/z): 492.4[M+H$^+$].

Example 170

(1R,2R)-2-(1-hydroxy-1-methyl-ethyl)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one and (1S,2S)-2-(1-hydroxy-1-methyl-ethyl)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BU and U and using procedure E, a mixture of the title compounds was obtained as a colourless foam (22 mg, 46% yield).
MS (ESI, m/z): 535.6[M+H$^+$].

Example 171

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one Starting from the compound of Example 132 and proceeding in analogy to Example 160, the title compound was obtained as a colourless foam (36% yield).
MS (ESI, m/z): 499.4[M+H$^+$].

Example 172

N-((RS)-9-fluoro-4-oxo-1,2-dihydro-4H-pyrrolo[3,2,1-ij]quinolin-1-yl)-N-{3-[(R)-2-oxo-3-(3-oxo-3,4-dihydro-2H-benzo[1,4]thiazin-6-yl)-oxazolidin-5-yl]-propyl}-acetamide and (RS)-1-{3-[(R)-3-(4-acetyl-3-oxo-3,4-dihydro-2H-benzo[1,4]thiazin-6-yl)-2-oxo-oxazolidin-5-yl]-propylamino}-9-fluoro-1,2-dihydro-pyrrolo[3,2,1-ij]quinolin-4-one A solution of the compound of Example 13 (20 mg) and DIPEA (14 µL) was reacted at 0° C. with Ac$_2$O (6 µL). The

Example 173

(S)-4-hydroxy-4-({2-[(S)-2-oxo-3-(3-oxo-3,4-dihydro-2H-benzo[1,4]thiazin-6-yl)-oxazolidin-5-yl]-ethylamino}-methyl)-4,5-dihydro-pyrrolo[3,2,1-de][1,5]naphthyridin-7-one To a solution of the compound of Preparation BD (75 mg) in EtOH (3 mL) were added the compound of Preparation AP (89 mg, 1.5 eq.) and $K_2CO_3$ (65 mg, 3 eq.). The mixture was stirred at rt for 3 days. The solvent was removed under reduced pressure and the residue was partitioned between water and DCM-MeOH (9:1). The phases were separated and the aq. layer was extracted two more times with DCM-MeOH (9:1). The combined org. layers were dried over $MgSO_4$ and concentrated. The residue was purified by CC (DCM/MeOH/$NH_4OH$ 1000:100:8) to afford the title compound as a yellow solid (26 mg, 26% yield).

MS (ESI, m/z): 494.2[M+H$^+$].

Example 174

(RS)-9-fluoro-1-hydroxy-1-({2-[(S)-2-oxo-3-(3-oxo-3,4-dihydro-2H-benzo[1,4]thiazin-6-yl)-oxazolidin-5-yl]-ethylamino}-methyl)-1,2-dihydro-pyrrolo[3,2,1-ij]quinolin-4-one Starting from 9-fluoro-1-hydroxy-4-oxo-1,2-dihydro-4H-pyrrolo[3,2,1-ij]quinolin-1-yl]methyl 4-methylbenzenesulfonate (prepared according to EP 1980251) and the compound of Preparation AP and using procedure C, the title compound was obtained as a yellow solid (85 mg, 65% yield).

MS (ESI, m/z): 511.2[M+H$^+$].

Example 175

(RS)-1-({[(S)-2-oxo-3-(3-oxo-3,4-dihydro-2H-pyrido[3,2-b][1,4]thiazin-6-yl)-oxazolidin-5-ylmethyl]-amino}-methyl)-1,2-dihydro-pyrrolo[3,2,1-ij]quinolin-4-one Starting from the compounds of Preparations AE and BW and using procedure C, the title compound was obtained as a beige solid (70 mg; 20% yield).

MS (ESI, m/z): 464.4[M+H$^+$].

Example 176

(RS)-1-({2-[(S)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one Starting from the compounds of Preparations AE and BX and using procedure C, the title compound was obtained as a colourless solid (130 mg; 36% yield).

MS (ESI, m/z): 478.2[M+H$^+$].

Example 177

(RS)-9-chloro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations BY and BK and using procedure E, the title compound was obtained as a pale yellow solid (31 mg; 58% yield).

$^1$H NMR (CDCl$_3$) δ: 8.33 (m, 1H), 7.84 (dd, J=8.8, 4.4 Hz, 1H), 7.66 (dd, J=9.4, 3.5 Hz, 1H), 7.57 (dd, J=8.5, 2.3 Hz, 1H), 7.41 (dd, J=8.2, 1.8 Hz, 1H), 7.11 (dd, J=8.5, 1.5 Hz, 1H), 6.66 (dd, J=9.4, 3.8 Hz, 1H), 4.91 (m, 1H), 4.62 (m, 1H), 4.45 (m, 1H), 4.25 (m, 2H), 3.75 (m, 1H), 3.45 (s, 2H), 2.61 (m, 2H), 1.78 (m, 5H).

MS (ESI, m/z): 512.3[M+H$^+$].

Example 178

(RS)-9-chloro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BY and U and using procedure E, the title compound was obtained as a colourless solid (14 mg; 26% yield).

$^1$H NMR (CDCl3) δ: 8.73 (s, 1H), 7.68 (d, J=9.7 Hz, 1H), 7.39 (m, 2H), 7.25 (m, 1H), 7.12 (d, J=8.2 Hz, 1H), 6.98 (m, 1H), 6.68 (d, J=9.4 Hz, 1H), 4.91 (dd, J=8.2, 3.5 Hz, 1H), 4.65 (m, 1H), 4.46 (m, 1H), 4.30 (dd, J=13.2, 3.2 Hz, 1H), 4.06 (m, 1H), 3.61 (m, 1H), 3.39 (s, 2H), 2.64 (m, 2H), 1.86 (m, 5H).

MS (ESI, m/z): 511.3[M+H$^+$].

Example 179

(RS)-9-ethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations BZ and U and using procedure E, the title compound was obtained as a colourless solid (11 mg; 36% yield).

$^1$H NMR (CDCl3) δ: 8.56 (m, 1H), 7.68 (d, J=9.4 Hz, 1H), 7.39 (m, 2H), 7.26 (m, 1H), 7.01 (m, 2H), 6.64 (d, J=9.4 Hz, 1H), 4.82 (t, J=5.3 Hz, 1H), 4.65 (m, 1H), 4.37 (d, J=5.3 Hz, 2H), 4.06 (m, 1H), 3.61 (dd, J=8.5, 7.0 Hz, 1H), 3.39 (s, 2H), 2.80 (m, 4H), 1.71 (m, 5H), 1.29 (m, 3H).

MS (ESI, m/z): 505.5[M+H$^+$].

Example 180

(RS)-9-ethynyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations CA and U and using procedure E, the title compound was obtained as a colourless solid (10 mg; 21% yield).

MS (ESI, m/z): 501.2[M+H$^+$].

---

(Top of page 195, continued from previous:)

reaction mixture was further stirred at rt for 5 h. The solvent was removed under reduced pressure and the residue was dissolved in DCM and sequentially washed with water and brine. The org. layer was dried over MgSO$_4$. The solvent was removed under reduced pressure and the residue was purified by CC (DCM/MeOH/NH$_4$OH; 1000:50:4), affording a 1:1-mixture of the two possible N-acetates as an off-white foam (18 mg; 83% yield).

MS (ESI, m/z): 537.5[M+H$^+$].

Example 181

(1R*,2R*)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid methyl ester Starting from the compounds of Preparations CB and U and using procedure E, the title compound was obtained as an off-white foam (23 mg; 20% yield).

MS (ESI, m/z): 553.6[M+H$^+$].

Example 182

(1R*,2R*)-9-fluoro-2-hydroxymethyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations CC and U and using procedure E, the title compound was obtained as a white foam (44 mg; 38% yield).

MS (ESI, m/z): 525.3[M+H$^+$].

Example 183

(1R*,2S*)-9-fluoro-2-methyl-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations CD and U and using procedure E, the title compound was obtained as an off-white foam (12 mg; 10% yield).

MS (ESI, m/z): 509.3[M+H$^+$].

Example 184

(1R*,2S*)-9-fluoro-2-methyl-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one Starting from the compounds of Preparations CD and AU and using procedure E, the title compound was obtained as an off-white foam (21 mg; 18% yield).

MS (ESI, m/z): 509.3[M+H$^+$].

Example 185

(1R*,2S*)-9-fluoro-2-methyl-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations CD and BK and using procedure E, the title compound was obtained as an off-white foam (64 mg; 55% yield).

MS (ESI, m/z): 510.3[M+H$^+$].

Example 186

(1R*,2R*)-9-fluoro-4-oxo-1-{3-[(R)-2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinoline-2-carboxylic acid hydrochloride A solution of the compound of Example 181 (20 mg) in dioxane (1 mL) was treated with aq. HCl (37%; 0.142 mL) and stirred at 50° C. for 3 h. The solution was concentrated under reduced pressure and the residue was suspended in EA/MeOH (4:1), filtered, washed with TBME and dried in HV, affording a gray solid (6 mg; 29% yield).

MS (ESI, m/z): 539.2[M+H$^+$].

Example 187

(RS)-9-fluoro-1-({2-[(S)-2-oxo-3-(3-oxo-3,4-dihydro-2H-benzo[1,4]oxazin-6-yl)-oxazolidin-5-yl]-ethylamino}-methyl)-1,2,5,6-tetrahydro-pyrrolo[3,2,1-ij]quinolin-4-one A solution of the compound of Example 2 (60 mg) in MeOH/AcOH (1:1, 2 mL) was hydrogenated over Pd/C (133 mg) overnight. The catalyst was filtered off and thoroughly washed with MeOH and MeOH/DCM. The filtrate was concentrated under reduced pressure. The residue was taken up in water and 28% aq. NH$_4$OH, filtered, washed with water and TBME and dried under reduced pressure, affording an off-white foam (45 mg; 75% yield).

MS (ESI, m/z): 481.5[M+H$^+$].

Example 188

(1R*,2S*)-2-aminomethyl-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one 188.i. (1R*,2S*)-methanesulfonic acid 9-fluoro-4-oxo-1-{3-[2-oxo-3-(3-oxo-3,4-dihydro-2H-benzo[1,4]thiazin-6-yl)-oxazolidin-5-yl]-propylamino}-1,2-dihydro-4H-pyrrolo[3,2,1-ij]quinolin-2-ylmethyl ester Starting from the compounds of Preparations CE and U and using procedure E, the title compound was obtained as an off-white foam (79 mg; 30% yield).

MS (ESI, m/z): 603.3[M+H$^+$].

188.ii. (1R*,2S*)-2-azidomethyl-9-fluoro-1-{3-[2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one NaN$_3$ (25 mg) was added to a solution of intermediate 188.i (77 mg) in DMF (1.5 mL) and the resulting mixture was stirred at 80° C. for 1 h. Water and EA were added and the phases separated. The aq. layer was extracted once more with EA and the combined org. layers were washed with water and brine, dried over MgSO$_4$ and concentrated. The residue was purified by CC (DCM/MeOH/NH$_4$OH 1000:50:4), affording a light yellow foam (57 mg; 81% yield).

MS (ESI, m/z): 550.5[M+H$^+$].

188.iii. (1R*,2S*)-2-aminomethyl-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one A solution of intermediate 188.ii (57 mg) in THF (1.5 mL) was treated with PPh₃ (30 mg) and water (19 μL). The mixture was heated at 70° C. overnight, concentrated under reduced pressure and the residue was taken in DCM. The DCM layer was extracted with 1M. HCl and the aq. layer was basified with NH₄OH. The aq. layer was extracted with DCM/MeOH (9:1) and the combined org. layers were dried over MgSO₄, concentrated and purified by CC (DCM/MeOH/NH₄OH 1000:100:8), affording a light yellow foam (26 mg; 48% yield).

MS (ESI, m/z): 524.3[M+H⁺].

Example 189

(S)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations CF and BJ and using procedure E, the title compound was obtained as an off-white foam (52 mg; 32% yield).

MS (ESI, m/z): 480.5[M+H⁺].

Example 190

(S)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations CF and AR and using procedure E, the title compound was obtained as an off-white foam (64 mg; 34% yield).

MS (ESI, m/z): 480.5[M+H⁺].

Example 191

(S)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations CF and BL and using procedure E, the title compound was obtained as an off-white foam (53 mg; 27% yield).

MS (ESI, m/z): 496.1[M+H⁺].

Example 192

(S)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations CF and BK and using procedure E, the title compound was obtained as an off-white solid (73 mg; 38% yield).

MS (ESI, m/z): 496.6[M+H⁺].

Example 193

(R)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations CG and BJ and using procedure E, the title compound was obtained as an off-white foam (56 mg; 34% yield).

MS (ESI, m/z): 480.6[M+H⁺].

Example 194

(R)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one Starting from the compounds of Preparations CG and AR and using procedure E, the title compound was obtained as an off-white foam (71 mg; 38% yield).

MS (ESI, m/z): 480.6[M+H⁺].

Example 195

(R)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations CG and BL and using procedure E, the title compound was obtained as a light yellow solid (52 mg; 27% yield).

MS (ESI, m/z): 496.5[M+H⁺].

Example 196

(R)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one Starting from the compounds of Preparations CG and BK and using procedure E, the title compound was obtained as a light yellow solid (55 mg; 28% yield).

MS (ESI, m/z): 496.6[M+H⁺].

Example 197

(RS)-9-fluoro-1-({2-[(R)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one Starting from the compounds of Preparations A and CH and using procedure C, the title compound was obtained as a pale yellow solid (40 mg; 22% yield).

MS (ESI, m/z): 496.6[M+H⁺].

Example 198

(RS)-9-fluoro-1-({2-[(S)-2-oxo-3-(3-oxo-3,4-dihydro-2H-pyrido[3,2-b][1,4]thiazin-6-yl)-oxazolidin-5-yl]-ethylamino}-methyl)-1,2-dihydro-pyrrolo[3,2,1-ij]quinolin-4-one Starting from the compounds of Preparations A and BX and using procedure C, the title compound was obtained as a pale yellow solid (10 mg; 11% yield).

MS (ESI, m/z): 496.4[M+H⁺].

Example 199

(RS)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one Starting from the compounds of Preparations CI and BK and using procedure E, the title compound was obtained as a light yellow solid (650 mg; 26% yield).
MS (ESI, m/z): 497.5[M+H$^+$].

Example 200

(RS)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one A solution of the compound of Preparation CI (0.2 g, 0.975 mmol) and the compound of Preparation BK (0.3 g, 0.975 mmol) in DCE/MeOH (1:1, 8 mL) was stirred at rt overnight. NaBH$_4$ (110 mg) was added and the mixture stirred at rt for 1 h. The mixture was quenched with HCl 1M and partitioned between DCM and diluted NH$_4$OH. The org. phase was dried over MgSO$_4$ and concentrated. The residue was purified by CC (DCM/MeOH 19:1 containing 1% NH$_4$OH). The title compound was obtained as a light rose foam (78 mg; 16% yield).
MS (ESI, m/z): 499.5[M+H$^+$].

Example 201

(RS)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-methyl-1,2,5,6-tetrahydro-pyrrolo[1,2,3-de]quinoxalin-3-one dihydrochloride 201.i. ((RS)-7-fluoro-3-oxo-5,6-dihydro-3H-pyrrolo[1,2,3-de]quinoxalin-6-yl)-{3-[(R)-2-oxo-3-(3-oxo-3,4-dihydro-2H-pyrido[3,2-b][1,4]thiazin-6-yl)-oxazolidin-5-yl]-propyl}-carbamic acid tert-butyl ester A suspension of the compound of Example 199 (0.6 g, 1.2 mmol) in DCM (10 mL), MeOH (2 mL) and THF (5 mL) was treated with Boc$_2$O (526 mg, 2 eq.) was heated at reflux overnight. The volatiles were removed under reduced pressure and the residue purified by CC (EA) to give the desired intermediate as a beige foam (0.61 g, 85% yield).
MS (ESI, m/z): 597.7[M+H$^+$].

201.ii. ((RS)-7-fluoro-3-oxo-2,3,5,6-tetrahydro-1H-pyrrolo[1,2,3-de]quinoxalin-6-yl)-{3-[(R)-2-oxo-3-(3-oxo-3,4-dihydro-2H-pyrido[3,2-b][1,4]thiazin-6-yl)-oxazolidin-5-yl]-propyl}-carbamic acid tert-butyl ester A solution of intermediate 201.i (610 mg) in MeOH/DCM (4:1; 20 mL) was treated with NaBH$_4$ (77 mg, 2 eq.) and stirred at rt for 2 h. The mixture was quenched with HCl 1M and partitioned between DCM and diluted NH$_4$OH. The org. phase was dried over MgSO$_4$ and concentrated. The residue was purified by CC (EA). The title compound was obtained as a beige foam (410 mg; 67% yield).
MS (ESI, m/z): 599.6[M+H$^+$].

201.iii. ((R)-7-fluoro-1-methyl-3-oxo-2,3,5,6-tetrahydro-1H-pyrrolo[1,2,3-de]quinoxalin-6-yl)-{3-[(R)-2-oxo-3-(3-oxo-3,4-dihydro-2H-pyrido[3,2-b][1,4]thiazin-6-yl)-oxazolidin-5-yl]-propyl}-carbamic acid tert-butyl ester A solution of intermediate 201.ii (100 mg) in MeOH (3 mL) was treated with AcOH (0.019 mL), aq. formaldehyde (37%, 0.026 mL) and NaCNBH$_3$ (30 mg). The mixture was stirred at rt for 3 h. The mixture was diluted with EA and water and the org. phase was washed with NaHCO$_3$ and brine, dried over MgSO$_4$ and concentrated. The residue was crystallized from ether to give the desired intermediate as a colourless solid (0.075 g, 73% yield).
MS (ESI, m/z): 613.7[M+H$^+$].

201.iv. (RS)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-methyl-1,2,5,6-tetrahydro-pyrrolo[1,2,3-de]quinoxalin-3-one dihydrochloride A suspension of intermediate 201.iii (0.068 g, 0.1 mmol) in HCl (4M in dioxane, 1 mL) was stirred at rt for 15 min. The volatiles were removed under reduced pressure and the solid was washed with ether and dried at HV. The title salt was isolated as a grey solid (0.068 g; quant.).
MS (ESI, m/z): 513.6[M+H$^+$].

Example 202

(RS)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-(3-hydroxypropyl)-1,2,5,6-tetrahydro-pyrrolo[1,2,3-de]quinoxalin-3-one dihydrochloride 202.i. ((R)-7-fluoro-1-(3-hydroxypropyl)-methyl-3-oxo-2,3,5,6-tetrahydro-1H-pyrrolo[1,2,3-de]quinoxalin-6-yl)-{3-[(R)-2-oxo-3-(3-oxo-3,4-dihydro-2H-pyrido[3,2-b][1,4]thiazin-6-yl)-oxazolidin-5-yl]-propyl}-carbamic acid tert-butyl ester A solution of intermediate 201.ii (100 mg) in MeOH (3 mL) was treated with AcOH (0.019 mL), aq. formaldehyde (37%, 0.026 mL) and 3-[(tert-butyldimethylsilyl)oxy]-1-propanal (88 mg, commercial). The mixture was stirred at rt for 5 h. The mixture was diluted with EA and water and the org. phase was washed with NaHCO$_3$ and brine, dried over MgSO$_4$ and concentrated. The residue was purified by CC (EA) to give the desired intermediate as a yellowish oil (0.11 g, 62% yield).
MS (ESI, m/z): 771.6[M+H$^+$].

202.ii. (RS)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1-(3-hydroxypropyl)-1,2,5,6-tetrahydro-pyrrolo[1,2,3-de]quinoxalin-3-one dihydrochloride A suspension of intermediate 202.i (0.11 g, 0.14 mmol) in HCl (4M in dioxane, 1.5 mL) was stirred at rt for 15 min. The volatiles were removed under reduced pressure and the solid was washed with ether and dried at HV. The title salt was isolated as a grey solid (0.071 g; 78% yield).
MS (ESI, m/z): 557.3[M+H$^+$].

Pharmacological Properties of the Invention Compounds
In Vitro Assays
Experimental Methods:

Minimal inhibitory concentrations (MICs; mg/l) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

Results:

All Example compounds were tested against several Gram positive and Gram negative bacteria such as S. aureus, E. faecalis, S. pneumoniae, M. catarrhalis, A. baumanii, E. coli or P. aeruginosa.

Typical antibacterial test results are given in the table hereafter (MIC in mg/l).

| Example No. | MIC for M. catarrhalis A894 | Example No. | MIC for M. catarrhalis A894 |
|---|---|---|---|
| 1 | ≤0.031 | 2 | ≤0.031 |
| 3 | ≤0.031 | 4 | ≤0.031 |
| 5 | ≤0.031 | 6 | 0.125 |
| 7 | ≤0.031 | 8 | ≤0.031 |
| 9 | ≤0.031 | 10 | ≤0.031 |
| 11 | 0.063 | 12 | ≤0.031 |
| 13 | ≤0.031 | 14 | ≤0.031 |
| 15 | ≤0.031 | 16 | ≤0.031 |
| 17 | ≤0.031 | 18 | ≤0.031 |
| 19 | ≤0.031 | 20 | ≤0.031 |
| 21 | ≤0.031 | 22 | ≤0.031 |
| 23 | ≤0.031 | 24 | ≤0.031 |
| 25 | ≤0.031 | 26 | 0.25 |
| 27 | 0.5 | 28 | ≤0.031 |
| 29 | ≤0.031 | 30 | 0.031 |
| 31 | 16 | 32 | 0.031 |
| 33 | 16 | 34 | ≤0.031 |
| 35 | ≤0.031 | 36 | 8 |
| 37 | 1 | 38 | 16 |
| 39 | ≤0.031 | 40 | 0.125 |
| 41 | 0.5 | 42 | 2 |
| 43 | 1 | 44 | 0.125 |
| 45 | 0.063 | 46 | ≤0.031 |
| 47 | ≤0.031 | 48 | ≤0.031 |
| 49 | ≤0.031 | 50 | ≤0.031 |
| 51 | ≤0.031 | 52 | ≤0.031 |
| 53 | ≤0.031 | 54 | 0.25 |
| 55 | ≤0.031 | 56 | ≤0.031 |
| 57 | ≤0.031 | 58 | ≤0.031 |
| 59 | 4 | 60 | ≤0.031 |
| 61 | ≤0.031 | 62 | ≤0.031 |
| 63 | 0.031 | 64 | ≤0.031 |
| 65 | ≤0.031 | 66 | ≤0.031 |
| 67 | ≤0.063 | 68 | ≤0.031 |
| 69 | ≤0.031 | 70 | ≤0.031 |
| 71 | ≤0.031 | 72 | ≤0.031 |
| 73 | ≤0.031 | 74 | ≤0.031 |
| 75 | ≤0.031 | 76 | ≤0.031 |
| 77 | 0.031 | 78 | ≤0.031 |
| 79 | ≤0.031 | 80 | ≤0.031 |
| 81 | ≤0.031 | 82 | 0.25 |
| 83 | ≤0.031 | 84 | 0.063 |
| 85 | ≤0.031 | 86 | ≤0.031 |
| 87 | ≤0.031 | 88 | ≤0.031 |
| 89 | 0.063 | 90 | ≤0.031 |
| 91 | ≤0.031 | 92 | ≤0.031 |
| 93 | ≤0.031 | 94 | ≤0.031 |
| 95 | ≤0.031 | 96 | ≤0.031 |
| 97 | ≤0.031 | 98 | 0.25 |
| 99 | ≤0.031 | 100 | 0.031 |
| 101 | ≤0.031 | 102 | ≤0.031 |
| 103 | ≤0.031 | 104 | ≤0.031 |
| 105 | ≤0.031 | 106 | ≤0.031 |
| 107 | 8 | 108 | ≤0.031 |
| 109 | ≤0.031 | 110 | ≤0.031 |
| 111 | 0.125 | 112 | ≤0.031 |
| 113 | ≤0.031 | 114 | ≤0.031 |
| 115 | ≤0.031 | 116 | ≤0.031 |
| 117 | ≤0.031 | 118 | ≤0.031 |
| 119 | ≤0.031 | 120 | 0.125 |
| 121 | 0.125 | 122 | 0.5 |
| 123 | 0.125 | 124 | ≤0.031 |
| 125 | ≤0.031 | 126 | ≤0.031 |
| 127 | ≤0.031 | 128 | ≤0.031 |
| 129 | ≤0.031 | 130 | ≤0.031 |
| 131 | ≤0.031 | 132 | ≤0.031 |
| 133 | ≤0.031 | 134 | ≤0.031 |
| 135 | ≤0.031 | 136 | ≤0.031 |
| 137 | ≤0.031 | 138 | ≤0.031 |
| 139 | ≤0.031 | 140 | ≤0.031 |
| 141 | ≤0.031 | 142 | ≤0.031 |
| 143 | ≤0.031 | 144 | ≤0.031 |
| 145 | ≤0.031 | 146 | ≤0.031 |
| 147 | ≤0.031 | 148 | ≤0.031 |
| 149 | ≤0.031 | 150 | ≤0.031 |
| 151 | ≤0.031 | 152 | ≤0.031 |
| 153 | ≤0.031 | 154 | ≤0.031 |
| 155 | ≤0.031 | 156 | ≤0.031 |
| 157 | 2 | 158 | ≤0.031 |
| 159 | ≤0.031 | 160 | ≤0.031 |
| 161 | 0.125 | 162 | 0.25 |
| 163 | 0.031 | 164 | 0.031 |
| 165 | 0.125 | 166 | ≤0.031 |
| 167 | ≤0.031 | 168 | ≤0.031 |
| 169 | ≤0.031 | 170 | 0.25 |
| 171 | ≤0.031 | 172 | 0.25 |
| 173 | 0.125 | 174 | ≤0.031 |
| 175 | ≤0.031 | 176 | ≤0.031 |
| 177 | ≤0.031 | 178 | ≤0.031 |
| 179 | ≤0.031 | 180 | ≤0.031 |
| 181 | ≤0.031 | 182 | ≤0.031 |
| 183 | ≤0.031 | 184 | ≤0.031 |
| 185 | ≤0.031 | 186 | 0.5 |
| 187 | ≤0.031 | 188 | ≤0.031 |
| 189 | ≤0.031 | 190 | ≤0.031 |
| 191 | ≤0.031 | 192 | ≤0.031 |
| 193 | ≤0.031 | 194 | ≤0.031 |
| 195 | ≤0.031 | 196 | ≤0.031 |
| 197 | ≤0.031 | 198 | ≤0.031 |
| 199 | ≤0.031 | 200 | ≤0.031 |
| 201 | ≤0.031 | 202 | 0.063 |

The invention claimed is:

1. A compound of formula I

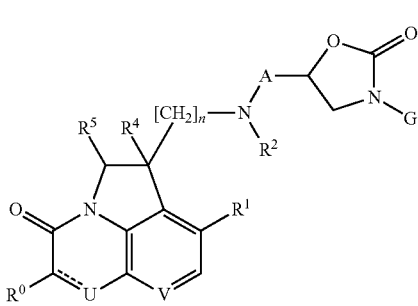

wherein

"-----" is a bond, V represents CH and U represents CH or N, or "-----" is absent and U represents NH;

$R^0$ represents H or, in the case "-----" is a bond, may also represent $(C_1-C_3)$alkoxy;

$R^1$ represents H or halogen;

R² represents H;
R⁴ represents H;
R⁵ represents H;
A represents —(CH₂)$_p$
G is the formula G¹ below

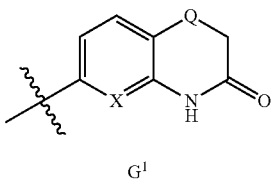

G¹ wherein Q is O or S and X is CH or N; and
n is 0 and p is 3; or a salt thereof.

2. The compound according to claim 1, wherein R¹ represents H or fluorine; or a salt thereof.

3. The compound according to claim 1, wherein "----" is a bond, V represents CH and U represents CH or N; or a salt thereof.

4. The compound according to claim 1, wherein "----" is absent and U represents NH; or a salt thereof.

5. The compound according to claim 1, which is:
9-fluoro-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;
6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;
1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(S)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(S)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;
(S)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(R)-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(R)-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;
9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;
(S)-7-fluoro-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;
(S)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(S)-1-{3-[(R)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;
(S)-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;
(R)-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;
(S)-7-fluoro-6-{3-[(S)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(S)-7-fluoro-6-{3-[(S)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;
(S)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(S)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;
(R)-7-fluoro-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;
(R)-7-fluoro-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(R)-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(R)-7-fluoro-2-methoxy-6-{3-[(R)-2-oxo-3-(3-oxo-3,4-dihydro-2H-benzo[1,4]oxazin-6-yl)-oxazolidin-5-yl]-propylamino}-5,6-dihydro-pyrrolo[1,2,3-de]quinoxalin-3-one;
(R)-7-fluoro-2-methoxy-6-{3-[(R)-2-oxo-3-(3-oxo-3,4-dihydro-2H-benzo[1,4]thiazin-6-yl)-oxazolidin-5-yl]-propylamino}-5,6-dihydro-pyrrolo[1,2,3-de]quinoxalin-3-one;
(S)-6-{3-[(R)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one;
6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;
9-bromo-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;
9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;
9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;
(R)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(S)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;
(R)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-7-fluoro-6-{3-[(S)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one;

(R)-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-benzo[1,4]oxazin-6-yl)-oxazolidin-5-yl]-propylamino}-1,2-dihydro-pyrrolo[3,2,1-ij]quinolin-4-one;

(R)-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-7-fluoro-6-{3-[(S)-2-oxo-3-(3-oxo-3,4-dihydro-2H-benzo[1,4]thiazin-6-yl)-oxazolidin-5-yl]-propylamino}-1,2,5,6-tetrahydro-pyrrolo[1,2,3-de]quinoxalin-3-one;

(R)-7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one;

9-chloro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

9-chloro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(S)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(S)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one;

(R)-9-fluoro-1-{3-[(S)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

(R)-9-fluoro-1-{3-[(R)-2-oxo-3-(3-oxo-3,4-dihydro-2H-pyrido[3,2-b][1,4]thiazin-6-yl)-oxazolidin-5-yl]-propylamino}-1,2-dihydro-pyrrolo[3,2,1-ij]quinolin-4-one;

7-fluoro-6-{3-[(R)-2-oxo-3-(3-oxo-3,4-dihydro-2H-pyrido[3,2-b][1,4]thiazin-6-yl)-oxazolidin-5-yl]-propylamino}-5,6-dihydro-pyrrolo[1,2,3-de]quinoxalin-3-one; or 7-fluoro-6-{3-[(R)-2-oxo-3-(3-oxo-3,4-dihydro-2H-pyrido[3,2-b][1,4]thiazin-6-yl)-oxazolidin-5-yl]-propylamino}-1,2,5,6-tetrahydro-pyrrolo[1,2,3-de]quinoxalin-3-one;

or a salt thereof.

6. A medicament comprising the compound according to claim 1, or a pharmaceutically acceptable salt thereof.

7. A pharmaceutical composition comprising a therapeutically effective amount of a compound according to claim 1, or a pharmaceutically acceptable salt thereof, and at least one therapeutically inert excipient.

8. A method of treating a bacterial infection in a subject comprising administering a therapeutically effective amount to a subject in need thereof, the compound according to claim 7, or a salt thereof.

9. A method of treating a bacterial infection in a subject comprising administering a therapeutically effective amount to a subject in need thereof, a pharmaceutical composition according to claim 7, or a salt thereof.

10. The compound according to claim 1, which has the stereochemistry as drawn below

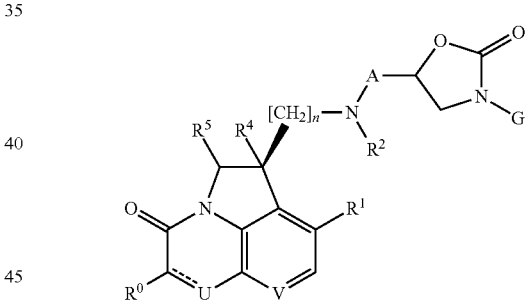

or a salt thereof.

11. The compound according to claim 10, which has the stereochemistry as drawn below

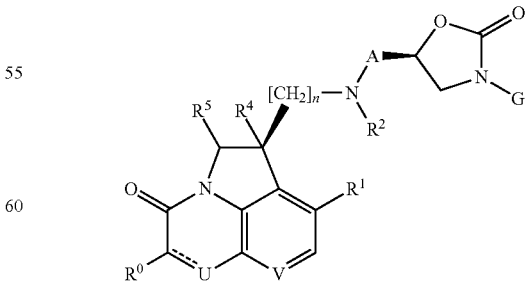

or a salt thereof.

12. The compound according to claim 10, which has the stereochemistry as drawn below

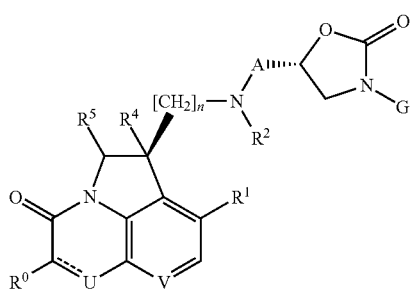

or a salt thereof.

13. The compound according to claim 1, which has the stereochemistry as drawn below

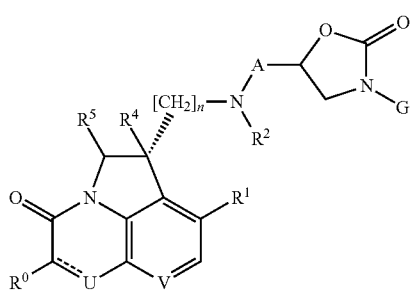

or a salt thereof.

14. The compound according to claim 13, which has the stereochemistry as drawn below

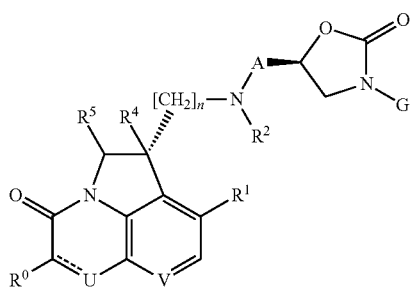

or a salt thereof.

15. The compound according to claim 13, which has the stereochemistry as drawn below

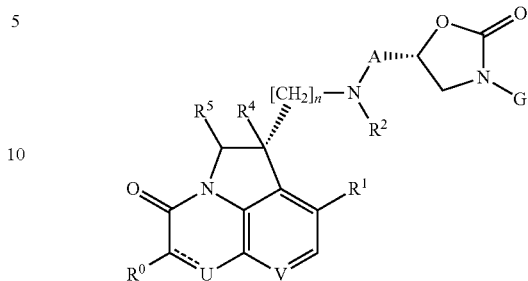

or a salt thereof.

16. The compound according to claim 1, which is (S)-7-fluoro-6-{3-[(R)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one; or a salt thereof.

17. The compound according to claim 1, which is (S)-9-fluoro-1-{3-[(R)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one; or a salt thereof.

18. The compound according to claim 1, which is (S)-9-fluoro-1-{3-[(S)-2-oxo-3-(3-oxo-3,4-dihydro-2H-benzo[1,4]thiazin-6-yl)-oxazolidin-5-yl]-propylamino}-1,2-dihydro-pyrrolo[3,2,1-ij]quinolin-4-one; or a salt thereof.

19. The compound according to claim 1, which is (R)-7-fluoro-6-{3-[(S)-2-oxo-3-(3-oxo-3,4-dihydro-2H-pyrido[3,2-b][1,4]oxazin-6-yl)-oxazolidin-5-yl]-propylamino}-5,6-dihydro-pyrrolo[1,2,3-de]quinoxalin-3-one; or a salt thereof.

20. The compound according to claim 1, which is (S)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one; or a salt thereof.

21. The compound according to claim 1, which is (S)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one; or a salt thereof.

22. The compound according to claim 1, which is (R)-9-fluoro-1-{3-[(S)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one; or a salt thereof.

23. The compound according to claim 1, which is (R)-9-fluoro-1-{3-[(R)-2-oxo-3-(3-oxo-3,4-dihydro-2H-pyrido[3,2-b][1,4]oxazin-6-yl)-oxazolidin-5-yl]-propylamino}-1,2-dihydro-pyrrolo[3,2,1-ij]quinolin-4-one; or a salt thereof.

* * * * *